US008853378B2

(12) United States Patent
Wellstein et al.

(10) Patent No.: US 8,853,378 B2
(45) Date of Patent: Oct. 7, 2014

(54) POLYNUCLEOTIDES THAT HOME TO ATHEROSCLEROTIC PLAQUE

(75) Inventors: Anton Wellstein, Washington, DC (US); Stephen E. Epstein, Rockville, MD (US); Mary Susan Burnett, Burke, VA (US)

(73) Assignees: Georgetown University, Washington, DC (US); MedStar Health Research Institute, Inc., Columbia, MD (US)

( * ) Notice: Subject to any disclaimer, the term of this patent is extended or adjusted under 35 U.S.C. 154(b) by 42 days.

(21) Appl. No.: 13/500,801

(22) PCT Filed: Oct. 9, 2010

(86) PCT No.: PCT/US2010/002717
§ 371 (c)(1),
(2), (4) Date: Jul. 2, 2012

(87) PCT Pub. No.: WO2011/043823
PCT Pub. Date: Apr. 14, 2011

(65) Prior Publication Data
US 2012/0269731 A1  Oct. 25, 2012

Related U.S. Application Data

(60) Provisional application No. 61/278,775, filed on Oct. 9, 2009.

(51) Int. Cl.
C07H 21/04 (2006.01)
C07K 14/47 (2006.01)
C12Q 1/68 (2006.01)

(52) U.S. Cl.
CPC .......... *C07K 14/4737* (2013.01); *C12Q 1/6883* (2013.01); *C12Q 2600/156* (2013.01)

USPC .......................................... 536/23.1; 514/1.9

(58) Field of Classification Search
None
See application file for complete search history.

(56) References Cited

U.S. PATENT DOCUMENTS

| 5,580,859 A * | 12/1996 | Felgner et al. ............ 514/44 R |
| 6,359,054 B1 * | 3/2002 | Lemieux et al. ............ 524/505 |
| 2004/0005309 A1 * | 1/2004 | LeBowitz et al. .......... 424/94.61 |

FOREIGN PATENT DOCUMENTS

| WO | WO 2007/086980 A2 | 8/2007 |
| WO | WO 2007/136336 A1 | 11/2007 |
| WO | WO 2008/069965 A2 | 6/2008 |

OTHER PUBLICATIONS

Khachigan et al., J Immunol Methods. 1991 Jul 5;140(2):249-58.*
Matthews et al., Clin. Sci. (Lond.), 1984, 67:541-549.*
The Merck Manual of Diagnosis and Therapy, 17th edition, editors Beers and Berkow, 1999, Merck Research Laboratories, pp. 2198-2210.*
Hong et al., "Phage display selection of peptides that home to atherosclerotic plaques: IL-4 receptor as a candidate target in atherosclerosis" *J Cell Mol Med*. Oct. 2008;12(5B):2003-14.

* cited by examiner

*Primary Examiner* — Michael Szperka
(74) *Attorney, Agent, or Firm* — Wolf, Greenfield & Sacks, P.C.

(57) ABSTRACT

Described herein are homing polypeptides that home to atherosclerotic plaque(s) in mammals and nucleic acids that encode such polypeptides. Also described are methods for detecting and treating conditions or disorders associated with, or characterized, by elevated levels of homing polypeptides that home to atherosclerotic plaque and/or vulnerable plaque.

2 Claims, 31 Drawing Sheets

FIGURE 2

A1: SEQ ID NO.: 24
GCCTGTAAGTGAGCCCAAACATCAATGAAGCTTCTGTCTTGTGGCTCAGCAGTTCCCCAC
CCCTGGTCCCCATCTCTCAGAGTGGAATGTTCATTAATTTCGTGAAATAAGAGTTGAGGA
GAGGAATGAAAAGCAGCCAAACACAACCATCACATTTTGCTGAAAGAGTTGATGGGGAAA
AAAAAACAGGCACCAATGGTTGTTGTATCACCTAACTGGGCTTTACATTGCTAGTTTCAT
TCCGTCCTTTATAAGTACACATTGTTGTGTGTTTTAACTTGGATTCAATACTTCAGCTAC
TTCTTATTTTCTACCATTGTAACATTAAAGGAAACTGCATCTCTGCATAAAACAAAAGGT
AATATAGCTTGTAGGTTTGCTTTGCATTGCAAAGAACATACTTGCTTAAGACAATCAAGT
GTCGAACCATGGACACCTGCTACGGAGATTCCAATTGTGGGATCTTCTTTTTATCAACTAA
AAAGCTTGCGGCCGCACTCGAGTAACTAGTTAACCCCTTGGGGCCTCTAAACGGGGGGGT
TATTTTGGTAAAGGGGGGGGGCCCATTTTTTTTTAAAAAAAAAAAACCCCTTGGGGACCC
CCCAGGGGGGGGGGGAAATTTTGTTTTTAAAGTTTTAAAGAACTAATATATACTTTGTA
GAGAGTCTTATGAGGAAAAAATACTGAGTATGAATCATAACCACATGGATATAAGGAATG
ACTAAGGCTAGATTGCAAAGGGGGGGGTCCCCCTGAGAACAGAAAAGATGCCGC

A8: SEQ ID NO.: 25
CTCAGCTTTTCCACTGTTATGTGTAAAGGACTTTAAAAATCTTATTCAGTCAAATATTAA
ATATCATCGTTGCTGTAATTAAGCTTGCGGCCGCACTCGAGTAACTAGTTAACCCCTTGG
GGCCTCTAAACGGGTCTTGAGGGGTTCCTAGTTACTCGAGTGCGGCCGCAAGCTTAATTA
CAAGCAACATGATATTTAATATTTGACTGCTAATAAGAATATTTTTAAAGTCCTCTAATA
CACAATTAAACAGTGATGGAAATAGCTTGAATTCGGATCCCCGAGCATCACACCTGACTG
GCAACACGCTCCTTTAGGCAAGCTAGAGGGATTTATTTTCCATTTTTAGGCCATAGGCAA
TTTTGTTTGCTTAAGCTTGCGGCCGCACTCGAGTAACTAGTTAACCCCTTGGGGCCTCTA
AC

B3: SEQ ID NO.: 26
TTCGGGTACAGAAAGATGTCCATGATTTTTACTCTTGAGTTAATCACTAAGATTCCAAAA
TTCCATAACCCTAAACAAGTCTATTTTCCAAGGGCAAAAAATAAATTTAATGGTAATTAT
TCAAGTCTTTAAAATTTTGTTTTGTTAAAAAGAGAAAATCAAAAGTATATCCTCTGCCT
CATGTTTAGGACTATAATAAAATGCTTTGTTCCATGAAATAAGCTTGCGGCCGCACTCGA
GTAACTAGTTAACCCCTTGGGGCCTCTAAACGGGTCTTGAAGGGGTTTACCGAGGGGCTA
GCGCAGCCGGGTAATTCCGGGAAAAAATTTTATTATAGCTACTGGGGGAGATATACTTGT
TTTCTTTTTTACAAACAAATTTTTAAAGAATAAATTTAAATTTATTTTTTCTTGGAAAATA
AATTGGTTATGGAATTGGAATCTTATGATTAACTCAAAGTAAAAATCATGGACATCTTAT
CTATATAACCCTGACTGGAATACGACAGCTTCCCAAA

B6: SEQ ID NO.: 27
GCGTTCTAGCTTTCCTTTTATCGATAGGCCAGATGGGTCTGTGGCATGTGAGATGAAATAC
AATGGGCCAGAAAGAAATCCTGGCTGGAGGTGAAAGGAAATCAGAGGGGTTGTGGGTCAA
CTTTAGGTTCAGGATTTAGGTACCAATCCCACCTCGATCAGTAAGTCACAACTAGAAGGA
AGCCCCTGTCTCAGTTTCCTCACCTGTAAAACCAAAGTGGTTGATCCATGATCTTCCTTG
GTTTTAGATGATTAGAAATGATATGTAGGAGGCAATTTGTGTGGGATCAGACATAAAAGC
ATAAGCTTGCGGCCGCACTCGAGTAACTAGTTAACCCCTTGGGGCCTCTAAACGGTAAAG
GGGTTGACTAGTTACTCGAGTGCGGCCGCAAGCTTATGCTTTTATGTCTGATCCCACACA
AATTGCCTCCTACATATCATTTCTAATCATCTAAAAGAAAGGAAGATCATGGATCAACCA
CTTTGGTTTTACAGGTGAGGAAACTGAGGAGGGGGTTTCCTTTGAAGTTGTGACTTACTG
TCCAAGGTGATTTATTCTGTTTTAAAGTTGATTTACAACCCCTCCGATTTCCTTTCACCT
CCGGGTTTGGGAATTTAATAAGAAATTGCCCCCCCCCCCTGCGGGAAGAAAAATCCCCA
ATCGATCAGGAAAGCTAGAATTCGGGATCCCGAGCATCACACCTGACTGGAATACGACCA
GCTTCCA

B9: SEQ ID NO.: 28
CTTCAGCATGATCCTGACGAGGCACTCCAAGAGGAACACAATTAAAAAATCGCAATGCAG

FIGURE 2
(continued)

TGTGTTGTAGCAGAGCAGAGAAATAACAAAGTAAAATAACAGATCACAATGTGGAGAGGT
AATCAGTTTTACTTGATGAGGGGAGAAAGGAGGAGAGACACATGTTGAGTTTTAAACAAT
CTGTATATAGGACCATAGAAATGGAAGCTGGCCAGACAGACTGGCATGCATATGAAAGAG
ATATGAAACAACATGGTTTAAGAACTGCATAGTTTAGAATGGTTAAAATATAAGCTTGCG
GCCGCACTCGAGTAACTAGTTAACCCCTTGGGGCCTCTAAACTTGGGGTAAAAGGGGGGG
GGGGGGGGCCCGATTATATTTTTACCTTTTAAAAATATGTGGTTTAAAACCCTTGGGTTA
TTTTTTCTTTTCAACGGGTGGGCTCGGGGGGCCTTCTTATCAGGAAAAGGGTAAAAAATC
AAGGGGTCCTCCTTTCCCCCCACCCCTGGGAGGGAATTTTAATTGGAAAATTTACGGGGG
AAAACGGGGATTATTTTTATTAAGGGGAAACCTCTGGGGGTACCCAGGGTCGGGACGGGTG
GGATCAAAAAAACCCC

C3: SEQ ID NO.: 29
CCTTTCCTGCACTTCCCAGACTTCTGTCAACAATAGCCACAGGAACAAAGCCTAAAGGAA
ACTGGACTTAGCCAAAAATAATTCTGTCTGCAAGCTTGCGGCCGCACTCGAGTAACTAGT
TAACCCCTTGGGGCCTCTAAACGGGTCTTGAGGGGTTCTAGTTACTCGAGTGCGGCCGCA
AGCTTGCAGACAGAATTATTTTTGGCTAAGTCCAGTTTCCTTTAGGCTTTGTTCCTGTGG
CTATTGTTGACAGCATAAGAAACTGTCTGGTGAAAGTGCAGGAAAGAATTCGTATCCCCG
AGCATCACACCTGACTGGAATACCACAGCTCCTCTCCTTAATCTGCCCACCCCCAATATT
TCCCTGTTTTTTTTTTTTTCTTCCTCCATACTT

C4: SEQ ID NO.: 30
GGGGTTCTTTCCTGCCTTTCACCAGACAGTTTCTTATGCTGTCAAAATAGCCACAGGAAC
AAAGCCTAAAGGAAACTGGACTTAGCCAAAAATAATTCTGTCTGCAAGCTTGCGGCCGCA
CTCGAGTAACTAGTTAACCCCTTGGGGCCTCTAAACGGGTCTTGAGGGGTTAGAGGCAAG
TAAGTCGCTCTTAGAGTTTGCTACTTTGCAGAGTGGTTACCCATAAGACTATTTTGGGAG
GGTTGTTGACGCACTAGACGACCTAGTGCTACACTTGTAGCCGCCGGCGGAAGCATCCCC
TGGAAAATACCATCCTAGCAGCTTCTCATAAAAATCATACCCTGTGGATCCTTTGCAAGC
AGAACTGACTGTTGTCCCTGAGTCCTTGGGGGTCGCATCCATCTCCACACTGGATATGGG
GAACATCATTTGAGTCTCTTCATCTCCCTGTTCTCTTAATCCATGTGTCCCACTAGTGGA
TGTGCACTCCAGGCCAGTGTGCAGAGCTTCTGTGAAAGCTGCTGGCACTGAGTCCAGGCA
GGGCTGCTGCCCCCAGGCACAGCTCTGCC

D5: SEQ ID NO.: 31
GCGATCTACAACTCAAATATTTAGTTAGACCACTTATACCAGATTCTTATCATTTCTGCC
TGAACTATTTGATTTTATTGATTAATAAATTGTAACTAAGAGTTTTAAAATGCCGCAATT
CAAATTTACCTTTGAACATTAAAATATTAACCCAGAGAATTATTTATAGAGGAGAGCCAC
AAGTCGCTATCCAAGTTTGCTTTACTTTGTAGATAATCAGGGGATAATTATCTATATTTC
AGAAGCTTGCGGCCGCACTCGAGTAACTAGTTAACCCCTTGGGGCCTCTAAACGCATGGG
GTTAAGGTACTCGAGAGTGGGCGCAAGGTTCTGAAATATAGATAATTATCCTGATTATCA
ACAAAGTATAGCAAACTTGGTAGCGCTCTTATAAAAAAAATTCTTGGGGAAATATTTTAA
GGGTTCAAGGTAAATTGGAAATGGGGTTTTTAAACTAAATTTTTAATATAAAACATAAGC
AAAGATAAATCGTATAAGGCTAATAAATATTGATTGTAAATTGGGAGGGGAAAAACACAC
CCCCCAA

D7: SEQ ID NO.: 32
GGCCGCACGGAACGGCCGCTAAACCCCAATACGAAAACAAAAGGCGCCGTAACAAGCCGC
GGCCGCACCCGAGTAACAGCAACCCCGGGGCCCCGCGGGCTAGGGTCGCTAGTTAACGAG
GGGGGCTGAAGCTTAATTACATGTAAAATGATATTTAATATTTTTTAGCCTCTAACAAT
ATTTTTAAAGTAAGTTGTATTGATTGACTCCACTGATGACTGACTCCTGCCTCGGGAAAG
GACGTGAGTGAAGTGCAGCTGCTGCGCCTGATGCTGGGACAGCCCCGCTCCCAGATGTAA
AGAACGCGACTTCCACAAACCTGGATTTTTTATGTACAACCCTGACCGTGACCGTTTGCT
ATATTCCTTTTTCTATGAAATAATGGGAATGATAATAAAACAGCTTTGACTTGGAAAAAC
CAAAAAAAAAAAAAAAAAAAAAAAAAAAAAAAAAAAAAACACCCCCAGATTCTTTTTTTTGT
ATTTTGCACCCCCCTACTTTCACAAA

F5: SEQ ID NO.: 33
GCTCTTTTGCACTTTCACCAGACAGTTTCTTATGCTGTCAACAATAGCCACAGGAACAAA
GCCTAAAGGAAACTGGACTTAGCCAAAAATAATTCTGTCTGCAAGCTTGCGGCCGCACTC
GAGTAACTAGTTAACCCCTTGGGGCCTCTAAACGGGCTTTGAGGGGTTCACTGAAGCCCG
CCGTCGCGGCGAGACCCTATTGGGCTGATTGGAGACCAGGAGGCCTCTTGGGGAAGAATG
GTTCAGGAATAAAAGGCAGGAGCATTGTAGAGATTTTCAGGGAGGCCTGAAGTGAGGTTG

FIGURE 2
(continued)

GAGGGAACCAAGGAGAATGTGGGGAGAGTGTGCAGATGATCCTGGAAGTAGAACTGAAAA
GGGAAGGACAGGTTGGGCAGTGGTTAAACCCTGGGCAGGAATGCCTCCTACGGCATCCCT
GAGGATTCGTTGTGAGGTACTGAGTGCCACTGCTGGGCTTGGGCTGAGTCACCTTGGTGC
ATTCTGCTTTGCCTGCACAGACTTTGTGTGCCAGAGCTGTGCCCAGAGAGGATGGAGGCC
TGGTCTCAGGGCACCTGGGCCCAGAGTAAGGCCTGTGGACCCAATCTGACGGCAGTGGAA
GATACTGTAGGGCCCAAAGAATGCCCAGCCTACAGGGCTGTCAAGTGCAGCTGGGTAAAA
AATGGATTGAGGAATTAGTGGGGGTTGGGAGGCAAGACCTGGTTGGGGAATGAAACACAG
AGAGAGCTCATAAACATGGACCAAGAAAATCCCTCTAGTATCAACACCTACTCTCTGGCC
AGGCGATGGCAAATTC

H4:     SEQ ID NO.: 34
TCGAAGAAGTAATTCAAAGTTCGCAGGTTCACTGTGGACCCCGAGCAAAACAAACACCT
AGTCCTAAAGAGGAGGGAGCCTCACCCACCCCCCAGCATGGGTCACTGAAAGGGGGCGAT
GTCTAAGTCACGTGAATGGGTTGGCAGAGAAATGGTAGAAGCCGAGACATAAGGACAGCC
TGCTTCCGAGTGTGCAAAGGAAGTGAAGCCAGCCAGCACCAGACCTTGTGCAGACCACCC
GCCCCCAGTGGCAGCTGGGGGAGTGGTCATCAGTTCAAGACCGTGGGAAGGGTTACAAAA
AAAGAAGCTTCGCGGCCGCACTGAGTAACTATTAACCCCTTGGGGCCTCTAAACGGTTTG
GGGGGGGTTAAAAAGTCGGGGGGGGGGGTCCTTTTTTTACCCCCCCCCCCTTAGGAAAAAA
AAAGATGACCCCCTCCCTCAAGGGAGGCTGATGGTGGTGGTGGTTCTTTCTTTGCACCT
CCGAAGGGTCCTTTAAGGTCGGTTTACAGTTTTTGCACCATTCTTTGTAAAAATTCCCCC
CTTATGCCCCGGGAAAAAGGGGGAAATTTAAAATTCTTCTTTTTTTTAAAAAAAAGGGTA
TTTAATTTTGGAAAGGGTTTCCCAAAAAACGGAGAGTTTTAAAGGTAATCAAATCGGACCC
AACTCCCCTGTGGAAAAAAACCATCCCGCGGGAAAACTAAATTAAAAACCATC

H6:     SEQ ID NO.: 35
CGTTCTGAGATTCCAAGGTAGAGCAAGAAACGGGGATACAGCTGACGTCTGTCTCCCCCT
GGGAGTTATGTCACTCCTTGATTTAATTCCTTCTGACATTTTCCCCATCATACTTTCTGC
TCTTCATCAAAATACATCCCTCTCGAAAAACAAATGTGCTTATTGACTACCCATGACAAT
CTTGGAAATGGTTGCAACTGTTCATGTGTAGGATTAAAAAAAAAATTAAAACAAAACAAA
ACAAAAAAACCACAGGCAAACAAAATCTAGAGACCTGTGCCATAAGGTCAGATGAGCACG
AAAGGGTTGGTTAGTCCATCCAAAGTCTCAGGGGTTTAGGCAAGCTAGAGGGATTTATTT
TCCATTTTTAGGCCATAGGCAATTTTGTTTGCTTAAGCTTGCGGCCGCACTCGAGTAACT
AGTTAACCCCTTGGGGCCTCTAAACGGGGGGGGGGGTAAGTTAATCGAGGGGGGGGGGG
GGAAGCTTAAGAAAAACAAAAATTGCCGATGGGCTAAAAAAATGGAAAATATCCCCTAGCT
TGCCTAAACTGGAGGACTTTGACTAACACAGGCCCCTTTGGGAGGGTTTTTGTTTTTTTG
GGGGGGGGGGTGTTTAAATTTTTTTTTTTTTTAACCCACCCTGAACCCATTGGGGAAAAAA
ATTGTTTTTTTGAGGGGAGGTTTTTGATAAAAAAAAAAAATGGGGGAAAAATGGGCAAA
GGAATAAATCCGGGGGGGGGAATCCCGCGGGAAAACTAAATTAAAAACCATC

H7:     SEQ ID NO.: 36
GGCGATCTGTGAACAAGACATGTGTAACAAATGCTTTTGCAAAATCATGTCGTCATTAAA
GCAGTTACTTTAATAAAGATCGGCTTCACAAGGGGTTTCCGGTACAACAGCTGCAGTTAA
ATATCTATACACTGTTAACATATTTTTTAAAATAAGCTTGCGGCCCCACTCGAGTAACTA
GTTAACCCCTTGGGGCCTCTAAACGGGTTTAAGGGGTACTAGTTACTCGAGTGCGGCCGC
AAGCTTATTTTAAAAAATATGTTAACAGTGAATAGTATTTATCTGGAGCGCTGCGGGGAA
CCCTTATTAAAAGCTTTTTTAATAAAGAATTTGCACAATGATCTGATTCTTGGGCAACCA
TATTGTGGAAAAAACCCCCCCCT

H8:     SEQ ID NO.: 37
GGCGATTCACCAGTGAGTAGATTGCACAAATCCTGCAGCCCATCTCTGCCACAGCTCAAA
GTAAGCAACTTTTACTCGTGTATTCTTAAATAGTCCCAAGGATCAAATTATATCTCTGCT
AAAACATTGTTAGGCCTAACTTCCTCACCAAGAATGTGGACTTTGGTCCGACTGCCAGGT
TAAGAGGGCGTTTCTTGAAAACTTTTGTTTCTTTGTAGGCACAGTATGTGCTCATTAGAT
ATAAAAGCTAATGGATTAACTAATTCCTTTAGCCTTTCCAAAATAGAGGTTTCATGGAAC
TATCTAGGCCCATAACAAATGTTTCTGTGATGAAACAAACTCAGGAAACTGTATATTTTC
TTTTTCCCTTAAAGCTTGCGGCCCGCACTCGAGTAACTAGTTAACCCCTTGGGGCCTCTAA
ACGGTGAGGGGGGGGGTAAGGCGGGGGGGGGGGGCACGGATTTAAGGAGGAAAATATAG
TTCCGGAGGGTTGTTTCCCCAAAAACAATTTGTGGGGCAAGAAACTTCCAGAACCTGGGG
AGGGGGGCGAATCCTTATTTTTATCTAATGGGAGGGAAAAAAAAATTCCAGAACTCCTAA

FIGURE 2
(continued)

```
CCGGGGGGGGGACCAAACCCATTTTTTGGGGGGGGAGGGGCCACAAAGGGTTTTAAAAAA
AAAAAAATGCCGGGGGGCTTTAAAAAAACTTTTTTTTTTTTTGTGGGAAAAAAAGGGGG
GAAATTTTTCGGGGCCCCCCCCCCCCCCAAC
```

```
GCAACACGCTCCTTTAGGCAAGCTAGAGGGATTTATTTTCCATTTTTAGGCCATAGGCAATTTTGTTTGCTTAAGCTTGCGGCCGCACTCGAGTAACTAG   < 400  SEQ ID NO.: 41
 A  T  R  S  F  R  Q  A  R  G  I  Y  F  P  F  L  G  H  R  Q  F  C  L  L  K  L  A  A  A  L  E  *  L  V           SEQ ID NO.: 42
  Q  R  A  P  L  G  K  L  E  G  F  I  F  R  V  *  A  I  G  N  F  V  C  L  S  L  R  P  H  S  S  N  *           SEQ ID NO.: 43
   N  T  L  L  *  A  S  *  R  D  L  F  S  I  F  R  P  *  A  I  L  F  A  *  A  C  G  R  T  R  V  T  S
CGTTGTGCGAGGAAATCCGTTCGATCTCCCTAAATAAAAGGTAAAAATCCGGTATCCGTTAAAACAAACGAATTCGAACGCCGGCGTGAGCTCATTGATC
       310       320       330       340       350       360       370       380       390

CviJI
              HaeIII
              FnuI
              Sau96I
              UnbI
              PssI
              EcoO109I
         BsaJI
         StyI    >HinI
    MseI     NlaIV
     |   |   |||  |
    TTAACCCCTTGGGGCCTCTAAC   < 422  SEQ ID NO.: 41
      N  P  L  G  P  L  *                 SEQ ID NO.: 42
     L  T  F  W  G  L  *  X               SEQ ID NO.: 43
      *  P  L  G  A  S  N
    AATTGGGGAACCCCGGAGATTG
      410       420
```

FIGURE 3
(continued)

```
            CviJI
              |
TACGACAGCTTCCCAAA  < 517   SEQ ID NO.: 44
 T  T  A  S  Q  X          SEQ ID NO.: 45
    R  Q  L  P  X
 Y  D  S  F  P  X          SEQ ID NO.: 46
ATGCTGTCGAAGGGTTT
       510
```

EST sequences:

A5: SEQ ID NO.: 1

GGGGATTCAGGGGCAGTTTATAATTCAGTCACATGTTAAAGAACAAAAAGGACGAAACAACAATA
AAGCAGATAGAATCGTGAAATGGGTTACATTATTTGCACCATAAAGTTTAAGTAAATCAAATTAT
TGGGAATATTCTGAGATAGAGCTAAAGTCTTTCTCAAGAGTCATGGTTGAAACCACATGTTGTGG
AGGAACTGATGGTGATTGTTGCCCCATTGTGGGATTCCTCCCTATGGTAATGACATCAAAATGAA
AAAAAAAAACACACACACAAAAAAATGACGCAAATTGTAATTAAAGGTGGAGCTGTTTATGA
TCTGGTTATCTCCACATTGTTCTGGGAAAAAATTGAAACATTACTGGGTCAAATCATGTCTGTGA
AACAAAATGAAAGGTAAAAATAGTGAATAAAAAAAAAAAAAATTAAAAACAAGCTT

A12: SEQ ID NO.: 2

GCGATTCAACACTCTATAAGAAAAAATATAATAATTTGATTTAAAAACTGGCAAAATATCTGAAT
AGATATTTCTCAAAACAAGCACATACGAATGGCAAACAAGCATACAAAAAGGTGTTCAACATCATT
GATCATCAGAGAAATGCAAATCAAAACTACAAGGAAAATATCATCTCACTCCTCTTAAAATGGCT
TTTATGCAAAAGTCAGACAATAACAAATGCTGAAAAGGATGTGGAAAAAAGGAAACCCTCATGCA
CTATTGGTGGAATGTAAATTAATACAGCCACTACGGAGAACAGTTTGCAGGTTCCTCAACAACAA
CAACAAAAAACTAAAAACAGAGCTATCTTACAATCCAACAATTCCACTCCCAGATATATATCAGA
AGTAAGGAAATGACACTAAGTTTTTGAAAAATGAAAAGCTT

B9 SEQ ID NO.: 3

GCGATTCTGGGACTGTGGATATAGCTTGCCACAGTATCTTATCAGTTAATTGCATTCTTGAATGT
GCTGGGAGTCAGCTTGCACAAGGTAAGTCCTTGAGGAAGCGGCTGCCAGTGTAAGAGCCAAGATG
GAGTCTGTCTGGCTCTCTTAGCTAAGGGAGAGTCAATTCAGGTGGAAACAAGGCTAGGTCATTAA
AGGAAAGGGACAGTCTAAAAACAGCGGTTAGTAAAAACCAGGTTGGGCATTACAGTATCACCCAGA
CAACCAAGTGTTCATGTTTAACCACAAAGCCCTCTTGTAATTGCTGAAGCGTATTTGCTTGTAAT
TGCTGCGACCATTCTTCAAGTTGTTTCTTTAACTCACATTCAAGAGTAGAAATTTGAGAAGAAAT
ACGGTTGTGATAAGCCCCTTGCAGGTGTGCTTTCACTCTCTCCCAAGCATATTGGGAGCTATTAT
ATGGCAGAGGTGTGACACAGATAGGATTATATTGCCAATCACAATGTAAATTTTGATGGGTAATC
AATGCCTGCTGCTGAGCCCCCAGCCATTCAACTGCGGCTTCAAGAGCCTCCAGGTGAGACAGAAT
AGTTTTATCAATATTTACCTGTTCCTGAAATTCATGGGTTACATTATATACCATGTGGTTCACCA
CTGAGGCTATGTGAATAGATCCTGTTAGAGAGACAGCTGCAGTAGCAGCAGTTGCTAGTATGATA
ATAGCTGAGACTAAAAAGTCAATTAAAGTGGCCAGAAATCTTTTTTTCTGAGCATGAGACAGTGC
TTTTCTAAATAGCTGCTGGGTGGAATTTCCTTCCCAGCTCCAGGTTAAATTTACAGGCAGCCACA
TTTCTGCATGCCGTTTTAATCATGACGTTATACTTAACTGTGTAACGTTTTGATAACAGCATGTA
GCATACCAGTACTGGAAGACTTTATACTATACTGATTCTGTTTTTGTAACCTCGCCAAAGTATAT
GGGTGCATAGTAACACTGTCAGTATATGCAAAGTGCTGCCTTATACTCCCTAAAACAATCAGAAA

C1: SEQ ID NO.: 4

ACATTCTGTGGGATGATGGTGATGGTAGCATAGCATATGAATGTGCTTAATGCCTCTGAAGGTAG
ACTTAAAAATGGTTAAGATGCCACATTTTATGTTATGTGTATTTGATGACGATTAAACATTTTAA
AAATTGAAAAAGGTAAACATTACAAAATAATTTAGTGAAGCCAGATATCATGTCACTTCATGTTT
CTGTTAAATTTATGTACAATTAGGCTGGTTTGTATTTAGAAAATTCTAGTTATAAAGATGAATGAA
TAACAGCCAAAGCTT

FIGURE 4
(continued)

C2: SEQ ID NO.: 5

GCATTCAGACCAGCTTGGTCACAGAGAGAGAGTCCATCTCTATAAAAAAATGTTTAAAAATTAGA
CGGGCATGATGGTGCTTGGTGCTTGCCTGTAGTCCCAGCTACTTGGGAGGCTGAGGTGGGAGGAC
TGCCTGAGCCCAGGAACTGGAGATTGCAGGAAGCTATGATCACATCACTGCACTCCAGCCTGGGT
GACAGAGCGAGACTCCGTCTCAAAAAAAAGTCTTTTGTTTTCAGTCATGGTGGTATACGCCTCTA
GTCTCAGCTACTTGGGAGACTGAGGCAGGAGGGTCACTTGAACCCACCAGTTCGAGTTCAGTCTG
GACAAAATAGCAAGACCCCATCTCTAAATCAAGCAAACAAAGCTT

C7 SEQ ID NO.: 6

CGATTCAGCGCTTGATTCCATTACTGGGTATATACCCAAAATAATATAAATTGTTGGACTATAAT
TATACATGCATGTGTGTGTTCATAACAGCACTATTCATAACAGCAAAGACATGAAATCAACCTAA
ATGCCCATCAAAGGCAGATTGAGCAAAGCAAATATGGTAGATACACACCATGGATGCTATGCAGC
CATAAAAATGAAAAAGATCATGTCCTTTCCAGAAACATGGATGAAGTTGGAGGCCATTATCCTTA
GCAAACTAATGCAGGAACAAAAAACCAAATGCTGCGTGTTCTCACTCATAAGTGGGAGCTAAATG
ATGAGAACAGCAGACACATAGAGGGGACAACAGACACTGGGGTCTACTGGAACGTGGAGGGTGAG
AGGAGGGAGAGGATCAGGAAAAATAACTAACAGGCACTAGGCTTAATACTTGGGTGACGAAATAA
TCTGTACGACAAACCCCTATGACAAGCGTTTACTTATATAATAAGCTT

E7: SEQ ID NO.: 7

CGATTGCAGAAGCGTCAGGTTTTGTAACCTACGCTTGCAGTTTACTCTCCCCATAGACTTGTAAT
GTTTATCTTTATAATGATAAGGAAAAAAACATCACTTTCTGTTATGGCTTTATGCCTATTTTATGT
AGTACAGAATAAACCTAATAAAATGATGTTGGGATTGTTCCATAAGGCATTCTAAAACTTCTTCT
TCCTAGTAGTTGAATTAGAGTTTTTAGTCATTAATAAGACACATGGCATCATAAAAACACAAAAT
CTGAAATAAAAAGAAAGATCTTTTCTCCAGGATTCAGAAAAATATTTTGTCTCCATTTTGCCATA
TGCTTCATGAGATCTTGTACTAAGCTT

E9: SEQ ID NO.: 8

GGGGAATAATTTTGTTATCGGCTAGTGAAAAGTATTTGCTTTCCTAAGGTATGAGCATGTACTGG
TTCACTAACTTCCCAGTTGTTTTTCTGGCTGAGAAGAGCTTTTCTTCTGGTGGCACATGTCCATG
ACAGCTGTTTATTCCACATGTTTCCATTGAAAGCATATTAACCTGAGCAAATGGGGATAATTATC
ACAGTGTAAAAATGCCTTTGGATGTTAATGATTCCTCTTCTGTCGTCTCCTTTGATTGGCCTGAC
CCTCGTATTACTATGTATTAATATCCTTAGATCTTCATGGTACCAAGGACATTCCAAAAGTCATC
CACATTGACTTTGGCTCAGAAAGCTT

E12-1: SEQ ID NO.: 9

GGATACTTGCTAGTAGGCTACTGCATTCATTTGGGCTCCACCCTTTAAGAGGGGCATTAACAAGG
TGAAGTGTATTCCTGGGTCAGTGGCAGCTGGTCTCACTAGCATGTCCCTAGGAGGACAGACAGCA
TAGAAGGGCCCTGGGAACTTGTGCCCTGGGAACTGGGTGCCAGAACTGGGGACGTTTAAAAATAA
CAATCTGGAGCAAATATGATGACTCCTTTTAATTTTTTCAAAGACTGAGATTTGGAAGAGGAGTT
GATCTGTGCTGGGAGACCCTGGCAAACAGTAGGTAGAAGTGACAGGGAGGTGGAGTGGTTAAACT
TTCTAATAATCAATGCTGGTTGACAACAAAATAGACTGCCTCAATTATATTGCATAGACACCTGC
AGTTGTATTACAACCCTCTTTAGCAAGCCACCAGGAAAATTGGTGCAAAGGAGAAAGATTGCTAT

FIGURE 4
(continued)

GGTATGAATCACTCTTTTGGCTGTGTAGATGGGTATGAATGTTTGTCTCTGTCACAGGAAGTATG
GATGCCACCTGGAAGATGACCTATGTGTAGAAGGAAACCCAAGCTT

E12-2: SEQ ID NO.: 10

GCAAGGTATAATACAGTTACGCATAATATGAGATTAGCGGACTTGCACGATTTAAGGTTTTGTTT
TAATTTTAATCACCCAGAGAGCTGCCAGTTGTTCTGATGCCTCTTTGGTTAAGTGAAGCTGAAAA
AAGGGTATAACTCAACTGTCACATGAATTACGGAAGCTT

F6 SEQ ID NO.: 11

GAATTGGGGCATATAATGAAAACAATGGTCGGGAAATGGAAGAGATATATTAACCGAATGGGTCT
GGAAATAAAATAAGTAAAGAACAACTTTATTCCCTGCTCTTTGTGGCTTGTGCAACCTCATGAGA
CAAATGGATGCACCAGGAATCCAGCTGTAATATACAACTGTCAGAGAAACACTTTTAAGCAAAGT
ACAATGTCCTGTGAGAGTACAGTAATGATTAATTTTGATTTGATTAACATTTTTGCTTAATAAAT
TTGTTATAGTAAATAAACTAATTTGTTTAGAAAACAGCACCAGTCCTTGTTCAACACATTTCATA
AAGAAGTTCATCCATGGTTTCAATATGCACCCTTGATTATTCTATGGAGAGTTAAATAATAATTT
TATAACTTTGGAGATATTAAGAGGGGGGTTATATATCTCTTCATTCAGTCTCCTATATATTCAGA
CAGAAAAACTGAGGACAAAATAAAGCTT

G12: SEQ ID NO.: 12

ATAAAAGGAAGCAGCTTTAAGGGAAGCAACTTCAATTGAGTGCATTGAGGGCAAAACAGCCAAAG
GGTGATCCTGAATTAGTTTATATGACGTAAAATGCAAAACAGTAAAGCCTGTTATCTAAAGGAAA
AGATAAAAGGCAAAGGCAGAGTCAAAGATAGCAGATTTCAGCAGTCATAGATTTCTCTCTCTGGA
AAGCACAGCTGTTTTTTGTATCTGCCAACCTAATGGAACTCCTCAAATGACTTTTGTTGAAAGCC
CACAGGTCCTGGCAGGGCATACAAGAACTTGAGAACACATGGATTCTTTCTTTCAGGACCTTACA
TTTTAAAAAGGATTCACCATGAGAACTCAATGGAAAACTGATCTGGTGAAGGGGGAAAGACAAGC
TT

H3: SEQ ID NO.: 13

CAAACACAGGGTGATTAAGTTACTCTCTAGAAGAACAAATACCATAGGAGCCCAGACTGGCTTTA
GTGATGATATAAGTAAAGAAAAGCACATTTCAAAAAGCAAAGAAATGACAGTGCTAATTTACTTG
CCCAAATGTTACTGAGAGAACTGTCACTTGAATGTCTCTCAGAAATCATAAGGTGGTGAATGACA
CTCTTTGTCATCAGTATATCCATAGGACAATGATTGTTCTGAAGCAAAATCTTGAATTTCTTACT
CTCTTAACAGGCGGACCTCAGGAAATAATGAATCTTGATAAAAGCATGTAATTTCACACTATTTT
AAATTGAGGTTCTATGTCATTTTACTGTGATATATTTCCTGTTGCTCCTTTAAAATGAGTATTTA
CATTAAAATTATTTCACTTAAATGAATAAAACATTAACAACAATAATGCAGCATGCACATTTAAA
TGGAGGATCGACATGATTAGAAGTGCATCTCAAAGGATTTCCCTTTCTTTTCTGATTGTTGCCCC
CTCTGATAGATTCATTAATTTCTTGTCACTTGGAGTAAATAGGTGGTTAGAAAGGTCTAGTA
TAAATAAAAATATTTTTCTACTTTGTTTTCATTTTTCAAAATTCTAACAAGCTT

FIGURE 5

```
Number of amimo acid:
123456789112345678921234567893123456789412345678951234567 89

>A5 [SEQ ID NO.: 14] frameshift -1
FKGQFIIQSHVKEQKGRKKNKADRIVKWVTLFAP = 34

>B9 [SEQ ID NO.: 15] FRAME-1
EFLGTVDIACHSILSVNCILECAGSQLAQGKSLRGLPV = 38

>C2 [SEQ ID NO.: 16] frameshift -1
FKTSLVNRERVHLYKKMFKN = 20

>C7 [SEQ ID NO.: 17] frameshift -1
FHYWVYTQNNINCWTIIIHACVCS = 24

>E7 [SEQ ID NO.: 18] frameshift -1
FSAKVEASGFSVTPTLAVYSPHRLVMFIFIMIRKKHHFLLWLYAYFM = 47

>E9 [SEQ ID NO.: 19] frameshift -1
FFQTLILSMGSVKSICFPKV = 20

>E12 [SEQ ID NO.: 20] frameshift -1
NSTGLSASQATAFHSGLHPFKRGINKVKCIPGSVAAGLTSMSLGGQTA = 48

>F6 [SEQ ID NO.: 21] frameshift -1
FFWGKSKYYIMKTMVGKWKMILFRPELGLEIK = 32

>G12 [SEQ ID NO.: 22] frameshift -1
FMIKELEASYFKGATQIECIEMAKQPKGDPELVYMTVKCKTVKPVI = 46

>H3 [SEQ ID NO.: 23] frameshift -1
FPYMYNHYWVKCELIREFTLLKKVNKYHRSSRIWL = 35

123456789112345678921234567893123456789412345678951234567 89
Number of amimo acid:
```

POLYNUCLEOTIDES THAT HOME TO ATHEROSCLEROTIC PLAQUE

RELATED APPLICATIONS

This application is a national stage filing under 35 U.S.C. §371 of International Application No. PCT/US2010/002717, filed on Oct. 9, 2010, which claims the benefit of the filing date of U.S. provisional application 61/278,775, entitled POLYPEPTIDES THAT HOME TO ATHEROSCLEROTIC PLAQUE, filed Oct. 9, 2009. The entire teachings of the referenced applications are incorporated by reference herein.

GOVERNMENT FUNDING

Not Applicable

BACKGROUND OF THE INVENTION

Acute coronary syndromes (ACS), characterized by either acute myocardial infarction (MI) or unstable angina, are most commonly precipitated by plaque rupture, which accounts for about 60-75% of fatal acute myocardial infarctions and/or sudden coronary deaths. The ruptured atherosclerotic plaques occur on a background of underlying atherosclerotic disease. Alarmingly, in patients presenting ACS, the recurrent cardiovascular event rate is high over the next two years, even with good medical management. The one year incidence of cardiovascular death, nonfatal MI, readmission for ACS and stroke is 8-12% during one year follow-up and 11-14% during two years follow-up.

This high rate of recurrent cardiovascular events, despite aggressive therapy, may be due to the now commonly held belief that ACS has a systemic inflammatory component, one manifestation of which is that many ACS patients have several vulnerable plaques in addition to the ruptured culprit lesion responsible for precipitating the ACS. The risk of rupture over the succeeding months posed by these additional vulnerable plaques accounts, in large part, for the high recurrence rate of cardiovascular events. While atherosclerotic plaques can be severe enough so that they compromise flow and therefore result in warning symptoms, they may be mild and not cause any warning symptoms. However, atherosclerotic plaques might still rupture and produce catastrophic clinical consequences.

Plaque rupture also plays an important role in stroke with the culprit lesions in these patients lying usually in the carotid artery.

SUMMARY OF THE INVENTION

Described herein are homing polypeptides that home to atherosclerotic plaques, homing polypeptides that home to vulnerable plaques, and nucleic acids that encode such polypeptides. Such homing polypeptides are referred to herein, respectively, as atherosclerotic-plaque-homing polypeptides, which are also referred to as atherosclerotic-lesion-homing polypeptides, and homing polypeptides that home to vulnerable plaque (vulnerable plaque-homing polypeptides). Also described are methods for detecting and treating conditions or disorders associated with or characterized by altered levels of homing polypeptides that home to atherosclerotic plaque and/or vulnerable plaque.

In one aspect the work described herein relates to atherosclerotic-plaque-homing polypeptides and nucleic acids encoding atherosclerotic-plaque-homing polypeptides that are useful, for example, for diagnostic and therapeutic purposes, particularly diagnosis and therapy of individuals in whom atherosclerotic plaques are developing or have developed, such as atherosclerotic plaque associated with vulnerable plaque, as well as for purposes of predicting or aiding in predicting the likelihood or risk that an individual will develop atherosclerotic plaque and/or vulnerable plaque. Such homing polypeptides and nucleic acids that encode such homing polypeptides are also useful for diagnosis and therapy of individuals in whom plaque rupture or acute ischemia has occurred and individuals who are at risk of ischemia or plaque rupture, which can lead to undesirable cardiovascular events, such as acute coronary syndrome or stroke. The work described herein further relates to atherosclerotic-plaque-homing polypeptides and nucleic acids encoding atherosclerotic-plaque-homing polypeptides, both of which are useful for predicting or aiding in predicting the likelihood or risk that an individual will develop plaque rupture (will experience rupture of vulnerable plaque) or acute ischemia. The atherosclerotic-plaque-homing polypeptides and nucleic acids encoding them are useful for diagnosis and therapy of atherosclerotic plaques, vulnerable plaque endothelia, developing and ruptured vulnerable plaque, and acutely ischemic myocardium.

Further described herein are uses of atherosclerotic-plaque-homing polypeptides, such as in methods of diagnosing or aiding in diagnosis of atherosclerotic plaque and vulnerable plaque, methods of predicting the likelihood that atherosclerotic plaque will develop in an individual; methods of diagnosing or aiding in the diagnosis of development of vulnerable plaque in an individual; methods of predicting or aiding in predicting the likelihood that an individual will experience disruptions of vulnerable plaque, including atheromatous plaque; methods of predicting or aiding in predicting the risk an individual will experience acute coronary syndrome; methods of predicting survival or aiding in predicting survival of an individual in whom vulnerable plaque, including atheromatous plaque, has developed; predicting or aiding in predicting how long it will be until an individual with vulnerable plaque will experience plaque rupture; methods of assessing the effectiveness of therapy; and methods of assessing the stage or progression of (atheromatous) plaque vulnerability (e.g., fragility) in an individual.

Also described herein is the use of atherosclerotic-plaque-homing polypeptides and vulnerable-plaque-homing polypeptides and the encoding polynucleotides for delivering agents, such as prophylactic or therapeutic drugs and detection or imaging agents, to atherosclerotic plaque and vulnerable plaque particularly; compositions, such as pharmaceutical compositions and compositions useful for detection and/or imaging of atherosclerotic plaques and vulnerable plaques, which comprise an (at least one, one or more) atherosclerotic-plaque-homing polypeptide or fragment thereof or a (at least one, one or more) polynucleotide that encodes an atherosclerotic-plaque-homing polypeptide and/or antibodies that bind atherosclerotic-plaque-homing polypeptide gene products or portions thereof, such as antibodies that bind homing domains of atherosclerotic plaques homing polypeptides.

Specific embodiments relate to atherosclerotic-plaque-homing polypeptides, including polypeptide fragments that are homing domains, encoded by nucleic acids whose sequences are presented herein or fragments thereof; methods in which one or more of the atherosclerotic plaque homing polypeptides or fragments thereof are used; methods in which one or more of the nucleic acids encoding atherosclerotic-plaques-homing-polypeptide is used; compositions comprising one or more of the atherosclerotic-plaque-horning-polypeptide-encoding polynucleotides or a portion(s)

thereof; compositions comprising (a) an atherosclerotic-lesion-homing polypeptide and (b) an agent to be targeted to atherosclerotic plaque and/or vulnerable plaque in an individual; and antibodies that bind (recognize) products (proteins, polypeptides) that are encoded by DNA whose sequences is provided herein or portions of any of the DNA.

The disclosure also encompasses SNPs (single nucleotide polymorphisms) in genes related to atherosclerotic-lesion-homing polypeptides, and methods for evaluating the risk or likelihood that an individual will develop a cardiovascular event, such as acute myocardial infarction (AMI) by determining if one or more of these SNPs are present.

The disclosure also encompasses SNPs (single nucleotide polymorphisms) in genes related to developing microvessel homing polypeptides, and methods for evaluating the risk or likelihood that an individual will develop a cardiovascular event, such as coronary artery disease, by determining if one or more of these SNPs are present.

In one aspect the disclosure provides an isolated homing polypeptide that homes to an atherosclerotic plaque and is encoded by a polynucleotide, wherein the polynucleotide comprises a sequence selected from the group consisting of: SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encodes the same polypeptide as a polypeptide encoded by any one of SEQ ID NO: 38-70 and SEQ ID NO: 127-137. In some embodiments, the atherosclerotic plaque is a vulnerable plaque. In some embodiments, the polypeptide is attached to a delivery agent. In some embodiments the delivery agent is a biodegradable delivery agent. In some embodiments, the polypeptide comprises the amino acid sequence of any one of: SEQ ID NO: 38-70 and SEQ ID NO: 127-137 or a fragment of any one of SEQ ID NO: 38-70 and SEQ ID NO: 127-137. In some embodiments, the polypeptide homes specifically to atherosclerotic plaque (preferentially to atherosclerotic-plaque than to microvessels). In some embodiments, the polypeptide homes specifically to microvessels in the atherosclerotic plaque (preferentially to microvessels than to atherosclerotic-plaque). In some embodiments, the polypeptide homes specifically to vulnerable plaque. In some embodiments, the polypeptide also homes to developing microvessels.

In one aspect the disclosure provides a polynucleotide encoding a homing polypeptide wherein the polynucleotide comprises a sequence selected from the group consisting of: SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encodes the same polypeptide as a polypeptide encoded by any one of SEQ ID NOs 24-37, complements thereof and nucleic acids that hybridize under stringent conditions to the polynucleotides.

In one aspect the disclosure provides an antibody, or a fragment thereof, that binds the homing polypeptides described herein.

In one aspect the disclosure provides an antibody, or a fragment thereof, that binds a homing polypeptide, wherein the polypeptide comprises a sequence selected from the group consisting of: SEQ ID NO: 38-70 and SEQ ID NO: 127-137.

In one aspect the disclosure provides an antibody, or a fragment thereof, that binds a homing polypeptide encoded by a polynucleotide, wherein the polynucleotide comprises a sequence selected from the group consisting of: SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encodes the same polypeptide as a polypeptide encoded by any one of SEQ ID NOs 24-37.

Antibodies described herein can be a monoclonal antibody, a polyclonal antibody, a chimeric antibody, a bispecific antibody, a heteroconjugate antibody, or a single chain (ScFv) antibody. In some embodiments the antibody is coupled to a therapeutic moiety. In some embodiments the therapeutic moiety is selected from the group consisting of ricin, a radioisotope, a clotting agent, a thrombolytic factor, a chemotherapeutic agent, a radiosensitizing agent, an anti-angiogenesis agent, an anti-motility agent, an anti-lipid agent, a statin, high density lipoprotein, a peptide with the functionality of a high density lipoprotein, and an immunomodulatory agent.

In some embodiments of the antibodies described herein, the antibody is coupled to a radiologic or other imaging molecule. In some embodiments, the radiologic or other imaging molecule is selected from the group consisting of a radioisotope, a dye, a pigment, a luciferase, fluorescein, a fluorescent molecule an MRI imaging agent, and an agent that can be imagined by computerized tomography (CT).

In one aspect the disclosure provides a method of determining the risk of a condition or disorder associated with, or characterized by, the presence of an altered (elevated or reduced) level of at least one atherosclerotic-plaque homing polypeptide in an individual, wherein the method comprises determining the presence of an altered (elevated or reduced) levels of at least one atherosclerotic-plaque-homing polypeptide or at least one polynucleotide encoding an atherosclerotic-plaque-homing polypeptide in a sample from an individual, wherein the presence of an elevated or reduced level of at least one homing polypeptide to an atherosclerotic plaque or at least one polynucleotide encoding a homing polypeptide to an atherosclerotic plaque, indicates an increased risk of a condition or disorder associated with, or characterized by, the presence of altered (elevated or reduced) levels of at least one atherosclerotic-plaque-homing polypeptide and wherein the at least one homing polypeptide to an atherosclerotic plaque is selected from the group consisting of: SEQ ID NO: 38-70 and SEQ ID NO: 127-137. As used herein the altered (elevated or reduced) level refers to an alteration compared to an individual who does not have atherosclerotic plaque or who is not at risk of a disorder associated with an atherosclerotic plaque.

In some embodiments of the methods described herein, the homing polypeptide to an atherosclerotic plaque is encoded by nucleic acid comprising a sequence selected from the group consisting of: SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encode the same polypeptide as a polypeptide encoded by one of the other members of the group.

In some embodiments of the methods described herein the determination of the presence of an altered level of at least one homing polypeptide that homes to an atherosclerotic plaque or at least one polynucleotide encoding a homing polypeptide that homes to an atherosclerotic plaque comprises using PCR analysis, RT-PCR, Northern analysis, DNA microarrays, isotope coded affinity tag reagents, MALDI TOF/TOF tandem mass spectrometry, 2D-gel/mass spectrometry technologies or ELISA.

In some embodiments of the methods described herein, the sample is a biological sample, such as a blood sample, a biopsy sample, a pathology sample, a urine sample or a cerebrospinal fluid sample. In some embodiments of the methods described herein, the condition or disorder associated with, or characterized by, a homing polypeptide to an atherosclerotic plaque is a cardiovascular condition, ischemia, myocardial infarction, stroke, acute coronary syndrome, cancer or a metabolic disorder.

In some embodiments of the homing polypeptides described herein the homing polypeptide is coupled to a therapeutic moiety. In some embodiments the therapeutic moiety is selected from the group consisting of ricin, a radioisotope, a clotting agent, a thrombolytic factor, a chemotherapeutic agent, a radiosensitizing agent, an anti-angiogenesis agent, an anti-motility agent, an anti-lipid agent, a statin, high density lipoprotein, a peptide with the functionality of a high density lipoprotein, and an immunomodulatory agent. In some embodiments the homing polypeptide is coupled to an imaging molecule. In some embodiments the imaging molecule is selected from the group consisting of a radiologic, a radioisotope, a dye, a pigment, a luciferase, fluorescein, a fluorescent molecule, an MRI imaging agent, and an agent that can be imaged by computerized tomography (CT).

In one aspect the disclosure provides a method of targeting an agent to an atherosclerotic plaque in an individual, wherein the method comprises administering to the individual in need thereof an effective amount of a composition comprising the homing polypeptides described herein coupled to the agent to be targeted to the atherosclerotic plaque, wherein the agent is a therapeutic moiety or an imaging molecule, and whereby the agent is targeted to the atherosclerotic plaque. In some embodiments the atherosclerotic plaque is a vulnerable plaque.

In one aspect the disclosure provides a method of treating a condition or disorder associated with, or characterized by, the presence of an elevated level of at least one homing polypeptide to an atherosclerotic plaque in an individual in need thereof, wherein the method comprises administering to the individual in need of such treatment a homing polypeptide that homes to an atherosclerotic plaque in an amount effective to treat the condition or disorder, wherein the homing polypeptide is coupled to a therapeutic moiety, wherein the at least one homing polypeptide that homes to an atherosclerotic plaque comprises a sequence selected from the group consisting of: SEQ ID NO: 38-70 and SEQ ID NO: 127-137.

In some embodiments of the methods described herein, the at least one homing polypeptide is encoded by a nucleic acid comprising a sequence selected from the group consisting of: SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encode the same polypeptide as a polypeptide encoded by one of the other members of the group. In some embodiments the therapeutic moiety is selected from the group consisting of ricin, a radioisotope, a clotting agent, a thrombolytic factor, a chemotherapeutic agent, a radiosensitizing agent, an anti-angiogenesis agent, an anti-motility agent, a statin, high density lipoprotein, a peptide with the functionality of a high density lipoprotein, and an immunomodulatory agent. In some embodiments the atherosclerotic plaque is a vulnerable plaque.

In one aspect the disclosure provides a pharmaceutical composition comprising (a) one or more homing polypeptides described herein, a portion of one or more homing polypeptides described herein; or a combination of one or more homing polypeptide described herein and a portion of one or more homing polypeptides described herein; (b) a therapeutic moiety, and (c) a pharmaceutically acceptable carrier.

In one aspect the disclosure provides a pharmaceutical composition comprising (a) one or more homing polypeptides described herein, a portion of one or more homing polypeptides described herein; or a combination of one or more homing polypeptide described herein and a portion of one or more homing polypeptides described herein; (b) one or more homing polypeptides of SEQ ID Nos. 14-23, a portion of one or more homing polypeptides of SEQ ID NOS. 14-23, or a combination of one or more homing polypeptides of SEQ ID NOS. 14-23 and a portion of one or more homing polypeptides of SEQ ID NOS. 14-23; (c) a therapeutic moiety and (d) a pharmaceutically acceptable carrier. In some embodiments the therapeutic moiety suppresses vulnerable plaque development.

In one aspect the disclosure provides a pharmaceutical composition comprising (a) one or more homing polypeptides described herein, a portion of one or more homing polypeptides described herein; or a combination of one or more homing polypeptide described herein and a portion of one or more homing polypeptides described herein; and (b) a pharmaceutically acceptable carrier.

In one aspect the disclosure provides a pharmaceutical composition comprising (a) one or more homing polypeptides described herein, a portion of one or more homing polypeptides described herein; or a combination of one or more homing polypeptide described herein and a portion of one or more homing polypeptides described herein; (b) one or more homing polypeptides of SEQ ID Nos. 14-23, a portion of one or more homing polypeptides of SEQ ID NOS. 14-23, or a combination of one or more homing polypeptides of SEQ ID NOS. 14-23 and a portion of one or more homing polypeptides of SEQ ID NOS. 14-23, each coupled to a therapeutic moiety or an imaging molecule, and (c) a pharmaceutically acceptable carrier.

In one aspect the disclosure provides a kit comprising one or more homing polypeptides described herein or portions thereof. In one aspect the disclosure provides a kit comprising one or more polynucleotides described herein, or at least one fragment thereof. In one aspect the disclosure provides a kit comprising one or more antibodies described herein or fragments thereof.

In one aspect the invention provides a method of determining the risk of a cardiovascular condition in an individual, the method comprising determining the presence of at least one SNP selected from the group consisting of a SNP shown in Table 1 and a SNP shown in Table 2.

In some embodiments the individual has a metabolic disorder or has one or more recognized risk factor of atherosclerosis.

In one aspect the invention provides a method of determining whether an individual is at increased risk of Acute Myocardial Infarction (AMI), the method comprising:

(a) obtaining a biological sample from the individual; and
(b) assessing the biological sample for the presence of at least one SNP selected from the group consisting of the SNPs shown in Table 3,
wherein the presence of the at least one SNP indicates that the individual has an increased risk of AMI.

In one aspect the invention provides a method of determining whether an individual is at increased risk of Acute Myocardial Infarction (AMI), the method comprising:
(a) obtaining a biological sample from the individual; and
(b) assessing the biological sample for SNPs selected from the group consisting of the SNPs shown in Table 3,
wherein the greater the number of SNPs in the biological sample, the greater the risk of AMI in the individual.

In one aspect the invention provides a method of determining whether an individual is at increased risk of Acute Myocardial Infarction (AMI), the method comprising:
(a) obtaining a biological sample from the individual; and
(b) determining the presence in the biological sample of at least one SNP selected from the group consisting of rs6982320 8p22, rs2830538 21q21.3 and rs463433 21q21.3
wherein the presence of the at least one SNP indicates that the individual is at risk of AMI.

In one aspect the invention provides a method of determining whether an individual is at increased risk of Acute Myocardial Infarction (AMI), the method comprising:
(a) obtaining a biological sample from the individual; and
(b) assessing the biological sample for SNPs selected from the group consisting rs6982320 8p22, rs2830538 21q21.3 and rs463433 21q21.3,
wherein the greater the number of SNPs in the biological sample, the greater the risk of AMI in the individual.

In one aspect the invention provides a method of determining an increased risk of Acute Myocardial Infarction (AMI) in an individual, the method comprising:
(a) obtaining a biological sample from the individual; and
(b) determining the presence in the biological sample of SNP rs6982320 8p22,
wherein the presence of the SNP indicates that the individual has an increased risk of AMI.

In one aspect the invention provides a method of determining an increased risk of Acute Myocardial Infarction (AMI) in an individual, the method comprising:
(a) obtaining a biological sample from the individual; and
(b) determining the presence in the biological sample of two alleles of SNP rs6982320 8p22,
wherein the presence of the alleles of the SNP indicates that the individual has an increased risk of AMI.

In one aspect the invention provides a method for determining an increased risk of Coronary Artery Disease (CAD) in an individual, the method comprising:
(a) obtaining a biological sample from the individual; and
(b) determining the presence in the biological sample of at least one SNP selected from the group consisting of the SNPs shown in Table 6
wherein the presence of the at least one SNP indicates that the individual has an increased risk of CAD.

In one aspect the invention provides a method of determining whether an individual is at increased risk of Coronary Artery Disease (CAD), the method comprising:
(a) obtaining a biological sample from the individual; and
(b) assessing the biological sample for SNPs selected from the group consisting of the SNPs shown in Table 6,
wherein the greater the number of SNPs in the biological sample, the greater the risk of CAD in the individual.

In one aspect the invention provides a method for determining an increased risk of Coronary Artery Disease (CAD) in an individual, the method comprising:
(a) obtaining a biological sample from the individual; and
(b) determining the presence in the biological sample of at least one SNP selected from the group consisting of rs10757493 9p21.3, rs988179 2p16.3, rs309137 2q21.3, rs17588757 9p23, and rs12475139 2q21.3,
wherein the presence of the at least one SNP indicates that the individual has an increased risk of CAD.

In one aspect the invention provides a method of determining whether an individual is at increased risk of Coronary Artery Disease (CAD), the method comprising:
(a) obtaining a biological sample from the individual; and
(b) assessing the biological sample for SNPs selected from the group consisting of rs10757493 9p21.3, rs988179 2p16.3, rs309137 2q21.3, rs17588757 9p23, and rs12475139 2q21.3,
wherein the greater the number of SNPs in the biological sample, the greater the risk of CAD in the individual.

Also described herein is a Genetic Risk Score (GRS) useful for estimating risk of AMI, including identifying individuals at high risk for AMI. The GRS was developed using the SNPs related to the ligands described herein and found to alter AMI risk and calculated for each patient. It was calculated by determining the number of risk alleles a patient had. An additive genetic model was assumed and weightings of 0, 1 or 2 were assigned, according to the number of risk alleles a patient had. The count method assumed that each SNP contributed equally to CAD risk and was calculated by summing the number of risk alleles across the panel of SNPs tested. This resulted in a score of 0 to twice the number of SNPs (representing the total number of risk alleles). The GRS was modeled as a continuous variable or as quartiles and tertiles, depending on the number of patients who could be assigned to each group. The GRS can be calculated using a variety of numbers of SNPs, such as three SNPs, (e.g., rs6982320 8p22; rs2830538 21q21.3; rs463433 21q21.3) or any combination of the SNPs shown in Table 3 and including any combination of the following: rs10812143 9p21.3; rs12005015 9p23; rs7025783 9p21.3; rs7639226 3p12.3; rs10757493 9p21.3; rs988179 2p16.3; rs309137 2q21.31rs17588757 9p23; rs12475139 2q21.3 or any additional SNP shown herein to be significantly associated with a greater risk of AMI.

Any number of SNPs (one or more, one) related to CAD, such as those described herein (e.g., one or more SNPs predisposing to AMI in individuals with documented CAD, one or more SNPs that predict risk for plaque rupture or risk for CAD development) can be used to create a GRS. The GRS for an individual can be compared with a standard or reference (e.g., a tertile or quartile such as described herein, which has been constructed based on GRS for a population of patients) in order to assess the risk for CAD for the individual.

A method of assessing risk for coronary artery disease (CAD) in an individual, comprising:
(a) developing a genetic risk score (GRS) for the individual; and
(b) comparing the genetic risk score for the individual with an appropriate reference,
wherein the genetic risk score is developed in (a) by determining the number of risk alleles the individual has and wherein the appropriate reference is a reference genetic risk score.

In the above method, the number of risk alleles the individual has is determined by assessing a sample obtained from the individual for at least one SNP associated with acute CAD or myocardial infarction; at least one SNP associated with stable CAD; or at least one SNP associated with acute CAD or myocardial infarction and at least one SNP associated with stable CAD.

At least one SNP is selected from the group consisting of the SNPs shown in Table 3.

In specific embodiments at least one SNP is selected from the group consisting of: rs6982320 8p22; rs2830538 21q21.3; rs463433 21q21.3; rs10812143 9p21.3; rs12005015

9p23; rs7025783 9p21.3; rs7639226 3p12.3; rs10757493 9p21.3; rs988179 2p16.3; rs309137 2q21.31 rs17588757 9p23; rs12475139 2q21.3.

In further specific embodiments at least three, at least four, or at least five SNPs are selected. Any number of SNPs shown herein can be combined to create the GRS.

BRIEF DESCRIPTION OF THE DRAWINGS

The figures are illustrative only and are not required for enablement of the disclosure provided herein.

FIG. 2 shows the nucleotide sequences of the identified homing polypeptides

FIG. 3 shows the amino acid sequences of the ligands identified.

FIG. 4 shows the nucleotide sequences of homing polypeptides identified by a developing microvessel model (See WO 2008/069965).

FIG. 5 shows the amino acid sequences of homing polypeptides identified by a developing microvessel model (See WO 2008/069965)

DETAILED DESCRIPTION OF THE INVENTION

Figure 1:
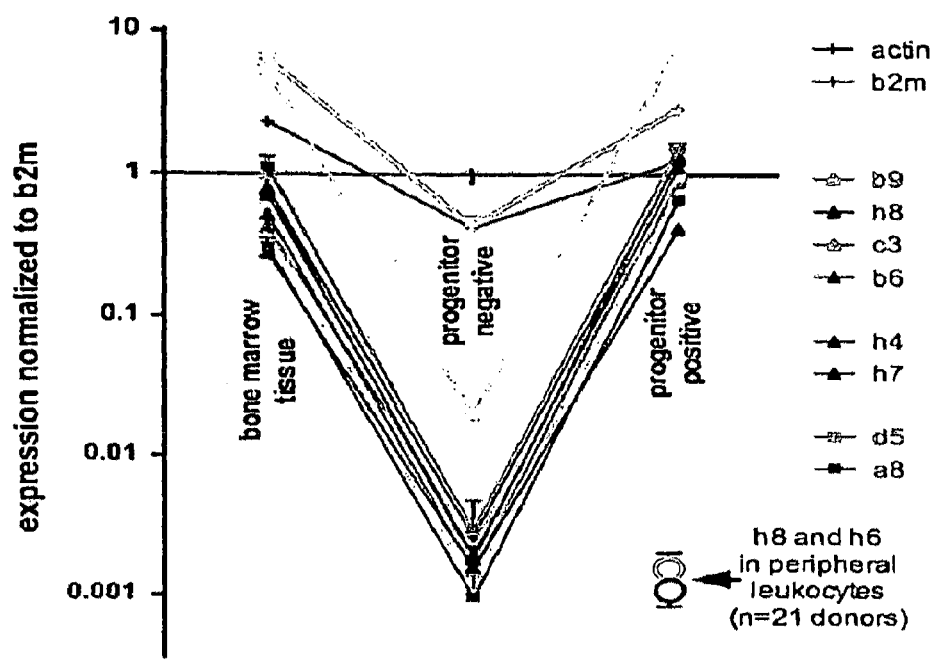
FIG. 1 is a graph of the mRNA expression levels, as fold-expression relative to beta-2-microglobulin, of the microvasculature homing gene fragments in bone marrow tissue.

Described herein are polypeptides that target or home to atherosclerotic plaques; nucleic acids (DNA, RNA) that encode the polypeptides; methods in which the polypeptides and encoding nucleic acids are used; compositions that comprise one or more of the polypeptides and/or one or more of the encoding nucleic acids; antibodies that bind to polypeptides that specifically target or home to atherosclerotic plaques; and kits that contain one or more of the polypeptides, one or more of the encoding nucleic acids and/or one or more antibodies that bind to polypeptides that specifically target or home to atherosclerotic plaques. In specific embodiments, the atherosclerotic lesion homing polypeptides home to atherosclerosis, independent of whether or not the plaque is prone to rupture. In some embodiments, the homing polypeptides home to atherosclerotic lesions with characteristics that make them prone to rupture (vulnerable plaque), such as that which develops before or in association with acute myocardial infarction or stroke.

Also provided herein are compositions and methods for determining the status of an individual or the risk that an individual will develop a condition in which atherosclerotic lesion plays a role or is indicative of a condition of interest or concern (e.g., vulnerable plaque, ischemia (e.g., in association with stroke or myocardial infarction)). Atherosclerotic lesion homing polypeptides of the present disclosure are also useful in methods of predicting the likelihood that an individual will develop atherosclerosis and/or a particular condition associated with atherosclerotic plaques (e.g., vulnerable plaque and, thus, myocardial infarction and/or stroke).

Rupture-prone plaque is characterized by a large necrotic lipid core, a thin fibrous cap (containing few or no smooth muscle cells, large numbers of activated inflammatory cells and neovascularization. Microvessels, originating from the adventitial vasa vasorum, form large neovascular plexi in the media and intima of atherosclerotic plaques. Microvessel number is increased in ruptured plaques, and vessel number directly relates to the amount of inflammation and intraplaque hemorrhage. These vessels also are more likely present in thin-cap fibroatheromas.

The vasa vasorum are thin-walled vessels, which are leaky and prone to rupture, thereby predisposing an individual to intraplaque hemorrhage. This contributes to plaque growth and thus to changed lesion morphology that might predispose mechanically to plaque rupture. The increased microvascular density caused by the neovascularization also facilitates delivery of inflammatory cells and inflammatory cells beget angiogenesis—another example of the interrelation among different processes that might synergize to increase the vulnerability of a given plaque to rupture.

As described herein, Applicants have identified polypeptides that specifically target or home to atherosclerotic plaques, independent of whether or not the plaque is prone to rupture, or homing polypeptides that home to atherosclerotic lesions with characteristics that make them prone to rupture (vulnerable plaque), such as that which develops before or in association with acute myocardial infarction or stroke. Such atherosclerotic plaque homing polypeptides are ligands that home to (target) any organ or tissue of the body and are useful to deliver compounds and molecules to the target or tissue to which they home. In doing so, Applicants used a human bone marrow cDNA phage display library that displays expressed genes from stem cells and precursor and mature monocytes and a biopanning technique. Applicants used such a phage display library and a method in which the phage display library is biopanned to a mouse vulnerable plaque model and identified polypeptides, referred to herein as atherosclerotic lesion homing polypeptides, that home to atherosclerotic plaques including vulnerable plaques. The insert sizes of cDNAs in the phage display library were between 100 and 2,000 nucleotides, with the majority between 300 and 900 nucleotides.

Also disclosed is the preparation of libraries that can be utilized for the identification of homing genes. In particular, described herein is the preparation of a human bone marrow cDNA phage display library that displays expressed genes from stem cells and precursor and mature monocytes and has been shown to be useful in identifying polypeptides that home to atherosclerotic plaques. In a specific embodiment, the library is used with an appropriate model (a vulnerable plaque mouse model) to identify polypeptides that home to vulnerable plaques. Such a library can be used in combination with a different model in order to identify polypeptides that home to atherosclerotic lesion associated with other conditions. The model is preferably a mammal, such as, for example, a human, a mouse or a rabbit, but may also be any other animal. Alternatively, the method may utilize any animal, including non-mammals, that allows for the injection of phage library and demonstrates a significant response.

Disclosed herein are homing polypeptides and nucleic acids encoding homing polypeptides that were identified by methods as disclosed herein, including the method comprising: (a) administering a phage displaying library comprising a collection of phages containing polynucleotides from human bone marrow to an individual, such as an appropriate animal model; (b) selecting phage that localize in a target organ or tissue (e.g., atherosclerotic lesion); (c) collecting phage from the selected organ or tissue; (d) repeating steps (a) and (c) for one or more cycles; and (e) identifying one or more polynucleotides encoding a polypeptide, or fragment thereof, from selected phage that home to or target a tissue(s) of interest, such as tissues in an ischemic hind limb animal model. Such polynucleotides include the polynucleotides of SEQ ID NOs. 24-37, shown in FIG. 2 and complements thereof. Such polypeptides include the polypeptides of SEQ ID NO: 38-70 and SEQ ID NO: 127-137, shown in FIG. 3 and fragments thereof.

Many types of phage may be used to create the library. Preferably, the phage used in the creation of the library has one or more of the following characteristics: the ability to contain and express relatively large polynucleotides, such as, for example, between about 300-3000 nucleotides. The polynucleotides are expressed from the library of phage at a copy number, such as, for example, between about 0.1 copy to about 1 copy per phage. Thus, on an average the library of phage expresses about 0.1 copy to about 1 copy per phage of the polypeptides. Such phages are commercially available (e.g., a T7Select vector using T7Select 1-1 phage). By way of example, a phage display library may comprise and express polynucleotides isolated from a primary tumor, such as, for example, colon cancer or from a cell line such as, for example, a colon cancer cell line (e.g., LSI74T; American tissue culture collection, ATCC, Rockville, Md.). Preferably, the phage themselves (phage without a recombinant insert) have a low relative retention to target organs or cells. Retention, which may relate to direct binding, non-specific association, or active uptake, will cause phage to non-specifically associate with target cells. By identifying and selecting only phage with low retentions by target cells, the highest selectivity can be achieved.

The library is administered to any subject, such as a mouse or other mammal. The animal may be a normal animal or an animal model of disease. Alternatively, the library may be contacted with in vitro systems or models. In an animal, such as a mouse, a volume of between about 3 microliters to about 100 microliters, 5 microliters to about 100 microliters, 10 microliters to about 100 microliters or other appropriate volume containing between about $10^7$ to about $10^{10}$ phage is administered. A volume sufficient to produce desanguination in the method used can be used. Phage, based on the expression product displayed, target to selected organs, tissues or other areas of the body. Accordingly, the library is administered and allowed to circulate for a time sufficient to allow binding to the target tissue and/or organ of the binding domains expressed in the library. The optimal circulation time will vary with the size/weight of the animal, volume and/or complexity of the library. By way of example, for a mouse circulation time may be between about one minute to about ten minutes.

After sufficient circulation time, the animal is euthanized and the target organs collected for analysis. In some embodiments of the method described herein may the anesthetized animal is perfused with an isotonic solution, such as an isotonic salt solution, with or without proteins (e.g., BSA) to minimize non-specific binding of phage. Examples of isotonic salt solutions include, but are not limited to, phosphate buffer. Perfusion is continued, preferably until desanguination (e.g., little or no blood exits the vena cava, organs appear white in color.) By way of example, volumes of between about 1 to about 100, such as about 3, 5, 10, 15 or 20 times the volume of the animal may be used.

Any organ or tissue may be harvested for analysis. By way of example, these include, but are not limited to, bone marrow, lung, skin, liver and/or brain. Generally the tissue or organ harvested will be selected based on the origin of the library. By way of example, metastasis in colon cancer is often to the liver, marrow, lung and/or bone marrow. If the library used in the method comprises polynucleotides from a primary colon cancer tumor or cell line, liver lung and/or bone marrow can be harvested. Phage are collected from the selected tissues and/or organs, amplified, if necessary, and injected into another animal. Through successive rounds of injection, selection, and amplification, a collection of phage can be isolated that are specific for the selection criteria. By way of example, between about two to about five rounds of injection, selection, and amplification may performed. These collections can be further selected or the polynucleotides from individual or groups of phage isolated and identified. Polynucleotides identified by these methods can be used for both diagnostic and therapeutic purposes.

The method described herein for identifying targeting polypeptides that home to atherosclerotic plaques and vulnerable plaque is also useful for identifying polypeptides that home to atherosclerotic plaques and vulnerable plaques in other tissues and/or in other conditions or diseases. By way of example, such diseases or disorders may include, but are not limited to, atherosclerosis, coronary artery disease, stroke, diabetic vascular damage (e.g., kidney vascular damage) or retinopathy. Examples of animals models to be used in the methods described herein include, but are not limited to, cardiovascular diseases in pig, rat, and rabbit.

Homing Polypeptides

In one aspect, the disclosure provides homing polypeptides that home to atherosclerotic plaques and vulnerable plaques.

Applicants' studies revealed VP-binding SNPs associated with increased risk of AMI, and collateral-binding SNPs associated with increased risk of CAD.

Analysis using SNPs associated with developing collateral-binding ligands demonstrated highly significant associations with CAD but not with AMI, whereas SNPs associated with vulnerable plaque-like binding ligands demonstrated significant associations with AMI but not with stable CAD—suggesting that the biology of these two different categories of ligands is different, and that the presented strategy allows for identification of each of these apparently different pathophysiological processes.

As described herein, Applicants show that there are signature polypeptides that home to (can bind) particular surface molecules that are exposed in distinct regions of the healthy or the diseased vasculature in humans. Furthermore, it is shown herein that these signature polypeptides are expressed by cells, such as stem cells, precursor cells and/or mature cells, in human bone marrow. Thus, as described herein, Applicants have identified signature polypeptides that home to atherosclerotic plaques, including vulnerable plaques (also referred to as "atherosclerotic plaque homing polypeptides" or "polypeptides that home to atherosclerotic plaques"). These polypeptides have been identified by panning a phage display library carrying fragments of proteins expressed by human bone marrow cells. The atherosclerotic plaques homing polypeptides bind to proteins exposed in atherosclerotic plaques and include ligands of tissue-specific receptors, and thus, ligands of the atherosclerotic plaques. The atherosclerotic plaques homing polypeptides can bind and target atherosclerotic plaques and vulnerable plaques.

Atherosclerotic plaques, as used herein, include both stable plaques and vulnerable plaques. Stable plaques include plaques that are not prone to rupture (and thus not prone to produce acute myocardial infarction or stroke). However, the plaques become problematic when increase in size and persistently block blood flow. Thus, expanding stable plaques can still lead to unwanted cardiovascular events. Vulnerable plaques are atherosclerotic plaques that have a greater chance of rupture than stable plaques. Rupture of a plaque may result in unwanted cardiovascular events, such as acute myocardial infarction and stroke. Atherosclerotic plaques, including vulnerable plaque, can be found in most organs of the body. In some embodiments the atherosclerotic plaques are atheromatous atherosclerotic plaque or plaques that are located in the carotid artery. The location of these plaques may result in the occurrence of unwanted cardiovascular events and stroke, respectively.

In some embodiments, atherosclerotic plaque homing polypeptides are ligands that home to (target) atherosclerotic plaques in any organ or tissue of interest. In some embodiments, the atherosclerotic lesion homing polypeptides provided herein home specifically to atherosclerotic plaques in one location (e.g., tissue or organ) and do not home to a significant extent to other tissues or organs. Atherosclerotic lesion homing polypeptides that bind specifically to atherosclerotic lesions in certain organs can be identified, for instance, by using models in which the atherosclerotic lesion is located in specific organs, according to the methods provided herein.

In some embodiments, atherosclerotic plaques homing polypeptides of the disclosure are homing polypeptides to vulnerable plaques. In some embodiments, atherosclerotic plaques homing polypeptides of the disclosure are homing polypeptides to stable plaques. In some embodiments, atherosclerotic plaques homing polypeptides of the disclosure are homing polypeptides that specifically home to vulnerable plaques. In some embodiments, atherosclerotic plaques homing polypeptides of the disclosure are homing polypeptides that specifically home to vulnerable plaques. Homing "specifically" as used herein refers to preferential binding of one plaque, lesion, location or target over another plaque, lesion, location or target. Thus, homing polypeptides that specifically home to vulnerable plaques will not significantly bind stable plaques.

In some embodiments, atherosclerotic lesion homing polypeptides are homing polypeptides that home to only one target (e.g., an atherosclerotic plaques in a specific organ) and do not home to a significant extent to another different target. In some embodiments, atherosclerotic lesion homing polypeptides are homing polypeptides that home to more than one target, such as (i) atherosclerotic plaques irrespective of the location, organ or tissue in which it develops (e.g., to atherosclerotic plaques in more than one organ or tissue); (ii) to atherosclerotic plaques that are stable plaques and to atherosclerotic plaques that are vulnerable plaque. In some embodiments, atherosclerotic lesion homing polypeptides are homing polypeptides that home to both stable plaques and vulnerable plaques, whether in the same location (same tissue or organ) or irrespective of where they develop/their location (e.g., in more than one organ or tissue).

In some embodiments, the atherosclerotic plaque homing polypeptides bind to specific structural elements of the atherosclerotic plaque, including specific structural elements of the vulnerable plaque or stable plaque. In some embodiments, the atherosclerotic plaque homing polypeptides bind to microvessels of the atherosclerotic plaque. Microvessels, as used herein, includes but is not limited to, vasa vasorum, microvasculature, arteriole, capillary, metarteriole, sinusois, venule and microcirculation. In some embodiments, the microvessels in the atherosclerotic plaque are vasa vasorum. It is thought that a higher number of microvessels in an atherosclerotic plaque is correlated to an increased chance of rupture.

In some embodiments, the homing polypeptides that home to atherosclerotic plaques can also home to developing microvessels. A model for the identification of homing polypeptides that home to developing microvessels is described in WO 2008/069965, the teachings of which are incorporated herein by reference. The term "developing microvessels" as used herein includes developing microvasculature, developing collateral vessels, developing collaterals and developing vasa vasorum. In some embodiments, homing polypeptides that bind to a developing microvasculature do not home (to a significant extent) to nondeveloping or pre-existing (stable, not presently expanding) microvasculature (microvessels) or pre-existing collateral vessels, respectively. However, developing microvessels and microvessels are thought to have overlapping receptors and therefore at least a subset of the homing polypeptides will bind both developing microvessels and microvessels.

In some embodiments the homing polypeptides that homes to an atherosclerotic plaque are encoded by a polynucleotide, wherein the polynucleotide comprises a sequence selected from the group consisting of: SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encodes the same polypeptide as a polypeptide encoded by any one of SEQ ID NO: 38-70 and SEQ ID NO: 127-137.

In some embodiments the homing polypeptide that homes to an atherosclerotic plaque comprises the amino acid sequence of any one of: SEQ ID NO: 38-70 and SEQ ID NO: 127-137 or a fragment of any of the foregoing. It should be appreciated that the disclosure also encompasses isolated atherosclerotic plaque homing polypeptides.

It should be appreciated that atherosclerotic lesion homing polypeptides also include portions of such atherosclerotic plaques homing polypeptides, including portions that exhibit substantially the same homing activity as the larger homing polypeptide of which they are a portion and portions that are characteristic of a larger homing polypeptide.

The homing polypeptides of the disclosure also included the polypeptides and proteins of which the homing polypeptides are a part. For instance, a homing polypeptide of 20 amino acids described herein can be part of a larger naturally expressed polypeptide (i.e., a protein). These larger polypeptides are also embraced by the disclosure.

The term polypeptide is used broadly herein to include peptide or protein or fragments thereof. Also intended to be encompassed are peptidomimetics, which include chemically modified peptides, peptide-like molecules containing nor-maturally occurring amino acids, peptoids and the like, have the selective binding of the targeting domains provided herein. ("Burger's Medicinal Chemistry and Drug Discovery" 5th ed., vols. I to III (ed. M. E. Wolff; Wiley Interscience 1995).

Figure 3:
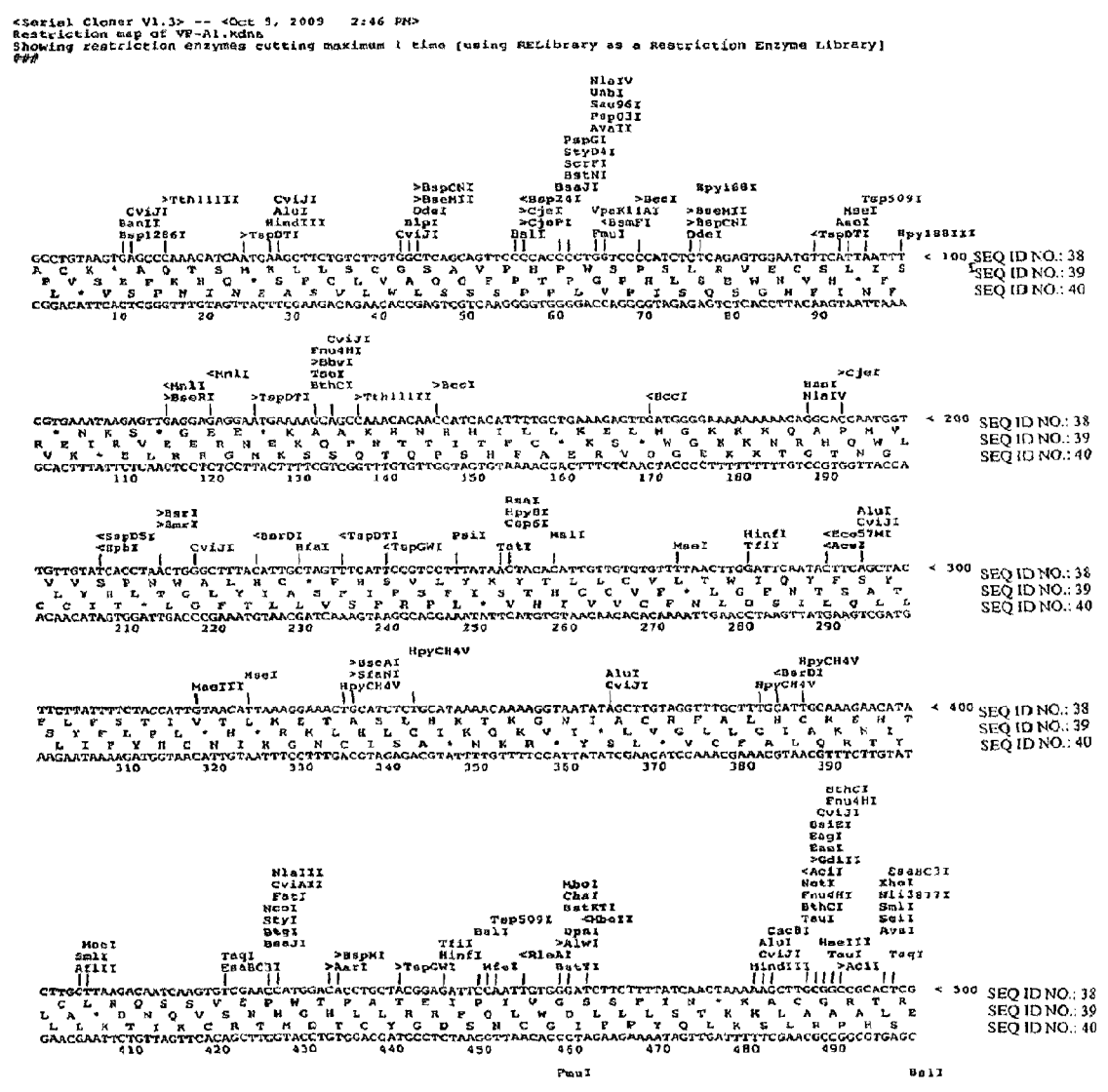
Figure 3:
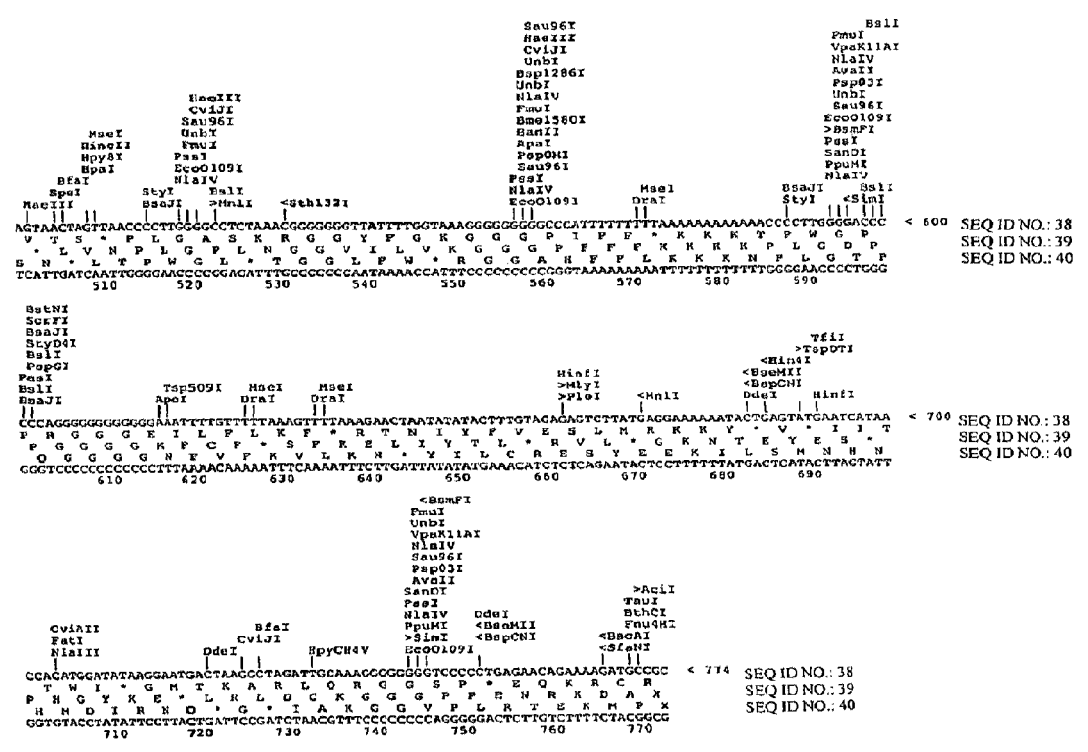
Figure 3:
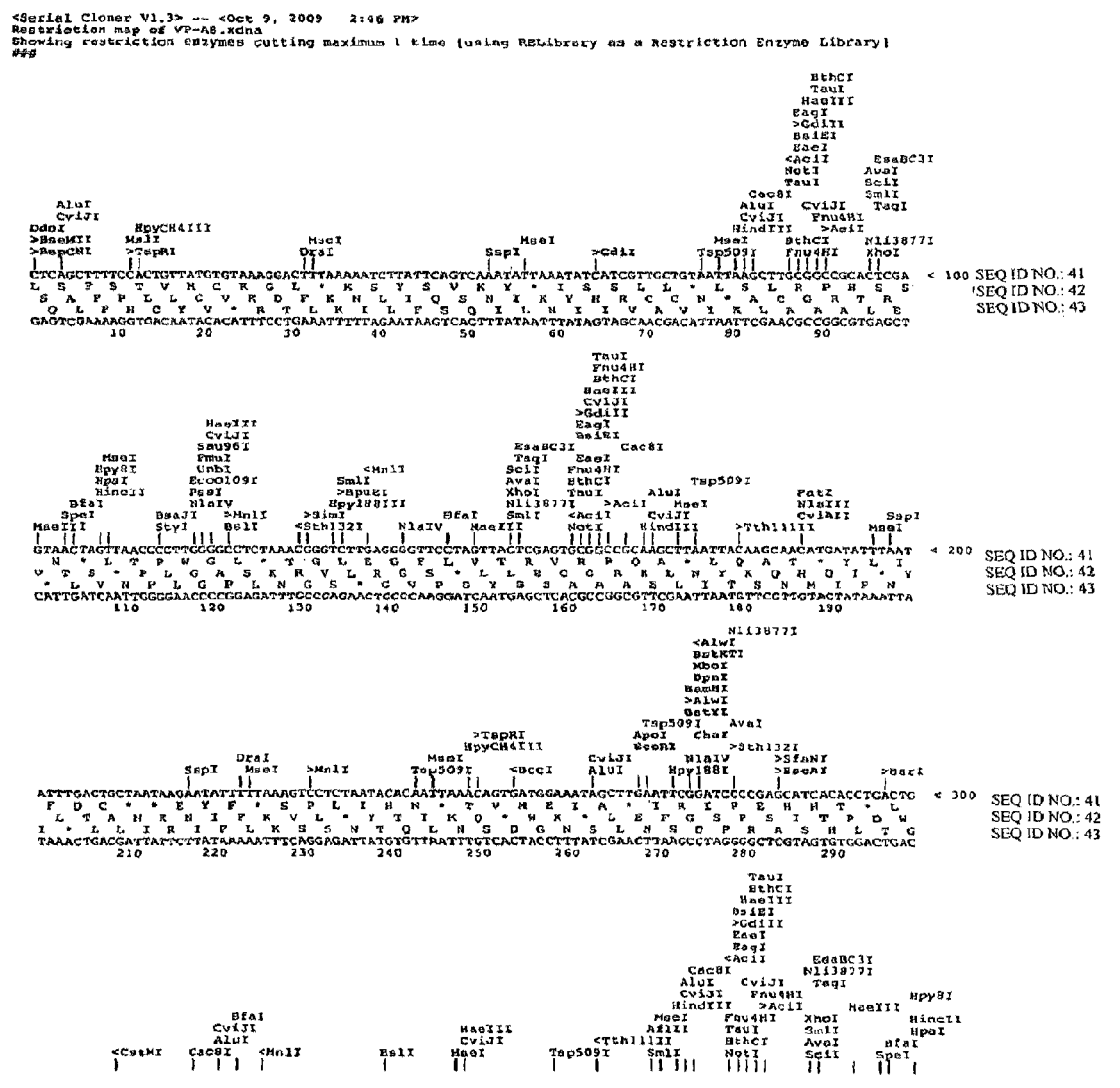
Figure 3:
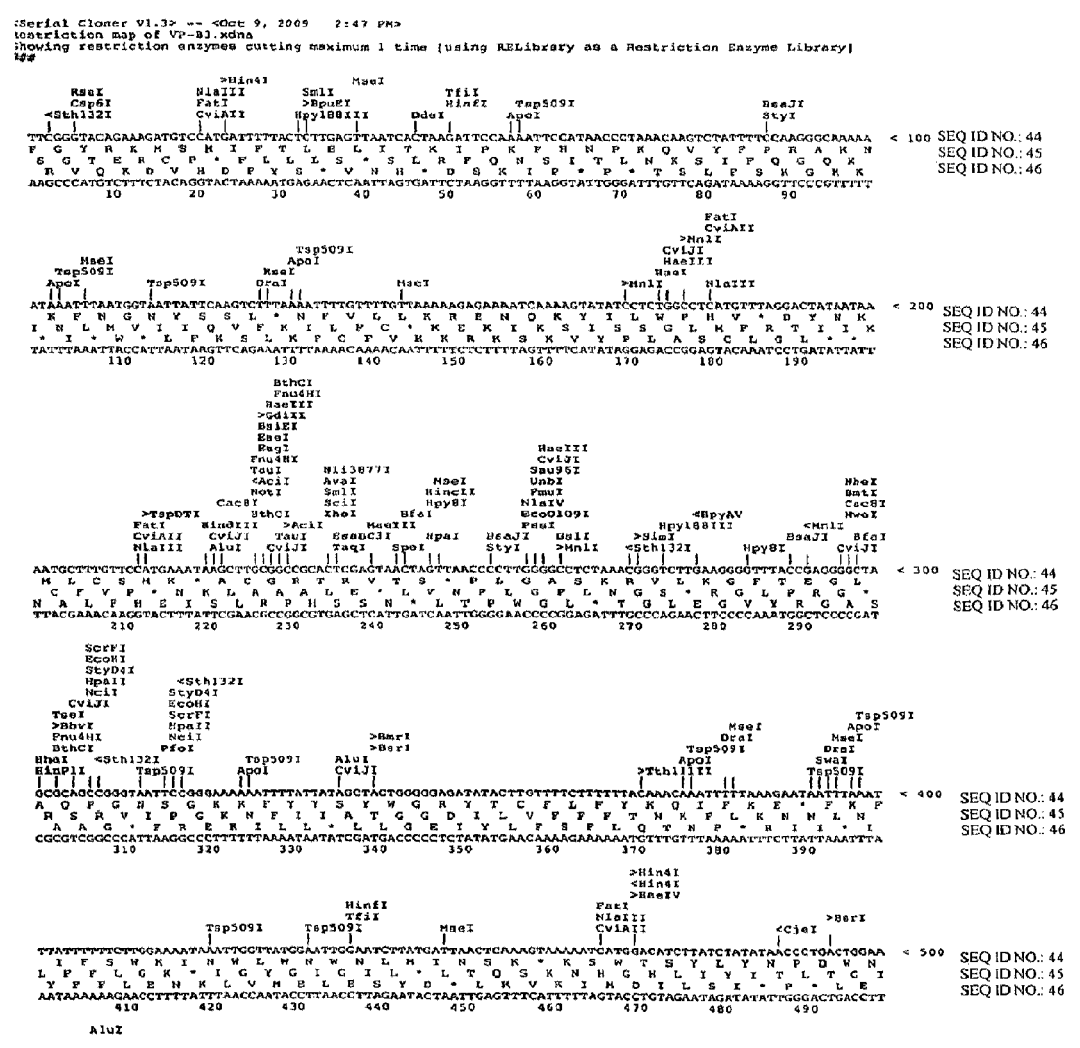
Figure 3:
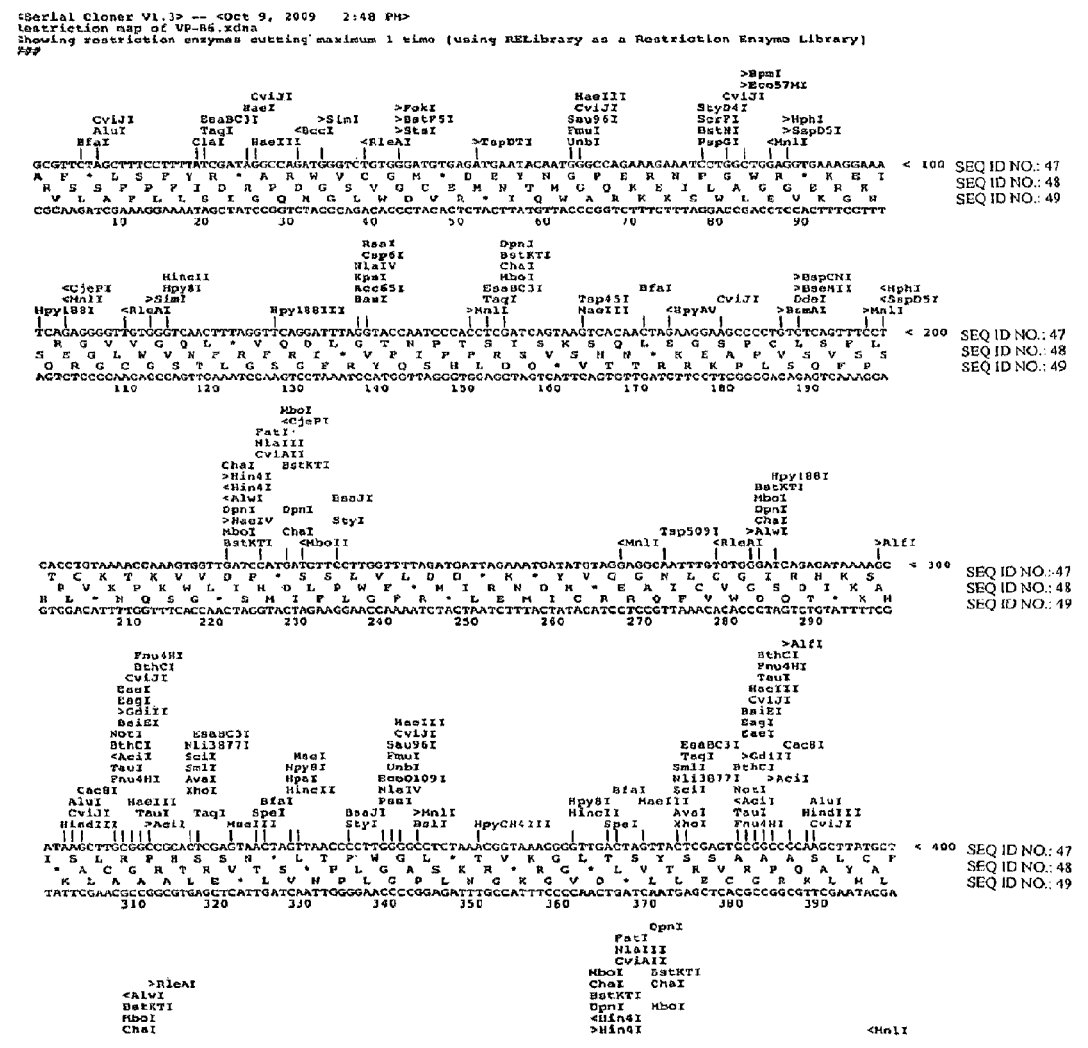
Figure 3:
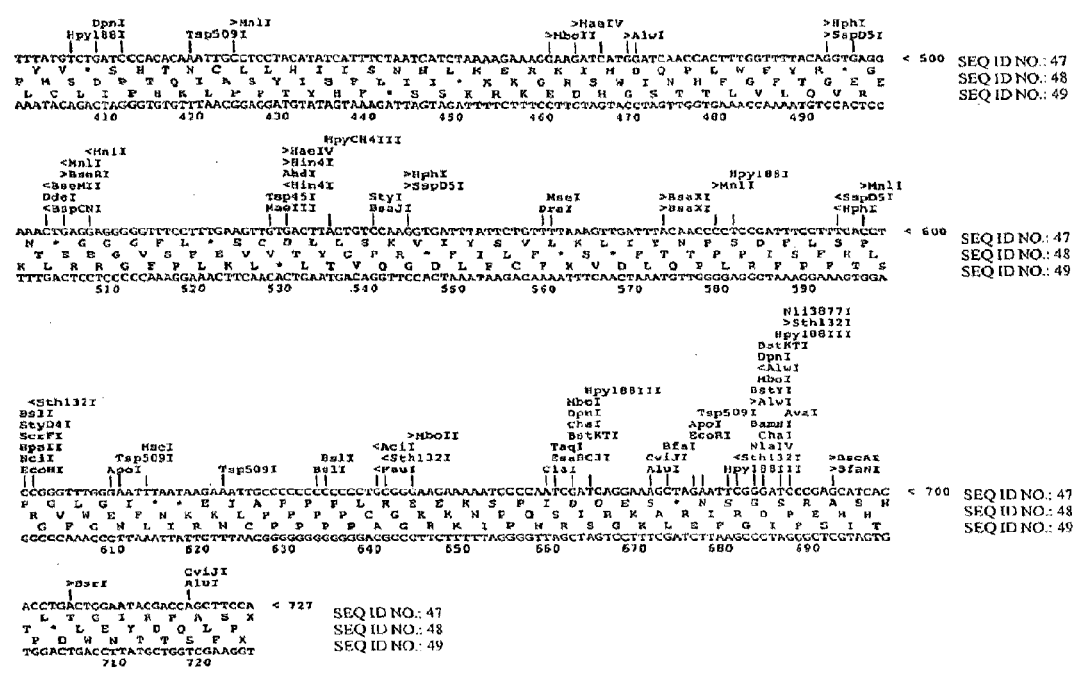
Figure 3:
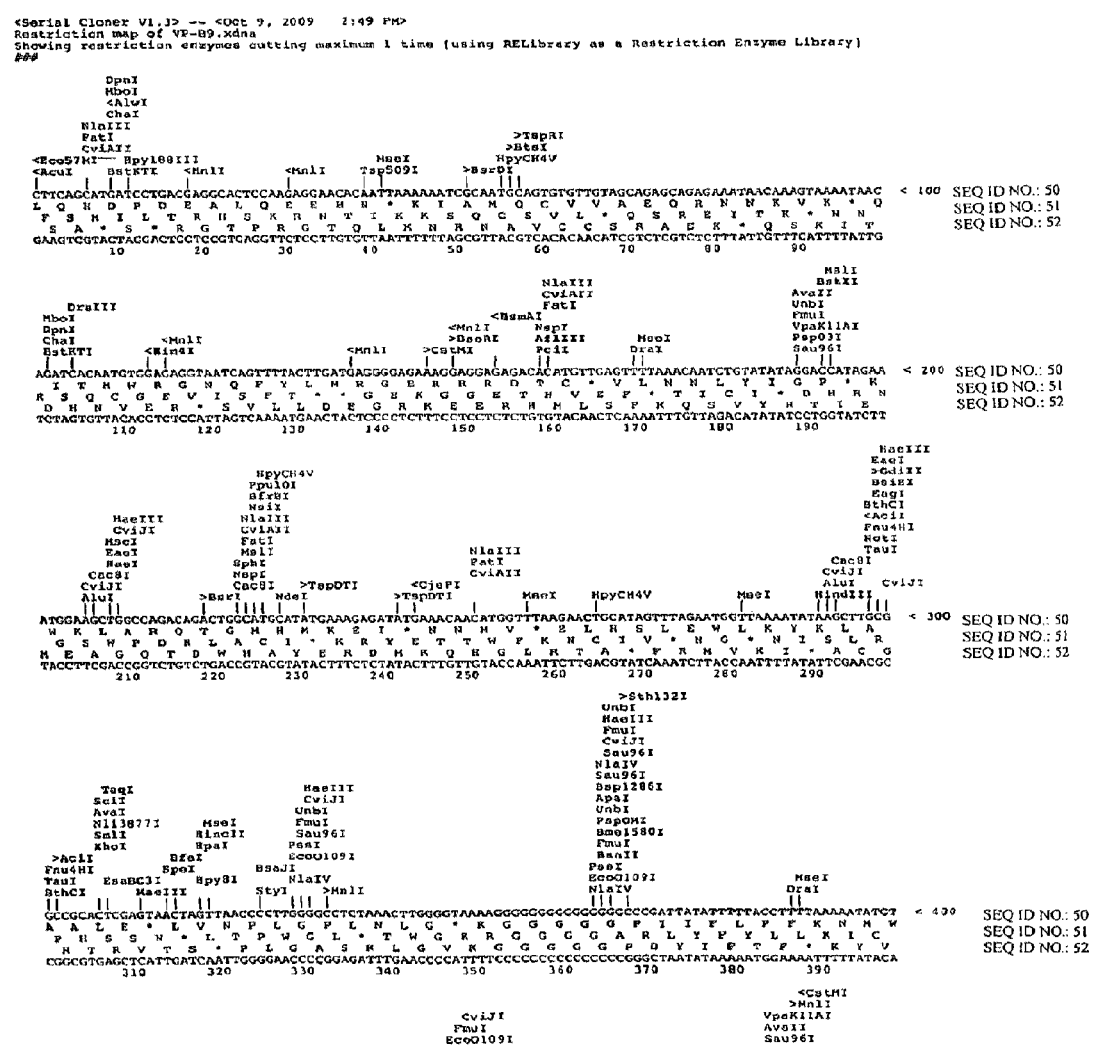
Figure 3:
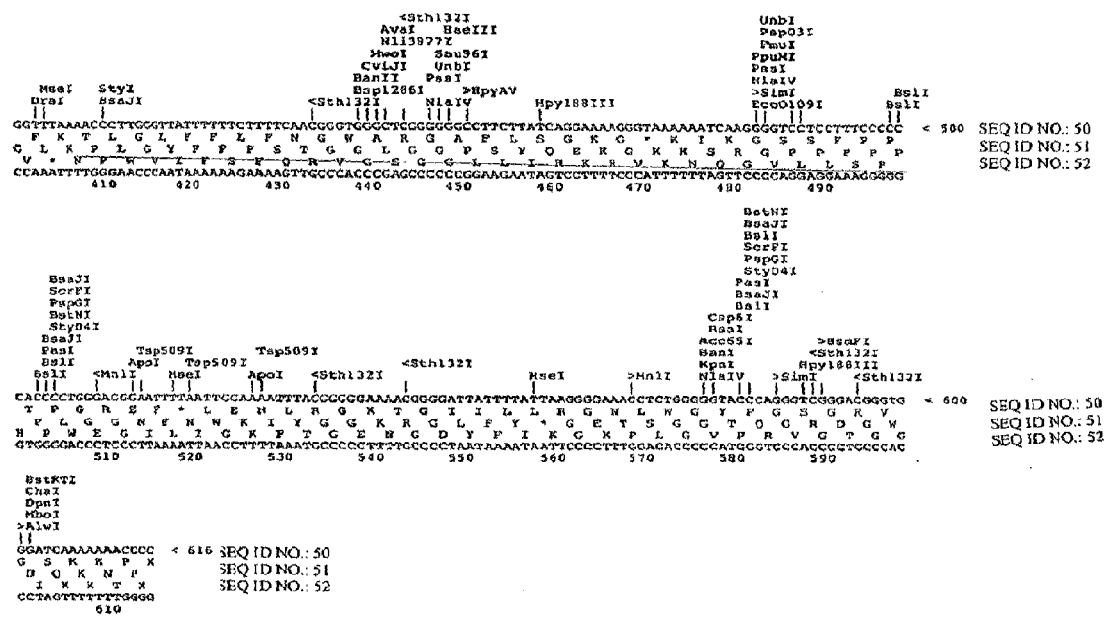
Figure 3:
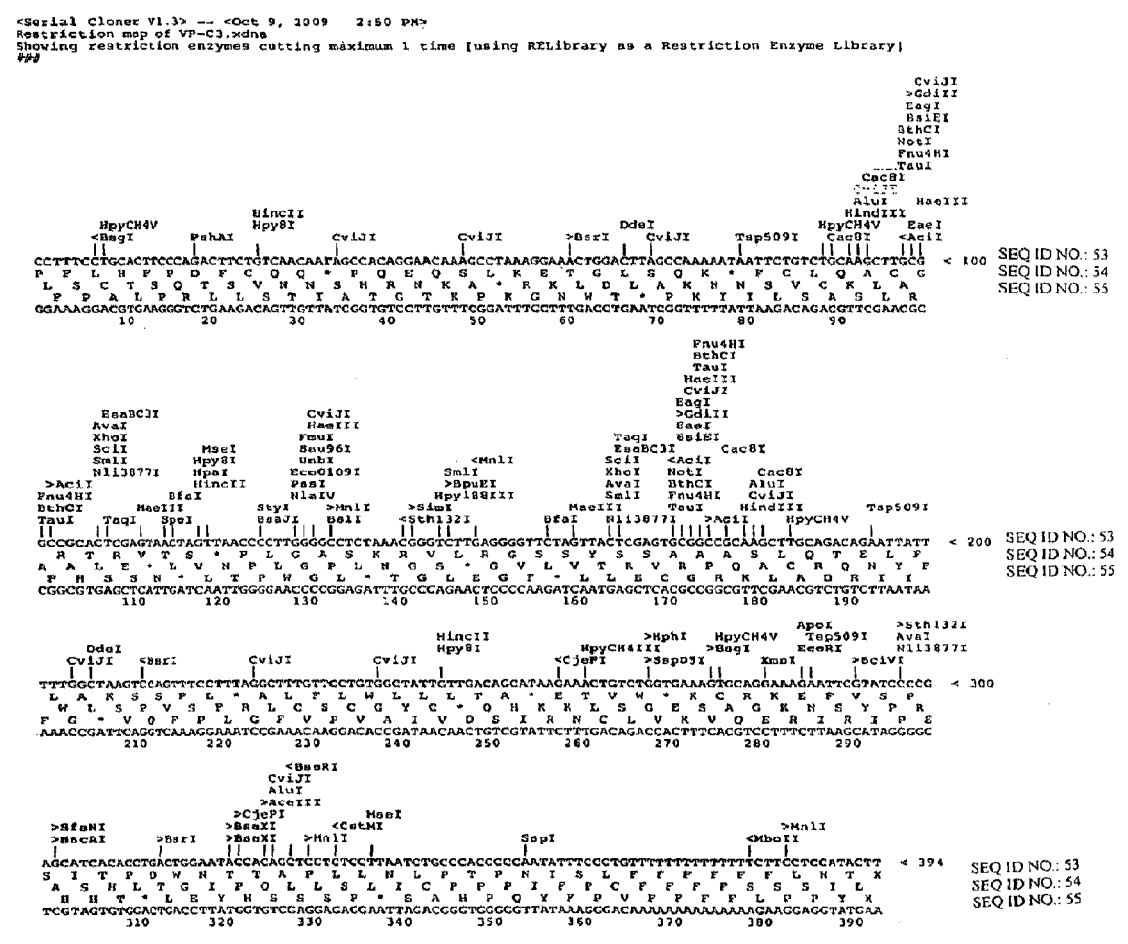
Figure 3:
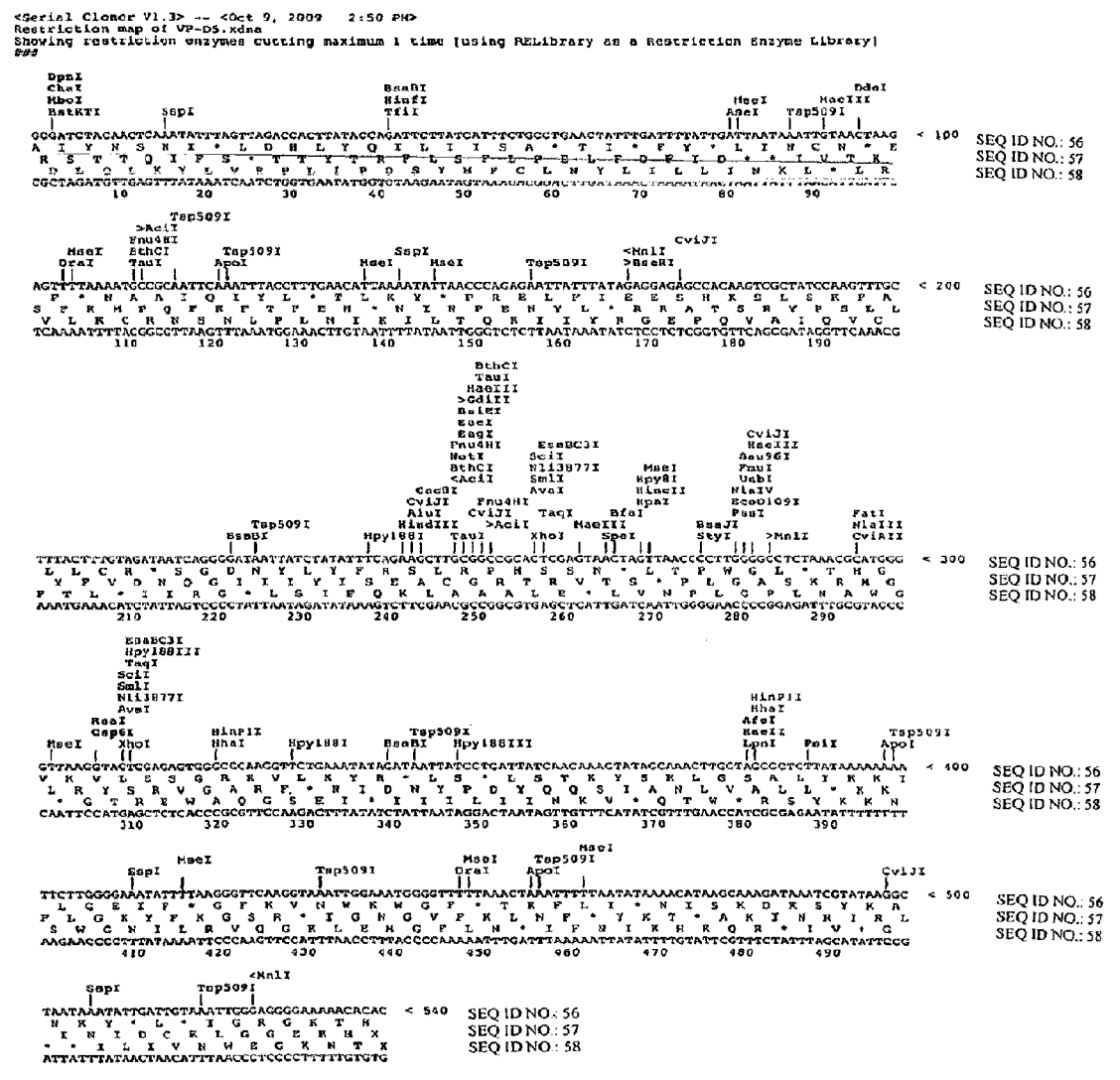
Figure 3:
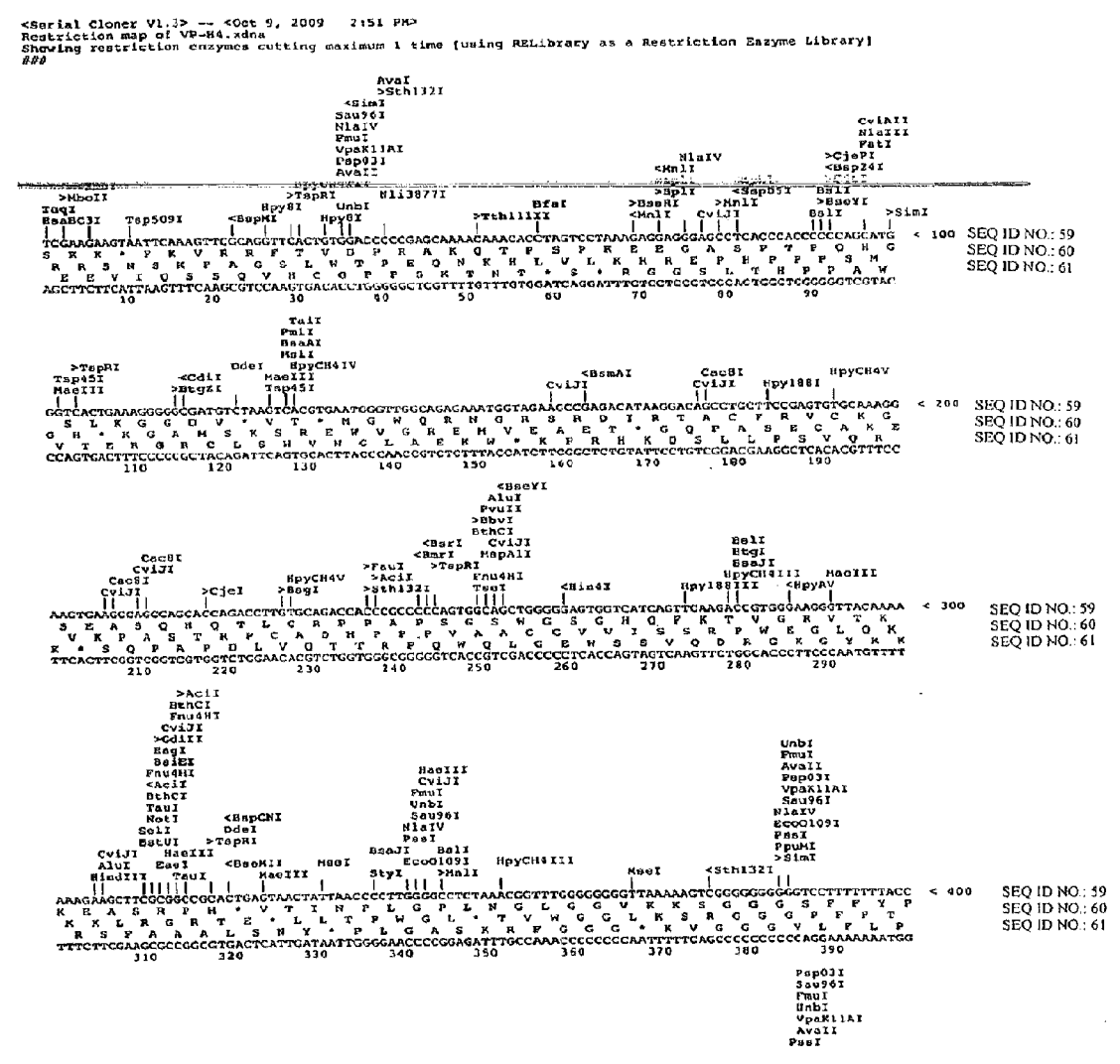
Figure 3:
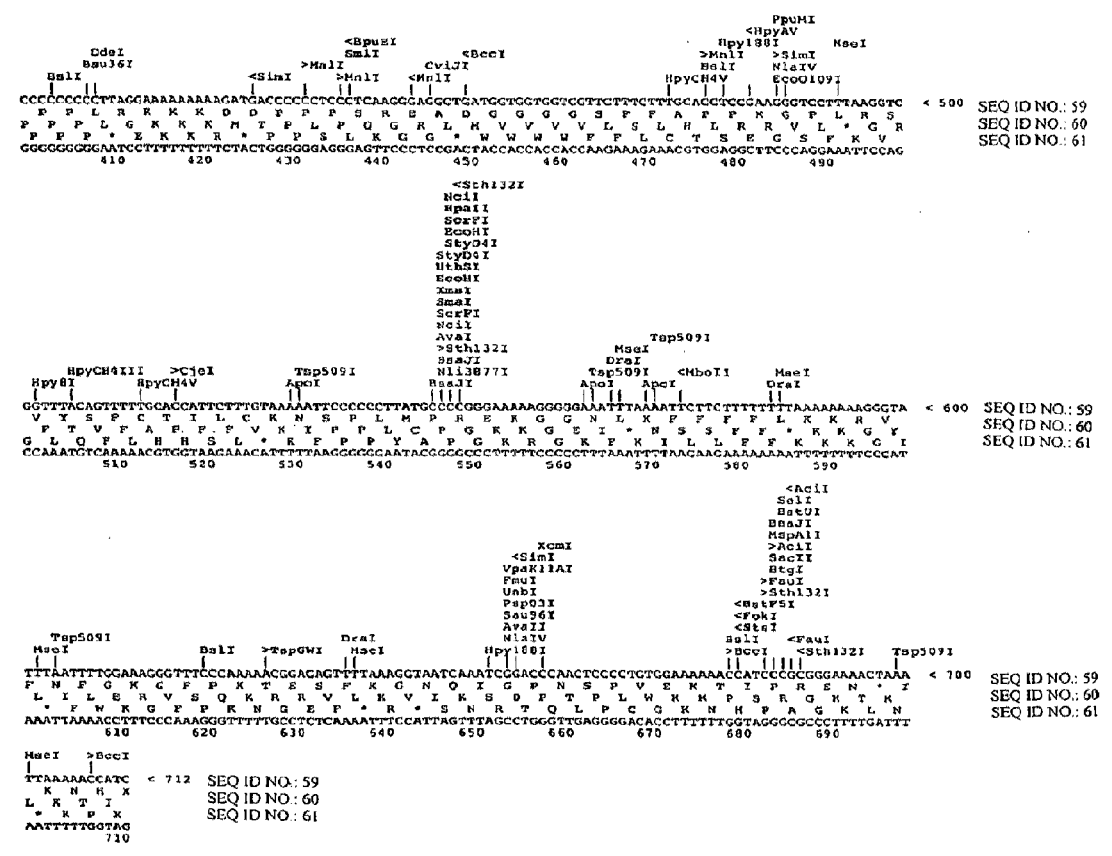
Figure 3:
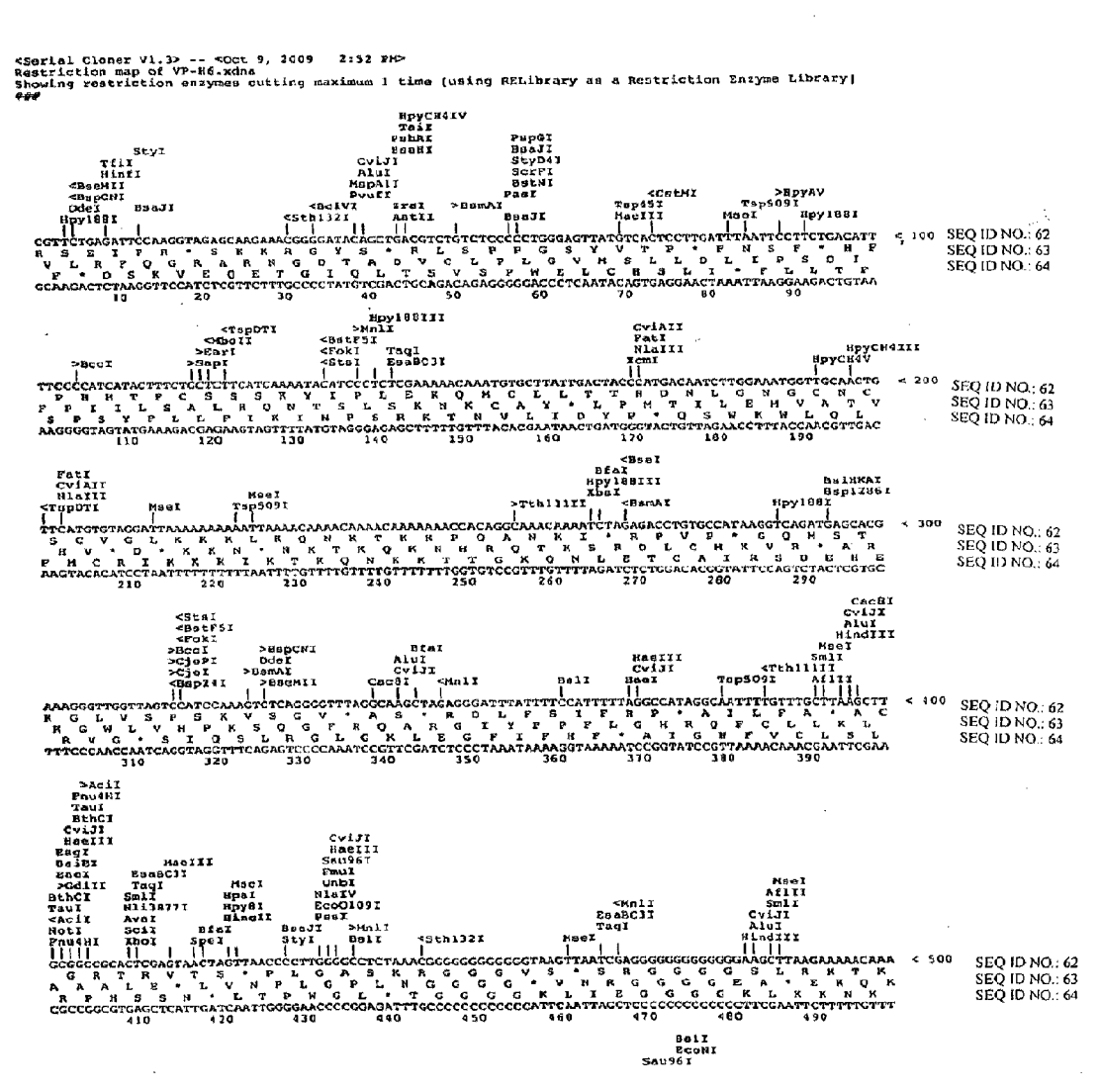
Figure 3:
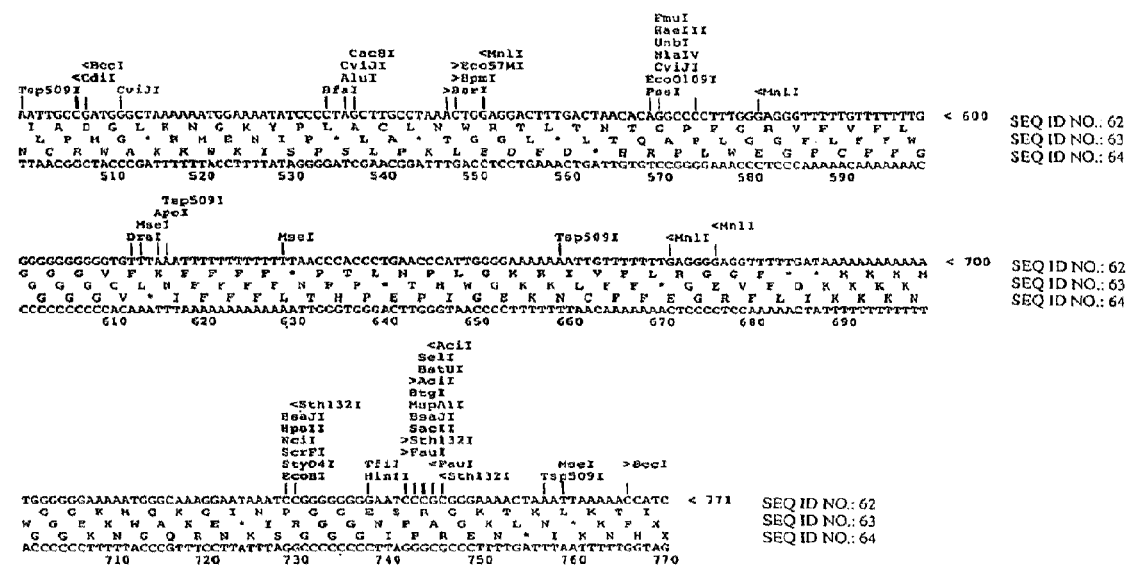
Figure 3:
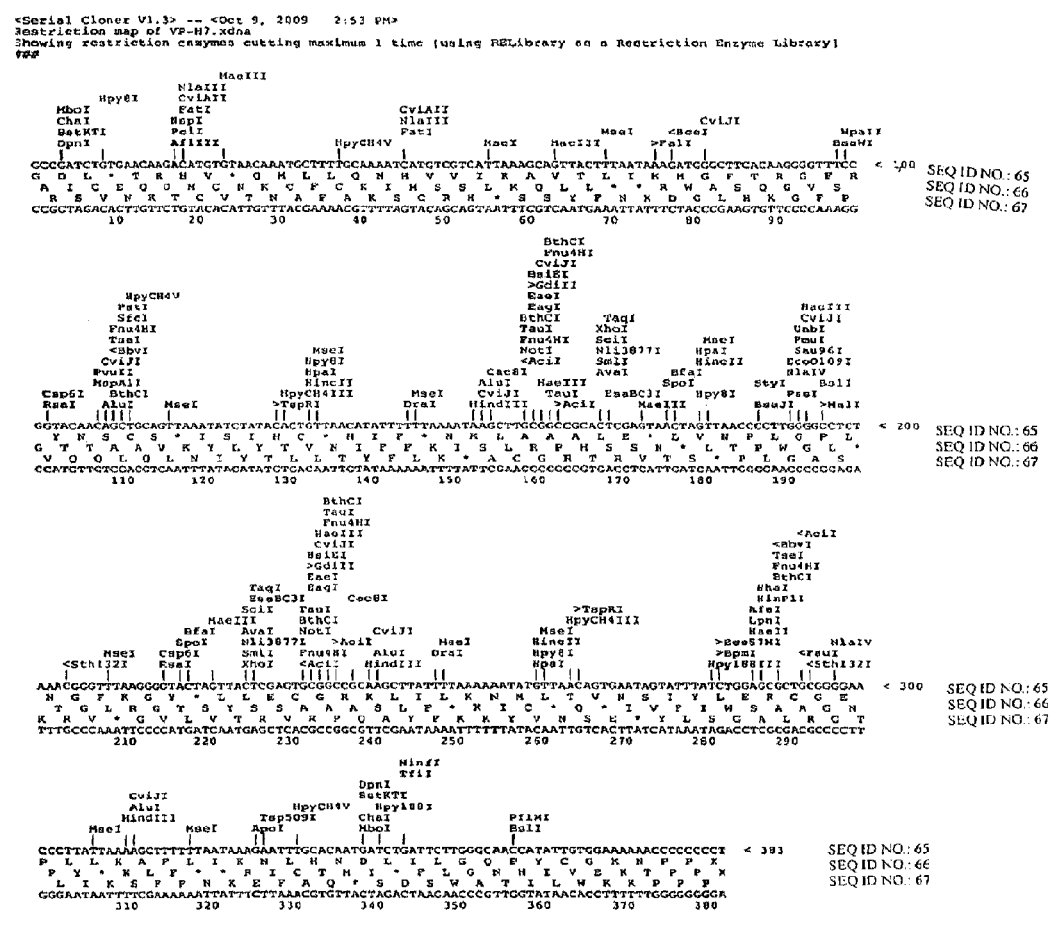
Figure 3:
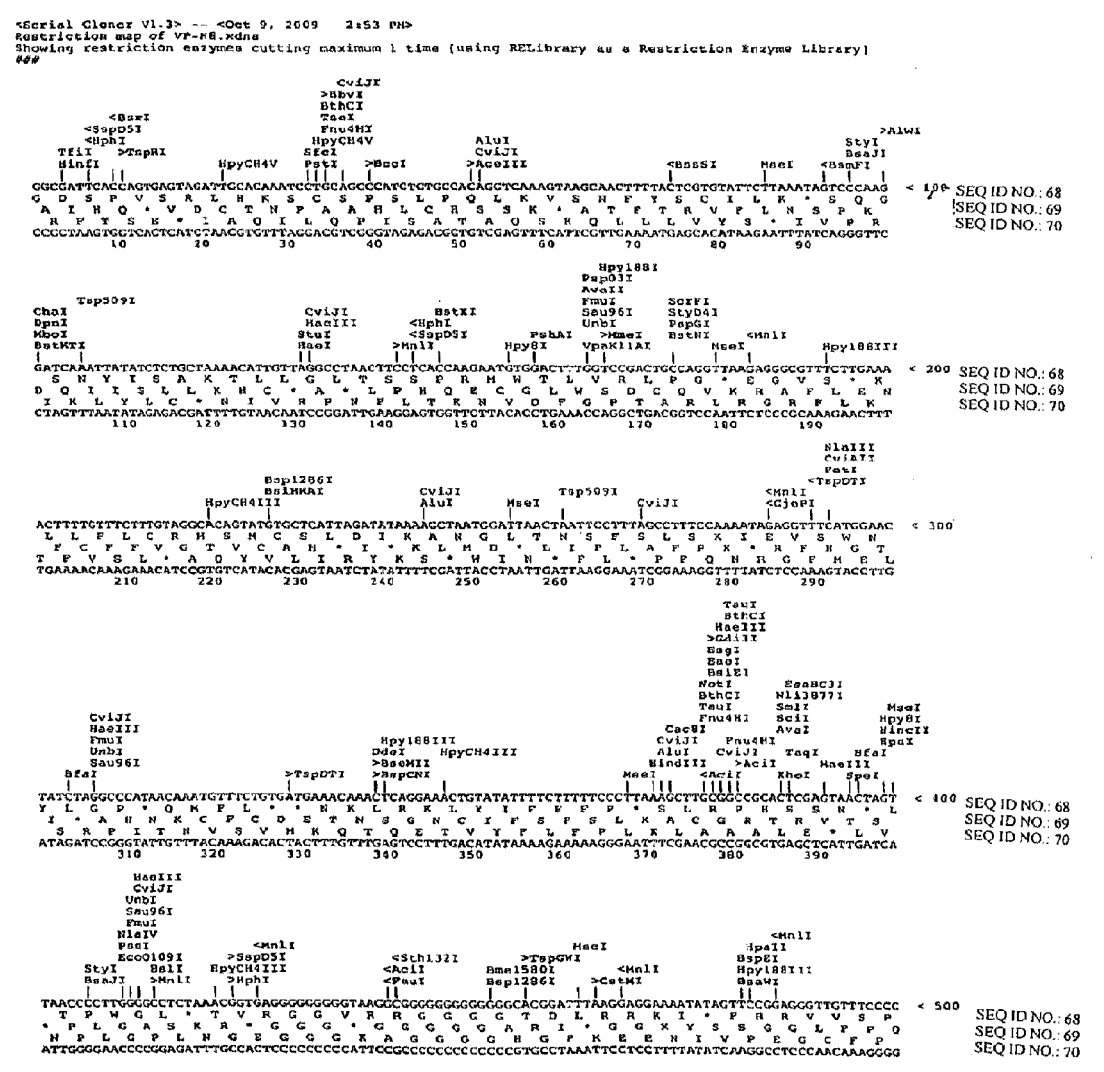
Figure 3:
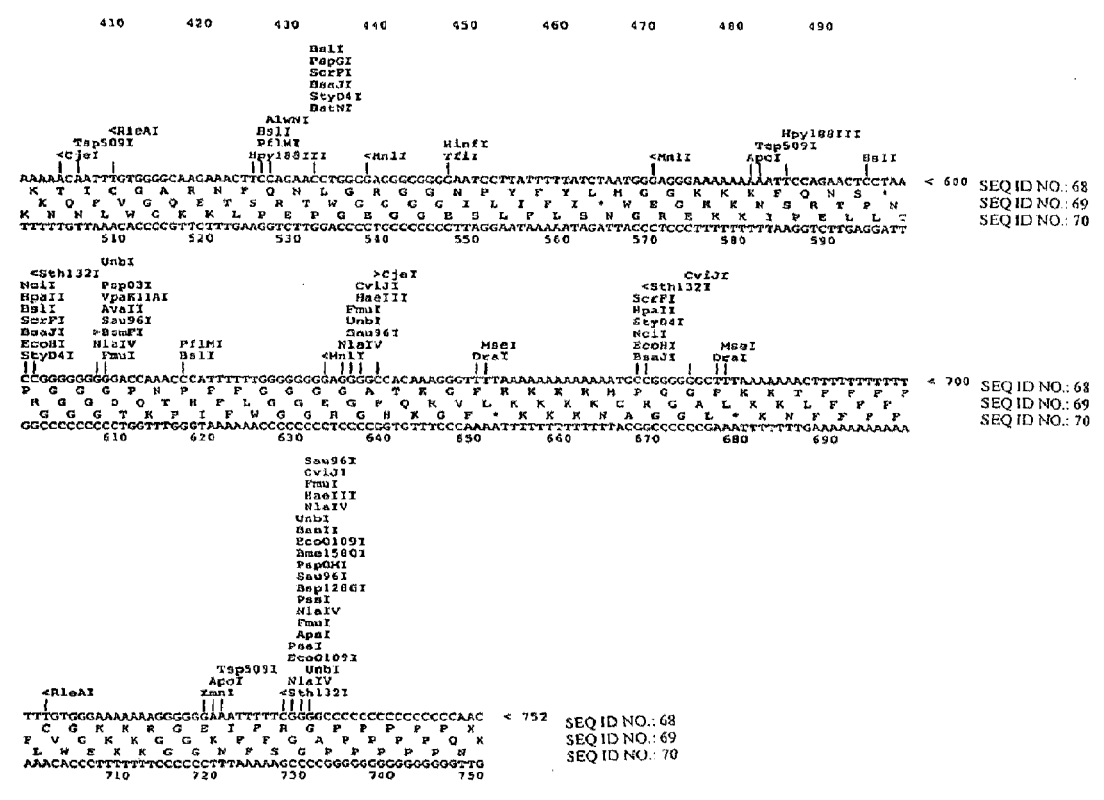

In some examples of the methods, the polypeptide comprises the amino acid sequence encoding by any one of SEQ ID NOs. 24-37 (FIG. 2), or the amino acid sequence of anyone of SEQ ID NO: 38-70 and SEQ ID NO: 127-137 (FIG. 3). This disclosure further includes polypeptides or analogs thereof having substantially the same function as the polypeptides of this disclosure. Such polypeptides include, but are not limited to, a substitution, addition or deletion mutant of the polypeptide. This disclosure also encompasses proteins or peptides that are substantially homologous to the polypeptides.

Homing polypeptides include the polypeptides themselves and portions thereof, including portions that exhibit substantially the same homing activity as that of the larger homing polypeptide of which they are a portion and portions that are characteristic of a larger homing polypeptide (e.g., an epitope to which an antibody binds).

Polynucleotides

The disclosure also embraces polynucleotides encoding homing polypeptides that homes to an atherosclerotic plaque. Polynucleotides embraced by the disclosure include the polynucleotides identified in the phage fishing protocol described herein, any polynucleotide that encodes an amino acid sequences encoded by the polynucleotides identified in the phage fishing protocol. The disclosure also embraces polynucleotides that encode any part of the protein or polypeptide that comprises the homing polypeptide. The polynucleotides also include the sequences flanking the polynucleotides encoding the homing polypeptides. These flanking sequences specifically include any single nucleotide polymorphism (SNP) in this sequences. The location of SNPs is known, for instance in the Affymatrix database.

Provided herein are polynucleotides identified by the method described herein. Such polynucleotides include the polynucleotides whose sequences are presented in FIG. 2, fragments thereof, and complements thereof. The term polynucleotide is used broadly and refers to polymeric nucleotides of any length (e.g., oligonucleotides, genes, small inhibiting RNA etc). The polynucleotide may be, for example, linear, circular, supercoiled, single stranded, double stranded or branched. It is, however, understood by one skilled in the art that due to the degeneracy of the genetic code, variations in the polynucleotide sequences shown will result in a polynucleotide sequence capable of encoding a polypeptide as disclosed herein in FIG. 2 it is understood that the polynucleotide sequences disclosed herein can encode a polypeptide of all three possible reading frames. The polypeptides encoded by the polynucleotides disclosed herein include all frame shifted variants. Such polynucleotide sequences are intended to be encompassed within the present disclosure. Further, a person of skill in the art will understand that there are naturally occurring allelic variations of the polynucleotide sequences shown herein. These variations are also encompassed by the present disclosure.

In some embodiments the polynucleotide comprises a sequence selected from the group consisting of: SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encodes the same polypeptide as a polypeptide encoded by any one of SEQ ID NOs 24-37, complements thereof and nucleic acids that hybridize under stringent conditions to the polynucleotides.

Provided herein are methods that comprise the use of one or more polynucleotides that comprise the polynucleotide sequence encoding polypeptides of any one of SEQ ID NOs. 24-37, shown in FIG. 2.

Polynucleotides that hybridize under stringent conditions to a polynucleotide that encodes a polypeptide of any one of SEQ ID NOS. 24-37 can also be used in the methods disclosed herein. Hybridization reactions can be performed under conditions of different stringency. Conditions that increase stringency of a hybridization reaction are widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 4×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. In a preferred embodiment hybridization and wash conditions are done at high stringency which permits only hybridization between nucleic acid sequences that are highly similar. By way of example hybridization under conditions of high stringency may be performed at 50% formamide and 4×SSC followed by washes of 2×SSC/formamide at 50° C. and with 1×SSC.

Antibodies

Antibodies that recognize (bind to) an atherosclerotic plaque homing polypeptide or portion of an atherosclerotic plaque homing polypeptide are also described. The antibodies include monoclonal or polyclonal antibodies and the antibodies can be produced using the information provided herein and art recognized methods. One or more such antibodies can be used in diagnostic methods and in therapeutic methods.

In some embodiments the disclosure provides an antibody, or a fragment thereof, that binds any of the atherosclerotic plaques described herein. In some embodiments, the disclosure provides an antibody, or a fragment thereof, that binds a homing polypeptide, wherein the polypeptide comprises a sequence selected from the group consisting of: SEQ ID NO: 38-70 and SEQ ID NO: 127-137.

In some embodiments, the disclosure provides an antibody, or a fragment thereof, that binds a homing polypeptides encoded by a polynucleotide, wherein the polynucleotide comprises a sequence selected from the group consisting of SEQ ID NO 24; SEQ ID NO 25; SEQ ID NO 26; SEQ ID NO 27; SEQ ID NO 28; SEQ ID NO 29; SEQ ID NO 30; SEQ ID NO 31; SEQ ID NO 32; SEQ ID NO 33; SEQ ID NO 34, SEQ ID NO 35; SEQ ID NO 36; SEQ ID NO 37, and a sequence that, due to the degeneracy of the genetic code, encodes the same polypeptide as a polypeptide encoded by any one of SEQ ID NOs 24-37.

In some embodiments, the antibody is a monoclonal antibody, a polyclonal antibody, a chimeric antibody, a bispecific antibody, a heteroconjugate antibody, or a single chain (ScFv) antibody.

Also provided herein are antibodies, or fragments thereof, that bind atherosclerotic lesion homing polypeptide(s) for use in the methods disclosed herein, or which bind one or more of the polypeptides disclosed herein in FIG. 3 (SEQ ID NO: 38-70 and SEQ ID NO: 127-137), or which are encoded by the polynucleotides of FIG. 2 (SEQ ID NOs 24-37). The antibodies can be monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv) antibodies, mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). The epitope(s) can be continuous or discontinuous. The antibodies may be made by any method known in the art and tested by the method described herein. In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; 6,265,150; and Winter et al., Annu. Rev. Immunol. 12:433-455 (1994). Alternatively, the phage display technology (McCafferty et al., Nature 348:552-553 (1990)) can be used to produce human antibodies and antibody fragments in vitro, from immunoglobulin variable (V) domain gene repertoires from unimmunized donors.

In one aspect the disclosure provides antibodies for the detection of atherosclerotic plaques and methods of treatment of atherosclerotic plaques. Antibodies for the detection of atherosclerotic plaques (and vulnerable plaques) include antibodies that bind to one or more of the homing polypeptides described herein, whereby the antibody is coupled to an imaging molecule (e.g., detection moiety). Examples of a detection moiety include, but are not limited to, radioisotopes, dyes, pigments, or fluorescent molecules such as luciferase, fluoroscein or commercially available fluorescent molecules from quantum-corn radioisotope, an MRI imaging agent, and an agent that can be imaged by computerized tomography (CT). Antibodies for the treatment of atherosclerotic plaques (and vulnerable plaques) include antibodies that bind to one or more of the homing polypeptides described herein, whereby the antibody is coupled to a therapeutic moiety. Examples of therapeutic moieties include, but are not limited to, ricin, radioisotopes, clotting agents, thrombolytic factors, chemotherapeutic and radiosensitizing agents, anti-angiogenesis agents, anti-motility agents, and ricin, a radioisotope, a clotting agent, a thrombolytic factor, a chemotherapeutic agent, an anti-angiogenesis agent, an anti-lipid agent, a statin, high density lipoprotein, a peptide with the functionality of a high density lipoprotein, and an immunomodulatory agent. The antibodies may be coupled to the therapeutic or imaging molecule by methods known in the art.

The antibodies, optionally coupled to an imaging agent or therapeutic agent, can be target to specific organs because the homing polypeptides will prudentially bind in specific organs.

Yet another aspect described herein relates to detection of a condition associated with, or characterized by, developing microvasculature homing polypeptide(s) in a subject, such as a human, utilizing one or more antibodies described herein, such as antibodies to any of the polypeptides, SEQ ID NO: 38-70 and SEQ ID NO: 127-137, or encoded by the polynucleotides of SEQ ID NOs 24-37, or fragments thereof, or epitopes thereof coupled to a radiologic (e.g., $I^{125}$) or other imaging molecules (e.g., dyes, pigments or fluorescent molecules such as luciferase, fluoroscein or commercially available fluorescent molecules from quantum.com).

Predicting Risk

Also described are uses of atherosclerotic plaques homing polypeptides, such as in methods of diagnosing or aiding in diagnosis of atherosclerotic plaques including methods of diagnosing or aiding in diagnosis of atherosclerotic plaques in association with ischemia (e.g., in association with stroke or myocardial infarction) or before ischemia develops; atherosclerotic plaques in the retina (e.g., in AMD).

Atherosclerotic plaques homing polypeptides, are also useful in methods of predicting or aiding in predicting the likelihood that an individual will suffer from a particular condition associated with atherosclerotic plaques (e.g., vulnerable plaque and, thus, myocardial infarction and/or stroke). Atherosclerotic plaques homing polypeptides or developing microvasculature homing polypeptides that home to developing collaterals are useful in methods of predicting or aiding in predicting the likelihood that an individual will develop or suffer from obstructive arterial disease.

Provided herein are compositions and methods for determining the presence of and/or the presence of elevated levels of one or more of the atherosclerotic lesion homing polypeptides described herein, or polynucleotides encoding them, in a sample from an individual at risk for or subject to developing a condition associated with or characterized by atherosclerotic plaques or in a sample from an individual at risk for or subject to developing vulnerable plaques. In a method of this type, levels of at least one atherosclerotic lesion homing polypeptides or at least one polynucleotide encoding such atherosclerotic lesion homing polypeptides distinct from levels evident in controls is correlated, for example, with increased risk of atherosclerotic lesion or pathologic development of vulnerable plaques, with resulting diseases.

Also provided herein are methods for determining survival rates (e.g., the probability of survival) or the recurrence of coronary artery or other vascular disease in an individual, such as an individual diagnosed as suffering from coronary artery or other vascular disease, comprising: 1) assessing the presence of and/or measuring the levels of one or more of the following: a) a polynucleotide disclosed herein in FIG. 2 (SEQ ID NOs 24-37), a complement thereof or the corresponding mRNA; b) a polypeptide encoded by any one of the polynucleotides disclosed in FIG. 2 (SEQ ID NO. 24-37) or a polypeptide disclosed in FIG. 3 (SEQ ID NO. 38-70) or a portion of such a polypeptide; or c) a polynucleotide that, through the degeneracy of the genetic code encodes a polypeptide having the same or substantially the same amino acid sequence and homing ability as an atherosclerotic lesion homing polypeptide encoded by any one of the polynucleotides of SEQ ID NOs. 24-37 and 2) comparing the results of 1) with results obtained in a control, wherein the presence of or presence of levels distinct from that of a control is indicative of a difference in survival rate. In some instances, a lower level in a sample from an individual being assessed of the component(s) being measured (polynucleotide or polypeptide) is indicative of a decrease in survival rate. In other instances, a higher level or the presence in a sample from an individual being assessed of the component(s) being measured is indicative of a decrease in survival rate. encoding them. In some instances, the presence of decreased levels or the presence of elevated levels of the component(s) being measured is indicative of an increase in survival rate. Alternatively, the presence of or the presence of elevated levels of the component(s) being measure is indicative of a decrease in survival rate. A variety of samples (e.g., blood, serum, vessel, organ or tissue such as heart tissue) can be assessed using this method of determining survival rate.

Also provided herein are compositions comprising such atherosclerotic lesion homing polypeptides and/or portions thereof and compositions comprising polynucleotides that encode atherosclerotic lesion homing polypeptides or portions thereof, as well as kits comprising such polypeptides and polynucleotides.

In one aspect the disclosure provides methods for determining if an individual is at risk for developing a cardiovascular disorder such as AMI or CAD comprising analyzing a biological sample taken from the individual for the presence of one or more SNPs, wherein if the sample has one or more of the SNPs the person is at risk for a cardiovascular disorder such as AMI or CAD The disclosure provides SNPs associated with atherosclerotic plaque (Table 3) and SNPs associated with developing collaterals (Table 6). The SNPs were identified by analyzing the genome flanking nucleic acid sequences that were shown to encode ligands that home to atherosclerotic plaque and developing collaterals, respectively, and parsing the SNPs against databases of SNPs known to be associated with AMI or CAD resulting in the sets of SNPs associated with AMI or CAD. It is shown herein that if an individual has one or more SNPs associated with atherosclerotic plaque (Table 3) that individual has an increased risk of having AMI. It is also shown herein that if an individual has one or more SNPs associated with developing collaterals (Table 6) that individual has an increased risk of having CAD.

The disclosure also demonstrates that the risk an individual has to develop AMI increases with the number of SNPs associated with atherosclerotic plaque that individual has acquired. Similarly, the disclosure also demonstrates that the risk an individual has to develop CAD increases with the number of SNPs associated with developing collaterals that individual has acquired.

It is shown herein that if a person has acquired one or more of the SNPs selected from rs6982320 8p22; rs2830538 21q21.3; rs463433 21q21.3, that person has an increased risk of developing AMI. Similarly, it is shown herein that if a person has acquired one or more of the SNPs selected from rs10757493 9p21.3, rs988179 2p16.3, rs309137 2q21.3, rs17588757 9p23 and rs12475139 2q21.3. that person has an increased risk for CAD.

The risk increases with the number of SNPs present in the sample. Thus in one embodiment, an individual is at risk for AMI if the individual has one SNP selected from the group consisting of rs6982320, 8p22; rs2830538, 21q21.3; rs463433 21q21.3; rs2830500, 21q21.3; rs457982, 21q21.3; rs468969, 21q21.3; rs2830492, 21q21.3; rs1602904, 8p22; rs229037, 21q21.3; rs4978541, 9q31.2; rs11176917, 12q15 and rs4749722, 10p11.22. However, in some embodiments the individual is at increased risk for AMI if the individual has 2, 3, 4, 5, 6, 7, 8, 9, 10, 11, 12, 13, 14, 15, 16, 17, 18, 19, 20, 21, 22, 23 up to 24 SNPs selected from the group consisting of rs6982320, 8p22; rs2830538, 21q21.3; rs463433 21q21.3; rs2830500, 21q21.3; rs457982, 21q21.3; rs468969, 21q21.3; rs2830492, 21q21.3; rs1602904, 8p22; rs229037, 21q21.3; rs4978541, 9q31.2; rs11176917, 12q15 and rs4749722, 10p11.22.

In one embodiment an individual is at risk for AMI if the individual has one SNP selected from the group consisting of rs6982320 8p22, rs2830538 21q21.3, and rs463433 21q21.3. In some embodiments the individual is at increased risk for AMI if the individual has 2, 3, 4, 5, up to 6, SNPs selected from the group consisting of rs6982320 8p22, rs2830538 21q21.3, and rs463433 21q21.3.

In one embodiment an individual is at risk for AMI if the individual has one or two SNPs corresponding to rs6982320 8p22.

In one embodiment an individual is at risk for CAD, it the individual has one SNP selected from the group consisting of rs10812143, 9p21.3; rs12005015, 9p23; rs7025783, 9p21.3; rs7639226, 3p12.3; rs10182729, 2p16.3, rs12618911, 2p16.3; rs2216784, 2p16.3, rs1592145, 9p21.2; rs13302855, 9p21.2; rs324501, 9p23; rs12005189, 9p23; rs2643801, 9p21.2; rs6558102, 8p21.1; rs10812622, 9p21.2; rs988179, 2p16.3; rs10193587, 2q22.1; rs4546115, 3q13.11; rs4971686, 2p16.3; rs10511521, 9p23; rs10966441, 9p21.3; rs309137, 2q21.3; rs9288812, 3q13.11; rs8396, 4q32.1; rs13391995, 2p16.3; rs10433373, 3q13.11; rs11759406, 6q21; rs10511245, 3q13.11; rs10433370, 3q13.11; rs6922304, 6q21; rs9838585, 3q13.11; rs629768, 8p21.1; rs6781390, 3p12.3; rs6921876, 6q21; rs4690909, 4q32.1; rs9320231, 6q21; rs17588757, 9p23; rs12664414, 6q21; rs10168838, 2p16.3; rs12475139, 2q21.3; rs629187, 3q13.11; rs10757493, 9p21.3; rs17059917, 8p21.1, rs17068440, 6q21 and rs3772551, 3q13.11.

In some embodiments the individual is at increased risk for CAD if the individual has 2, 3, 4, 5, 6, 7, 8, 9, 10, 11, 12, 13, 14, 15, 16, 17, 18, 19, 20, 21, 22, 23., 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 up to 86 SNPs selected from the group consisting of rs10812143, 9p21.3; rs12005015, 9p23; rs7025783, 9p21.3; rs7639226, 3p12.3; rs10182729, 2p16.3, rs12618911, 2p16.3; rs2216784, 2p16.3, rs1592145, 9p21.2; rs13302855, 9p21.2; rs324501, 9p23; rs12005189, 9p23; rs2643801, 9p21.2; rs6558102, 8p21.1; rs10812622, 9p21.2; rs988179, 2p16.3; rs10193587, 2q22.1; rs4546115, 3q13.11; rs4971686, 2p16.3; rs10511521, 9p23; rs10966441, 9p21.3; rs309137, 2q21.3; rs9288812, 3q13.11; rs8396, 4q32.1; rs13391995, 2p16.3; rs10433373, 3q13.11; rs11759406, 6q21; rs10511245, 3q13.11; rs10433370, 3q13.11; rs6922304, 6q21; rs9838585, 3q13.11; rs629768, 8p21.1; rs6781390, 3p12.3; rs6921876, 6q21; rs4690909, 4q32.1; rs9320231, 6q21; rs17588757, 9p23; rs12664414, 6q21; rs10168838, 2p16.3; rs12475139, 2q21.3; rs629187, 3q13.11; rs10757493, 9p21.3; rs17059917, 8p21.1, rs17068440, 6q21 and rs3772551, 3q13.11.

In one embodiment an individual is at risk for CAD, it the individual has one SNP selected from the group consisting of rs10757493 9p21.3, rs988179 2p16.3, rs309137 2q21.3, rs17588757 9p23 and rs12475139 2q21.3. In some embodiments the individual is at increased risk for CAD if the individual has 2, 3, 4, 5, 6, 7, 8, 9, up to 10 SNPs selected from the group consisting of rs10757493 9p21.3, rs988179 2p16.3, rs309137 2q21.3, rs17588757 9p23 and rs12475139 2q21.3.

Provided herein are methods for determining the presence of developing atherosclerotic lesion polypeptides or polynucleotides encoding them, in a sample from an individual at risk for developing a condition associated with or characterized by developing microvasculature, wherein the presence of, or presence of elevated levels of, a atherosclerotic lesion homing polypeptide(s), or polynucleotides encoding them, is correlated with increased risk of a condition or disorder associated with, or characterized by, atherosclerotic lesion homing polypeptides. In some embodiments, the presence of an elevated level of a atherosclerotic lesion homing peptide correlated with increased risk that an individual will develop vulnerable plaque is determined and its presence at an elevated level (relative to the level of the same atherosclerotic lesion homing peptide in an appropriate control, such as an individual not at increased risk of developing vulnerable plaque) indicates that the individual is at increased risk of developing of developing vulnerable plaque (e.g., is indicative of increased risk in the individual of developing vulnerable plaque). In other embodiments, the levels of more than one (two or more) atherosclerotic lesion homing polypeptide correlated with increased risk that an individual will develop vulnerable plaque are determined and their presence at elevated levels indicates that the individual is at increased risk of developing of developing vulnerable plaque (is indicative of increased risk in the individual of developing vulnerable plaque). In one embodiment, the cumulative level (sum of the levels) of the two or more atherosclerotic lesion homing peptide correlated with increased risk that an individual will develop vulnerable plaque is assessed and indicates that the individual is at increased risk of developing of developing vulnerable plaque (is indicative of increased risk in the individual of developing vulnerable plaque). In a further embodiment, a pattern of increased levels is the basis for the assessment In each embodiment in which elevated level(s) of one or more than one atherosclerotic lesion homing polypeptides, is determined, the polypeptide(s) are those encoded, for example, by any one of SEQ ID NOs 24-37, or polypeptides having the amino acid sequence of any one of SEQ ID NOs 38-70. An appropriate control is, for example, an individual of the same age and/or gender and/or ethnicity and/or dietary pattern and/or physical activity pattern as the individual whose risk is being assessed. The appropriate control individual may be a "normal" or "healthy" individual that is believed not to have vulnerable plaque. Controls may be selected using methods that are well known in the art. Once a level has become well established for a control population, the levels of the test biological samples can be directly compared with the known levels.

Also provided herein are methods for determining the risk of a condition or disorder associated with or characterized by developing microvasculature homing polypeptides in an individual, such as cardiovascular conditions, ischemia and related conditions, such as myocardial infarction and stroke. Such methods comprise detecting the presence of and/or measuring the levels of one or more of the polypeptides such as those encoded by the nucleotides of SEQ ID NOs 24-37, or polypeptides having the amino acid sequence of SEQ ID NOs. 38-70 in a sample from the individual, wherein the presence and/or presence of elevated levels of one or more of the polypeptides or polynucleotides encoding them is correlated with an increased risk of developing the condition.

The methods provided herein may be used to detect subclinical conditions, detect subclinical metastasis in at risk patients, assess the risk of developing a condition associated with or characterized by atherosclerotic lesion homing polypeptides or used for diagnostic purposes (e.g., detect the condition, monitor disease progression or treatment). One embodiment provides methods of diagnosing a cardiovascular disorder in a subject. In one embodiment, the method comprises detecting the level of a polynucleotide encoding an atherosclerotic lesion homing polypeptide in a sample obtained from a subject, wherein a level of the polynucleotide that is abnormal (e.g., higher or lower) relative to a control sample is indicative of the condition. In another embodiment, the method comprises detecting the presence or absence of a polynucleotide encoding a atherosclerotic-lesion-homing polypeptide in a sample obtained from the subject, wherein the presence of the polynucleotide is indicative of the associated condition. Conventional methodology may be used to detect the polynucleotides in the method described herein. Examples include, but are not limited to, PCR analysis, RT-PCR, Northern analysis or microarrays as described herein below. Examples of a sample obtained from a subject include, but is not limited to, blood, biopsy sample, pathology sample, urine or cerebrospinal fluid.

Yet another aspect of this disclosure provides methods of prognosing, imaging and/or diagnosing a condition associated with or characterized by atherosclerotic lesion homing polypeptide(s) in a subject. In one embodiment, the method comprises detecting the level of such a polypeptide(s) in a sample obtained from an individual, wherein a higher level of the polypeptide relative to a control sample is indicative of the condition. In another embodiment, the method comprises detecting the presence or absence of an atherosclerotic lesion homing polypeptide(s) in a sample obtained from the individual, wherein the presence of the polypeptide is indicative of the condition. Conventional methodology may be used to detect the polypeptides in the method described herein.

Examples include, but are not limited to, Western blot analysis or protein microarrays. Other methods of quantitative analysis of proteins include, for example, proteomics technologies such as isotope coded affinity tag reagents, MALDI TOF/TOF tandem mass spectrometry, and 2D-gel/mass spectrometry technologies. These technologies are commercially available from, for example, Large Scale Proteomics, Inc. (Germantown, Md.) and Oxford Glycosystems (Oxford UK). Methods for quantitatively measuring proteins such as ELISA analyses are well known. Kits for measuring levels of many proteins using ELISA assays are commercially available from many suppliers. In addition, methods for developing ELISA assays in the laboratory are well known. See for example Antibodies: A Laboratory Manual (Harlow and Lane Eds. Cold Spring Harbor Press). Antibodies for use in such ELISA methods either are commercially available or are prepared using well-known methods. Examples of a sample obtained from a subject include, but is not limited to, blood, biopsy sample, pathology sample, urine or cerebrospinal fluid.

The methods as described herein, as well as methods that predict or identify survival rates, such as for example, five and ten year survival rates, can be used to design appropriate therapeutic intervention. For example, for an individual with an early stage of a condition, methods for detecting the presence of elevated cumulative levels of any one or more of a polypeptide of SEQ ID NOs 38-70 and 127-137, or polynucleotides encoding such polypeptides (SEQ ID NOs 24-37), can help a physician determine if frequent diagnostic assessment is necessary or if therapeutic intervention is necessary. A physician will be able to determine appropriate therapeutic intervention based on the methods disclosed herein and conventional methods known in the art.

Methods of Treatment and Imaging

The disclosure further relates to use of atherosclerotic plaques homing polypeptides, and encoding polynucleotides for delivering agents to atherosclerotic plaques. In one embodiment, an atherosclerotic plaque homing polypeptide or an encoding polynucleotide is used to deliver prophylactic or therapeutic drug(s) to atherosclerotic plaques, in order to prevent or treat a condition associated with atherosclerotic plaques.

In further specific embodiments, the compositions of the present disclosure are useful for detection and/or imaging of atherosclerotic plaques and vulnerable plaque. In some embodiments, the atherosclerotic lesion homing polypeptides or encoding DNA are bound to a label which can be a fluorescent label, an enzyme label, an enzyme substrate label, a radioactive label, a nuclear magnetic resonance active label, a luminescent label or a chromophore label. In some embodiments, the atherosclerotic lesion homing polypeptides are bound to a radioisotope. Some radioisotopes could emit α radiations. Others could emit β radiations. Other radioisotopes could emit γ radiations. Examples of radioisotopes that may be used in this disclosure include but are not limited to $^{225}AC$, $^{211}At$, $^{212}Bi$, $^{213}Bi$, $^{186}Rh$, $^{188}Rh$, $^{177}Lu$, $^{90}Y$, $^{131}I$ or $^{67}Cu$, $^{125}I$, $^{123}I$ or $^{77}Br$.

In another embodiment, an atherosclerotic plaques homing polypeptide or an encoding polynucleotide is used to deliver detection or imaging agents to assess the atherosclerotic plaques, such as the extent to which they have developed in an untreated individual or the degree to which they have regressed or stopped developing in a treated individual. In one embodiment, for example, atherosclerotic plaques homing polypeptides are attached or affixed to a biocompatible or biodegradable delivery agent, such as a nanoparticles, to produce a targeting biocompatible or biodegradable delivery agent, such as targeting biocompatible or biodegradable nanoparticles. The targeting biocompatible or biodegradable delivery agents, such as targeting biocompatible or biodegradable nanoparticles, can be designed to target any organ or tissue of the body and, in specific embodiments, to home to a specific atherosclerotic plaques, such as a vulnerable plaque, and such as that in association with ischemia. Such targeting biodegradable delivery agents, such as targeting biodegradable nanoparticles, or a collection of same, can be used for therapeutic purposes. For example, targeting biodegradable delivery agents, such as targeting biodegradable nanoparticles, carrying a therapeutic agent can be administered to an individual, making it possible to deliver the therapeutic agent to a selected tissue or organ. Using this approach, high levels of therapeutic agent(s) can be delivered to a targeted tissue or organ without the risk of high, potentially toxic, systemic concentrations. For example, therapeutic agents can be delivered, using targeting biodegradable delivery agents, such as targeting biodegradable nanoparticles, to atherosclerotic plaques and vulnerable plaques, such as in association with ischemia.

Such targeting biocompatible or biodegradable delivery agents, such as targeting biocompatible or biodegradable nanoparticles, or a collection of same, can also be used for imaging. For example, targeting biodegradable delivery agents, such as targeting biodegradable nanoparticles carrying an imaging agent, such as gadolinium, that can be imaged by MRI, make noninvasive imaging possible. For example, individuals can be assessed for the presence and/or extent of atherosclerotic plaques and/or vulnerable plaques. For example, individuals shown to have vulnerable plaques (who are at risk of plaque rupture and, thus, acute coronary syndrome or stroke) can be treated earlier and more rigorously than would otherwise be possible. Specific plaques can also be identified using targeting biodegradable delivery vehicles, such as targeting biodegradable nanoparticles.

In certain embodiments, the present disclosure provides a method of targeting an agent to vulnerable plaque in an individual, comprising administering to an individual in need thereof an effective amount of a composition comprising a atherosclerotic lesion homing polypeptide that homes to vulnerable plaque and the agent to be targeted to vulnerable plaque in the individual, whereby the agent is targeted to the vulnerable plaque. For example, the agent to be targeted to vulnerable plaque is a therapeutic drug or a detection/imaging agent (e.g., radioisotopes, dyes, fluorescent molecules, and pigments).

In some embodiments, the method comprises administering to a subject in need of such treatment a homing polypeptide linked to a therapeutic agent in an amount effective to treat the condition, or an effective amount of a composition that inhibits the condition (e.g., collection of phage or phage expression products identified by the method herein; a homing polypeptide linked to a therapeutic agent and/or an antibody directed against a polypeptide comprising a targeting domain).

Pharmaceutical Compositions

Also described are compositions, such as pharmaceutical compositions and compositions useful for therapy or prevention of conditions in which atherosclerotic plaques a role, and compositions used for detection and/or imaging of atherosclerotic plaques. Such compositions are useful, for example, in treating and detecting conditions such as cardiovascular conditions, ischemia and related conditions, such as myocardial infarction and stroke; retinal conditions, such as AMD.

In one aspect, the pharmaceutical compositions comprise an atherosclerotic lesion homing polypeptide and one or more therapeutic agents. The therapeutic agent can be an agent that suppresses the formation of atherosclerotic plaques, such as radioisotopes and chemotherapeutic agents.

In other examples, provided herein are kits and compositions comprising one or more polynucleotide (e.g., one or more of SEQ ID NOs 24-37, or polynucleotides that, due to the degeneracy of the genetic code, encode the same or substantially the same amino acid sequence as that encoded by one of the specified polynucleotides) or reagents specific thereto, such as antibodies, specific for couple moieties described herein.

In addition, the present disclosure provides kits comprising primers specific for polynucleotides encoding any one or more of developing microvasculature homing polypeptide(s), such as atherosclerotic lesion homing polypeptides (e.g., any one of the polypeptides encoded by any of SEQ ID NOs 24-37). Such kits comprising primers specific for such polynucleotides, and, optionally, primers for control polynucleotides and instructions for use.

In specific embodiments, compositions are pharmaceutical compositions that comprise (a) one or more atherosclerotic lesion homing polypeptides or portions thereof (e.g., one or more of the homing polypeptides encoded by any one of the DNAs represented by SEQ ID NOs 24-37) or one or more DNA encoding an atherosclerotic lesion homing polypeptide, such as DNA encoding one or more atherosclerotic lesion homing polypeptide (e.g., one or more DNA of SEQ ID NOs 24-37, each of which encodes an atherosclerotic lesion homing polypeptide) or one or more of atherosclerotic lesion homing polypeptides of SEQ ID NO: 38-70 and SEQ ID NO: 127-137, and (b) a therapeutic agent (a drug) to be delivered to atherosclerotic plaques and/or vulnerable plaques. In some embodiments, the pharmaceutical compositions also include one or more homing polypeptides of SEQ ID Nos. 14-23 shown in FIG. 5. Therapeutic agents that can be included in a pharmaceutical composition of the present disclosure include those that decrease the developments of atherosclerotic plaques, such as radioisotopes and chemotherapeutic drugs, that would favorably influence vulnerable plaque or modify the extent to which it occurs in an individual. In some embodiments, the polypeptides may be coupled to a therapeutic agent or an imaging molecule. Imaging molecules that can be used include a radioisotope, a dye, a pigment and a fluorescent molecule (such as luciferase, and fluorescein).

A pharmaceutical can include a pharmaceutically acceptable carrier, which is a compound suitable for administration to individuals, such as humans. The pharmaceutical compositions can contain other components useful in formulating pharmaceutical preparations for administration to subjects, preferably humans, including surfactants, solvents, preservatives, diluents, buffering agents and the like, all of which are standard in the pharmaceutical arts.

Suitable surfactants for use with the present disclosure include nonionic agents, such as long-chain fatty acids and their water-insoluble derivatives. These include fatty amines such as lauryl acetyl and stearyl amine, glyceryl esters such as the naturally occurring mono-, di- and triglycerides, and fatty acid esters of fatty amines, such as propylene glycol, polyethylene glycol, sorbitan, sucrose and cholesterol. Also useful are compounds that have polyoxyethylene groups added through an ether linkage with an amine group. Compounds that are also useful in the present disclosure include the polyoxyethylene sorbitan fatty acid esters and polyoxyethylene glycerol and steroidal esters. Some of the preferred surfactants are Cremophor® EL and Cremophor® EL-P, which are polyoxyethylated castor oil surfactants.

It is contemplated that other surfactants may be used to solubilize the compositions described herein. For example, it is contemplated that polysorbate 80, polysorbate 20, sodium laurate, sodium oleate, and sorbitan monooleate may be useful in certain embodiments of the present disclosure. Anionic surfactants may also be useful in the practice of the present disclosure. Examples of these include, but are not limited to, sodium cholate, sodium lauryl sulfate, sodium deoxycholate, sodium laurate, sodium oleate, and potassium laurate.

In certain embodiments, dehydrated ethanol may be used as a solvent for the compositions described herein. In other embodiments, glycols such as propylene glycol or polyethylene glycol are within the scope of the disclosure. Simple complex polyols may also be suitable solvents. Moreover, the use of non-dehydrated amines may also be suitable within the scope of the present disclosure.

Suitable buffering agents include: acetic acid and a salt (1-2% W/V); citric acid and a salt (1-3% W/V); and phosphoric acid and a salt (0.8-2% W/V).

Suitable preservatives include antimicrobial agents, such as, benzalkonium chloride (0.003-0.03% W/V); chlorobutanol (0.3-0.9% W/V); parabens (0.01-0.25% W/V) and thimerosal (0.004-0.02% W/V) and/or suitable antioxidants, such as, ascorbic acid, ascorbyl pamitate, BHA, BHT, hypophosphorous acid, monothioglycerol, potassium metabisulfite, propyl gallate, sodium formaldehyde sulfoxylate, sodium metabisulfite, sodium bisulfite, sodium thiosulfate, sulfur dioxide, tocopherol and/or tocopherols excipient.

The practice of the present disclosure will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

The present disclosure is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Generation of cDNA Phage Libraries

The specific strategy developed is based on the capacity to genetically alter millions of bacteriophage so that each phage expresses a single relatively large peptide. This is achieved by inserting a random library of millions of cDNAs into the genome of a bacteriophage that have been specially designed so that each phage displays on its surface one copy of a single fusion protein of 100 to 1,000 amino acids. In an experiment to determine which peptides bind to endothelium within the target tissue ("fishing" for the phage), millions of genetically altered phage are injected into an animal. Those that bind to the tissue are isolated and expanded by infecting susceptible bacteria and harvesting the expanded phage particles. In aggregate, therefore, millions of different peptides can be examined as potential targeting molecules. Thus, the phage fishing technique, through the binding of phage-expressed ligands to tissue-specific endothelial receptors, allows identification of tissue-specific ligands that are, in effect, functioning as molecules that home to the target tissue.

A phage library carrying large fragments of expressed proteins from the bone marrow (BM) was generated. As a source of BM expressed genes, the particulate fractions (>50 micron particles filtered out) that are discarded after human bone marrow harvests were used. This particulate fraction cannot be transfused to patients receiving BM transplant due to the large particle size, but, contains bone marrow matrix-bound cells (stem and progenitor cells not released into the circulation), precursor cells and differentiated cells. Cells were derived from different donors and stimulated by attachment and with growth factors. cDNA libraries of human bone marrow cells were constructed as follows: Human bone marrow cells were harvested from healthy donors and filtered through a 200 µm filter. Mononuclear cells were isolated by gradient centrifugation (Ficoll-Paque PLUS™, GE Healthcare, Piscataway, N.J.). Mononuclear cells were grown in DMEM cell culture medium containing 50 ug/ml SCF, 10 ng/ml GM-CSF and 10 ng/ml IL-3 and the non-attached cells were harvested after 3 weeks in order to select for hemapoetic precursor cells. Mononuclear cells were cultivated in MesenCult (Stemcell Technologies Inc; Vancouver, Calif.) for two weeks and the resulting attached mesenchymal precursor cells were isolated. Mononuclear cells were isolated by utilizing a negative selection system (Stemcell Technologies Inc). Monocytes were isolated by utilizing a negative selection system (Stemcell Technologies Inc.) from mononuclear cells, which were previously harvested by gradient centrifugation. From each cell type cDNA was generated by reverse transcribing mRNA using random primers and oligo-dT oligonucleotide. From the RNA of the four collected pools of bone marrow derived cells (mononuclear cells, hematopoetic precursor cells, mesenchymal precursor cells and monocytes) cDNA was generated by reverse transcribing using random primers and oligo-dT oligonucleotides. Following second strand synthesis, gel filtration was performed to size fractionate the cDNA, which resulted in exclusion of all products less than 200 base pairs in size. Subsequently, the cDNA was EcoR1/HindIII double digested and directionally cloned into a multiple cloning site within the capsid encoding gene 10B of bacteriophage T7 using the OrientExpress Cloning System (Novagen, Darmstadt, Germany). The quality of the resulting inserts was verified by gel electrophoresis. The insert sizes of cDNA in the phage display library ranged between 100 to 2,000 with the majority between 300 and 900 nucleotides, which results in the display of a majority of 100 to 300 amino acids of protein fragments to be expressed on the phage surface.

The resulting phage libraries were estimated to comprise between 1 and $4 \times 10^6$ clonal species. Amplification of phage libraries was carried out by inoculation of BLT5615 *E. coli* stocks (Novagen, Madison, Wis.). Following *E. coli* lysis, phage was isolated by collection of the media supernatant;

titering of the phage stock was performed using a serial dilution plating assay. For phage in vivo selection assays all phage libraries were pooled.

Bacteriophage (or "phage"), are viruses that infect bacteria. After binding to the bacterial cell surface, they inject their DNA into the host, capture the bacterial biosynthetic machinery, and then proliferate, resulting in millions of virus copies. The success of the phage fishing strategy derives from the ability to genetically alter the phage to: 1) express molecules of interest; 2) use in one experiment millions of phage with millions of different peptides to be examined for targeting capacity; and 3) expand individual phage so that millions of the particular phage of interest are easily available for further study.

Example 2

Homing to Atherosclerotic Plaques

For the selection of particles binding to atherosclerotic plaques, the genetically altered vulnerable plaque mouse model was used. It is thought that both vulnerable plaques and stable plaques are present in the vulnerable plaque mouse model. The plaques present in the mouse model are phenotypically similar to human plaques. These mice showed a number of type of lesions with marked inflammation, large necrotic lipid cores, thin fibrous caps, lipid laden macrophages, dissolution of elastic laminae neovascularization and intraplaque hemorrhage.

Polypeptides that home to atherosclerotic plaques were identified using the following protocol: ("phage fishing")

Step 1: A human bone marrow phage display cDNA library, as described above, is injected into the vena cava inferior. Step 2: The brachiocephalic artery and the lesion it contained were identified and the lesion was scraped off and harvested. Step 3: Phage that had bound were expanded and reinjected into another eight mice. The phage were again harvested from the lesions and subsequently sequenced.

About $10^9$ phage, containing >1 million different human proteins on their surfaces (one/phage), were injected into each of eight mice. Unbound phage was washed out with the blood by injecting 10 ml saline directly through the heart. Selected phage retained in the vulnerable plaque was harvested, amplified and reinjected repeatedly into the next mouse. In order to harvest the bound phage, the brachiocephalic artery and control organs were removed from the mouse and homogenized. The bound phage in the supernatant was amplified in *E. coli*. Titering of the selective phage after each round was performed using a serial dilution assay. In parallel with animals with vulnerable plaques, control animals were also assessed for phage homing by a parallel injection and harvesting of phage from the same organs.

From each last round, single phage were isolated, amplified and the cDNA-insert was sequenced using the T7-UP primer (Novagen, Darmstadt, Germany).

Two rounds of phage fishing in the mouse vulnerable plaque model were performed. There were two ligands that bound to the plaque lesions in each of the eight mice, another three that bound to the lesion in each of seven mice, and another three that bound to the lesion of four to six mice, suggesting that five to eight ligands exhibited robust binding to lesions present in our mouse model, which contains lesions phenotypically similar to human vulnerable plaque. The eight clones (30% of all the clones found) that bound to the lesions of at least four mice accounted for 84% of the total number of clones that grew out after harvesting and plating. The sequences of identified phage inserts are shown in FIG. 2.

Example 3

Imaging in the Absence of Phage and Phage Protein

The assay was verified by determining that the identified ligands (polypeptides) homed to the target tissue when removed from the context of the phage and phage proteins and that these ligands could be used to image the target tissue. Images were obtained after i.v. injection of a recombinant homing polypeptide isolated by phage display of liver metastatic cancer cell cDNA libraries. The targeting polypeptide was linked with a 655 nm Q-dot. The images show the background, with gut fluorescence from food having a distinct spectrum, while the 655 nm scan (i.e., the Q-dot) with the liver lighting up brightly.

Other images show a time course measurement of the 655 nm scan signal appearance in different organs after injection of the Q-dot labeled protein. Upon injection the signal increases in the liver but does not increase above background in any of the other organs evaluated.

Example 4

Homing Gene Expression

To verify the expression of the identified homing polypeptides in bone-marrow cells, RNA was isolated from cells, reverse transcribed and the resulting cDNA was analyzed by real-time PCR with primer pairs specific for each phage insert (see FIG. 1). For these measurements, RNA was extracted from human bone marrow tissues (BM) and from subpopulations of precursor and non-precursor cells selected from the BM tissues by magnetic separation. A series of differentiated white blood cells (leukocytes) from donors' blood was screened for expression of two randomly chosen of the genes: H6 and H8. Extracted RNA was then reverse transcribed and the levels of expression detected real-time PCR with specific primer pairs. The normalization was done using beta-2-microglobulin as a house keeping gene. Actin and GAPDH are other loading and quality controls used. The expression levels are presented on a logarithmic scale since they cover a wide range of one million-fold when comparing the highest and lowest levels observed. The results show that the genes are expressed at a very high level in BM and in precursor cells. They are expressed at a 100- to 1,000-fold lower level in differentiated BM cells and that is reflected in peripheral leukocytes as shown for two of the genes picked randomly. Thus, these genes are expressed in progenitor and stem cells present in bone marrow tissues and highly downregulated upon differentiation.

Example 5

Identification of the Peptide Sequence of Expressed Homing Genes

FIG. 3 presents the sequences of fusion proteins with gene 10 identified by mass spectrometry of T7 phage expressing the different collateral homing sequences. Additional amino acid sequences of ligands that home to vulnerable plaque/atherosclerotic plaque are indicated below:

>VP-A1 frameshift -1
(SEQ ID NO: 127)
SPNINEASVLWLSSSPPLVPISQSGMFINFVK

>VP-A8 frameshift -1
(SEQ ID NO: 128)
FPSLFNCVLEDFKNILISSQILNIMLLVIKLAAALE

>VP-B3 frameshift -1
(SEQ ID NO: 129)
FGYRKMSMIFTLELITKIPKFHNPKQVYFPRAKNKFNGNYSSL >VP-B6 frameshift -1
(SEQ ID NO: 130)
RSSFPFIDRPDGSVGCEMNTMGQKEILAGGERKSEGLWVNFRFRI >VP-B9 frameshift -1
(SEQ ID NO: 131)
RGTPRGTQLKNRNAVCCSRAEK >VP-C3 frameshift -1
(SEQ ID NO: 132)
PFLHFPDFCQQPQEQSLKETGLSQK*

>VP-D5 frameshift -1
(SEQ ID NO: 133)
TTYTRFLSFLPELFDFID

>VP-H4 ORF of ADAMTS1
(SEQ ID NO: 134)
AWVIEEWGECSKSCELGWQRRLVECRDINGQPASECAKEVKPASTRPCADHPCPQWQLGEWSSCSKTCGKGYKK
RSL

>VP-H6 in frame
(SEQ ID NO: 135)
RSEISKVEQETGNTADVCLPLGVMSLLDLIPSDIFPIILSALHQNTSLSKNKCAY VP-H7 frameshift-1
(SEQ ID NO: 136)
RSVNKTCVTNAFAKSCRH VP-H8 in frame
(SEQ ID NO: 137)
RFTSEMRIAQILQPISATAQSKQLLLVYS Example 6

Identification of SNPs

A unique phage fishing strategy was employed, using a human bone marrow-derived cDNA library, to fish for ligands using both a mouse model of vulnerable plaque-like lesions, and a model of developing collaterals in an ischemic mouse hindlimb model. These studies led to identification of previously unrecognized genes encoding novel vulnerable plaque-binding ligands and encoding ligands of developing collaterals.

The studies show that these binding sequences are expressed by human stem/progenitor cells, and in circulating mononuclear cells. A new class of homing ligands that are associated with stem cell homing to injured vessels and in tissue repair was thereby identified. Genetic variations in the genes encoding these ligands (or in proximity to the actual genes) could alter the propensity of plaque rupture and of CAD development. Database analysis characterized SNPs present within +/−100 kb of the binding sequences (See Table 1 below). The SNPs were tested for association with AMI risk and with risk of having CAD by using the DNA banks of a consortium of 5 centers that had performed GWAS analysis in over 7000 patients with coronary disease demonstrated by coronary angiography.

The studies revealed VP-binding SNPs that were associated with increased risk of AMI, and collateral-binding SNPs that were associated with increased risk of CAD. Moreover, an aggregate genetic risk score (GRS), based on the number of risk alleles an individual has, markedly improves identification of high risk subgroups, conveying a maximal odds ratio of having the propensity to develop plaque rupture (e.g., develop AMI) of almost 7-fold, and a maximal odds ratio of having the propensity to develop CAD of over 2-fold.

GRS analysis using SNPs associated with developing collateral-binding ligands demonstrated highly significant associations with CAD but not with AMI, whereas SNPs associated with vulnerable plaque-like binding ligands demonstrated significant associations with AMI but not with stable CAD—suggesting that the biology of these two different categories of ligands is different, and that the presented strategy allows for identification of each of these apparently different pathophysiological processes.

In studies using different mouse model ligands that home to developing microvessels were identified. SNPs present within +/−100 kb of these homing sequences are shown in Table 2 below.

The data in both Table 1 and 2 are based on the UCSC Genome Browser on Human March 2006 (NCBI36/hg18) Assembly.

TABLE I

ATHEREOSCLEROTIC PLAQUE

| chr9: 77,877,195-78,064,394 Physical Position | | | chr8: 84,157,963-84,371,712 Physical Position |
|---|---|---|---|
| 77896027 | 77932826 | 77955771 | 84221577 |
| 77970398 | 77952616 | 77975095 | 84296493 |
| 78013514 | 77965390 | 78030807 | 84353372 |
| 77912756 | 77967757 | 77944920 | 84290131 |
| 77981132 | 77969652 | 78046409 | 84278815 |
| 77935150 | 77976038 | 77896612 | 84263681 |
| 77995982 | 78001755 | 77974145 | 84317832 |
| 77984871 | 78021235 | 77921291 | 84188140 |
| 77941503 | 78006320 | 78024292 | 84353645 |
| 77897682 | 78063721 | 77918656 | 84237668 |
| 77932517 | 78044132 | 78001197 | 84183459 |
| 77965467 | 78019266 | 77919033 | 84276448 |
| 77884791 | 77902252 | 78034186 | 84250995 |
| 78019970 | 77883625 | 78031221 | 84277905 |
| 77942584 | 78002731 | 78062383 | 84183812 |
| 78002292 | 77972056 | | 84263445 |
| 77932601 | 78018985 | | 84249978 |
| 78033797 | 78048821 | | 84266229 |
| 77946987 | 77889693 | | 84295735 |
| 77935318 | 77949525 | | 84174852 |
| 77998313 | 78062666 | | 84174551 |
| 78005912 | 77971147 | | 84296606 |
| 77963029 | 77889895 | | 84238621 |
| 77896771 | 77970169 | | 84169473 |
| 77975710 | 78043736 | | 84182166 |
| 78006072 | 77990101 | | 84284267 |
| 77971080 | 77989934 | | 84207495 |
| 77994662 | 77995241 | | 84264048 |
| 77912868 | 78047503 | | 84365983 |
| 77986342 | 77903120 | | 84262321 |
| 78013455 | 77919956 | | 84192952 |
| 77977581 | 77954821 | | 84318794 |
| 77932971 | 77974130 | | 84187981 |
| 78005218 | 77941990 | | 84172094 |
| 77974918 | 77883052 | | 84171465 |
| 77904900 | 78017871 | | 84277486 |
| 77930847 | 77941452 | | 84251306 |
| 77932174 | 77934997 | | 84240387 |
| 78032200 | 77977040 | | 84182673 |
| 77962279 | 78000707 | | 84283166 |
| 77983094 | 77949108 | | |
| 78001973 | 77978363 | | |
| 78030136 | 77909466 | | |
| 78059344 | 77916433 | | |
| 78007108 | 77918996 | | |
| 77885146 | 77981076 | | |
| 77904070 | 77935280 | | |
| 77910229 | 77981597 | | |

| chr9: 109,370,971-109,631,637 Physical Position | | | chr1: 49,375,478-49,595,477 Physical Position |
|---|---|---|---|
| 109561555 | 109517708 | 109561408 | 49438023 |
| 109606999 | 109491458 | 109528469 | 49572650 |
| 109437701 | 109396498 | 109404115 | 49415285 |
| 109570145 | 109488370 | 109408916 | 49503955 |
| 109478033 | 109465353 | 109608393 | 49538025 |
| 109458037 | 109457162 | 109459101 | 49570391 |
| 109488475 | 109429636 | 109475506 | 49438227 |
| 109521846 | 109426833 | 109510453 | 49493666 |
| 109466790 | 109513104 | 109557711 | 49559783 |
| 109478412 | 109403385 | 109415487 | 49544413 |
| 109465616 | 109559903 | 109488111 | 49544440 |
| 109505417 | 109560249 | 109533933 | 49595020 |
| 109529592 | 109562562 | 109380958 | 49492490 |
| 109372390 | 109478297 | 109572668 | 49571908 |
| 109540242 | 109606932 | 109371225 | 49526716 |
| 109502658 | 109591656 | 109611773 | 49589970 |
| 109549158 | 109596423 | 109465379 | 49428017 |
| 109450788 | 109372401 | 109447407 | 49439184 |
| 109381539 | 109419388 | 109401996 | 49517287 |
| 109491400 | 109470229 | 109426555 | 49573279 |
| 109488545 | 109399379 | 109502141 | 49487859 |
| 109475120 | 109534029 | | 49547479 |
| 109593488 | 109529372 | | |

TABLE I-continued

| ATHEREOSCLEROTIC PLAQUE | |
|---|---|
| 109401821 | 109509765 |
| 109401866 | 109505195 |
| 109402367 | 109585778 |
| 109402402 | 109450466 |
| 109403631 | 109452468 |
| 109421938 | 109513614 |
| 109559510 | 109491068 |
| 109576753 | 109505684 |
| 109582865 | 109551757 |
| 109542206 | 109534865 |
| 109463841 | 109465481 |
| 109537772 | 109584553 |
| 109426897 | 109470068 |
| 109529527 | 109507319 |
| 109404366 | 109616405 |
| 109491337 | 109458102 |
| 109458769 | 109509746 |
| 109486525 | 109450709 |
| 109407217 | 109405361 |
| 109458174 | 109546695 |
| 109412229 | 109629627 |
| 109508006 | 109444604 |
| 109488305 | 109491757 |
| 109523938 | 109450582 |
| 109488248 | 109538094 |
| 109464558 | 109584228 |

| chr8: 16,655,319-16,838,318 Physical Position | | |
|---|---|---|
| 16749276 | 16801933 | 16707741 |
| 16798673 | 16670100 | |
| 16708689 | 16687505 | |
| 16748328 | 16688797 | |
| 16803309 | 16700145 | |
| 16687869 | 16722533 | |
| 16723732 | 16758362 | |
| 16740641 | 16758568 | |
| 16769576 | 16770542 | |
| 16770478 | 16660421 | |
| 16767711 | 16667644 | |
| 16815574 | 16708530 | |
| 16770206 | 16657519 | |
| 16731145 | 16742980 | |
| 16692762 | 16683846 | |
| 16669543 | 16754548 | |
| 16756732 | 16708933 | |
| 16746473 | 16712593 | |
| 16697002 | 16734306 | |
| 16674398 | 16763340 | |
| 16715581 | 16787794 | |
| 16815214 | 16684394 | |
| 16746418 | 16673095 | |
| 16779732 | 16832525 | |
| 16832384 | 16735019 | |
| 16762389 | 16732622 | |
| 16815909 | 16746366 | |
| 16733338 | 16664362 | |
| 16708504 | 16695913 | |
| 16715916 | 16696573 | |
| 16781883 | 16758252 | |
| 16709079 | 16709175 | |
| 16748470 | 16832443 | |
| 16678934 | 16743081 | |
| 16730934 | 16766827 | |
| 16832074 | 16732897 | |
| 16748188 | 16746343 | |
| 16756372 | 16762900 | |
| 16772600 | 16708332 | |
| 16832618 | 16787552 | |
| 16709202 | 16683642 | |
| 16749310 | 16669896 | |
| 16766657 | 16735427 | |
| 16688945 | 16700652 | |
| 16689526 | 16741462 | |
| 16692554 | 16754603 | |
| 16816208 | 16672685 | |

TABLE I-continued

ATHEREOSCLEROTIC PLAQUE

| chr10: 32,638,733-32,871,832 Physical Position | | chr7: 126,828,912-127,052,911 Physical Position | |
|---|---|---|---|
| 32763837 | 32752813 | 126846472 | 126890691 |
| 32645195 | 32720645 | 126842023 | 126946171 |
| 32664921 | 32657126 | 126867613 | 126901375 |
| 32733491 | 32710992 | 126931415 | 126964535 |
| 32667085 | 32771985 | 126898001 | 126962472 |
| 32719838 | 32666012 | 126957133 | 126858699 |
| 32709243 | 32639470 | 126898714 | 126965398 |
| 32803119 | 32738919 | 126990579 | 126913421 |
| 32711123 | 32642466 | 127021213 | 126892947 |
| 32678422 | 32667175 | 126846369 | 126940529 |
| 32691867 | 32802302 | 126945525 | 127007431 |
| 32679099 | 32693900 | 126912730 | 126847532 |
| 32715336 | 32727834 | 126839168 | 126972486 |
| 32720715 | 32667984 | 126861195 | 126957251 |
| 32754344 | 32727671 | 126861374 | 126888423 |
| 32737763 | 32738038 | 126896104 | 126997218 |
| 32667609 | 32708076 | 126896213 | 127045687 |
| 32801068 | 32727503 | 126901791 | 126960584 |
| 32655451 | 32726549 | 126926139 | 127044734 |
| 32678315 | | 126926444 | 127045620 |
| 32679055 | | 126934999 | 127034139 |
| 32743427 | | 126935389 | 127024239 |
| 32766535 | | 126935868 | 127006137 |
| 32766966 | | 126936527 | 126849152 |
| 32756263 | | 126976838 | 126848032 |
| 32688699 | | 126996023 | 126932802 |
| 32794766 | | 126876593 | 127008063 |
| 32663556 | | 126945593 | 126837870 |
| 32743813 | | 126833389 | 126867052 |
| 32744471 | | 127006653 | 126991301 |
| 32709300 | | 126908717 | 127045444 |
| 32732494 | | 126837730 | 127027330 |
| 32679221 | | 126960898 | 126977473 |
| 32644946 | | 126991874 | |
| 32732726 | | 126931117 | |
| 32715716 | | 126842141 | |
| 32643720 | | 126866707 | |
| 32737662 | | 126905161 | |
| 32739553 | | 126849607 | |
| 32733859 | | 126905338 | |
| 32680145 | | 126898322 | |
| 32708873 | | 126980903 | |
| 32716690 | | 126869733 | |
| 32651124 | | 126990487 | |
| 32739882 | | 126918847 | |
| 32803978 | | | |
| 32843490 | | | |

| chr7: 81,192,700-81,412,299 Physical Position | | chr21: 27,015,991-27,247,990 Physical Position | | |
|---|---|---|---|---|
| 81247165 | 81212690 | 27018884 | 27214966 | 27050253 |
| 81210092 | 81404437 | 27030694 | 27218195 | 27061287 |
| 81201833 | 81402800 | 27030745 | 27219725 | 27072901 |
| 81241905 | 81373286 | 27031839 | 27219920 | 27076079 |
| 81208200 | 81250538 | 27037800 | 27224226 | 27076613 |
| 81240449 | 81409669 | 27038485 | 27227083 | 27078585 |
| 81324694 | 81337209 | 27079625 | 27227348 | 27079748 |
| 81242564 | 81373695 | 27093463 | 27227518 | 27085871 |
| 81402565 | 81275233 | 27093620 | 27228179 | 27088226 |
| 81256532 | 81298425 | 27093797 | 27232045 | 27093711 |
| 81193438 | 81359002 | 27105880 | 27232611 | 27096496 |
| 81259692 | 81381238 | 27141178 | 27247646 | 27097629 |
| 81260298 | 81341979 | 27165468 | 27206844 | 27115113 |
| 81271054 | 81324587 | 27201834 | 27208724 | 27116399 |
| 81376245 | 81290882 | 27202222 | 27046037 | 27130339 |
| 81209555 | 81405055 | 27204531 | 27146707 | 27149776 |
| 81362823 | 81341235 | 27209349 | 27206021 | 27151657 |
| 81409867 | 81363117 | 27213326 | 27221375 | 27152424 |
| 81304177 | 81314535 | 27221719 | 27304217 | 27152913 |
| 81225978 | 81193002 | 27224018 | 27030799 | 27162263 |
| 81202371 | 81193385 | 27021099 | 27049363 | 27166543 |
| 81200126 | 81296288 | 27035541 | 27126295 | 27174700 |
| 81241830 | 81395727 | 27049551 | 27126375 | 27184300 |
| 81381822 | 81409497 | 27050077 | 27180389 | 27187963 |

TABLE I-continued

| ATHEREOSCLEROTIC PLAQUE | | | |
|---|---|---|---|
| 81272020 | 27061136 | 27206818 | 27218260 |
| 81376443 | 27067239 | 27227726 | 27231899 |
| 81261213 | 27068060 | 27227742 | 27247481 |
| 81207355 | 27076325 | 27246439 | 27031856 |
| 81381562 | 27077671 | 27025515 | 27167220 |
| 81271260 | 27078727 | 27101653 | 27087201 |
| 81301322 | 27087769 | 27105523 | 27031695 |
| 81315172 | 27092657 | 27167103 | 27038989 |
| 81300383 | 27093843 | 27221589 | 27078897 |
| 81210388 | 27095922 | 27207802 | 27094577 |
| 81260361 | 27113787 | 27214988 | 27102264 |
| 81195996 | 27114559 | 27161868 | 27145567 |
| 81196125 | 27114861 | 27016284 | 27165252 |
| 81373908 | 27116745 | 27017026 | 27181794 |
| 81266243 | 27121943 | 27023664 | 27204705 |
| 81409636 | 27129261 | 27027688 | 27206392 |
| 81335975 | 27146591 | 27032440 | 27228483 |
| 81196011 | 27168978 | 27034627 | 27238687 |
| 81196987 | 27197332 | 27035051 | 27238792 |
| 81197771 | 27206861 | 27035748 | 27244377 |
| 81212901 | 27207255 | 27040866 | 27105813 |
| 81336087 | 27208461 | 27049635 | 27023850 |

| chr9: 109,413,329-109,589,278 Physical Position | | chr10: 97,389,255-97,595,804 Physical Position | chr12: 66,524,408-65,691,807 Physical Position | |
|---|---|---|---|---|
| 109561555 | 109559903 | 97580816 | 66590436 | 66662806 |
| 109437701 | 109560249 | 97519261 | 66672279 | 66575803 |
| 109570145 | 109562562 | 97540730 | 66666773 | 66690900 |
| 109478033 | 109478297 | 97504607 | 66596751 | 66533143 |
| 109458037 | 109419388 | 97421359 | 66657808 | 66664693 |
| 109488475 | 109470229 | 97497463 | 66574675 | 66601826 |
| 109521846 | 109534029 | 97405897 | 66574845 | 66568024 |
| 109466790 | 109529372 | 97484134 | 66642650 | 66588136 |
| 109478412 | 109509765 | 97503352 | 66574174 | 66572776 |
| 109465616 | 109505195 | 97574534 | 66674393 | 66622011 |
| 109505417 | 109585778 | 97589987 | 66571501 | 66682402 |
| 109529592 | 109450466 | 97581287 | 66575033 | 66682621 |
| 109540242 | 109452468 | 97513770 | 66679947 | 66682901 |
| 109502658 | 109513614 | 97594931 | 66593789 | 66568062 |
| 109549158 | 109491068 | 97497484 | 66689365 | 66606236 |
| 109450788 | 109505684 | 97595047 | 66629807 | 66664589 |
| 109491400 | 109551757 | 97501891 | 66627312 | 66663868 |
| 109488545 | 109534865 | 97529130 | 66620081 | 66561463 |
| 109475120 | 109465481 | 97416076 | 66604479 | 66602278 |
| 109421938 | 109584553 | 97456381 | 66688646 | 66687658 |
| 109559510 | 109470068 | 97548769 | 66579618 | 66543473 |
| 109576753 | 109507319 | 97431316 | 66553869 | 66534699 |
| 109582865 | 109458102 | 97506754 | 66662916 | 66610157 |
| 109542206 | 109509746 | 97458758 | 66575178 | 66599300 |
| 109463841 | 109450709 | 97458579 | 66591996 | 66567673 |
| 109537772 | 109546695 | 97529077 | 66617382 | 66568385 |
| 109426897 | 109444604 | 97529166 | 66532700 | 66537370 |
| 109529527 | 109491757 | 97551931 | 66609559 | 66561761 |
| 109491337 | 109450582 | 97532442 | 66630479 | 66619505 |
| 109458769 | 109538094 | 97401670 | 66630101 | 66686138 |
| 109486525 | 109584228 | 97526785 | 66665748 | 66602571 |
| 109458174 | 109561408 | 97430384 | 66627089 | 66599776 |
| 109508006 | 109528469 | 97540395 | 66658216 | 66532862 |
| 109488305 | 109459101 | 97575004 | 66565988 | 66649309 |
| 109523938 | 109475506 | 97456417 | 66668104 | 66565377 |
| 109488248 | 109510453 | 97549167 | 66600288 | |
| 109464558 | 109557711 | 97419342 | 66631240 | |
| 109517708 | 109415487 | 97420847 | 66672133 | |
| 109491458 | 109488111 | 97593820 | 66571409 | |
| 109488370 | 109533933 | 97431184 | 66573585 | |
| 109465353 | 109572668 | | 66622069 | |
| 109457162 | 109465379 | | 66613229 | |
| 109429636 | 109447407 | | 66642695 | |
| 109426833 | 109426555 | | 66543553 | |
| 109513104 | 109502141 | | 66624461 | |

TABLE 2

COLLATERAL SNPs

| chrX: 33,116,271-33,285,358 Physical Position | chr9: 27,588,019-27,810,685 Physical Position | | | chr8: 29,121,505-29,344,171 Physical Position | | chr4: 159,637,107-159,859,773 Physical Position |
|---|---|---|---|---|---|---|
| 33260026 | 27723456 | 27716731 | 27746019 | 29128829 | 29255475 | 159664766 |
| 33205761 | 27756700 | 27716911 | 27625480 | 29306465 | 29135138 | 159723224 |
| 33199098 | 27662182 | 27759781 | 27619389 | 29277653 | 29139865 | 159848601 |
| 33155701 | 27678778 | 27673813 | 27761268 | 29199260 | 29208956 | 159654523 |
| 33164832 | 27768250 | 27696803 | 27770310 | 29143820 | 29200434 | 159838876 |
| 33179680 | 27654432 | 27743785 | 27691892 | 29135215 | 29215392 | 159720416 |
| 33213219 | 27701197 | 27750946 | 27713713 | 29192544 | 29309728 | 159822419 |
| 33203624 | 27720552 | 27755416 | 27626655 | 29123150 | 29206203 | 159659826 |
| 33214791 | 27696404 | 27701270 | 27592921 | 29271088 | 29139935 | 159663764 |
| 33259700 | 27743654 | 27661310 | 27796130 | 29126531 | 29187088 | 159652379 |
| 33243806 | 27715305 | 27794540 | 27749359 | 29209798 | 29258142 | 159660115 |
| 33200815 | 27651834 | 27715384 | 27794977 | 29122639 | 29287003 | 159836469 |
| 33204266 | 27792613 | 27631463 | 27693432 | 29138530 | 29193239 | 159650151 |
| 33188438 | 27809540 | 27723456 | 27765949 | 29139390 | 29269477 | 159649919 |
| 33259999 | 27673762 | 27723472 | | 29282859 | 29295757 | 159664766 |
| 33265834 | 27600657 | 27701260 | | 29163307 | 29236517 | 159648487 |
| 33280487 | 27617023 | 27693109 | | 29254724 | 29318137 | 159723061 |
| 33267513 | 27652118 | 27661294 | | 29286054 | 29275544 | 159770971 |
| 33277974 | 27678029 | 27600116 | | 29142862 | 29305619 | 159663277 |
| 33217078 | 27678904 | 27617123 | | 29285985 | 29171847 | 159808234 |
| 33132703 | 27720125 | 27617336 | | 29254981 | | 159661614 |
| 33155964 | 27758409 | 27651753 | | 29123004 | | 159680172 |
| 33184448 | 27800651 | 27668194 | | 29236107 | | 159654646 |
| 33143880 | 27642540 | 27678290 | | 29152772 | | 159656697 |
| 33205186 | 27636697 | 27692974 | | 29311503 | | 159655136 |
| 33257727 | 27619304 | 27797373 | | 29132656 | | 159684182 |
| 33156591 | 27662338 | 27608779 | | 29321457 | | 159667707 |
| 33158327 | 27782012 | 27808941 | | 29164906 | | 159835658 |
| 33205095 | 27695949 | 27661898 | | 29254175 | | 159670674 |
| 33207175 | 27731749 | 27743923 | | 29126907 | | 159673729 |
| 33184263 | 27798093 | 27746625 | | 29147554 | | 159839873 |
| 33143757 | 27708916 | 27810352 | | 29125106 | | 159766592 |
| 33255163 | 27808130 | 27777022 | | 29138884 | | 159661077 |
| 33240478 | 27715556 | 27764181 | | 29140479 | | 159666071 |
| 33226988 | 27763059 | 27731361 | | 29309586 | | 159637129 |
| 33119101 | 27792678 | 27590698 | | 29310010 | | 159728609 |
| 33211614 | 27610642 | 27709394 | | 29294870 | | 159765777 |
| 33207078 | 27800414 | 27629810 | | 29307123 | | 159781579 |
| 33277236 | 27768662 | 27592277 | | 29317076 | | 159660974 |
| | 27589202 | 27810493 | | 29213585 | | 159651896 |
| | 27678488 | 27618537 | | 29279149 | | 159850267 |
| | 27756591 | 27696835 | | 29161447 | | 159782597 |
| | 27743085 | 27799668 | | 29277149 | | 159821126 |
| | 27743227 | 27739775 | | 29305366 | | 159664478 |
| | 27617074 | 27617785 | | 29230698 | | 159654119 |
| | 27667544 | 27786645 | | 29170820 | | 159653131 |
| | 27590645 | 27766146 | | 29274182 | | 159660470 |
| | 27644050 | 27662820 | | 29276809 | | |
| | 27654162 | 27659412 | | 29279783 | | |

| chr6: 107,940,113-108,162,779 Physical Position | | | chr2: 50,505,741-50,728,407 Physical Position | | chr3: 78,053,017-78,275,238 Physical Position |
|---|---|---|---|---|---|
| 108036069 | 108073161 | 108038495 | 50638682 | 50641150 | 78148591 |
| 108047154 | 108124555 | 108059866 | 50607199 | 50673550 | 78193644 |
| 108124975 | 108107418 | 108127089 | 50670974 | 50511289 | 78066038 |
| 108046980 | 107968243 | 107952171 | 50577506 | 50675554 | 78102348 |
| 108148370 | 108125057 | 108024845 | 50714553 | 50673310 | 78187009 |
| 108021470 | 108099428 | 108127168 | 50558602 | 50579172 | 78098419 |
| 108113355 | 108113615 | 108146847 | 50568460 | 50539877 | 78127379 |
| 108144382 | 107958993 | 108108383 | 50722055 | 50555061 | 78207025 |
| 108162596 | 108098738 | 108133564 | 50522978 | 50724922 | 78170285 |
| 108089618 | 108136781 | 108137532 | 50547618 | 50690998 | 78128239 |
| 108036069 | 108100857 | 108072977 | 50547858 | 50673595 | 78102438 |
| 108089658 | 108079480 | 108064209 | 50548604 | 50536900 | 78095449 |
| 108106673 | 108101021 | 108147139 | 50579684 | 50704190 | 78267488 |
| 108077755 | 108035718 | 108054095 | 50579975 | 50692710 | 78219298 |
| 107973208 | 108160599 | 108081771 | 50608317 | 50616765 | 78098350 |
| 108027947 | 108132338 | 108117785 | 50608980 | 50557221 | 78249676 |
| 108088549 | 108132663 | 108119511 | 50619511 | 50518671 | 78188898 |
| 108140588 | 107972002 | 108119713 | 50682535 | 50524754 | 78187398 |
| 108075191 | 108067426 | 108126012 | 50682648 | 50616645 | 78076008 |
| 108075563 | 107952875 | 108160057 | 50703228 | 50598324 | 78170143 |
| 108107159 | 108162412 | 108004825 | 50523758 | 50578981 | 78170155 |
| 108117633 | 108013345 | 108051260 | 50569986 | 50635527 | 78098242 |

TABLE 2-continued

COLLATERAL SNPs

| | | | | | |
|---|---|---|---|---|---|
| 108158265 | 108147548 | 107963111 | 50675967 | 50724116 | 78155469 |
| 108161863 | 107953518 | 108098586 | 50589711 | 50623689 | 78238673 |
| 108132109 | 108073622 | 108108177 | 50666395 | 50683307 | 78053309 |
| 108135535 | 108024122 | 108029977 | 50568825 | 50538079 | 78096017 |
| 107969771 | 108010827 | | 50566914 | 50663502 | 78274507 |
| 107972837 | 108039974 | | 50543537 | 50518986 | 78184267 |
| 107972481 | 108107667 | | 50685238 | 50671075 | 78060317 |
| 108135572 | 108109696 | | 50570272 | 50513796 | 78101740 |
| 108113892 | 108076670 | | 50561680 | 50530852 | |
| 108149027 | 108033069 | | 50589502 | 50579828 | |
| 108139874 | 108003867 | | 50603932 | 50620492 | |
| 107966814 | 108090509 | | 50523365 | 50651965 | |
| 108155735 | 108115711 | | 50584706 | 50714954 | |
| 108124252 | 108090969 | | 50523466 | 50726443 | |
| 108135402 | 108084633 | | 50602259 | 50620595 | |
| 108099494 | 108108771 | | 50691212 | 50640976 | |
| 108072999 | 108145349 | | 50546323 | 50568510 | |
| 108137098 | 108147898 | | 50571840 | 50598005 | |
| 108031503 | 108124364 | | 50652013 | 50647285 | |
| 108059503 | 108110624 | | 50580033 | 50516691 | |
| 108088690 | 107972580 | | 50612161 | 50551658 | |
| 107952377 | 108023704 | | 50589447 | 50716777 | |
| 108106656 | 108099641 | | 50623197 | | |
| 107962211 | 107990473 | | 50544383 | | |
| 107983797 | 108075894 | | 50584725 | | |
| 108106634 | 108056326 | | 50511733 | | |
| 108162613 | 108018850 | | 50547737 | | |

| chr9: 9,016,328-9,238,994 Physical Position | | | chr2: 136,420,723-136,643,389 Physical Position | chr9: 24,727,073-24,949,739 Physical Position | | |
|---|---|---|---|---|---|---|
| 9173823 | 9075811 | 9186661 | 136638231 | 24846402 | 24802191 | 24746027 |
| 9088121 | 9029395 | 9187160 | 136496458 | 24924491 | 24871105 | 24761431 |
| 9224411 | 9034347 | 9020039 | 136523244 | 24799640 | 24731204 | 24870658 |
| 9187324 | 9123196 | 9076923 | 136451611 | 24949252 | 24749031 | 24801059 |
| 9067607 | 9145721 | 9054648 | 136486979 | 24840192 | 24789940 | |
| 9051331 | 9163304 | 9179356 | 136482421 | 24896802 | 24892466 | |
| 9048949 | 9176346 | 9206980 | 136602611 | 24790910 | 24898448 | |
| 9186248 | 9051819 | 9148221 | 136490614 | 24949467 | 24837477 | |
| 9136300 | 9170897 | 9098336 | 136506078 | 24943245 | 24747755 | |
| 9228929 | 9170827 | 9215919 | 136530579 | 24764620 | 24874945 | |
| 9229154 | 9173542 | 9185670 | 136525419 | 24949557 | 24839641 | |
| 9178957 | 9080834 | 9139128 | 136452590 | 24892741 | 24873179 | |
| 9152669 | 9048285 | 9236647 | 136452468 | 24902430 | 24792002 | |
| 9198635 | 9147088 | 9075941 | 136609695 | 24902363 | 24854508 | |
| 9043770 | 9215463 | 9228528 | 136435643 | 24740179 | 24765747 | |
| 9044621 | 9123593 | 9193316 | 136534128 | 24762803 | 24906557 | |
| 9044913 | 9048319 | 9097265 | 136451084 | 24792015 | 24759908 | |
| 9131628 | 9189165 | 9206368 | 136586343 | 24727360 | 24761927 | |
| 9175515 | 9118101 | 9211297 | 136502239 | 24740255 | 24730388 | |
| 9178533 | 9141640 | 9017331 | 136638173 | 24776754 | 24790338 | |
| 9228714 | 9139387 | 9075530 | 136626743 | 24776843 | 24745397 | |
| 9237105 | 9066214 | | 136503121 | 24825444 | 24799985 | |
| 9051283 | 9046791 | | 136482394 | 24825638 | 24745137 | |
| 9016815 | 9060768 | | 136571975 | 24885885 | 24778179 | |
| 9121375 | 9196006 | | 136601149 | 24895439 | 24727563 | |
| 9172216 | 9078734 | | 136521871 | 24922377 | 24818167 | |
| 9040722 | 9163714 | | 136531099 | 24787824 | 24856799 | |
| 9129951 | 9046867 | | 136584543 | 24778834 | 24805436 | |
| 9192872 | 9166176 | | 136623906 | 24925108 | 24734456 | |
| 9136140 | 9125857 | | 136535189 | 24897576 | 24948749 | |
| 9134115 | 9149868 | | 136639142 | 24943447 | 24760750 | |
| 9092409 | 9016457 | | 136548852 | 24853948 | 24778197 | |
| 9125223 | 9080876 | | 136443037 | 24933020 | 24727593 | |
| 9166870 | 9178615 | | 136617983 | 24895678 | 24806304 | |
| 9035011 | 9096511 | | 136547110 | 24923878 | 24892495 | |
| 9052189 | 9051234 | | 136472154 | 24900506 | 24797137 | |
| 9067555 | 9228776 | | 136468439 | 24856097 | 24776605 | |
| 9221961 | 9102698 | | 136476134 | 24943301 | 24759439 | |
| 9082345 | 9214376 | | 136505949 | 24840287 | 24739214 | |
| 9222484 | 9087111 | | 136523429 | 24791362 | 24831971 | |
| 9055718 | 9178865 | | 136584346 | 24835867 | 24759578 | |
| 9190590 | 9138168 | | 136501823 | 24895365 | 24924859 | |
| 9029222 | 9205776 | | 136641909 | 24895556 | 24766197 | |
| 9039072 | 9182961 | | 136580286 | 24778126 | 24759723 | |
| 9048076 | 9032345 | | | 24827608 | 24888150 | |
| 9047632 | 9044075 | | | 24818651 | 24888926 | |
| 9052032 | 9077205 | | | 24933729 | 24922289 | |

TABLE 2-continued

COLLATERAL SNPs

| 9132828 | 9075698 | 24839802 |  |
| 9199488 | 9211800 | 24901868 |  |

| chr3: 106,580,698-106,791,809 Physical Position | | chr11: 116,166,738-116,367,550 Physical Position | |
|---|---|---|---|
| 106737399 | 106741551 | 116209813 | 116208850 |
| 106744838 | 106762147 | 116202131 | 116180028 |
| 106762324 | 106681064 | 116253524 | 116173721 |
| 106633384 | 106761095 | 116289902 | 116236470 |
| 106716949 | 106659325 | 116265034 | 116210778 |
| 106784432 | 106670239 | 116203058 | 116284709 |
| 106614596 | 106716829 | 116202554 | 116210310 |
| 106598882 | 106614698 | 116253431 | 116263664 |
| 106750596 | 106685882 | 116230513 | 116233146 |
| 106787174 | 106618473 | 116332080 | 116362838 |
| 106779003 | 106634735 | 116334863 | 116289586 |
| 106749226 | 106759285 | 116353858 | 116338060 |
| 106769977 | 106626356 | 116248872 | 116198373 |
| 106749021 | 106750231 | 116361852 | 116195788 |
| 106734452 | 106741142 | 116189238 | 116189977 |
| 106702230 | 106617541 | 116189374 | 116263903 |
| 106731659 | 106649375 | 116294845 | 116233487 |
| 106617293 | 106768187 | 116272109 | 116334186 |
| 106779439 | 106750126 | 116365666 | 116202948 |
| 106748964 | 106650788 | 116350314 | 116352372 |
| 106691352 | 106765714 | 116319189 | 116189954 |
| 106702201 | 106773218 | 116333932 | 116236415 |
| 106702389 | 106595927 | 116245869 | 116361399 |
| 106783827 | 106587497 | 116186218 | 116220898 |
| 106783905 | 106717176 | 116317838 | 116171525 |
| 106610059 | 106721305 | 116246456 | 116210929 |
| 106787709 | 106604904 | 116294648 | 116202748 |
| 106659717 | 106717573 | 116260794 | 116167789 |
| 106753240 | 106744170 | 116202276 | 116335471 |
| 106782468 | 106660954 | 116261393 | |
| 106669733 | 106744577 | 116359581 | |
| 106762230 | 106759659 | 116172547 | |
| 106660369 | | 116335297 | |
| 106661546 | | 116202097 | |
| 106752911 | | 116188704 | |
| 106747807 | | 116175886 | |
| 106753286 | | 116252492 | |
| 106784358 | | 116175392 | |
| 106658336 | | 116349489 | |
| 106745798 | | 116350748 | |
| 106747643 | | 116269311 | |
| 106660178 | | 116269792 | |
| 106735067 | | 116215449 | |
| 106598426 | | 116222873 | |
| 106731901 | | 116186128 | |
| 106616747 | | 116217184 | |
| 106746314 | | 116229414 | |
| 106632991 | | 116333694 | |
| 106772830 | | 116240998 | |

Example 7

Identification of SNPs Associated with AMI

The studies presented herein identified ligands that bind reproducibly to vulnerable plaques. Fascinatingly, none of the nucleic acid sequences encoding these ligands have previously been recognized as genes. The novel ligands are expressed by human stem/progenitor cells, and in circulating mononuclear cells, thereby identifying a new class of homing ligands that play a role in stem cell homing to injured vessels and in tissue repair. As such, the ligands and the stem/progenitor/inflammatory cells they deliver to injured tissue probably alter plaque stability/vulnerability. Genetic variations in the genes encoding these ligands (or in proximity to the actual genes) are therefore associated with altered propensity of plaques to rupture in patients.

Genetic variation (SNPs) present within +/−100 kb of the binding sequences were characterized using Affymetrix 6.0 SNP chips (See Table 1). Association analysis of the resulting SNPs with AMI risk was performed using the DNA banks of a consortium of 5 centers that had performed Genome Wide Association Studies (GWAS) analysis in over 7000 patients with coronary disease demonstrated by coronary angiography. Angiographic documentation of CAD allows for characterizing patients with CAD as patients with no history of plaque rupture (no history of AMI) and patients with prior plaque rupture (prior AMI).

Discovery analysis was performed using the Washington Hospital Center (WHC) cohort of 1000 CAD patients. The 12 SNPs (shown in Table 3A-B below) that were found to be associated with AMI were tested in the WHC cohort and the findings confirmed using 5 distinct cohorts consisting of a total of 5,624 individuals with angiographically normal coronary arteries (0 to <20% obstruction) and 7,247 patients with angiographically documented CAD (>50% obstruction). The latter group consisted of 3,700 patients who had experienced an AMI and 3,547 patients who, although having significant coronary artery disease, had never had an AMI (stable CAD). The results of the analysis are presented in Table 4 below. Three SNPs were identified that were "significantly" associated with AMI: rs6982320 8p22, rs2830538 21q21.3, and rs463433 21q21.3.

TABLE 3A

Unstable Plaque Acute Vs. Chronic

| SNP name | Locus | Bound to: | Meta-analysis p-value | Meta-analysis Odds Ratio | 95% Confidence Interval | | Sequence Context |
|---|---|---|---|---|---|---|---|
| rs6982320 | 8p22 | Unstable Plaque | 0.0179 | 0.75 | 0.60 | 0.95 | TGTCTCTAACTGGAAA ACCAAGAAAC[A/G]TT ACTATGCTAGAACTGT TTTTTTA (SEQ ID NO: 71) |
| rs2830538 | 21q21.3 | Unstable Plaque | 0.0388 | 1.21 | 1.01 | 1.45 | TCAGATTGCAGAGCA GCCCTGACTGA[C/T]C TTGAAGAGTCACTCCC AGGCCCTT (SEQ ID NO: 72) |
| rs463433 | 21q21.3 | Unstable Plaque | 0.0416 | 1.25 | 1.01 | 1.55 | CCATAGAGCTCAAGC AAAATGGCTTA[A/G]T GCTGGAAAAAGGACC CCACACGAG (SEQ ID NO: 73) |
| rs2830500 | 21q21.3 | Unstable Plaque | 0.0742 | 0.91 | 0.81 | 1.01 | ATGCATCAATTTCCCA CACTCCAGAT[A/C]AT CTAGAACTCAGAGTG CTGTTAAA (SEQ ID NO: 74) |
| rs457982 | 21q21.3 | Unstable Plaque | 0.0943 | 1.10 | 0.99 | 1.22 | TGGGCTACTTAGATAG AAAACCCTCT[A/T]CA AGCCAGTCTAGCAAG GTCTCACT (SEQ ID NO: 75) |
| rs468969 | 21q21.3 | Unstable Plaque | 0.1034 | 0.74 | 0.52 | 1.05 | AACAGAATACAGTAT GTACACCATTA[A/G]G TACTTTGCTGTCTTCA TATGAATT (SEQ ID NO: 76) |
| rs2830492 | 21q21.3 | Unstable Plaque | 0.1507 | 1.10 | 0.97 | 1.26 | TAAATAACAAGCAAC GCTGTGTACCA[A/T]T GTAAACATTTATTAAA TTCTAATC (SEQ ID NO: 77) |
| rs1602904 | 8p22 | Unstable Plaque | 0.1565 | 1.16 | 0.95 | 1.43 | CTATTCTGTTGAGCGC TTTTTATGAT[A/G]AAT GAGTATTGGAAATAG TTAAATG (SEQ ID NO: 78) |
| rs229037 | 21q21.3 | Unstable Plaque | 0.3227 | 1.06 | 0.95 | 1.09 | TTCCTATGAGAAAGC ATAATTTACTT[C/T]GT TGAGAAAACACGTAG ATGAACCA (SEQ ID NO: 79) |
| rs4978541 | 9q31.2 | Unstable Plaque | 0.4451 | 0.91 | 0.72 | 1.19 | TAACTGCAACATGCA ATGTTTACCCC[C/T]GT GCTATAGAGTGTCTGA CAATGAA (SEQ ID NO: 80) |
| rs1117691 | 712q15 | Unstable Plaque | 0.4496 | 1.05 | 0.93 | 1.15 | AAGTCTGATTCTCCTT ATTTCCAGAG[A/C]TG ATGAAAGCTACAATT AACACATG (SEQ ID NO: 81) |

TABLE 3A-continued

Unstable Plaque Acute Vs. Chronic

| SNP name | Locus | Bound to: | Meta-analysis p-value | Meta-analysis Odds Ratio | 95% Confidence Interval | Sequence Context |
|---|---|---|---|---|---|---|
| rs4749722 | 10p11.22 | Unstable Plaque | 0.4670 | 1.04 | 0.94 1.17 | TTTTATTCTAAGTGCC CCGATTATGC[A/G]GA ATACCTAAGACAGCC GCCCATTT (SEQ ID NO: 82) |

TABLE 3B

Unstable Plaque CAD Vs. Control

| rs # | Locus | Bound to: | Meta-analysis p-value | Meta-analysis Odds Ratio (95% CI) |
|---|---|---|---|---|
| rs463433 | 21q21.3 | Unstable Plaque | 0.1118 | 1.17 (0.97 1.40) |
| rs2830500 | 21q21.3 | Unstable Plaque | 0.116 | 0.92 (0.85 1.02) |
| rs4978541 | 9q31.2 | Unstable Plaque | 0.15 | 0.95 (0.88 1.02) |
| rs2830538 | 21q21.3 | Unstable Plaque | 0.2136 | 1.11 (0.95 1.290 |
| rs2830492 | 21q21.3 | Unstable Plaque | 0.3025 | 0.94 (0.84 1.05) |
| rs457982 | 21q21.3 | Unstable Plaque | 0.36 | 1.09 (0.95 1.29) |
| rs6982320 | 8p22 | Unstable Plaque | 0.397 | 1.03 (0.96 1.11) |
| rs11176917 | 12q15 | Unstable Plaque | 0.5236 | 1.12 (0.83 1.51) |
| rs1602904 | 8p22 | Unstable Plaque | 0.5373 | 1.07 (0.95 1.29) |
| rs468969 | 21q21.3 | Unstable Plaque | 0.6894 | 1.08 (0.79 1.46) |
| rs4749722 | 10p11.22 | Unstable Plaque | 0.809 | 0.99 (0.92 1.07) |
| rs229037 | 21q21.3 | Unstable Plaque | 0.8676 | 0.99 (0.90 1.09) |

TABLE 4

Table 4. Acute AMI vs. Stable CAD. (SNPs within ± 100 kb of vulnerable plaque binding sequence. Displayed: SNPs with p < 0.05). There were 3 SNPs that were significantly associated with AMI.

| Locus | Minor allele/Risk Allele | % pop with risk allele | Meta-analysis p-value | Meta-analysis Odds Ratio (95% CI) |
|---|---|---|---|---|
| 8p22 rs6982320 | G/G | 5 | 0.018 | 1.33 (1.05-1.67) |
| 21q21.3 rs2830538 | A/A | 19 | 0.039 | 1.21 (1.01-1.45) |
| T 21q21.3 rs463433 | A/G | 29 | 0.042 | 1.25 (1.01-1.55) |

To further explore the biological relevance of these SNPs it was investigated if these SNPs alter expression of their associated ligands. The analysis of the SNP rs6982320 8p22, which is within 200 bps of a ligand coding region is associated with an increased risk of AMI (odds ratio of 1.33 when CAD pts with AMI are compared to those without AMI). Patients homozygous for the SNP have increased expression of the ligand in their circulating mononuclear cells, with a p value of 0.0007. This finding demonstrates that the SNP has functional consequences and shows the biological and clinical relevance of the association between the SNP and increased risk of acute myocardial infarction (For instance, since the SNP increases the expression of the ligand in circulating inflammatory cells, the ligand is likely involved in processes exerting deleterious effects on plaque biology that predispose to plaque instability)

Example 8

Aggregate Risk SNP Burden in AMI Risk

Figure 6:
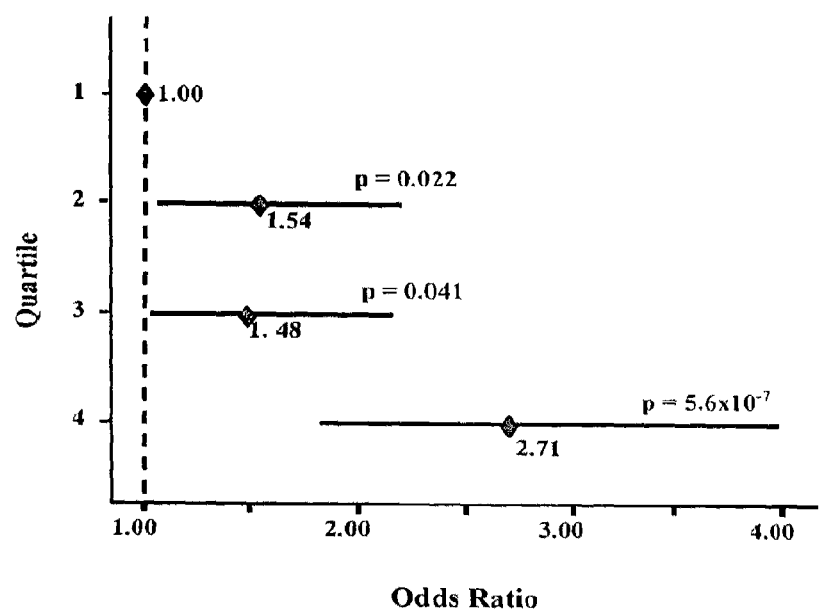
FIG. 6 shows the Genetic Risk Scores based on 12 SNPs associated with AMI.

It follows that if an individual SNP alters risk of plaque rupture, then multiple SNPs, influencing multiple pathways involved in plaque vulnerability might improve the ability to identify patients at particularly high risk for AMI. A genetic risk score (GSR) for each patient was calculated using those 12 SNPs related to the 11 ligands binding to mouse vulnerable plaque and found to alter AMI risk (See also Anderson et al. Am Heart J 2010: 160, 250-256). The GSR was calculated by determining the number of risk alleles in each patient. A dominant/recessive model was assumed with an individual assigned either a 0 or 1 for the presence or absence of a dominant or recessive effect. according to the number of risk alleles present. The count method assumed that each SNP contributed equally to CAD risk and was calculated by summing the number of risk alleles across the panel of SNPs tested. This produced a score between 0 and twice the number of SNPs, that is, representing the total number of risk alleles. The GRS was modeled as a continuous variable and as quartiles or tertiles, depending on the number of patients that could be assigned to each group. The data are displayed in FIG. 6 showing a major increase in the ability to identify a high risk cohort. GRS quartiles 2-4 were at significantly greater risk of AMI than those patients in the first quartile. Of potential clinical importance, quartile 4, with 22.5% of the total cohort (197/875), had a 2.7 fold greater risk of AMI.

The following are results of analysis (univariate logistic regressions) of the significance of SNPs described herein (Acute v. Chronic; CAD vs. Control).

| ACUTE VS CHRONIC | | | | | | |
|---|---|---|---|---|---|---|
| Collateral - significant only | | | | | | |
| | | | Log likelihood = −598.56788 | | Number of obs = 875 LR chi2(1) = 14.63 Prob > chi2 = 0.0001 Pseudo R2 = 0.0121 | |
| a_vs_c_new | Odds Ratio | Std. Err. | z | P > \|z\| | [95% Conf. | Interval] |

-continued

| | | | | | | |
|---|---|---|---|---|---|---|
| a__vs__c__sig~l | 1.300896 | .0904099 | 3.79 | 0.000 | 1.135234 | 1.490732 | logistic a__vs__c__new a__vs__c__sig__coll

Collateral - all

Log likelihood = −602.51943

Number of obs = 875
LR chi2(1) = 6.72
Prob > chi2 = 0.0095
Pseudo R2 = 0.0055

| a__vs__c__new | Odds Ratio | Std. Err. | z | P > \|z\| | [95% Conf. | Interval] |
|---|---|---|---|---|---|---|
| a__vs__c__all~l | 1.052309 | .0208042 | 2.58 | 0.010 | 1.012314 | 1.093885 | logistic a__vs__c__new a__vs__c__all__coll

Unstable - significant only

Log likelihood = −599.77395

Number of obs = 875
LR chi2(1) = 12.21
Prob > chi2 = 0.0005
Pseudo R2 = 0.0101

| a__vs__c__new | Odds Ratio | Std. Err. | z | P > \|z\| | [95% Conf. | Interval] |
|---|---|---|---|---|---|---|
| a__vs__c__sig~e | 1.541451 | .1964499 | 3.40 | 0.001 | 1.200739 | 1.978841 | logistic a__vs__c__new a__vs__c__sig__unstable

Unstable - all

Log likelihood = −594.39618

Number of obs = 875
LR chi2(1) = 22.97
Prob > chi2 = 0.0000
Pseudo R2 = 0.0190

| a__vs__c__new | Odds Ratio | Std. Err. | z | P > \|z\| | [95% Conf. | Interval] |
|---|---|---|---|---|---|---|
| a__vs__c__all~e | 1.166377 | .0382359 | 4.69 | 0.000 | 1.093793 | 1.243778 | logistic a__vs__c__new a__vs__c__all__unstable

CAD VS CONTROL

Collateral - significant only

Log likelihood = −837.58191

Number of obs = 1322
LR chi2(1) = 16.42
Prob > chi2 = 0.0001
Pseudo R2 = 0.0097

| c__vs__cont | Odds Ratio | Std. Err. | z | P > \|z\| | [95% Conf. | Interval] |
|---|---|---|---|---|---|---|
| c__vs__~g__coll | 1.382351 | .1133519 | 3.95 | 0.000 | 1.177119 | 1.623366 | logistic c__vs__cont c__vs__cont__sig__coll

Collateral - all

Log likelihood = −845.72397

Number of obs = 1322
LR chi2(1) = 0.14
Prob > chi2 = 0.7091
Pseudo R2 = 0.0001

| c__vs__cont | Odds Ratio | Std. Err. | z | P > \|z\| | [95% Conf. | Interval] |
|---|---|---|---|---|---|---|
| c__vs__~l__coll | 1.007206 | .019399 | 0.37 | 0.709 | .9698934 | 1.045954 | logistic c__vs__cont c__vs__cont__all__coll

Unstable - significant only

Log likelihood = −843.74045

Number of obs = 1322
LR chi2(1) = 4.11
Prob > chi2 = 0.0427
Pseudo R2 = 0.0024

| c__vs__cont | Odds Ratio | Std. Err. | z | P > \|z\| | [95% Conf. | Interval] |
|---|---|---|---|---|---|---|
| c~g__unstable | 1.28082 | .1559848 | 2.03 | 0.042 | 1.008845 | 1.626116 | logistic c__vs__cont c__vs__cont__sig__unstable

Unstable - all

Log likelihood = −844.55211

Number of obs = 1322
LR chi2(1) = 2.48
Prob > chi2 = 0.1151
Pseudo R2 = 0.0015

| c__vs__cont\| | Odds Ratio | Std. Err. | z | P > \|z\| | [95% Conf. | Interval] |
|---|---|---|---|---|---|---|
| c~l__unstable\| | 1.055908 | .0365848 | 1.57 | 0.116 | .9865835 | 1.130103 | logistic c__vs__cont c__vs__cont__all__unstable

Figure 7:
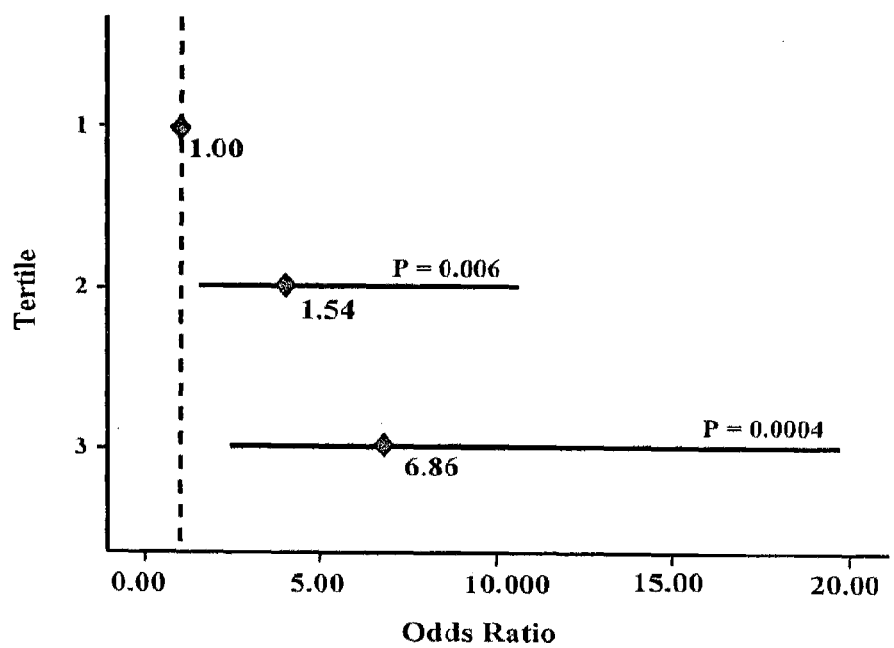
FIG. 7 shows the Genetic Risk Scores based on 3 SNPs that show significant association with AMI.

Three individual SNPs that were found to be significantly associated with AMI (rs6982320 8p22; rs2830538 21q21.3; rs463433 21q21.3) and were used to calculate a GRS for these risk alleles. This identified a smaller group of patients with an even greater risk of AMI. The data are displayed in FIG. 7. If only the 3 SNPs that were found to be significantly associated with AMI were used in the analysis, an even greater increase in the ability to identify a high risk cohort was displayed. GRS tertiles 2-3 were at significantly greater risk of AMI that those patients in the first tertile; of clinical importance, tertile 3, with 10% of the total cohort (87/875) had a 6.9-fold increase in AMI risk (p=0.0004).

These results confirm the validity and power of the experimental strategy presented herein. The results also confirm that the mouse model of "vulnerable" plaque models human vulnerable plaque. Thus, the phage fishing strategy, using a human bone marrow-derived cDNA library to fish for ligands in a unique mouse model of VP, led to identification of previously unrecognized genes encoding novel VP-binding ligands that, through genetic association, revealed SNPs predisposing to AMI in individuals with angiographically documented CAD. Moreover, an aggregate genetic risk score (GRS), based on the number of risk alleles an individual has, markedly improves identification of high risk subgroups, conveying a maximal odds ratio of having the propensity to develop plaque rupture (e.g., develop AMI) of almost 7-fold.

Example 9

Collateral Binding Ligands/Single SNP Association with CAD

In addition to performing phage fishing on mouse vulnerable plaque, ligands were identified that bind to developing collaterals in a mouse model of acute hindlimb ischemia (See also PCT/US2007/024629). The studies identified 12 ligands that preferentially bound to developing collaterals, 10 of which are shown in FIGS. 4 and 5. All but one of these ligands, similarly the vulnerable plaque-binding ligands, was encoded by genes not previously recognized as being genes. There was no overlap between the VP-binding ligands and collateral-binding ligands. A discovery analysis was performed using the WHC cohort of patients. The 44 SNPs that were found to be associated with AMI and/or CAD were tested in the discovery phase using the Washington Hospital Center cohort and the findings confirmed using the 5 distinct cohorts as described above for the VP-binding sequences. The data are presented in Table 6A and 6B below.

5 SNPs were identified that were significantly associated with the risk of having stable CAD: rs10757493 9p21.3, rs988179 2p16.3, rs309137 2q21.3, rs17588757 9p23 and rs12475139 2q21.3. Four of these SNPs are shown in Table 5 below

TABLE 5

Table 5. SNPs involving collateral-binding sequences and association with stable CAD. Displayed are those SNPs that have p values of <0.05. There were 4 SNPs that were significantly associated with the risk of having stable CAD.

| Locus | Minor allele/Risk Allele | % pop with risk allele | Meta-analysis p-value | Meta-analysis Odds Ratio (95% CI) |
|---|---|---|---|---|
| 2p16.3 rs988179 | A/A | 33 | 0.0079 | 1.11 (1.03-1.19) |
| 2q21.3 rs309137 | T/T | 18 | 0.0120 | 1.17 (1.04-1.31) |
| 9p23 rs17588757 | T/T | 10 | 0.0165 | 1.37 (1.04-1.77) |
| 2q21.3 Rs12475139 | A/A | 21 | 0.0401 | 1.13 (1.01-1.27) |

In addition, four SNPs near the collateral sequences were associated with Acute Myocardial Infarction: rs10812143 9p21.3, rs12005015 9p23, rs7025783 9p21.3 and rs7639226 3p12.3

TABLE 6A

Collateral Acute Vs. Chronic

| SNP name | Locus | Bound to: | Position | Genetic Model | Meta-analysis p-value | Meta-analysis Odds Ratio | 95% Confidence Interval | Sequence Context |
|---|---|---|---|---|---|---|---|---|
| rs10812143 | 9p21.3 | Collateral | 24933020 | DOM | 0.0013 | 0.84 | 0.76 0.93 | AAAGTCAGATA GATAGCTAGAT AATA[C/G]ATAT ACACACAGCTA AAGATGACAG (SEQ ID NO: 83) |
| rs12005015 | 9p23 | Collateral | 9048285 | DOM | 0.0053 | 0.74 | 0.6 0.91 | GAATAAAGCAG TGTCTTATGCAA TGT[C/T]ACAAC CCATGAAGCAT AAAAGGAGC (SEQ ID NO: 84) |
| rs7025783 | 9p21.3 | Collateral | 24933729 | DOM | 0.0059 | 0.87 | 0.78 0.96 | GAAATGTCAGT GCGTTTTTCAAT TAC[A/G]TATAC TGGTCACTGGCA AACAGGAT (SEQ ID NO: 85) |
| rs7639226 | 3p12.3 | Collateral | 78193644 | Rec | 0.0442 | 0.83 | 0.7 0.99 | TGACTTAGACAA AATCTCACCTCC TT[A/G]CAAGGC AGTCACAAACG TCACTATT (SEQ ID NO: 86) |
| rs10182729 | 2p16.3 | Collateral | 50724922 | Rec | 0.0669 | 1.19 | 0.99 1.44 | ACTTCTACCCTG ATTATGTTAGGT AA[C/T]TGAATT |

TABLE 6A-continued

Collateral Acute Vs. Chronic

| SNP name | Locus | Bound to: | Position | Genetic Model | Meta-analysis p-value | Meta-analysis Odds Ratio | 95% Confidence Interval | | Sequence Context |
|---|---|---|---|---|---|---|---|---|---|
| | | | | | | | | | GGAAAGAAAAA TATTTATT (SEQ ID NO: 87) |
| rs12618911 | 2p16.3 | Collateral | 50724115 | Rec | 0.0945 | 1.14 | 0.98 | 1.33 | CTTTTTACTTCA TGGCAAGCTGCT TT[G/T]ATTTCTA ATTAAGAAAAC ATTCCTG (SEQ ID NO: 88) |
| rs2216784 | 2p16.3 | Collateral | 50682648 | Rec | 0.098 | 1.17 | 0.98 | 1.41 | CTGGACCAAGA ATCATAAGACCC AGT[C/T]ATGAG TTGTTAAAAGTG AGGGTGAA (SEQ ID NO: 89) |
| rs1592145 | 9p21.2 | Collateral | 27731749 | DOM | 0.1279 | 1.18 | 0.96 | 1.45 | TTTCTGTAGGAC TGCTGTGGTATG CT[C/T]GGGGCC CGCTCCAATTCC CAGTCAC (SEQ ID NO: 90) |
| rs13302855 | 9p21.2 | Collateral | 27585995 | DOM | 0.142 | 1.21 | 0.95 | 1.56 | CTCACTTCCTCA CACATCCCTCAC CG[C/T]TTCGCTC CAGTCTCTTTGG AGGCAT (SEQ ID NO: 91) |
| rs324501 | 9p23 | Collateral | 27072901 | Rec | 0.1441 | 1.12 | 0.97 | 1.29 | ATTTCTCTCAGC TGGTCAAATAA ACA[A/G]CTCTT CTATCCTCCTGT AGAGAGGC (SEQ ID NO: 92) |
| rs12005189 | 9p23 | Collateral | 9044075 | DOM | 0.1788 | 0.89 | 0.76 | 1.05 | TAACAATTAAA GTCCCATATCAT GTA[C/T]TGAGC TCCTGGTCCATG CACCAAAT (SEQ ID NO: 93) |
| rs2643801 | 9p21.2 | Collateral | 27642540 | Rec | 0.1852 | 0.8 | 0.59 | 1.09 | CTTAGGAAAAC ATGTACTAACCA TCC[A/G]CATCTT TGTTTTTTTTTT AAGAGT (SEQ ID NO: 94) |
| rs6558102 | 8p21.1 | Collateral | 29152772 | Rec | 0.1906 | 0.83 | 0.63 | 1.08 | CTCTAAAAGAG CTGGAAGTATAC TAC[A/G]ACAAT TTTCACTGCACA CTTCCTTG (SEQ ID NO: 95) |
| rs10812622 | 9p21.2 | Collateral | 27610641 | Rec | 0.2106 | 1.1 | 0.95 | 1.27 | CAGGCCACTGAT CCTGAGTATGTG AA[A/C]CGACCA ATGCTCTGACCC GATAAAT (SEQ ID NO: 96) |
| rs988179 | 2p16.3 | Collateral | 50682535 | DOM | 0.2268 | 0.94 | 0.86 | 1.04 | TAGTCAGACAC AAACCGGTGTTA TCA[A/C]ACAGA ACTGTCACGTAT TTGATCTG (SEQ ID NO: 97) |

TABLE 6A-continued

Collateral Acute Vs. Chronic

| SNP name | Locus | Bound to: | Position | Genetic Model | Meta-analysis p-value | Meta-analysis Odds Ratio | 95% Confidence Interval | | Sequence Context |
|---|---|---|---|---|---|---|---|---|---|
| rs10193587 | 2q22.1 | Collateral | 136641909 | DOM | 0.229 | 1.07 | 0.96 | 1.19 | CTGGGCCAGGCT CTCCCTGCCCAA TT[C/T]GGTAAA TGTGTGCTAGAG GAAACAT (SEQ ID NO: 98) |
| rs4546115 | 3q13.11 | Collateral | 78207025 | DOM | 0.2799 | 1.05 | 0.96 | 1.16 | ATGTATACATTG AAGCCCTAGCCC CC[A/G]AAGTGA CTCTGGAGATGG TACCTTT (SEQ ID NO: 99) |
| rs4971686 | 2p16.3 | Collateral | 50685238 | Rec | 0.2868 | 1.12 | 0.92 | 1.35 | ACCTTTTCTCCA ACTTTTCCTGTC TC[A/G]ACTCTT ATCTCTATTTTT GTTTACT (SEQ ID NO: 100) |
| rs10511521 | 9p23 | Collateral | 9123196 | DOM | 0.3009 | 0.67 | 0.35 | 1.29 | AGATTCCAGGG CCTATCCTAAAA CCA[C/T]TGGAA GAGAATTACAC AGAGGTAGG (SEQ ID NO: 101) |
| rs10966441 | 9p21.3 | Collateral | 24739214 | DOM | 0.302 | 1.07 | 0.94 | 1.22 | TTACAGAGCTCA GAAACAGTGCT GCT[C/G]AATTA AAGCTTCCAGG AGTAAGATT (SEQ ID NO: 102) |
| rs309137 | 2q21.3 | Collateral | 136765951 | DOM | 0.363 | 1.06 | 0.94 | 1.18 | TCACTTCTGCTG TTGCCACCAACC CT[C/T]GCGTTTC CCTTTGTCACTT CCCCCT (SEQ ID NO: 103) |
| rs9288812 | 3q13.11 | Collateral | 106783826 | DOM | 0.3671 | 1.05 | 0.95 | 1.15 | GCCTAATTAGGT TTTCAGTAATTC AT[A/G]TCATTG GTCATTAGGACA ATCATAC (SEQ ID NO: 104) |
| rs8396 | 4q32.1 | Collateral | 159850267 | Rec | 0.3765 | 0.93 | 0.81 | 1.08 | ATAAGAAAATG TAAAGGTTTTG TCT[A/G]TGAAT ATGATCCCTAAT GTGTTTCT (SEQ ID NO: 105 |
| rs13391995 | 2p16.3 | Collateral | 50716776 | DOM | 0.3948 | 0.88 | 0.67 | 1.16 | GTTAATTAAGGC TCATTACATAAG AA[C/T]GAGATT GAAGTATTGTAA ATAGAAA (SEQ ID NO: 106) |
| rs10433373 | 3q13.11 | Collateral | 106784431 | DOM | 0.4157 | 1.04 | 0.95 | 1.15 | ACATGATCTGTA GGATGGCAGCA ATA[C/T]TAATT GTATCAGAGCTT GTTGCTCT (SEQ ID NO: 107) |
| rs11759406 | 6q21 | Collateral | 108171828 | Rec | 0.4207 | 1.11 | 0.87 | 1.41 | TTTGTTGAATGC GCTAAACCTGTC TG[C/T]GAGCAC |

TABLE 6A-continued

Collateral Acute Vs. Chronic

| SNP name | Locus | Bound to: | Position | Genetic Model | Meta-analysis p-value | Meta-analysis Odds Ratio | 95% Confidence Interval | | Sequence Context |
|---|---|---|---|---|---|---|---|---|---|
| | | | | | | | | | ATACCTGCAGAT GTATCTG (SEQ ID NO: 108) |
| rs10511245 | 3q13.11 | Collateral | 106783905 | DOM | 0.4314 | 1.04 | 0.95 | 1.14 | ACACTAAATGG AGACACGAATC TAAA[A/G]GATC ACCGGCAACAG CCCTAAAAGA (SEQ ID NO: 109) |
| rs10433370 | 3q13.11 | Collateral | 106784358 | DOM | 0.4515 | 1.04 | 0.94 | 1.14 | AATGAATACTAT GGATCTACAACT TA[C/T]TAGAAG TGAGGCCTTGAG CATAATA (SEQ ID NO: 110) |
| rs6922304 | 6q21 | Collateral | 108172837 | Rec | 0.4583 | 1.1 | 0.87 | 1.40 | GTCCCTGCAGGT GGGGGAAGCAG GAC[A/G]AGGCC TACCTGATTCCA TCCTCCCT (SEQ ID NO: 111) |
| rs9838585 | 3q13.11 | Collateral | 106779438 | DOM | 0.4646 | 1.04 | 0.94 | 1.14 | GCATATAACTTT GTCACAATTCCA GA[C/T]ACAGAG TGGTTGAGCCAG GACCCAT (SEQ ID NO: 112) |
| rs629768 | 8p21.1 | Collateral | 29199260 | DOM | 0.5135 | 0.96 | 0.85 | 1.08 | GAGCCACCGAG TTCACAGTCTGT TCA[A/G]GGGAA CTCAAGACATTA AAATCAAC (SEQ ID NO: 113) |
| rs6781390 | 3p12.3 | Collateral | 78184267 | Rec | 0.5203 | 0.95 | 0.8 | 1.11 | TTAAACCCAAG ATAGGATATAA GGAG[A/C]CTGT TAAAAAGTAAG GTATCTTAAG (SEQ ID NO: 114) |
| rs6921876 | 6q21 | Collateral | 108172532 | Rec | 0.6195 | 1.07 | 0.84 | 1.36 | CCCAGAGTTTCA ATGAGAGGAGA GTG[A/C]AGAAA CTTACTTGTTAC ATATGATG (SEQ ID NO: 115) |
| rs4690909 | 4q32.1 | Collateral | 159848601 | Rec | 0.6457 | 0.96 | 0.84 | 1.11 | AACAGAAACGT GTTCTGACTGAC AAT[C/G]TAAGT TGAGTACTACCT GAGGTTTC (SEQ ID NO: 116) |
| rs9320231 | 6q21 | Collateral | 108176932 | Rec | 0.6516 | 1.06 | 0.82 | 1.38 | CGGCCAGATTA ACAAGTCTGGG CTTC[A/G]TCTA AAAGCAATGGG AGGGACTGAA (SEQ ID NO: 117) |
| rs17588757 | 9p23 | Collateral | 9052188 | DOM | 0.6543 | 1.03 | 0.92 | 1.14 | AATCACATAAAT GGTCTTGAATAT AG[C/T]GTTACC AAAACATAAGA CAAAACAA (SEQ ID NO: 118) |

TABLE 6A-continued

Collateral Acute Vs. Chronic

| SNP name | Locus | Bound to: | Position | Genetic Model | Meta-analysis p-value | Meta-analysis Odds Ratio | 95% Confidence Interval | | Sequence Context |
|---|---|---|---|---|---|---|---|---|---|
| rs12664414 | 6q21 | Collateral | 108176526 | Rec | 0.6585 | 1.06 | 0.84 | 1.35 | AGAAAAATCTA ATAAGAGACCTT CAT[A/G]CAGGC ACTATGCCATGC CCTACAAA (SEQ ID NO: 119) |
| rs10168838 | 2p16.3 | Collateral | 50546322 | DOM | 0.6965 | 1.05 | 0.84 | 1.33 | ACAGATGATAT GTCCAAACTAGT TTT[G/T]AAAGTT CTAGTTCACACA CCTGAAT (SEQ ID NO: 120) |
| rs12475139 | 2q21.3 | Collateral | 136503120 | Rec | 0.7977 | 1.02 | 0.88 | 1.19 | TTCAACAGTTAT TATCAAGCATGG AC[A/T]TTCCTTG TGTCAGGTCCTG GGTCAG (SEQ ID NO: 121) |
| rs629187 | 3q13.11 | Collateral | 106747807 | DOM | 0.8476 | 1.01 | 0.91 | 1.12 | AACTCTAGAAA AATATTTCTCCA CAG[C/T]TTCTTA TAAAGGTAATTC TTGTCAA (SEQ ID NO: 122) |
| rs10757493 | 9p21.3 | Collateral | 24874944 | Rec | 0.8490 | 0.99 | 0.88 | 1.11 | TGGATAATGCCT TGAAAAATGATT TT[A/G]TAGCTG ATGCAGAAGCC GTCTGCGT (SEQ ID NO: 123) |
| rs17059917 | 8p21.1 | Collateral | 29230697 | DOM | 0.8955 | 1.01 | 0.91 | 1.12 | TTTTTGCAAGCT CAAGCTGATCAT TG[C/T]TTTTTTT TTCATTAGAACG CCCACA (SEQ ID NO: 124) |
| rs17068440 | 6q21 | Collateral | 108073160 | DOM | 0.9009 | 1.01 | 0.9 | 1.13 | ATACTTAATTCA TATATTACAATC TG[C/T]GAAACT TAATAACTCCTC ATCATAT (SEQ ID NO: 125) |
| rs3772551 | 3q13.11 | Collateral | 106741142 | DOM | 0.9885 | 1 | 0.9 | 1.11 | TATATGAATCTT ATAGTTTGGAAG GA[C/T]AAAAAT CAGCTAGCAAA TAGCTAAA (SEQ ID NO: 126) |

TABLE 6B

Collateral CAD Vs. Control

| rs # | Locus | Condition | Meta-analysis p-value | Meta-analysis Odds Ratio | 95% Confidence Interval | |
|---|---|---|---|---|---|---|
| rs10757493 | 9p21.3 | Collateral | 0.0053 | 1.12 | 1.04 | 1.22 |
| rs988179 | 2p16.3 | Collateral | 0.0067 | 0.9 | 0.84 | 0.97 |
| rs309137 | 2q21.3 | Collateral | 0.012 | 1.17 | 1.04 | 1.31 |
| rs17588757 | 9p23 | Collateral | 0.0202 | 1.35 | 1.06 | 1.72 |
| rs12475139 | 2q21.3 | Collateral | 0.0401 | 1.13 | 1.01 | 1.27 |
| rs10966441 | 9p21.3 | Collateral | 0.0609 | 0.86 | 0.74 | 1.00 |
| rs2643801 | 9p21.2 | Collateral | 0.1422 | 0.85 | 0.69 | 1.05 |
| rs1592145 | 9p21.2 | Collateral | 0.2175 | 0.89 | 0.74 | 1.06 |
| rs629768 | 8p21.1 | Collateral | 0.2302 | 1.25 | 0.89 | 1.75 |
| rs10433370 | 3q13.11 | Collateral | 0.2811 | 0.91 | 0.77 | 1.07 |
| rs10812622 | 9p21.2 | Collateral | 0.2841 | 0.93 | 0.82 | 1.06 |
| rs10511245 | 3q13.11 | Collateral | 0.3085 | 0.92 | 0.78 | 1.08 |

TABLE 6B-continued

Collateral CAD Vs. Control

| rs # | Locus | Condition | Meta-analysis p-value | Meta-analysis Odds Ratio | 95% Confidence Interval | |
|---|---|---|---|---|---|---|
| rs324501 | 9p23 | Collateral | 0.3319 | 0.96 | 0.89 | 1.04 |
| rs10433373 | 3q13.11 | Collateral | 0.3321 | 0.92 | 0.78 | 1.08 |
| rs3772551 | 3q13.11 | Collateral | 0.3403 | 1.13 | 0.90 | 1.42 |
| rs629187 | 3q13.11 | Collateral | 0.3482 | 1.12 | 0.89 | 1.41 |
| rs13302855 | 9p21.2 | Collateral | 0.3569 | 0.94 | 0.83 | 1.07 |
| rs13391995 | 2p16.3 | Collateral | 0.3630 | 0.88 | 0.70 | 1.12 |
| rs9288812 | 3q13.11 | Collateral | 0.3649 | 0.92 | 0.79 | 1.09 |
| rs17068440 | 6q21 | Collateral | 0.3888 | 1.04 | 0.95 | 1.14 |
| rs6558102 | 8p21.1 | Collateral | 0.4325 | 0.87 | 0.63 | 1.20 |
| rs10511521 | 9p23 | Collateral | 0.4617 | 1.24 | 0.76 | 2.02 |
| rs10168838 | 2p16.3 | Collateral | 0.5104 | 0.94 | 0.78 | 1.13 |
| rs9838585 | 3q13.11 | Collateral | 0.5442 | 0.94 | 0.79 | 1.13 |
| rs7639226 | 3p12.3 | Collateral | 0.5625 | 0.96 | 0.85 | 1.09 |
| rs10182729 | 2p16.3 | Collateral | 0.6195 | 1.04 | 0.91 | 1.19 |
| rs12005189 | 9p23 | Collateral | 0.6242 | 0.97 | 0.85 | 1.10 |
| rs2216784 | 2p16.3 | Collateral | 0.6250 | 1.04 | 0.90 | 1.21 |
| rs10812143 | 9p21.3 | Collateral | 0.6322 | 0.94 | 0.75 | 1.18 |
| rs6922304 | 6q21 | Collateral | 0.6961 | 1.02 | 0.94 | 1.10 |
| rs6781390 | 3p12.3 | Collateral | 0.7026 | 0.97 | 0.86 | 1.11 |
| rs17059917 | 8p21.1 | Collateral | 0.7058 | 0.97 | 0.83 | 1.13 |
| rs11759406 | 6q21 | Collateral | 0.7352 | 1.01 | 0.94 | 1.10 |
| rs4971686 | 2p16.3 | Collateral | 0.7498 | 1.03 | 0.88 | 1.20 |
| rs12664414 | 6q21 | Collateral | 0.7627 | 1.04 | 0.85 | 1.26 |
| rs7025783 | 9p21.3 | Collateral | 0.7807 | 0.96 | 0.77 | 1.20 |
| rs6921876 | 6q21 | Collateral | 0.7852 | 1.01 | 0.94 | 1.09 |
| rs4690909 | 4q32.1 | Collateral | 0.7952 | 1.01 | 0.94 | 1.09 |
| rs12618911 | 2p16.3 | Collateral | 0.8108 | 0.98 | 0.87 | 1.11 |
| rs9320231 | 6q21 | Collateral | 0.8139 | 1.03 | 0.85 | 1.25 |
| rs12005015 | 9p23 | Collateral | 0.8551 | 0.98 | 0.83 | 1.16 |
| rs4546115 | 3q13.11 | Collateral | 0.8884 | 0.99 | 0.87 | 1.12 |
| rs10193587 | 2q22.1 | Collateral | 0.9325 | 1.01 | 0.88 | 1.15 |
| rs8396 | 4q32.1 | Collateral | 0.9867 | 1.00 | 0.93 | 1.08 |

Example 10

Aggregate Risk Snp Burden for CAD Risk

Figure 8:
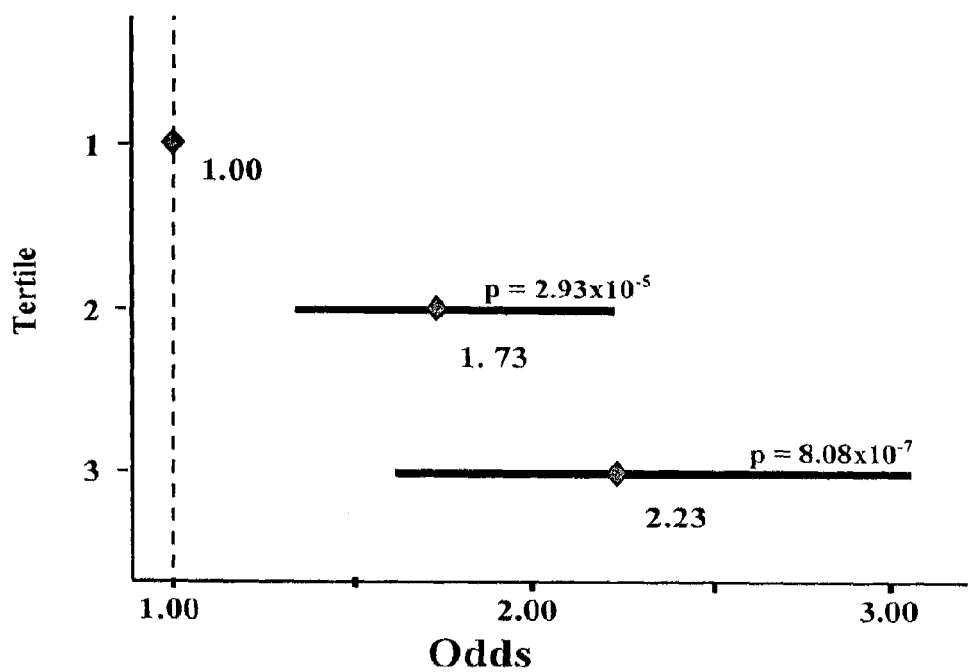
FIG. 8 shows the Genetic Risk Scores based on 44 SNPs associated with CAD.

Similarly to the VP-binding sequences, if an individual SNP indicates altered CAD risk, then multiple SNPs, influencing multiple pathways involved in atherogenesis, might improve the ability to identify patients at particularly high risk. The SNPs related to the 12 ligands that bound to developing collaterals that were found to alter CAD risk were used to calculate a genetic risk score (GSR) for each patient. The results are shown in FIG. 8.

These analyses indicate the GRS results in a greater ability to identify a cohort at high risk for CAD. GRS tertiles 2-3 were at significantly greater risk of having CAD than patients in the first tertile. Of clinical importance, tertile 3, with 22% of the total cohort (289/1322) had a 2.2-fold increase in CAD risk ($p=8 \times 10^{-7}$).

Thus, the phage fishing strategy, using a human bone marrow-derived cDNA library to fish for ligands in a mouse model of acute hindlimb ischemia, led to identification of previously unrecognized genes encoding novel ligands binding to developing collaterals that, through genetic association, revealed SNPs predisposing to CAD. Moreover, an aggregate genetic risk score (GRS), based on the number of risk alleles an individual has, markedly improves identification of high risk subgroups, conveying a maximal odds ratio of having the propensity to develop CAD of over 2-fold.

What is claimed is:

1. A complementary DNA (cDNA) encoding a homing polypeptide, wherein the cDNA comprises the nucleotide sequence as set forth in SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

2. The cDNA of claim 1, wherein the cDNA comprises the nucleotide sequence as set forth in SEQ ID NO: 24.

* * * * *

SEQUENCE LISTING

<160> NUMBER OF SEQ ID NOS: 429

<210> SEQ ID NO 1
<211> LENGTH: 445
<212> TYPE: DNA
<213> ORGANISM: H. sapiens

<400> SEQUENCE: 1

```
ggggattcag gggcagttta taattcagtc acatgttaaa gaacaaaaag gacgaaagaa      60
gaataaagca gatagaatcg tgaaatgggt tacattattt gcaccataaa gtttaagtaa     120
atcaaattat tgggaatatt ctgagataga gctaaagtct ttctcaagag tcatggttga     180
aaccacatgt tgtggaggaa ctgatggtga ttgttgcccc attgtgggat tcctccctat     240
ggtaatgaca tcaaaatgaa aaaaaaaaaa cacacacaca caaaaaaatg acgcaaattg     300
taattaaagg tggagctgtt tatgatctgg ttatctccac attgttctgg gaaaaaattg     360
aaacattact gggtcaaatc atgtctgtga aacaaaatga aaggtaaaaa tagtgaataa     420
aaaaaaaaaa attaaaaaca agctt                                          445
```

<210> SEQ ID NO 2
<211> LENGTH: 431
<212> TYPE: DNA
<213> ORGANISM: H. sapiens

<400> SEQUENCE: 2

```
gcgattcaac actctataag aaaaaatata ataatttgat ttaaaaactg gcaaaatatc      60
```

```
tgaatagata tttctcaaaa gaagacatac gaatggcaaa caagcataca aaaaggtgtt      120
caacatcatt gatcatcaga gaaatgcaaa tcaaaactac aaggaaaata tcatctcact      180
cctgttaaaa tggcttttat gcaaaagtca gacaataaca aatgctgaaa aggatgtgga      240
aaaaaggaaa ccctcatgca ctattggtgg aatgtaaatt aatacagcca ctacggagaa      300
cagtttgcag gttcctcaac aacaacaaca aaaaactaaa aacagagcta tcttacaatc      360
caacaattcc actcccagat atatatcaga gtaaggaaa tgacactaag ttttttgaaaa      420 atgaaaagct t                                                          431

<210> SEQ ID NO 3
<211> LENGTH: 1040
<212> TYPE: DNA
<213> ORGANISM: H. sapiens

<400> SEQUENCE: 3
gcgattctgg gactgtggat atagcttgcc acagtatctt atcagttaat tgcattcttg       60
aatgtgctgg gagtcagctt gcacaaggta agtccttgag gaaggggctg ccagtgtaag      120
agccaagatg gagtctgtct ggctctctta gctaagggag agtcaattca ggtggaaaca      180
aggctaggtg attaaaggaa agggagagtc taaaaacagg gttagtaaaa accaggttgg      240
gcattacagt atcacccaga caaccaagtg ttcatgttta accacaaagc cctcttgtaa      300
ttgctgaagg gtatttgctt gtaattgctg cgaccattct tcaagttgtt tctttaactc      360
acattcaaga gtagaaattt gagaagaaat acggttgtga taagcccctt gcaggtgtgc      420
tttcactctc tcccaagcat attgggagct attatatggc agaggtgtga cacagatagg      480
attatattgc caatcacaat gtaaattttg atgggtaatg aatgcctgct gctgacccc       540 cagccattca actgcggctt caagagcctc caggtgagac agaatagttt tatcaatatt      600
tacctgttcc tgaaattcat gggttacatt ataaccatg tggttcacca ctgaggctat       660
gtgaatagat cctgttagag agacagctgc agtagcagca gttgctagta tgataatagc      720
tgagactaaa aagtcaatta aagtggccag aaatcttttt ttctgagcat gagacagtgc      780
ttttctaaat agctgctggg tggaatttcc ttcccagctc caggttaaat ttacaggcag      840
ccacatttct gcatgccgtt ttaatcatga cgttatactt aactgtgtaa cgttttgata      900
acagcatgta gcataccagt actggaagac tttatactat actgattctg ttttttgtaac     960 ctcgccaaag tatatgggtg catagtaaca ctgtcagtat atgcaaagtg ctgccttata    1020
ctccctaaaa caatcagaaa                                                1040

<210> SEQ ID NO 4
<211> LENGTH: 275
<212> TYPE: DNA
<213> ORGANISM: H. sapiens

<400> SEQUENCE: 4
acattctgtg ggatgatggt gatggtagca tagcatatga atgtgcttaa tgcctctgaa       60
ggtagactta aaaatggtta agatgccaca ttttatgtta tgtgtatttg atgacgatta      120
aacattttaa aaattgaaaa aggtaaacat tacaaaataa tttagtgaag ccagatatca      180
tgtcacttca tgtttctgtt aaatttatgt acaattaggc tggtttgtat ttagaaattc      240
tagttataaa gatgaatgaa taacagccaa agctt                                275

<210> SEQ ID NO 5
```

```
<211> LENGTH: 370
<212> TYPE: DNA
<213> ORGANISM: H. sapiens

<400> SEQUENCE: 5
gcattcagac cagcttggtc acagagagag agtccatctc tataaaaaaa tgtttaaaaa      60
ttagacgggc atgatggtgc ttggtgcttg cctgtagtcc cagctacttg ggaggctgag     120
gtgggaggac tgcctgagcc caggaactgg agattgcagg aagctatgat cacatcactg     180
cactccagcc tgggtgacag agcgagactc cgtctcaaaa aaagtctttt gtttttcagt     240
catggtggta tacgcctcta gtctcagcta cttgggagac tgaggcagga gggtcacttg     300
aacccaggag ttcgagttca gtctggacaa atagcaaga ccccatctct aaatcaagca     360
aacaaagctt                                                           370

<210> SEQ ID NO 6
<211> LENGTH: 503
<212> TYPE: DNA
<213> ORGANISM: H. sapiens

<400> SEQUENCE: 6
cgattcagcg cttgattcca ttactgggta tatacccaaa ataatataaa ttgttggact      60
ataattatac atgcatgtgt gtgttcataa cagcactatt cataacagca agacatgaa     120
atcaacctaa atgcccatca aggcagatt gagcaaagca aatatggtag atacacacca     180
tggatgctat gcagccataa aaatgaaaaa gatcatgtcc tttccagaaa catggatgaa     240
gttggaggcc attatcctta gcaaactaat gcaggaacaa aaaccaaat gctgcgtgtt     300
ctcactgata gtgggagct aaatgatgag aacagcagac acatagaggg gacaacagac     360
actgggtct actggaaggt ggagggtgag aggaggggaga ggatcaggaa aaataactaa     420
caggcactag gcttaatact tgggtgacga aataatctgt acgacaaacc cctatgacaa     480
gggtttactt atataataag ctt                                           503

<210> SEQ ID NO 7
<211> LENGTH: 352
<212> TYPE: DNA
<213> ORGANISM: H. sapiens

<400> SEQUENCE: 7
cgattgcaga agcgtcaggt tttgtaacct acgcttgcag tttactctcc ccatagactt      60
gtaatgttta tctttataat gataaggaaa aacatcact ttctgttatg gctttatgcc     120
tattttatgt agtacagaat aaacctaata aaatgatgtt gggattgttc cataaggcat     180
tctaaaactt cttcttccta gtagttgaat tagagttttt agtcattaat aagcacatg     240
gcatcataaa aacacaaaat ctgaaataaa agaaagatg ttttgtccag gattcagaaa     300
aatattttgt ctccattttg ccatatgctt catgagatct tgtactaagc tt           352

<210> SEQ ID NO 8
<211> LENGTH: 351
<212> TYPE: DNA
<213> ORGANISM: H. sapiens

<400> SEQUENCE: 8
ggggaataat tttgttatgg gctagtgaaa agtatttgct ttcctaaggt atgagcatgt      60
actggttcac taacttccca gttgtttttc tggctgagaa gagcttttct ctggtggca     120
catgtccatg acagctgttt attccacatg tttccattga aagcatatta acctgagcaa     180
```

```
atgggqataa ttatcacagt gtaaaaatgc ctttggatgt taatgattcc tcttctgtcg    240
tctcctttga ttggcctgac cctcgtatta ctatgtatta atatccttag atcttcatgg    300
taccaaggac attccaaaag tcatccacat tgactttggc tcagaaagct t             351
```

<210> SEQ ID NO 9
<211> LENGTH: 566
<212> TYPE: DNA
<213> ORGANISM: H. sapiens

<400> SEQUENCE: 9

```
ggatacttgc tagtaggcta ctgcattcat ttgggctcca ccctttaaga ggggcattaa     60
caaggtgaag tgtattcctg gtcagtggc agctggtctc actagcatgt ccctaggagg    120
acagacagca tagaagggcc ctgggaactt gtgccctggg aactgggtgc agaactggg     180 gacgtttaaa aataacaatc tggagcaaat atgatgactc cttttaattt tttcaaagac    240
tgagatttgg aagaggagtt gatctgtgct gggagaccct ggcaaacagt aggtagaagt    300
gacagggagg tggagtggtt aaactttcta ataatcaatg ctggttgaca acaaaataga    360
ctgcctcaat tatattgcat agagacctgc agttgtatta caaccctctt tagcaagcca    420
ccaggaaaat tggtgcaaag gagaaagatt gctatggtat gaatcactct tttggctgtg    480
tagatgggta tgaatgtttg tctctgtcac aggaagtatg gatgccacct ggaagatgac    540
ctatgtgtag aaggaaaccc aagctt                                          566
```

<210> SEQ ID NO 10
<211> LENGTH: 169
<212> TYPE: DNA
<213> ORGANISM: H. sapiens

<400> SEQUENCE: 10

```
gcaaggtata atacagttac gcataatatg agattagcgg acttgcacga tttaaggttt     60
tgttttaatt ttaatcaccc agagagctgc cagttgttct gatgcctctt tggttaagtg    120
aagctgaaaa aagggtataa ctcaactgtc acatgaatta cggaagctt                 169
```

<210> SEQ ID NO 11
<211> LENGTH: 483
<212> TYPE: DNA
<213> ORGANISM: H. sapiens

<400> SEQUENCE: 11

```
gaattggggc atataatgaa aacaatggtc gggaaatgga agagatatat taaccgaatg     60
ggtctggaaa taaataagt aaagaacaac tttattccct gctctttgtg gcttgtgcaa    120
cctcatgaga caaatggatg caccaggaat ccagctgtaa tatacaactg tcagagaaac    180 actttaagc aaagtacaat gtcctgtgag agtacagtaa tgattaattt tgatttgatt    240 aacattttg cttaataaat ttgttatagt aaataaacta atttgtttag aaaacagcac    300
cagtccttgt tcaacacatt tcataaagaa gttcatccat ggtttcaata tgcacccttg    360
attattctat ggagagttaa ataataattt tataactttg gagatattaa gaggggggtt    420
atatatctct tcattcagtc tcctatatat tcagacagaa aaactgagga caaaataaag    480
ctt                                                                   483
```

<210> SEQ ID NO 12
<211> LENGTH: 392
<212> TYPE: DNA

<213> ORGANISM: H. sapiens

<400> SEQUENCE: 12

| | |
|---|---|
| ataaaaggaa gcagctttaa gggaagcaac ttcaattgag tgcattgagg gcaaaacagc | 60 |
| caaagggtga tcctgaatta gtttatatga cgtaaaatgc aaaacagtaa agcctgttat | 120 |
| ctaaaggaaa agataaaagg caaaggcaga gtcaaagata gcagatttca gcagtcatag | 180 |
| atttctctct ctggaaagca cagctgtttt ttgtatctgc caacctaatg gaactcctca | 240 |
| aatgactttt gttgaaagcc cacaggtcct ggcagggcat acaagaactt gagaacacat | 300 |
| ggattctttc tttcaggacc ttacatttta aaaggattc accatgagaa ctcaatggaa | 360 |
| aactgatctg gtgaaggggg aaagacaagc tt | 392 |

<210> SEQ ID NO 13
<211> LENGTH: 639
<212> TYPE: DNA
<213> ORGANISM: H. sapiens

<400> SEQUENCE: 13

| | |
|---|---|
| caaacacagg gtgattaagt tactctctag aagaacaaat accataggag cccagactgg | 60 |
| ctttagtgat gatataagta aagaaaagca catttcaaaa agcaaagaaa tgacagtgct | 120 |
| aatttacttg cccaaatgtt actgagagaa ctgtcacttg aatgtctctc agaaatcata | 180 |
| aggtggtgaa tgcacactct tgtcatcagt atatccatag acaatgatt gttctgaagc | 240 |
| aaaatcttga atttcttact ctcttaacag gcggacctca ggaaataatg aatcttgata | 300 |
| aaagcatgta atttcacact attttaaatt gaggttctat gtcattttac tgtgatatat | 360 |
| ttcctgttgc tcctttaaaa tgagtattta cattaaaatt atttcactta aatgaataaa | 420 |
| acattaacaa caataatgca gcatgcacat ttaaatggag gatcgacatg attagaagtg | 480 |
| catctcaaag gatttccctt gttttctga ttgttgcccc ctctgataga tgattcatta | 540 |
| atttcttgtc acttggagta aataggtggt tagaaaggtc tagtataaat aaaaatattt | 600 |
| ttctactttg ttttcatttt tcaaaattct aacaagctt | 639 |

<210> SEQ ID NO 14
<211> LENGTH: 34
<212> TYPE: PRT
<213> ORGANISM: H. sapiens

<400> SEQUENCE: 14

Phe Lys Gly Gln Phe Ile Ile Gln Ser His Val Lys Glu Gln Lys Gly
1               5                   10                  15

Arg Lys Lys Asn Lys Ala Asp Arg Ile Val Lys Trp Val Thr Leu Phe
            20                  25                  30

Ala Pro

<210> SEQ ID NO 15
<211> LENGTH: 38
<212> TYPE: PRT
<213> ORGANISM: H. sapiens

<400> SEQUENCE: 15

Glu Phe Leu Gly Thr Val Asp Ile Ala Cys His Ser Ile Leu Ser Val
1               5                   10                  15

Asn Cys Ile Leu Glu Cys Ala Gly Ser Gln Leu Ala Gln Gly Lys Ser
            20                  25                  30

Leu Arg Gly Leu Pro Val

```
<210> SEQ ID NO 16
<211> LENGTH: 20
<212> TYPE: PRT
<213> ORGANISM: H. sapiens

<400> SEQUENCE: 16

Phe Lys Thr Ser Leu Val Asn Arg Glu Arg Val His Leu Tyr Lys Lys
1               5                   10                  15

Met Phe Lys Asn
            20

<210> SEQ ID NO 17
<211> LENGTH: 24
<212> TYPE: PRT
<213> ORGANISM: H. sapiens

<400> SEQUENCE: 17

Phe His Tyr Trp Val Tyr Thr Gln Asn Asn Ile Asn Cys Trp Thr Ile
1               5                   10                  15

Ile Ile His Ala Cys Val Cys Ser
            20

<210> SEQ ID NO 18
<211> LENGTH: 47
<212> TYPE: PRT
<213> ORGANISM: H. sapiens

<400> SEQUENCE: 18

Phe Ser Ala Lys Val Glu Ala Ser Gly Phe Ser Val Thr Pro Thr Leu
1               5                   10                  15

Ala Val Tyr Ser Pro His Arg Leu Val Met Phe Ile Phe Ile Met Ile
            20                  25                  30

Arg Lys Lys His His Phe Leu Leu Trp Leu Tyr Ala Tyr Phe Met
        35                  40                  45

<210> SEQ ID NO 19
<211> LENGTH: 20
<212> TYPE: PRT
<213> ORGANISM: H. sapiens

<400> SEQUENCE: 19

Phe Phe Gln Thr Leu Ile Leu Ser Met Gly Ser Val Lys Ser Ile Cys
1               5                   10                  15

Phe Pro Lys Val
            20

<210> SEQ ID NO 20
<211> LENGTH: 48
<212> TYPE: PRT
<213> ORGANISM: H. sapiens

<400> SEQUENCE: 20

Asn Ser Thr Gly Leu Ser Ala Ser Gln Ala Thr Ala Phe His Ser Gly
1               5                   10                  15

Leu His Pro Phe Lys Arg Gly Ile Asn Lys Val Lys Cys Ile Pro Gly
            20                  25                  30

Ser Val Ala Ala Gly Leu Thr Ser Met Ser Leu Gly Gly Gln Thr Ala
        35                  40                  45
```

<210> SEQ ID NO 21
<211> LENGTH: 32
<212> TYPE: PRT
<213> ORGANISM: H. sapiens

<400> SEQUENCE: 21

Phe Phe Trp Gly Lys Ser Lys Tyr Tyr Ile Met Lys Thr Met Val Gly
1               5                   10                  15

Lys Trp Lys Met Ile Leu Phe Arg Pro Glu Leu Gly Leu Glu Ile Lys
            20                  25                  30

<210> SEQ ID NO 22
<211> LENGTH: 46
<212> TYPE: PRT
<213> ORGANISM: H. sapiens

<400> SEQUENCE: 22

Phe Met Ile Lys Glu Leu Glu Ala Ser Tyr Phe Lys Gly Ala Thr Gln
1               5                   10                  15

Ile Glu Cys Ile Glu Met Ala Lys Gln Pro Lys Gly Asp Pro Glu Leu
            20                  25                  30

Val Tyr Met Thr Val Lys Cys Lys Thr Val Lys Pro Val Ile
        35                  40                  45

<210> SEQ ID NO 23
<211> LENGTH: 35
<212> TYPE: PRT
<213> ORGANISM: H. sapiens

<400> SEQUENCE: 23

Phe Pro Tyr Met Tyr Asn His Tyr Trp Val Lys Cys Glu Leu Ile Arg
1               5                   10                  15

Glu Phe Thr Leu Leu Lys Lys Val Asn Lys Tyr His Arg Ser Ser Arg
            20                  25                  30

Ile Trp Leu
        35

<210> SEQ ID NO 24
<211> LENGTH: 774
<212> TYPE: DNA
<213> ORGANISM: H. sapiens

<400> SEQUENCE: 24
gcctgtaagt gagcccaaac atcaatgaag cttctgtctt gtggctcagc agttccccac      60
ccctggtccc catctctcag agtggaatgt tcattaattt cgtgaaataa gagttgagga     120
gaggaatgaa aagcagccaa acacaaccat cacattttgc tgaaagagtt gatggggaaa     180
aaaaaacagg caccaatggt tgttgtatca cctaactggg ctttacattg ctagtttcat     240
tccgtccttt ataagtacac attgttgtgt gttttaactt ggattcaata cttcagctac     300
ttcttatttt ctaccattgt aacattaaag gaaactgcat ctctgcataa aacaaaaggt     360
aatatagctt gtaggtttgc tttgcattgc aaagaacata cttgcttaag acaatcaagt     420
gtcgaaccat ggacacctgc tacggagatt ccaattgtgg gatcttcttt tatcaactaa     480
aaagcttgcg gccgcactcg agtaactagt taacccttg gggcctctaa acggggggt      540 tattttggta aagggggggg gcccattttt ttttaaaaaa aaaaaacccc ttggggaccc     600 cccaggggg ggggggaaat tttgttttta agtttttaaa gaactaatat atactttgta      660
gagagtctta tgaggaaaaa atactgagta tgaatcataa ccacatggat ataaggaatg     720
actaaggcta gattgcaaag ggggggtcc ccctgagaac agaaaagatg ccgc        774

<210> SEQ ID NO 25
<211> LENGTH: 422
<212> TYPE: DNA
<213> ORGANISM: H. sapiens

<400> SEQUENCE: 25
ctcagctttt ccactgttat gtgtaaagga cttaaaaat cttattcagt caaatattaa     60
atatcatcgt tgctgtaatt aagcttgcgg ccgcactcga gtaactagtt aaccccttgg   120
ggcctctaaa cgggtcttga ggggttccta gttactcgag tgcggccgca agcttaatta   180
caagcaacat gatatttaat atttgactgc taataagaat attttaaag tcctctaata   240
cacaattaaa cagtgatgga aatagcttga attcggatcc ccgagcatca cacctgactg   300
gcaacacgct cctttaggca agctagaggg atttattttc cattttagg ccataggcaa   360
ttttgtttgc ttaagcttgc ggccgcactc gagtaactag ttaaccccctt ggggcctcta   420
ac                                                                  422

<210> SEQ ID NO 26
<211> LENGTH: 517
<212> TYPE: DNA
<213> ORGANISM: H. sapiens

<400> SEQUENCE: 26
ttcgggtaca gaaagatgtc catgattttt actcttgagt taatcactaa gattccaaaa     60
ttccataacc ctaaacaagt ctattttcca agggcaaaaa ataaatttaa tggtaattat   120
tcaagtcttt aaaatttgt tttgttaaaa agagaaaatc aaaagtatat cctctggcct   180
catgtttagg actataataa aatgctttgt tccatgaaat aagcttgcgg ccgcactcga   240
gtaactagtt aaccccttgg ggcctctaaa cgggtcttga aggggtttac cgaggggcta   300
gcgcagccgg gtaattccgg gaaaaaattt tattatagct actgggggag atatacttgt   360
tttcttttt acaaacaaat tttaaagaa taatttaaat ttattttttc ttggaaaata   420
aattggttat ggaattggaa tcttatgatt aactcaaagt aaaaatcatg gacatcttat   480
ctatataacc ctgactggaa tacgacagct cccaaa                             517

<210> SEQ ID NO 27
<211> LENGTH: 727
<212> TYPE: DNA
<213> ORGANISM: H. sapiens

<400> SEQUENCE: 27
gcgttctagc tttccttta tcgataggcc agatgggtct gtgggatgtg agatgaatac     60
aatgggccag aaagaaatcc tggctggagg tgaaaggaaa tcagaggggt tgtgggtcaa   120
ctttaggttc aggatttagg taccaatccc acctcgatca gtaagtcaca actagaagga   180
agcccctgtc tcagtttcct cacctgtaaa accaaagtgg ttgatccatg atcttccttg   240
gtttagatg attagaaatg atatgtagga ggcaatttgt gtgggatcag acataaaagc   300
ataagcttgc ggccgcactc gagtaactag ttaaccccctt ggggcctcta acggtaaag   360
gggttgacta gttactcgag tgcggccgca agcttatgct tttatgtctg atcccacaca   420
aattgcctcc tacatatcat ttctaatcat ctaaaagaaa ggaagatcat ggatcaacca   480
cttttggtttt acaggtgagg aaactgagga gggggtttcc tttgaagttg tgacttactg   540
tccaaggtga tttattctgt tttaaagttg atttacaacc cctccgattt cctttcacct   600

```
ccgggtttgg gaatttaata agaaattgcc cccccccccc tgcgggaaga aaaatcccca    660
atcgatcagg aaagctagaa ttcgggatcc cgagcatcac acctgactgg aatacgacca    720
gcttcca                                                              727
```

<210> SEQ ID NO 28
<211> LENGTH: 616
<212> TYPE: DNA
<213> ORGANISM: H. sapiens

<400> SEQUENCE: 28

```
cttcagcatg atcctgacga ggcactccaa gaggaacaca attaaaaaat cgcaatgcag     60
tgtgttgtag cagagcagag aaataacaaa gtaaataaac agatcacaat gtggagaggt    120
aatcagtttt acttgatgag gggagaaagg aggagagaca catgttgagt tttaaacaat    180
ctgtatatag gaccatagaa atggaagctg ccagacaga ctggcatgca tatgaaagag     240
atatgaaaca acatggttta agaactgcat agtttagaat ggttaaaata taagcttgcg    300
gccgcactcg agtaactagt tacccccttg gggcctctaa acttggggta aaggggggg    360 gggggggggcc cgattatatt tttaccttt aaaaatatgt ggtttaaaac ccttgggtta    420
ttttttcttt tcaacgggtg ggctcggggg gccttcttat caggaaaagg gtaaaaaatc    480
aaggggtcct cctttccccc caccctggg agggaatttt aattgaaaa ttacgggg      540 aaaacgggga ttatttat aaggggaaac ctctggggg acccagggtc gggacgggtg      600
ggatcaaaaa aacccc                                                    616
```

<210> SEQ ID NO 29
<211> LENGTH: 394
<212> TYPE: DNA
<213> ORGANISM: H. sapiens

<400> SEQUENCE: 29

```
cctttcctgc acttcccaga cttctgtcaa caatagccac aggaacaaag cctaaaggaa     60
actggactta gccaaaaata attctgtctg caagcttgcg gccgcactcg agtaactagt    120 taccccttg gggcctctaa acgggtcttg aggggttcta gttactcgag tgcggccgca    180
agcttgcaga cagaattatt tttggctaag tccagtttcc tttaggcttt gttcctgtgg    240
ctattgttga cagcataaga aactgtctgg tgaaagtgca ggaaagaatt cgtatccccg    300
agcatcacac ctgactggaa taccacagct cctctcctta atctgcccac ccccaatatt    360
tccctgtttt ttttttttt cttcctccat actt                                 394
```

<210> SEQ ID NO 30
<211> LENGTH: 569
<212> TYPE: DNA
<213> ORGANISM: H. sapiens

<400> SEQUENCE: 30

```
ggggttcttt cctgcctttc accagacagt ttcttatgct gtcaaaatag ccacaggaac     60
aaagcctaaa ggaaactgga cttagccaaa ataattctg tctgcaagct tgcggccgca    120
ctcgagtaac tagttaaccc cttggggcct ctaaacgggt cttgagggt tagaggcaag    180 taagtcgctc ttagagtttg ctactttgca gagtggttac ccataagact attttgggag    240
ggttgttgac gcactagacg acctagtgct acacttgtag ccgccggcgg aagcatcccc    300
tggaaaatac catcctagca gcttctcata aaaatcatac cctgtggatc ctttgcaagc    360
```

```
agaactgact gttgtccctg agtccttggg ggtcgcatcc atctccacac tggatatggg    420
gaacatcatt tgagtctctt catctccctg ttctcttaat ccatgtgtcc cactagtgga    480
tgtgcactcc aggccagtgt gcagagcttc tgtgaaagct gctggcactg agtccaggca    540
gggctgctgc ccccaggcac agctctgcc                                     569

<210> SEQ ID NO 31
<211> LENGTH: 547
<212> TYPE: DNA
<213> ORGANISM: H. sapiens

<400> SEQUENCE: 31
gcgatctaca actcaaatat ttagttagac cacttatacc agattcttat catttctgcc     60
tgaactattt gattttattg attaataaat tgtaactaag agttttaaaa tgccgcaatt    120
caaatttacc tttgaacatt aaaatattaa cccagagaat tatttataga ggagagccac    180
aagtcgctat ccaagtttgc tttactttgt agataatcag gggataatta tctatatttc    240
agaagcttgc ggccgcactc gagtaactag ttaaccccct tgggcctcta aacgcatggg    300
gttaaggtac tcgagagtgg gcgcaaggtt ctgaaatata gataattatc ctgattatca    360
acaaagtata gcaaacttgg tagcgctctt ataaaaaaaa ttcttgggga atatttttaa    420
gggttcaagg taaattggaa atggggtttt taaactaaat ttttaatata aaacataagc    480
aaagataaat cgtataaggc taataaatat tgattgtaaa ttgggagggg aaaaacacac    540
cccccaa                                                             547

<210> SEQ ID NO 32
<211> LENGTH: 506
<212> TYPE: DNA
<213> ORGANISM: H. sapiens

<400> SEQUENCE: 32
ggccgcacgg aacggccgct aaaccccaat acgaaaacaa aaggcgccgt aacaagccgc     60
ggccgcaccc gagtaacagc aaccccgggg ccccgcgggc tagggtcgct agttaacgag    120
gggggctgaa gcttaattac atgtaaaatg atatttaata tttttttagc ctctaagaat    180
atttttaaag taagttgtat tgattgactc cactgatgac tgactcctgc ctcgggaaag    240
gacgtgagtg aagtgcagct gctgcgcctg atgctgggac agccccgctc ccagatgtaa    300
agaacgcgac ttccacaaac ctggattttt tatgtacaac cctgaccgtg accgtttgct    360
atattccttt ttctatgaaa aatgggaat gataataaaa cagctttgac ttggaaaaac    420
caaaaaaaaa aaaaaaaaa aaaaaaaaa aaaaacacc cccagattct ttttttttgt    480
attttgcacc cccctacttt cacaaa                                        506

<210> SEQ ID NO 33
<211> LENGTH: 796
<212> TYPE: DNA
<213> ORGANISM: H. sapiens

<400> SEQUENCE: 33
gctcttttgc actttcacca gacagtttct tatgctgtca acaatagcca caggaacaaa     60
gcctaaagga aactggactt agccaaaaat aattctgtct gcaagcttgc ggccgcactc    120
gagtaactag ttaaccccct tgggcctcta aacgggcttt gaggggttca ctgaagcccg    180
ccgtggcggc gagaccctat tgggctgatt ggagaccagg aggcctcttg ggagaatg     240 gttcaggaat aaaaggcagg agcattgtag agattttcag ggaggcctga agtgaggttg    300
```

```
gagggaaccaa aggagaatgt ggggagagtg tgcagatgat cctggaagta gaactgaaaa    360
gggaaggaca ggttgggcag tggttaaacc ctgggcagga atgcctccta cggcatccct    420
gaggattcgt tgtgaggtac tgagtgccac tgctgggctt gggctgagtc accttggtgc    480
attctgcttt gcctgcacag actttgtgtg ccagagctgt gcccagagag gatggaggcc    540
tggtctcagg gcacctgggc ccagagtaag gcctgtggac ccaatctgag ggcagtggaa    600
gatactgtag gcccaaaga atgcccagcc tacagggctg tcaagtgcag ctgggtaaaa     660
aatggattga ggaattagtg ggggttggga ggcaagacct ggttggggaa tgaaacacag    720
agagagctca taaacatgga ccaagaaaat ccctctagta tcaacaccta ctctctggcc    780
aggcgatggc aaattc                                                     796

<210> SEQ ID NO 34
<211> LENGTH: 712
<212> TYPE: DNA
<213> ORGANISM: H. sapiens

<400> SEQUENCE: 34
tcgaagaagt aattcaaagt tcgcaggttc actgtggacc cccgagcaaa acaaacacct     60
agtcctaaag aggagggagc ctcacccacc ccccagcatg ggtcactgaa agggggcgat    120
gtctaagtca cgtgaatggg ttggcagaga atggtagaa gccgagacat aaggacagcc    180
tgcttccgag tgtgcaaagg aagtgaagcc agccagcacc agaccttgtg cagaccaccc    240
gcccccagtg gcagctgggg gagtggtcat cagttcaaga ccgtgggaag ggttacaaaa    300
aaagaagctt cgcggccgca ctgagtaact attaacccct tggggcctct aaacggtttg    360 ggggggggtta aaaagtcggg ggggggtcc ttttttttacc ccccccccct taggaaaaaa    420
aaagatgacc cccctccctc aagggaggct gatggtggtg gtggttcttt ctttgcacct    480
ccgaagggtc ctttaaggtc ggtttacagt ttttgcacca ttctttgtaa aaattccccc    540
cttatgcccc gggaaaaagg gggaaattta aaattcttct tttttttaaa aaaagggta    600 tttaattttg gaaagggttt cccaaaaacg gagagtttta aaggtaatca aatcggaccc    660 aactccctg tggaaaaaac catcccgcgg gaaaactaaa ttaaaaacca tc             712

<210> SEQ ID NO 35
<211> LENGTH: 771
<212> TYPE: DNA
<213> ORGANISM: H. sapiens

<400> SEQUENCE: 35
cgttctgaga ttccaaggta gagcaagaaa cggggataca gctgacgtct gtctcccct      60 gggagttatg tcactccttg atttaattcc ttctgacatt tccccatca tactttctgc    120 tcttcatcaa atacatccc tctcgaaaaa caaatgtgct tattgactac ccatgacaat    180
cttggaaatg gttgcaactg ttcatgtgta ggattaaaaa aaaattaaa acaaacaaa     240 acaaaaaaac cacaggcaaa caaaatctag agacctgtgc cataaggtca gatgagcacg    300
aaagggttgg ttagtccatc caaagtctca ggggttagg caagctagag ggatttattt     360 tccatttta ggccataggc aatttttgttt gcttaagctt cgcggccgcac tcgagtaact   420 agttaacccc ttggggcctc taaacggggg ggggggtaa gttaatcgag ggggggggg     480 ggaagcttaa gaaaacaaa aattgccgat gggctaaaaa atggaaaata tcccctagct   540
tgcctaaact ggaggacttt gactaacaca ggcccctttg ggagggtttt tgttttttg    600
```

```
gggggggggg tgtttaaatt ttttttttttt taacccaccc tgaacccatt ggggaaaaaa      660 attgttttttt tgagggggagg tttttgataa aaaaaaaaaa tggggggaaa aatgggcaaa     720
ggaataaatc cggggggggga atcccgcggg aaaactaaat taaaaaccat c               771
```

```
<210> SEQ ID NO 36
<211> LENGTH: 383
<212> TYPE: DNA
<213> ORGANISM: H. sapiens

<400> SEQUENCE: 36
ggcgatctgt gaacaagaca tgtgtaacaa atgcttttgc aaaatcatgt cgtcattaaa        60
gcagttactt taataaagat gggcttcaca agggggtttcc ggtacaacag ctgcagttaa      120
atatctatac actgttaaca tattttttaa aataagcttg cggccgcact cgagtaacta      180
gttaacccct tggggcctct aaacgggttt aagggggtact agttactcga gtgcggccgc     240
aagcttattt taaaaaatat gttaacagtg aatagtattt atctggagcg ctgcggggaa      300
cccttattaa aagcttttttt aataaagaat ttgcacaatg atctgattct tgggcaacca    360
tattgtggaa aaaccccccc cct                                             383
```

```
<210> SEQ ID NO 37
<211> LENGTH: 752
<212> TYPE: DNA
<213> ORGANISM: H. sapiens

<400> SEQUENCE: 37
ggcgattcac cagtgagtag attgcacaaa tcctgcagcc catctctgcc acagctcaaa       60
gtaagcaact tttactcgtg tattcttaaa tagtcccaag gatcaaatta tatctctgct     120
aaaacattgt taggcctaac ttcctcacca agaatgtgga ctttggtccg actgccaggt    180
taagagggcg tttcttgaaa acttttgttt cttttgtaggc acagtatgtg ctcattagat    240
ataaaagcta atggattaac taattccttt agcctttcca aaatagaggt ttcatggaac     300
tatctaggcc cataacaaat gtttctgtga tgaaacaaac tcaggaaact gtatattttc      360 ttttttccctt aaagcttgcg gccgcactcg agtaactagt taacccctttg gggcctctaa   420 acggtgaggg ggggggtaag gcggggggggg gggggcacgg atttaaggag gaaaatatag     480
ttccggaggg ttgtttcccc aaaaacaatt tgtgggcaa gaaacttcca gaacctgggg      540 aggggggggga atccttattt ttatctaatg ggagggaaaa aaaaattcca gaactcctaa   600
ccgggggggg gaccaaaccc atttttttggg ggggagggg ccacaagggg ttttaaaaaa    660
aaaaaaatgc cggggggctt taaaaaaact tttttttttt tttgtgggaa aaaaggggg     720 gaaattttttc gggggcccccc ccccccccccca ac                                752
```

```
<210> SEQ ID NO 38
<211> LENGTH: 30
<212> TYPE: PRT
<213> ORGANISM: H. sapiens

<400> SEQUENCE: 38

Ala Gln Thr Ser Met Lys Leu Leu Ser Cys Gly Ser Ala Val Pro His
1               5                   10                  15

Pro Trp Ser Pro Ser Leu Arg Val Glu Cys Ser Leu Ile Ser
            20                  25                  30
```

```
<210> SEQ ID NO 39
<211> LENGTH: 8
```

```
<212> TYPE: PRT
<213> ORGANISM: H. sapiens

<400> SEQUENCE: 39

Pro Val Ser Glu Pro Lys His Gln
1               5

<210> SEQ ID NO 40
<211> LENGTH: 33
<212> TYPE: PRT
<213> ORGANISM: H. sapiens

<400> SEQUENCE: 40

Val Ser Pro Asn Ile Asn Glu Ala Ser Val Leu Trp Leu Ser Ser
1               5                   10                  15

Pro Pro Leu Val Pro Ile Ser Gln Ser Gly Met Phe Ile Asn Phe Val
            20                  25                  30

Lys

<210> SEQ ID NO 41
<211> LENGTH: 11
<212> TYPE: PRT
<213> ORGANISM: H. sapiens

<400> SEQUENCE: 41

Leu Ser Phe Ser Thr Val Met Cys Lys Gly Leu
1               5                   10

<210> SEQ ID NO 42
<211> LENGTH: 26
<212> TYPE: PRT
<213> ORGANISM: H. sapiens

<400> SEQUENCE: 42

Ser Ala Phe Pro Leu Leu Cys Val Lys Asp Phe Lys Asn Leu Ile Gln
1               5                   10                  15

Ser Asn Ile Lys Tyr His Arg Cys Cys Asn
            20                  25

<210> SEQ ID NO 43
<211> LENGTH: 7
<212> TYPE: PRT
<213> ORGANISM: H. sapiens

<400> SEQUENCE: 43

Gln Leu Phe His Cys Tyr Val
1               5

<210> SEQ ID NO 44
<211> LENGTH: 43
<212> TYPE: PRT
<213> ORGANISM: H. sapiens

<400> SEQUENCE: 44

Phe Gly Tyr Arg Lys Met Ser Met Ile Phe Thr Leu Glu Leu Ile Thr
1               5                   10                  15

Lys Ile Pro Lys Phe His Asn Pro Lys Gln Val Tyr Phe Pro Arg Ala
            20                  25                  30

Lys Asn Lys Phe Asn Gly Asn Tyr Ser Ser Leu
        35                  40

<210> SEQ ID NO 45
```

<210> SEQ ID NO 45
<211> LENGTH: 7
<212> TYPE: PRT
<213> ORGANISM: H. sapiens

<400> SEQUENCE: 45

Ser Gly Thr Glu Arg Cys Pro
1               5

<210> SEQ ID NO 46
<211> LENGTH: 11
<212> TYPE: PRT
<213> ORGANISM: H. sapiens

<400> SEQUENCE: 46

Arg Val Gln Lys Asp Val His Asp Phe Tyr Ser
1               5                   10

<210> SEQ ID NO 47
<211> LENGTH: 5
<212> TYPE: PRT
<213> ORGANISM: H. sapiens

<400> SEQUENCE: 47

Leu Ser Phe Tyr Arg
1               5

<210> SEQ ID NO 48
<211> LENGTH: 45
<212> TYPE: PRT
<213> ORGANISM: H. sapiens

<400> SEQUENCE: 48

Arg Ser Ser Phe Pro Phe Ile Asp Arg Pro Asp Gly Ser Val Gly Cys
1               5                   10                  15

Glu Met Asn Thr Met Gly Gln Lys Glu Ile Leu Ala Gly Gly Glu Arg
            20                  25                  30

Lys Ser Glu Gly Leu Trp Val Asn Phe Arg Phe Arg Ile
        35                  40                  45

<210> SEQ ID NO 49
<211> LENGTH: 17
<212> TYPE: PRT
<213> ORGANISM: H. sapiens

<400> SEQUENCE: 49

Val Leu Ala Phe Leu Leu Ser Ile Gly Gln Met Gly Leu Trp Asp Val
1               5                   10                  15

Arg

<210> SEQ ID NO 50
<211> LENGTH: 14
<212> TYPE: PRT
<213> ORGANISM: H. sapiens

<400> SEQUENCE: 50

Leu Gln His Asp Pro Asp Glu Ala Leu Gln Glu Glu His Asn
1               5                   10

<210> SEQ ID NO 51
<211> LENGTH: 22
<212> TYPE: PRT
<213> ORGANISM: H. sapiens

<400> SEQUENCE: 51

```
Phe Ser Met Ile Leu Thr Arg His Ser Lys Arg Asn Thr Ile Lys Lys
1               5                   10                  15

Ser Gln Cys Ser Val Leu
            20
```

<210> SEQ ID NO 52
<211> LENGTH: 22
<212> TYPE: PRT
<213> ORGANISM: H. sapiens

<400> SEQUENCE: 52

```
Arg Gly Thr Pro Arg Gly Thr Gln Leu Lys Asn Arg Asn Ala Val Cys
1               5                   10                  15

Cys Ser Arg Ala Glu Lys
            20
```

<210> SEQ ID NO 53
<211> LENGTH: 11
<212> TYPE: PRT
<213> ORGANISM: H. sapiens

<400> SEQUENCE: 53

```
Pro Phe Leu His Phe Pro Asp Phe Cys Gln Gln
1               5                   10
```

<210> SEQ ID NO 54
<211> LENGTH: 17
<212> TYPE: PRT
<213> ORGANISM: H. sapiens

<400> SEQUENCE: 54

```
Leu Ser Cys Thr Ser Gln Thr Ser Val Asn Asn Ser His Arg Asn Lys
1               5                   10                  15

Ala
```

<210> SEQ ID NO 55
<211> LENGTH: 22
<212> TYPE: PRT
<213> ORGANISM: H. sapiens

<400> SEQUENCE: 55

```
Phe Pro Ala Leu Pro Arg Leu Leu Ser Thr Ile Ala Thr Gly Thr Lys
1               5                   10                  15

Pro Lys Gly Asn Trp Thr
            20
```

<210> SEQ ID NO 56
<211> LENGTH: 7
<212> TYPE: PRT
<213> ORGANISM: H. sapiens

<400> SEQUENCE: 56

```
Ala Ile Tyr Asn Ser Asn Ile
1               5
```

<210> SEQ ID NO 57
<211> LENGTH: 8
<212> TYPE: PRT
<213> ORGANISM: H. sapiens

<400> SEQUENCE: 57

```
Arg Ser Thr Thr Gln Ile Phe Ser
```

```
<210> SEQ ID NO 58
<211> LENGTH: 30
<212> TYPE: PRT
<213> ORGANISM: H. sapiens

<400> SEQUENCE: 58

Asp Leu Gln Leu Lys Tyr Leu Val Arg Pro Leu Ile Pro Asp Ser Tyr
1               5                   10                  15

His Phe Cys Leu Asn Tyr Leu Ile Leu Leu Ile Asn Lys Leu
            20                  25                  30

<210> SEQ ID NO 59
<211> LENGTH: 37
<212> TYPE: PRT
<213> ORGANISM: H. sapiens

<400> SEQUENCE: 59

Phe Lys Val Arg Arg Phe Thr Val Asp Pro Arg Ala Lys Gln Thr Pro
1               5                   10                  15

Ser Pro Lys Glu Glu Gly Ala Ser Pro Thr Pro Gln His Gly Ser Leu
            20                  25                  30

Lys Gly Gly Asp Val
        35

<210> SEQ ID NO 60
<211> LENGTH: 35
<212> TYPE: PRT
<213> ORGANISM: H. sapiens

<400> SEQUENCE: 60

Arg Arg Ser Asn Ser Lys Phe Ala Gly Ser Leu Trp Thr Pro Glu Gln
1               5                   10                  15

Asn Lys His Leu Val Leu Lys Arg Arg Glu Pro His Pro Pro Pro Ser
            20                  25                  30

Met Gly His
        35

<210> SEQ ID NO 61
<211> LENGTH: 19
<212> TYPE: PRT
<213> ORGANISM: H. sapiens

<400> SEQUENCE: 61

Glu Glu Val Ile Gln Ser Ser Gln Val His Cys Gly Pro Pro Ser Lys
1               5                   10                  15

Thr Asn Thr

<210> SEQ ID NO 62
<211> LENGTH: 6
<212> TYPE: PRT
<213> ORGANISM: H. sapiens

<400> SEQUENCE: 62

Arg Ser Glu Ile Pro Arg
1               5

<210> SEQ ID NO 63
<211> LENGTH: 54
<212> TYPE: PRT
<213> ORGANISM: H. sapiens
```

```
<400> SEQUENCE: 63

Val Leu Arg Phe Gln Gly Arg Ala Arg Asn Gly Asp Thr Ala Asp Val
1               5                   10                  15

Cys Leu Pro Leu Gly Val Met Ser Leu Leu Asp Leu Ile Pro Ser Asp
            20                  25                  30

Ile Phe Pro Ile Ile Leu Ser Ala Leu His Gln Asn Thr Ser Leu Ser
        35                  40                  45

Lys Asn Lys Cys Ala Tyr
    50

<210> SEQ ID NO 64
<211> LENGTH: 25
<212> TYPE: PRT
<213> ORGANISM: H. sapiens

<400> SEQUENCE: 64

Asp Ser Lys Val Glu Gln Glu Thr Gly Ile Gln Leu Thr Ser Val Ser
1               5                   10                  15

Pro Trp Glu Leu Cys His Ser Leu Ile
            20                  25

<210> SEQ ID NO 65
<211> LENGTH: 4
<212> TYPE: PRT
<213> ORGANISM: H. sapiens

<400> SEQUENCE: 65

Thr Arg His Val
1

<210> SEQ ID NO 66
<211> LENGTH: 23
<212> TYPE: PRT
<213> ORGANISM: H. sapiens

<400> SEQUENCE: 66

Ala Ile Cys Glu Gln Asp Met Cys Asn Lys Cys Phe Cys Lys Ile Met
1               5                   10                  15

Ser Ser Leu Lys Gln Leu Leu
            20

<210> SEQ ID NO 67
<211> LENGTH: 18
<212> TYPE: PRT
<213> ORGANISM: H. sapiens

<400> SEQUENCE: 67

Arg Ser Val Asn Lys Thr Cys Val Thr Asn Ala Phe Ala Lys Ser Cys
1               5                   10                  15

Arg His

<210> SEQ ID NO 68
<211> LENGTH: 30
<212> TYPE: PRT
<213> ORGANISM: H. sapiens

<400> SEQUENCE: 68

Gly Asp Ser Pro Val Ser Arg Leu His Lys Ser Cys Ser Pro Ser Leu
1               5                   10                  15

Pro Gln Leu Lys Val Ser Asn Phe Tyr Ser Cys Ile Leu Lys
```

<210> SEQ ID NO 69
<211> LENGTH: 4
<212> TYPE: PRT
<213> ORGANISM: H. sapiens

<400> SEQUENCE: 69

Ala Ile His Gln
1

<210> SEQ ID NO 70
<211> LENGTH: 5
<212> TYPE: PRT
<213> ORGANISM: H. sapiens

<400> SEQUENCE: 70

Arg Phe Thr Ser Glu
1               5

<210> SEQ ID NO 71
<211> LENGTH: 53
<212> TYPE: DNA
<213> ORGANISM: H. sapiens

<400> SEQUENCE: 71
tgtctctaac tggaaaacca agaaacagtt actatgctag aactgttttt tta         53

<210> SEQ ID NO 72
<211> LENGTH: 53
<212> TYPE: DNA
<213> ORGANISM: H. sapiens

<400> SEQUENCE: 72
tcagattgca gagcagccct gactgactct tgaagagtca ctcccaggcc ctt         53

<210> SEQ ID NO 73
<211> LENGTH: 53
<212> TYPE: DNA
<213> ORGANISM: H. sapiens

<400> SEQUENCE: 73
ccatagagct caagcaaaat ggcttaagtg ctggaaaaag daccccacac gag         53

<210> SEQ ID NO 74
<211> LENGTH: 53
<212> TYPE: DNA
<213> ORGANISM: H. sapiens

<400> SEQUENCE: 74
atgcatcaat ttcccacact ccagatacat ctagaactca gagtgctgtt aaa         53

<210> SEQ ID NO 75
<211> LENGTH: 53
<212> TYPE: DNA
<213> ORGANISM: H. sapiens

<400> SEQUENCE: 75
tgggctactt agatagaaaa ccctctatca agccagtcta gcaaggtctc act         53

<210> SEQ ID NO 76
<211> LENGTH: 53
<212> TYPE: DNA
<213> ORGANISM: H. sapiens

```
<400> SEQUENCE: 76
aacagaatac agtatgtaca ccattaaggt actttgctgt cttcatatga att          53

<210> SEQ ID NO 77
<211> LENGTH: 53
<212> TYPE: DNA
<213> ORGANISM: H. sapiens

<400> SEQUENCE: 77
taaataacaa gcaacgctgt gtaccaattg taaacattta ttaaattcta atc          53

<210> SEQ ID NO 78
<211> LENGTH: 53
<212> TYPE: DNA
<213> ORGANISM: H. sapiens

<400> SEQUENCE: 78
ctattctgtt gagcgctttt tatgatagaa tgagtattgg aaatagttaa atg          53

<210> SEQ ID NO 79
<211> LENGTH: 53
<212> TYPE: DNA
<213> ORGANISM: H. sapiens

<400> SEQUENCE: 79
ttcctatgag aaagcataat ttacttctgt tgagaaaaca cgtagatgaa cca          53

<210> SEQ ID NO 80
<211> LENGTH: 53
<212> TYPE: DNA
<213> ORGANISM: H. sapiens

<400> SEQUENCE: 80
taactgcaac atgcaatgtt taccccctgt gctatagagt gtctgacaat gaa          53

<210> SEQ ID NO 81
<211> LENGTH: 53
<212> TYPE: DNA
<213> ORGANISM: H. sapiens

<400> SEQUENCE: 81
aagtctgatt ctccttattt ccagagactg atgaaagcta caattaacac atg          53

<210> SEQ ID NO 82
<211> LENGTH: 53
<212> TYPE: DNA
<213> ORGANISM: H. sapiens

<400> SEQUENCE: 82
ttttattcta agtgccccga ttatgcagga atacctaaga cagccgccca ttt          53

<210> SEQ ID NO 83
<211> LENGTH: 53
<212> TYPE: DNA
<213> ORGANISM: H. sapiens

<400> SEQUENCE: 83
aaagtcagat agatagctag ataatacgat atacacacag ctaaagatga cag          53

<210> SEQ ID NO 84
<211> LENGTH: 53
<212> TYPE: DNA
```

<213> ORGANISM: H. sapiens

<400> SEQUENCE: 84
gaataaagca gtgtcttatg caatgtctac aacccatgaa gcataaaagg agc                53

<210> SEQ ID NO 85
<211> LENGTH: 53
<212> TYPE: DNA
<213> ORGANISM: H. sapiens

<400> SEQUENCE: 85
gaaatgtcag tgcgttttc aattacagta tactggtcac tggcaaacag gat                53

<210> SEQ ID NO 86
<211> LENGTH: 53
<212> TYPE: DNA
<213> ORGANISM: H. sapiens

<400> SEQUENCE: 86
tgacttagac aaaatctcac ctccttagca aggcagtcac aaacgtcact att                53

<210> SEQ ID NO 87
<211> LENGTH: 53
<212> TYPE: DNA
<213> ORGANISM: H. sapiens

<400> SEQUENCE: 87
acttctaccc tgattatgtt aggtaacttg aattggaaag aaaaatattt att                53

<210> SEQ ID NO 88
<211> LENGTH: 53
<212> TYPE: DNA
<213> ORGANISM: H. sapiens

<400> SEQUENCE: 88
ctttttactt catggcaagc tgctttgtat ttctaattaa gaaaacattc ctg                53

<210> SEQ ID NO 89
<211> LENGTH: 53
<212> TYPE: DNA
<213> ORGANISM: H. sapiens

<400> SEQUENCE: 89
ctggaccaag aatcataaga cccagtctat gagttgttaa aagtgagggt gaa                53

<210> SEQ ID NO 90
<211> LENGTH: 53
<212> TYPE: DNA
<213> ORGANISM: H. sapiens

<400> SEQUENCE: 90
tttctgtagg actgctgtgg tatgctctgg ggcccgctcc aattcccagt cac                53

<210> SEQ ID NO 91
<211> LENGTH: 53
<212> TYPE: DNA
<213> ORGANISM: H. sapiens

<400> SEQUENCE: 91
ctcacttcct cacacatccc tcaccgcttt cgctccagtc tctttggagg cat                53

<210> SEQ ID NO 92
<211> LENGTH: 53

```
<212> TYPE: DNA
<213> ORGANISM: H. sapiens

<400> SEQUENCE: 92
atttctctca gctggtcaaa taaacaagct cttctatcct cctgtagaga ggc      53

<210> SEQ ID NO 93
<211> LENGTH: 53
<212> TYPE: DNA
<213> ORGANISM: H. sapiens

<400> SEQUENCE: 93
taacaattaa agtcccatat catgtacttg agctcctggt ccatgcacca aat      53

<210> SEQ ID NO 94
<211> LENGTH: 53
<212> TYPE: DNA
<213> ORGANISM: H. sapiens

<400> SEQUENCE: 94
cttaggaaaa catgtactaa ccatccagca tctttgtttt ttttttaag agt       53

<210> SEQ ID NO 95
<211> LENGTH: 53
<212> TYPE: DNA
<213> ORGANISM: H. sapiens

<400> SEQUENCE: 95
ctctaaaaga gctggaagta tactacagac aattttcact gcacacttcc ttg      53

<210> SEQ ID NO 96
<211> LENGTH: 53
<212> TYPE: DNA
<213> ORGANISM: H. sapiens

<400> SEQUENCE: 96
caggccactg atcctgagta tgtgaaaccg accaatgctc tgacccgata aat      53

<210> SEQ ID NO 97
<211> LENGTH: 53
<212> TYPE: DNA
<213> ORGANISM: H. sapiens

<400> SEQUENCE: 97
tagtcagaca caaaccggtg ttatcaacac agaactgtca cgtatttgat ctg      53

<210> SEQ ID NO 98
<211> LENGTH: 53
<212> TYPE: DNA
<213> ORGANISM: H. sapiens

<400> SEQUENCE: 98
ctgggccagg ctctccctgc ccaattctgg taaatgtgtg ctagaggaaa cat      53

<210> SEQ ID NO 99
<211> LENGTH: 53
<212> TYPE: DNA
<213> ORGANISM: H. sapiens

<400> SEQUENCE: 99
atgtatacat tgaagcccta gcccccagaa gtgactctgg agatggtacc ttt      53

<210> SEQ ID NO 100
```

```
-continued

<211> LENGTH: 53
<212> TYPE: DNA
<213> ORGANISM: H. sapiens

<400> SEQUENCE: 100
accttttctc caacttttcc tgtctcagac tcttatctct attttttgttt act      53

<210> SEQ ID NO 101
<211> LENGTH: 53
<212> TYPE: DNA
<213> ORGANISM: H. sapiens

<400> SEQUENCE: 101
agattccagg gcctatccta aaaccacttg gaagagaatt acacagaggt agg       53

<210> SEQ ID NO 102
<211> LENGTH: 53
<212> TYPE: DNA
<213> ORGANISM: H. sapiens

<400> SEQUENCE: 102
ttacagagct cagaaacagt gctgctcgaa ttaaagcttc caggagtaag att       53

<210> SEQ ID NO 103
<211> LENGTH: 53
<212> TYPE: DNA
<213> ORGANISM: H. sapiens

<400> SEQUENCE: 103
tcacttctgc tgttgccacc aaccctctgc gtttcccttt gtcacttccc cct       53

<210> SEQ ID NO 104
<211> LENGTH: 53
<212> TYPE: DNA
<213> ORGANISM: H. sapiens

<400> SEQUENCE: 104
gcctaattag gttttcagta attcatagtc attggtcatt aggacaatca tac       53

<210> SEQ ID NO 105
<211> LENGTH: 53
<212> TYPE: DNA
<213> ORGANISM: H. sapiens

<400> SEQUENCE: 105
ataagaaaat gtaaaggttt ttgtctagtg aatatgatcc ctaatgtgtt tct       53

<210> SEQ ID NO 106
<211> LENGTH: 53
<212> TYPE: DNA
<213> ORGANISM: H. sapiens

<400> SEQUENCE: 106
gttaattaag gctcattaca taagaactga gattgaagta ttgtaaatag aaa       53

<210> SEQ ID NO 107
<211> LENGTH: 53
<212> TYPE: DNA
<213> ORGANISM: H. sapiens

<400> SEQUENCE: 107
acatgatctg taggatggca gcaatactta attgtatcag agcttgttgc tct       53
```

<210> SEQ ID NO 108
<211> LENGTH: 53
<212> TYPE: DNA
<213> ORGANISM: H. sapiens

<400> SEQUENCE: 108
tttgttgaat gcgctaaacc tgtctgctga gcacatacct gcagatgtat ctg    53

<210> SEQ ID NO 109
<211> LENGTH: 53
<212> TYPE: DNA
<213> ORGANISM: H. sapiens

<400> SEQUENCE: 109
acactaaatg gagacacgaa tctaaaagga tcaccggcaa cagccctaaa aga    53

<210> SEQ ID NO 110
<211> LENGTH: 53
<212> TYPE: DNA
<213> ORGANISM: H. sapiens

<400> SEQUENCE: 110
aatgaatact atggatctac aacttactta gaagtgaggc cttgagcata ata    53

<210> SEQ ID NO 111
<211> LENGTH: 53
<212> TYPE: DNA
<213> ORGANISM: H. sapiens

<400> SEQUENCE: 111
gtccctgcag gtgggggaag caggacagag gcctacctga ttccatcctc cct    53

<210> SEQ ID NO 112
<211> LENGTH: 53
<212> TYPE: DNA
<213> ORGANISM: H. sapiens

<400> SEQUENCE: 112
gcatataact ttgtcacaat tccagactac agagtggttg agccaggacc cat    53

<210> SEQ ID NO 113
<211> LENGTH: 53
<212> TYPE: DNA
<213> ORGANISM: H. sapiens

<400> SEQUENCE: 113
gagccaccga gttcacagtc tgttcaaggg gaactcaaga cattaaaatc aac    53

<210> SEQ ID NO 114
<211> LENGTH: 53
<212> TYPE: DNA
<213> ORGANISM: H. sapiens

<400> SEQUENCE: 114
ttaaacccaa gataggatat aaggagacct gttaaaaagt aaggtatctt aag    53

<210> SEQ ID NO 115
<211> LENGTH: 53
<212> TYPE: DNA
<213> ORGANISM: H. sapiens

<400> SEQUENCE: 115
cccagagttt caatgagagg agagtgacag aaacttactt gttacatatg atg    53

```
<210> SEQ ID NO 116
<211> LENGTH: 53
<212> TYPE: DNA
<213> ORGANISM: H. sapiens

<400> SEQUENCE: 116
aacagaaacg tgttctgact gacaatcgta agttgagtac tacctgaggt ttc      53

<210> SEQ ID NO 117
<211> LENGTH: 53
<212> TYPE: DNA
<213> ORGANISM: H. sapiens

<400> SEQUENCE: 117
cggccagatt aacaagtctg ggcttcagtc taaaagcaat gggagggact gaa      53

<210> SEQ ID NO 118
<211> LENGTH: 53
<212> TYPE: DNA
<213> ORGANISM: H. sapiens

<400> SEQUENCE: 118
aatcacataa atggtcttga atatagctgt taccaaaaca taagacaaaa caa      53

<210> SEQ ID NO 119
<211> LENGTH: 53
<212> TYPE: DNA
<213> ORGANISM: H. sapiens

<400> SEQUENCE: 119
agaaaaatct aataagagac cttcatagca ggcactatgc catgccctac aaa      53

<210> SEQ ID NO 120
<211> LENGTH: 53
<212> TYPE: DNA
<213> ORGANISM: H. sapiens

<400> SEQUENCE: 120
acagatgata tgtccaaact agttttgtaa agttctagtt cacacacctg aat      53

<210> SEQ ID NO 121
<211> LENGTH: 53
<212> TYPE: DNA
<213> ORGANISM: H. sapiens

<400> SEQUENCE: 121
ttcaacagtt attatcaagc atggacattt ccttgtgtca ggtcctgggt cag      53

<210> SEQ ID NO 122
<211> LENGTH: 53
<212> TYPE: DNA
<213> ORGANISM: H. sapiens

<400> SEQUENCE: 122
aactctagaa aaatatttct ccacagcttt cttataaagg taattcttgt caa      53

<210> SEQ ID NO 123
<211> LENGTH: 53
<212> TYPE: DNA
<213> ORGANISM: H. sapiens

<400> SEQUENCE: 123
tggataatgc cttgaaaaat gattttagta gctgatgcag aagccgtctg cgt      53
```

```
<210> SEQ ID NO 124
<211> LENGTH: 53
<212> TYPE: DNA
<213> ORGANISM: H. sapiens

<400> SEQUENCE: 124
tttttgcaag ctcaagctga tcattgcttt ttttttttcat tagaacgccc aca        53

<210> SEQ ID NO 125
<211> LENGTH: 53
<212> TYPE: DNA
<213> ORGANISM: H. sapiens

<400> SEQUENCE: 125
atacttaatt catatattac aatctgctga aacttaataa ctcctcatca tat        53

<210> SEQ ID NO 126
<211> LENGTH: 53
<212> TYPE: DNA
<213> ORGANISM: H. sapiens

<400> SEQUENCE: 126
tatatgaatc ttatagtttg gaaggactaa aaatcagcta gcaaatagct aaa        53

<210> SEQ ID NO 127
<211> LENGTH: 32
<212> TYPE: PRT
<213> ORGANISM: H. sapiens

<400> SEQUENCE: 127

Ser Pro Asn Ile Asn Glu Ala Ser Val Leu Trp Leu Ser Ser Pro
1               5                   10                  15

Pro Leu Val Pro Ile Ser Gln Ser Gly Met Phe Ile Asn Phe Val Lys
            20                  25                  30

<210> SEQ ID NO 128
<211> LENGTH: 36
<212> TYPE: PRT
<213> ORGANISM: H. sapiens

<400> SEQUENCE: 128

Phe Pro Ser Leu Phe Asn Cys Val Leu Glu Asp Phe Lys Asn Ile Leu
1               5                   10                  15

Ile Ser Ser Gln Ile Leu Asn Ile Met Leu Leu Val Ile Lys Leu Ala
            20                  25                  30

Ala Ala Leu Glu
        35

<210> SEQ ID NO 129
<211> LENGTH: 43
<212> TYPE: PRT
<213> ORGANISM: H. sapiens

<400> SEQUENCE: 129

Phe Gly Tyr Arg Lys Met Ser Met Ile Phe Thr Leu Glu Leu Ile Thr
1               5                   10                  15

Lys Ile Pro Lys Phe His Asn Pro Lys Gln Val Tyr Phe Pro Arg Ala
            20                  25                  30

Lys Asn Lys Phe Asn Gly Asn Tyr Ser Ser Leu
        35                  40
```

<210> SEQ ID NO 130
<211> LENGTH: 45
<212> TYPE: PRT
<213> ORGANISM: H. sapiens

<400> SEQUENCE: 130

Arg Ser Ser Phe Pro Phe Ile Asp Arg Pro Asp Gly Ser Val Gly Cys
1               5                   10                  15

Glu Met Asn Thr Met Gly Gln Lys Glu Ile Leu Ala Gly Gly Glu Arg
            20                  25                  30

Lys Ser Glu Gly Leu Trp Val Asn Phe Arg Phe Arg Ile
        35                  40                  45

<210> SEQ ID NO 131
<211> LENGTH: 22
<212> TYPE: PRT
<213> ORGANISM: H. sapiens

<400> SEQUENCE: 131

Arg Gly Thr Pro Arg Gly Thr Gln Leu Lys Asn Arg Asn Ala Val Cys
1               5                   10                  15

Cys Ser Arg Ala Glu Lys
            20

<210> SEQ ID NO 132
<211> LENGTH: 25
<212> TYPE: PRT
<213> ORGANISM: H. sapiens

<400> SEQUENCE: 132

Pro Phe Leu His Phe Pro Asp Phe Cys Gln Gln Pro Gln Glu Gln Ser
1               5                   10                  15

Leu Lys Glu Thr Gly Leu Ser Gln Lys
            20                  25

<210> SEQ ID NO 133
<211> LENGTH: 18
<212> TYPE: PRT
<213> ORGANISM: H. sapiens

<400> SEQUENCE: 133

Thr Thr Tyr Thr Arg Phe Leu Ser Phe Leu Pro Glu Leu Phe Asp Phe
1               5                   10                  15

Ile Asp

<210> SEQ ID NO 134
<211> LENGTH: 77
<212> TYPE: PRT
<213> ORGANISM: H. sapiens

<400> SEQUENCE: 134

Ala Trp Val Ile Glu Glu Trp Gly Glu Cys Ser Lys Ser Cys Glu Leu
1               5                   10                  15

Gly Trp Gln Arg Arg Leu Val Glu Cys Arg Asp Ile Asn Gly Gln Pro
            20                  25                  30

Ala Ser Glu Cys Ala Lys Glu Val Lys Pro Ala Ser Thr Arg Pro Cys
        35                  40                  45

Ala Asp His Pro Cys Pro Gln Trp Gln Leu Gly Glu Trp Ser Ser Cys
    50                  55                  60

Ser Lys Thr Cys Gly Lys Gly Tyr Lys Lys Arg Ser Leu

```
                65                  70                  75

<210> SEQ ID NO 135
<211> LENGTH: 55
<212> TYPE: PRT
<213> ORGANISM: H. sapiens

<400> SEQUENCE: 135

Arg Ser Glu Ile Ser Lys Val Glu Gln Glu Thr Gly Asn Thr Ala Asp
1               5                   10                  15

Val Cys Leu Pro Leu Gly Val Met Ser Leu Leu Asp Leu Ile Pro Ser
                20                  25                  30

Asp Ile Phe Pro Ile Ile Leu Ser Ala Leu His Gln Asn Thr Ser Leu
            35                  40                  45

Ser Lys Asn Lys Cys Ala Tyr
        50                  55

<210> SEQ ID NO 136
<211> LENGTH: 18
<212> TYPE: PRT
<213> ORGANISM: H. sapiens

<400> SEQUENCE: 136

Arg Ser Val Asn Lys Thr Cys Val Thr Asn Ala Phe Ala Lys Ser Cys
1               5                   10                  15

Arg His

<210> SEQ ID NO 137
<211> LENGTH: 29
<212> TYPE: PRT
<213> ORGANISM: H. sapiens

<400> SEQUENCE: 137

Arg Phe Thr Ser Glu Met Arg Ile Ala Gln Ile Leu Gln Pro Ile Ser
1               5                   10                  15

Ala Thr Ala Gln Ser Lys Gln Leu Leu Leu Val Tyr Ser
            20                  25

<210> SEQ ID NO 138
<211> LENGTH: 34
<212> TYPE: PRT
<213> ORGANISM: H. sapiens

<400> SEQUENCE: 138

Lys Ala Ala Lys His Asn His His Ile Leu Leu Lys Glu Leu Met Gly
1               5                   10                  15

Lys Lys Lys Gln Ala Pro Met Val Val Val Ser Pro Asn Trp Ala Leu
            20                  25                  30

His Cys

<210> SEQ ID NO 139
<211> LENGTH: 81
<212> TYPE: PRT
<213> ORGANISM: H. sapiens

<400> SEQUENCE: 139

Phe His Ser Val Leu Tyr Lys Tyr Thr Leu Leu Cys Val Leu Thr Trp
1               5                   10                  15

Ile Gln Tyr Phe Ser Tyr Phe Leu Phe Ser Thr Ile Val Thr Leu Lys
            20                  25                  30
```

```
Glu Thr Ala Ser Leu His Lys Thr Lys Gly Asn Ile Ala Cys Arg Phe
             35                  40                  45

Ala Leu His Cys Lys Glu His Thr Cys Leu Arg Gln Ser Ser Val Glu
         50                  55                  60

Pro Trp Thr Pro Ala Thr Glu Ile Pro Ile Val Gly Ser Ser Phe Ile
65                  70                  75                  80

Asn

<210> SEQ ID NO 140
<211> LENGTH: 10
<212> TYPE: PRT
<213> ORGANISM: H. sapiens

<400> SEQUENCE: 140

Lys Ala Cys Gly Arg Thr Arg Val Thr Ser
1               5                   10

<210> SEQ ID NO 141
<211> LENGTH: 20
<212> TYPE: PRT
<213> ORGANISM: H. sapiens

<400> SEQUENCE: 141

Pro Leu Gly Ala Ser Lys Arg Gly Gly Tyr Phe Gly Lys Gly Gly Gly
1               5                   10                  15

Pro Ile Phe Phe
            20

<210> SEQ ID NO 142
<211> LENGTH: 20
<212> TYPE: PRT
<213> ORGANISM: H. sapiens

<400> SEQUENCE: 142

Lys Lys Lys Thr Pro Trp Gly Pro Pro Arg Gly Gly Gly Glu Ile Leu
1               5                   10                  15

Phe Leu Lys Phe
            20

<210> SEQ ID NO 143
<211> LENGTH: 15
<212> TYPE: PRT
<213> ORGANISM: H. sapiens

<400> SEQUENCE: 143

Arg Thr Asn Ile Tyr Phe Val Glu Ser Leu Met Arg Lys Lys Tyr
1               5                   10                  15

<210> SEQ ID NO 144
<211> LENGTH: 6
<212> TYPE: PRT
<213> ORGANISM: H. sapiens

<400> SEQUENCE: 144

Ile Ile Thr Thr Trp Ile
1               5

<210> SEQ ID NO 145
<211> LENGTH: 12
<212> TYPE: PRT
<213> ORGANISM: H. sapiens

<400> SEQUENCE: 145
```

Gly Met Thr Lys Ala Arg Leu Gln Arg Gly Gly Ser
1               5                   10

<210> SEQ ID NO 146
<211> LENGTH: 6
<212> TYPE: PRT
<213> ORGANISM: H. sapiens

<400> SEQUENCE: 146

Glu Gln Lys Arg Cys Arg
1               5

<210> SEQ ID NO 147
<211> LENGTH: 22
<212> TYPE: PRT
<213> ORGANISM: H. sapiens

<400> SEQUENCE: 147

Ser Phe Cys Leu Val Ala Gln Gln Phe Pro Thr Pro Gly Pro His Leu
1               5                   10                  15

Ser Glu Trp Asn Val His
            20

<210> SEQ ID NO 148
<211> LENGTH: 21
<212> TYPE: PRT
<213> ORGANISM: H. sapiens

<400> SEQUENCE: 148

Phe Arg Glu Ile Arg Val Glu Glu Arg Asn Glu Lys Gln Pro Asn Thr
1               5                   10                  15

Thr Ile Thr Phe Cys
            20

<210> SEQ ID NO 149
<211> LENGTH: 34
<212> TYPE: PRT
<213> ORGANISM: H. sapiens

<400> SEQUENCE: 149

Trp Gly Lys Lys Asn Arg His Gln Trp Leu Leu Tyr His Leu Thr Gly
1               5                   10                  15

Leu Tyr Ile Ala Ser Phe Ile Pro Ser Phe Ile Ser Thr His Cys Cys
            20                  25                  30

Val Phe

<210> SEQ ID NO 150
<211> LENGTH: 14
<212> TYPE: PRT
<213> ORGANISM: H. sapiens

<400> SEQUENCE: 150

Leu Gly Phe Asn Thr Ser Ala Thr Ser Tyr Phe Leu Pro Leu
1               5                   10

<210> SEQ ID NO 151
<211> LENGTH: 12
<212> TYPE: PRT
<213> ORGANISM: H. sapiens

<400> SEQUENCE: 151

Arg Lys Leu His Leu Cys Ile Lys Gln Lys Val Ile

```
1               5                   10
```

<210> SEQ ID NO 152
<211> LENGTH: 13
<212> TYPE: PRT
<213> ORGANISM: H. sapiens

<400> SEQUENCE: 152

```
Leu Val Gly Leu Leu Cys Ile Ala Lys Asn Ile Leu Ala
1               5                   10
```

<210> SEQ ID NO 153
<211> LENGTH: 31
<212> TYPE: PRT
<213> ORGANISM: H. sapiens

<400> SEQUENCE: 153

```
Asp Asn Gln Val Ser Asn His Gly His Leu Leu Arg Arg Phe Gln Leu
1               5                   10                  15

Trp Asp Leu Leu Leu Ser Thr Lys Lys Leu Ala Ala Ala Leu Glu
            20                  25                  30
```

<210> SEQ ID NO 154
<211> LENGTH: 41
<212> TYPE: PRT
<213> ORGANISM: H. sapiens

<400> SEQUENCE: 154

```
Leu Val Asn Pro Leu Gly Pro Leu Asn Gly Gly Val Ile Leu Val Lys
1               5                   10                  15

Gly Gly Gly Pro Phe Phe Phe Lys Lys Lys Pro Leu Gly Asp Pro
            20                  25                  30

Pro Gly Gly Gly Gly Lys Phe Cys Phe
        35                  40
```

<210> SEQ ID NO 155
<211> LENGTH: 9
<212> TYPE: PRT
<213> ORGANISM: H. sapiens

<400> SEQUENCE: 155

```
Ser Phe Lys Glu Leu Ile Tyr Thr Leu
1               5
```

<210> SEQ ID NO 156
<211> LENGTH: 8
<212> TYPE: PRT
<213> ORGANISM: H. sapiens

<400> SEQUENCE: 156

```
Gly Lys Asn Thr Glu Tyr Glu Ser
1               5
```

<210> SEQ ID NO 157
<211> LENGTH: 6
<212> TYPE: PRT
<213> ORGANISM: H. sapiens

<400> SEQUENCE: 157

```
Pro His Gly Tyr Lys Glu
1               5
```

<210> SEQ ID NO 158

<211> LENGTH: 17
<212> TYPE: PRT
<213> ORGANISM: H. sapiens

<400> SEQUENCE: 158

```
Leu Arg Leu Asp Cys Lys Gly Gly Pro Pro Glu Asn Arg Lys Asp
1               5                   10                  15

Ala
```

<210> SEQ ID NO 159
<211> LENGTH: 34
<212> TYPE: PRT
<213> ORGANISM: H. sapiens

<400> SEQUENCE: 159

```
Glu Leu Arg Arg Gly Met Lys Ser Ser Gln Thr Gln Pro Ser His Phe
1               5                   10                  15

Ala Glu Arg Val Asp Gly Glu Lys Lys Thr Gly Thr Asn Gly Cys Cys
                20                  25                  30

Ile Thr
```

<210> SEQ ID NO 160
<211> LENGTH: 12
<212> TYPE: PRT
<213> ORGANISM: H. sapiens

<400> SEQUENCE: 160

```
Leu Gly Phe Thr Leu Leu Val Ser Phe Arg Pro Leu
1               5                   10
```

<210> SEQ ID NO 161
<211> LENGTH: 31
<212> TYPE: PRT
<213> ORGANISM: H. sapiens

<400> SEQUENCE: 161

```
Val His Ile Val Val Cys Phe Asn Leu Asp Ser Ile Leu Gln Leu Leu
1               5                   10                  15

Leu Ile Phe Tyr His Cys Asn Ile Lys Gly Asn Cys Ile Ser Ala
                20                  25                  30
```

<210> SEQ ID NO 162
<211> LENGTH: 44
<212> TYPE: PRT
<213> ORGANISM: H. sapiens

<400> SEQUENCE: 162

```
Val Cys Phe Ala Leu Gln Arg Thr Tyr Leu Leu Lys Thr Ile Lys Cys
1               5                   10                  15

Arg Thr Met Asp Thr Cys Tyr Gly Asp Ser Asn Cys Gly Ile Phe Phe
                20                  25                  30

Tyr Gln Leu Lys Ser Leu Arg Pro His Ser Ser Asn
                35                  40
```

<210> SEQ ID NO 163
<211> LENGTH: 6
<212> TYPE: PRT
<213> ORGANISM: H. sapiens

<400> SEQUENCE: 163

```
Leu Thr Pro Trp Gly Leu
1               5
```

<210> SEQ ID NO 164
<211> LENGTH: 6
<212> TYPE: PRT
<213> ORGANISM: H. sapiens

<400> SEQUENCE: 164

Thr Gly Gly Leu Phe Trp
1               5

<210> SEQ ID NO 165
<211> LENGTH: 31
<212> TYPE: PRT
<213> ORGANISM: H. sapiens

<400> SEQUENCE: 165

Arg Gly Gly Ala His Phe Phe Leu Lys Lys Asn Pro Leu Gly Thr
1               5                   10                  15

Pro Gln Gly Gly Gly Gly Asn Phe Val Phe Lys Val Leu Lys Asn
            20                  25                  30

<210> SEQ ID NO 166
<211> LENGTH: 25
<212> TYPE: PRT
<213> ORGANISM: H. sapiens

<400> SEQUENCE: 166

Tyr Ile Leu Cys Arg Glu Ser Tyr Glu Glu Lys Ile Leu Ser Met Asn
1               5                   10                  15

His Asn His Met Asp Ile Arg Asn Asp
            20                  25

<210> SEQ ID NO 167
<211> LENGTH: 14
<212> TYPE: PRT
<213> ORGANISM: H. sapiens

<400> SEQUENCE: 167

Ile Ala Lys Gly Gly Val Pro Leu Arg Thr Glu Lys Met Pro
1               5                   10

<210> SEQ ID NO 168
<211> LENGTH: 7
<212> TYPE: PRT
<213> ORGANISM: H. sapiens

<400> SEQUENCE: 168

Lys Ser Tyr Ser Val Lys Tyr
1               5

<210> SEQ ID NO 169
<211> LENGTH: 5
<212> TYPE: PRT
<213> ORGANISM: H. sapiens

<400> SEQUENCE: 169

Ile Ser Ser Leu Leu
1               5

<210> SEQ ID NO 170
<211> LENGTH: 9
<212> TYPE: PRT
<213> ORGANISM: H. sapiens

```
<400> SEQUENCE: 170

Leu Ser Leu Arg Pro His Ser Ser Asn
1               5

<210> SEQ ID NO 171
<211> LENGTH: 6
<212> TYPE: PRT
<213> ORGANISM: H. sapiens

<400> SEQUENCE: 171

Leu Thr Pro Trp Gly Leu
1               5

<210> SEQ ID NO 172
<211> LENGTH: 15
<212> TYPE: PRT
<213> ORGANISM: H. sapiens

<400> SEQUENCE: 172

Thr Gly Leu Glu Gly Phe Leu Val Thr Arg Val Arg Pro Gln Ala
1               5                   10                  15

<210> SEQ ID NO 173
<211> LENGTH: 4
<212> TYPE: PRT
<213> ORGANISM: H. sapiens

<400> SEQUENCE: 173

Leu Gln Ala Thr
1

<210> SEQ ID NO 174
<211> LENGTH: 6
<212> TYPE: PRT
<213> ORGANISM: H. sapiens

<400> SEQUENCE: 174

Tyr Leu Ile Phe Asp Cys
1               5

<210> SEQ ID NO 175
<211> LENGTH: 6
<212> TYPE: PRT
<213> ORGANISM: H. sapiens

<400> SEQUENCE: 175

Ser Pro Leu Ile His Asn
1               5

<210> SEQ ID NO 176
<211> LENGTH: 6
<212> TYPE: PRT
<213> ORGANISM: H. sapiens

<400> SEQUENCE: 176

Thr Val Met Glu Ile Ala
1               5

<210> SEQ ID NO 177
<211> LENGTH: 8
<212> TYPE: PRT
<213> ORGANISM: H. sapiens

<400> SEQUENCE: 177
```

```
Ile Arg Ile Pro Glu His His Thr
1               5
```

\<210\> SEQ ID NO 178
\<211\> LENGTH: 32
\<212\> TYPE: PRT
\<213\> ORGANISM: H. sapiens

\<400\> SEQUENCE: 178

```
Leu Ala Thr Arg Ser Phe Arg Gln Ala Arg Gly Ile Tyr Phe Pro Phe
1               5                   10                  15
Leu Gly His Arg Gln Phe Cys Leu Leu Lys Leu Ala Ala Ala Leu Glu
            20                  25                  30
```

\<210\> SEQ ID NO 179
\<211\> LENGTH: 8
\<212\> TYPE: PRT
\<213\> ORGANISM: H. sapiens

\<400\> SEQUENCE: 179

```
Leu Val Asn Pro Leu Gly Pro Leu
1               5
```

\<210\> SEQ ID NO 180
\<211\> LENGTH: 9
\<212\> TYPE: PRT
\<213\> ORGANISM: H. sapiens

\<400\> SEQUENCE: 180

```
Ala Cys Gly Arg Thr Arg Val Thr Ser
1               5
```

\<210\> SEQ ID NO 181
\<211\> LENGTH: 12
\<212\> TYPE: PRT
\<213\> ORGANISM: H. sapiens

\<400\> SEQUENCE: 181

```
Pro Leu Gly Ala Ser Lys Arg Val Leu Arg Gly Ser
1               5                   10
```

\<210\> SEQ ID NO 182
\<211\> LENGTH: 15
\<212\> TYPE: PRT
\<213\> ORGANISM: H. sapiens

\<400\> SEQUENCE: 182

```
Leu Leu Glu Cys Gly Arg Lys Leu Asn Tyr Lys Gln His Asp Ile
1               5                   10                  15
```

\<210\> SEQ ID NO 183
\<211\> LENGTH: 12
\<212\> TYPE: PRT
\<213\> ORGANISM: H. sapiens

\<400\> SEQUENCE: 183

```
Tyr Leu Thr Ala Asn Lys Asn Ile Phe Lys Val Leu
1               5                   10
```

\<210\> SEQ ID NO 184
\<211\> LENGTH: 5
\<212\> TYPE: PRT
\<213\> ORGANISM: H. sapiens

\<400\> SEQUENCE: 184

Tyr Thr Ile Lys Gln
1               5

<210> SEQ ID NO 185
<211> LENGTH: 27
<212> TYPE: PRT
<213> ORGANISM: H. sapiens

<400> SEQUENCE: 185

Leu Glu Phe Gly Ser Pro Ser Ile Thr Pro Asp Trp Gln His Ala Pro
1               5                   10                  15

Leu Gly Lys Leu Glu Gly Phe Ile Phe His Phe
            20                  25

<210> SEQ ID NO 186
<211> LENGTH: 16
<212> TYPE: PRT
<213> ORGANISM: H. sapiens

<400> SEQUENCE: 186

Ala Ile Gly Asn Phe Val Cys Leu Ser Leu Arg Pro His Ser Ser Asn
1               5                   10                  15

<210> SEQ ID NO 187
<211> LENGTH: 6
<212> TYPE: PRT
<213> ORGANISM: H. sapiens

<400> SEQUENCE: 187

Leu Thr Pro Trp Gly Leu
1               5

<210> SEQ ID NO 188
<211> LENGTH: 25
<212> TYPE: PRT
<213> ORGANISM: H. sapiens

<400> SEQUENCE: 188

Arg Thr Leu Lys Ile Leu Phe Ser Gln Ile Leu Asn Ile Ile Val Ala
1               5                   10                  15

Val Ile Lys Leu Ala Ala Ala Leu Glu
            20                  25

<210> SEQ ID NO 189
<211> LENGTH: 11
<212> TYPE: PRT
<213> ORGANISM: H. sapiens

<400> SEQUENCE: 189

Leu Val Asn Pro Leu Gly Pro Leu Asn Gly Ser
1               5                   10

<210> SEQ ID NO 190
<211> LENGTH: 21
<212> TYPE: PRT
<213> ORGANISM: H. sapiens

<400> SEQUENCE: 190

Gly Val Pro Ser Tyr Ser Ser Ala Ala Ala Ser Leu Ile Thr Ser Asn
1               5                   10                  15

Met Ile Phe Asn Ile
            20

<210> SEQ ID NO 191
<211> LENGTH: 36
<212> TYPE: PRT
<213> ORGANISM: H. sapiens

<400> SEQUENCE: 191

Leu Leu Ile Arg Ile Phe Leu Lys Ser Ser Asn Thr Gln Leu Asn Ser
1               5                   10                  15
Asp Gly Asn Ser Leu Asn Ser Asp Pro Arg Ala Ser His Leu Thr Gly
            20                  25                  30
Asn Thr Leu Leu
            35

<210> SEQ ID NO 192
<211> LENGTH: 9
<212> TYPE: PRT
<213> ORGANISM: H. sapiens

<400> SEQUENCE: 192

Arg Asp Leu Phe Ser Ile Phe Arg Pro
1               5

<210> SEQ ID NO 193
<211> LENGTH: 5
<212> TYPE: PRT
<213> ORGANISM: H. sapiens

<400> SEQUENCE: 193

Ala Ile Leu Phe Ala
1               5

<210> SEQ ID NO 194
<211> LENGTH: 9
<212> TYPE: PRT
<213> ORGANISM: H. sapiens

<400> SEQUENCE: 194

Ala Cys Gly Arg Thr Arg Val Thr Ser
1               5

<210> SEQ ID NO 195
<211> LENGTH: 6
<212> TYPE: PRT
<213> ORGANISM: H. sapiens

<400> SEQUENCE: 195

Pro Leu Gly Ala Ser Asn
1               5

<210> SEQ ID NO 196
<211> LENGTH: 18
<212> TYPE: PRT
<213> ORGANISM: H. sapiens

<400> SEQUENCE: 196

Asn Phe Val Leu Leu Lys Arg Glu Asn Gln Lys Tyr Ile Leu Trp Pro
1               5                   10                  15
His Val

<210> SEQ ID NO 197
<211> LENGTH: 10
<212> TYPE: PRT
<213> ORGANISM: H. sapiens

<400> SEQUENCE: 197

Asp Tyr Asn Lys Met Leu Cys Ser Met Lys
1               5                   10

<210> SEQ ID NO 198
<211> LENGTH: 9
<212> TYPE: PRT
<213> ORGANISM: H. sapiens

<400> SEQUENCE: 198

Ala Cys Gly Arg Thr Arg Val Thr Ser
1               5

<210> SEQ ID NO 199
<211> LENGTH: 46
<212> TYPE: PRT
<213> ORGANISM: H. sapiens

<400> SEQUENCE: 199

Pro Leu Gly Ala Ser Lys Arg Val Leu Lys Gly Phe Thr Glu Gly Leu
1               5                   10                  15

Ala Gln Pro Gly Asn Ser Gly Lys Lys Phe Tyr Tyr Ser Tyr Trp Gly
            20                  25                  30

Arg Tyr Thr Cys Phe Leu Phe Tyr Lys Gln Ile Phe Lys Glu
        35                  40                  45

<210> SEQ ID NO 200
<211> LENGTH: 22
<212> TYPE: PRT
<213> ORGANISM: H. sapiens

<400> SEQUENCE: 200

Phe Lys Phe Ile Phe Ser Trp Lys Ile Asn Trp Leu Trp Asn Trp Asn
1               5                   10                  15

Leu Met Ile Asn Ser Lys
            20

<210> SEQ ID NO 201
<211> LENGTH: 18
<212> TYPE: PRT
<213> ORGANISM: H. sapiens

<400> SEQUENCE: 201

Lys Ser Trp Thr Ser Tyr Leu Tyr Asn Pro Asp Trp Asn Thr Thr Ala
1               5                   10                  15

Ser Gln

<210> SEQ ID NO 202
<211> LENGTH: 5
<212> TYPE: PRT
<213> ORGANISM: H. sapiens

<400> SEQUENCE: 202

Phe Leu Leu Leu Ser
1               5

<210> SEQ ID NO 203
<211> LENGTH: 34
<212> TYPE: PRT
<213> ORGANISM: H. sapiens

<400> SEQUENCE: 203

```
Ser Leu Arg Phe Gln Asn Ser Ile Thr Leu Asn Lys Ser Ile Phe Gln
1               5                   10                  15

Gly Gln Lys Ile Asn Leu Met Val Ile Ile Gln Val Phe Lys Ile Leu
            20                  25                  30

Phe Cys

<210> SEQ ID NO 204
<211> LENGTH: 22
<212> TYPE: PRT
<213> ORGANISM: H. sapiens

<400> SEQUENCE: 204

Lys Glu Lys Ile Lys Ser Ile Ser Ser Gly Leu Met Phe Arg Thr Ile
1               5                   10                  15

Ile Lys Cys Phe Val Pro
            20

<210> SEQ ID NO 205
<211> LENGTH: 8
<212> TYPE: PRT
<213> ORGANISM: H. sapiens

<400> SEQUENCE: 205

Asn Lys Leu Ala Ala Ala Leu Glu
1               5

<210> SEQ ID NO 206
<211> LENGTH: 11
<212> TYPE: PRT
<213> ORGANISM: H. sapiens

<400> SEQUENCE: 206

Leu Val Asn Pro Leu Gly Pro Leu Asn Gly Ser
1               5                   10

<210> SEQ ID NO 207
<211> LENGTH: 6
<212> TYPE: PRT
<213> ORGANISM: H. sapiens

<400> SEQUENCE: 207

Arg Gly Leu Pro Arg Gly
1               5

<210> SEQ ID NO 208
<211> LENGTH: 39
<212> TYPE: PRT
<213> ORGANISM: H. sapiens

<400> SEQUENCE: 208

Arg Ser Arg Val Ile Pro Gly Lys Asn Phe Ile Ile Ala Thr Gly Gly
1               5                   10                  15

Asp Ile Leu Val Phe Phe Phe Thr Asn Lys Phe Leu Lys Asn Asn Leu
            20                  25                  30

Asn Leu Phe Phe Leu Gly Lys
            35

<210> SEQ ID NO 209
<211> LENGTH: 8
<212> TYPE: PRT
<213> ORGANISM: H. sapiens
```

<400> SEQUENCE: 209

Ile Gly Tyr Gly Ile Gly Ile Leu
1               5

<210> SEQ ID NO 210
<211> LENGTH: 23
<212> TYPE: PRT
<213> ORGANISM: H. sapiens

<400> SEQUENCE: 210

Leu Thr Gln Ser Lys Asn His Gly His Leu Ile Tyr Ile Thr Leu Thr
1               5                   10                  15

Gly Ile Arg Gln Leu Pro Lys
            20

<210> SEQ ID NO 211
<211> LENGTH: 5
<212> TYPE: PRT
<213> ORGANISM: H. sapiens

<400> SEQUENCE: 211

Asp Ser Lys Ile Pro
1               5

<210> SEQ ID NO 212
<211> LENGTH: 9
<212> TYPE: PRT
<213> ORGANISM: H. sapiens

<400> SEQUENCE: 212

Thr Ser Leu Phe Ser Lys Gly Lys Lys
1               5

<210> SEQ ID NO 213
<211> LENGTH: 26
<212> TYPE: PRT
<213> ORGANISM: H. sapiens

<400> SEQUENCE: 213

Leu Phe Lys Ser Leu Lys Phe Cys Phe Val Lys Arg Lys Ser Lys
1               5                   10                  15

Val Tyr Pro Leu Ala Ser Cys Leu Gly Leu
            20                  25

<210> SEQ ID NO 214
<211> LENGTH: 15
<212> TYPE: PRT
<213> ORGANISM: H. sapiens

<400> SEQUENCE: 214

Asn Ala Leu Phe His Glu Ile Ser Leu Arg Pro His Ser Ser Asn
1               5                   10                  15

<210> SEQ ID NO 215
<211> LENGTH: 6
<212> TYPE: PRT
<213> ORGANISM: H. sapiens

<400> SEQUENCE: 215

Leu Thr Pro Trp Gly Leu
1               5

<210> SEQ ID NO 216

```
<211> LENGTH: 14
<212> TYPE: PRT
<213> ORGANISM: H. sapiens

<400> SEQUENCE: 216

Thr Gly Leu Glu Gly Val Tyr Arg Gly Ala Ser Ala Ala Gly
1               5                   10

<210> SEQ ID NO 217
<211> LENGTH: 7
<212> TYPE: PRT
<213> ORGANISM: H. sapiens

<400> SEQUENCE: 217

Phe Arg Glu Lys Ile Leu Leu
1               5

<210> SEQ ID NO 218
<211> LENGTH: 15
<212> TYPE: PRT
<213> ORGANISM: H. sapiens

<400> SEQUENCE: 218

Leu Leu Gly Glu Ile Tyr Leu Phe Ser Phe Leu Gln Thr Asn Phe
1               5                   10                  15

<210> SEQ ID NO 219
<211> LENGTH: 17
<212> TYPE: PRT
<213> ORGANISM: H. sapiens

<400> SEQUENCE: 219

Ile Tyr Phe Phe Leu Glu Asn Lys Leu Val Met Glu Leu Glu Ser Tyr
1               5                   10                  15

Asp

<210> SEQ ID NO 220
<211> LENGTH: 11
<212> TYPE: PRT
<213> ORGANISM: H. sapiens

<400> SEQUENCE: 220

Leu Lys Val Lys Ile Met Asp Ile Leu Ser Ile
1               5                   10

<210> SEQ ID NO 221
<211> LENGTH: 7
<212> TYPE: PRT
<213> ORGANISM: H. sapiens

<400> SEQUENCE: 221

Leu Glu Tyr Asp Ser Phe Pro
1               5

<210> SEQ ID NO 222
<211> LENGTH: 7
<212> TYPE: PRT
<213> ORGANISM: H. sapiens

<400> SEQUENCE: 222

Ala Arg Trp Val Cys Gly Met
1               5

<210> SEQ ID NO 223
```

<211> LENGTH: 13
<212> TYPE: PRT
<213> ORGANISM: H. sapiens

<400> SEQUENCE: 223

Asp Glu Tyr Asn Gly Pro Glu Arg Asn Pro Gly Trp Arg
1               5                   10

<210> SEQ ID NO 224
<211> LENGTH: 10
<212> TYPE: PRT
<213> ORGANISM: H. sapiens

<400> SEQUENCE: 224

Lys Glu Ile Arg Gly Val Val Gly Gln Leu
1               5                   10

<210> SEQ ID NO 225
<211> LENGTH: 34
<212> TYPE: PRT
<213> ORGANISM: H. sapiens

<400> SEQUENCE: 225

Val Gln Asp Leu Gly Thr Asn Pro Thr Ser Ile Ser Lys Ser Gln Leu
1               5                   10                  15

Glu Gly Ser Pro Cys Leu Ser Phe Leu Thr Cys Lys Thr Lys Val Val
            20                  25                  30

Asp Pro

<210> SEQ ID NO 226
<211> LENGTH: 7
<212> TYPE: PRT
<213> ORGANISM: H. sapiens

<400> SEQUENCE: 226

Ser Ser Leu Val Leu Asp Asp
1               5

<210> SEQ ID NO 227
<211> LENGTH: 22
<212> TYPE: PRT
<213> ORGANISM: H. sapiens

<400> SEQUENCE: 227

Tyr Val Gly Gly Asn Leu Cys Gly Ile Arg His Lys Ser Ile Ser Leu
1               5                   10                  15

Arg Pro His Ser Ser Asn
            20

<210> SEQ ID NO 228
<211> LENGTH: 6
<212> TYPE: PRT
<213> ORGANISM: H. sapiens

<400> SEQUENCE: 228

Leu Thr Pro Trp Gly Leu
1               5

<210> SEQ ID NO 229
<211> LENGTH: 19
<212> TYPE: PRT
<213> ORGANISM: H. sapiens

<400> SEQUENCE: 229

```
Thr Val Lys Gly Leu Thr Ser Tyr Ser Ala Ala Ala Ser Leu Cys
1               5                   10                  15

Phe Tyr Val

<210> SEQ ID NO 230
<211> LENGTH: 28
<212> TYPE: PRT
<213> ORGANISM: H. sapiens

<400> SEQUENCE: 230

Ser His Thr Asn Cys Leu Leu His Ile Ile Ser Asn His Leu Lys Glu
1               5                   10                  15

Arg Lys Ile Met Asp Gln Pro Leu Trp Phe Tyr Arg
            20                  25

<210> SEQ ID NO 231
<211> LENGTH: 5
<212> TYPE: PRT
<213> ORGANISM: H. sapiens

<400> SEQUENCE: 231

Gly Gly Gly Phe Leu
1               5

<210> SEQ ID NO 232
<211> LENGTH: 30
<212> TYPE: PRT
<213> ORGANISM: H. sapiens

<400> SEQUENCE: 232

Ser Cys Asp Leu Leu Ser Lys Val Ile Tyr Ser Val Leu Lys Leu Ile
1               5                   10                  15

Tyr Asn Pro Ser Asp Phe Leu Ser Pro Pro Gly Leu Gly Ile
            20                  25                  30

<210> SEQ ID NO 233
<211> LENGTH: 18
<212> TYPE: PRT
<213> ORGANISM: H. sapiens

<400> SEQUENCE: 233

Glu Ile Ala Pro Pro Leu Arg Glu Glu Lys Ser Pro Ile Asp Gln
1               5                   10                  15

Glu Ser

<210> SEQ ID NO 234
<211> LENGTH: 16
<212> TYPE: PRT
<213> ORGANISM: H. sapiens

<400> SEQUENCE: 234

Asn Ser Gly Ser Arg Ala Ser His Leu Thr Gly Ile Arg Pro Ala Ser
1               5                   10                  15

<210> SEQ ID NO 235
<211> LENGTH: 11
<212> TYPE: PRT
<213> ORGANISM: H. sapiens

<400> SEQUENCE: 235

Val Pro Ile Pro Pro Arg Ser Val Ser His Asn
1               5                   10
```

<210> SEQ ID NO 236
<211> LENGTH: 23
<212> TYPE: PRT
<213> ORGANISM: H. sapiens

<400> SEQUENCE: 236

Lys Glu Ala Pro Val Ser Val Ser Ser Pro Val Lys Pro Lys Trp Leu
1               5                   10                  15

Ile His Asp Leu Pro Trp Phe
            20

<210> SEQ ID NO 237
<211> LENGTH: 6
<212> TYPE: PRT
<213> ORGANISM: H. sapiens

<400> SEQUENCE: 237

Met Ile Arg Asn Asp Met
1               5

<210> SEQ ID NO 238
<211> LENGTH: 11
<212> TYPE: PRT
<213> ORGANISM: H. sapiens

<400> SEQUENCE: 238

Glu Ala Ile Cys Val Gly Ser Asp Ile Lys Ala
1               5                   10

<210> SEQ ID NO 239
<211> LENGTH: 9
<212> TYPE: PRT
<213> ORGANISM: H. sapiens

<400> SEQUENCE: 239

Ala Cys Gly Arg Thr Arg Val Thr Ser
1               5

<210> SEQ ID NO 240
<211> LENGTH: 7
<212> TYPE: PRT
<213> ORGANISM: H. sapiens

<400> SEQUENCE: 240

Pro Leu Gly Ala Ser Lys Arg
1               5

<210> SEQ ID NO 241
<211> LENGTH: 28
<212> TYPE: PRT
<213> ORGANISM: H. sapiens

<400> SEQUENCE: 241

Leu Val Thr Arg Val Arg Pro Gln Ala Tyr Ala Phe Met Ser Asp Pro
1               5                   10                  15

Thr Gln Ile Ala Ser Tyr Ile Ser Phe Leu Ile Ile
            20                  25

<210> SEQ ID NO 242
<211> LENGTH: 31
<212> TYPE: PRT
<213> ORGANISM: H. sapiens

-continued

<400> SEQUENCE: 242

Lys Lys Gly Arg Ser Trp Ile Asn His Phe Gly Phe Thr Gly Glu Glu
1               5                   10                  15

Thr Glu Glu Gly Val Ser Phe Glu Val Val Thr Tyr Cys Pro Arg
            20                  25                  30

<210> SEQ ID NO 243
<211> LENGTH: 4
<212> TYPE: PRT
<213> ORGANISM: H. sapiens

<400> SEQUENCE: 243

Phe Ile Leu Phe
1

<210> SEQ ID NO 244
<211> LENGTH: 44
<212> TYPE: PRT
<213> ORGANISM: H. sapiens

<400> SEQUENCE: 244

Phe Thr Thr Pro Pro Ile Ser Phe His Leu Arg Val Trp Glu Phe Asn
1               5                   10                  15

Lys Lys Leu Pro Pro Pro Cys Gly Lys Lys Asn Pro Gln Ser Ile
            20                  25                  30

Arg Lys Ala Arg Ile Arg Asp Pro Glu His His Thr
        35                  40

<210> SEQ ID NO 245
<211> LENGTH: 7
<212> TYPE: PRT
<213> ORGANISM: H. sapiens

<400> SEQUENCE: 245

Leu Glu Tyr Asp Gln Leu Pro
1               5

<210> SEQ ID NO 246
<211> LENGTH: 35
<212> TYPE: PRT
<213> ORGANISM: H. sapiens

<400> SEQUENCE: 246

Ile Gln Trp Ala Arg Lys Lys Ser Trp Leu Glu Val Lys Gly Asn Gln
1               5                   10                  15

Arg Gly Cys Gly Ser Thr Leu Gly Ser Gly Phe Arg Tyr Gln Ser His
            20                  25                  30

Leu Asp Gln
        35

<210> SEQ ID NO 247
<211> LENGTH: 14
<212> TYPE: PRT
<213> ORGANISM: H. sapiens

<400> SEQUENCE: 247

Val Thr Thr Arg Arg Lys Pro Leu Ser Gln Phe Pro His Leu
1               5                   10

<210> SEQ ID NO 248
<211> LENGTH: 4
<212> TYPE: PRT

<213> ORGANISM: H. sapiens

<400> SEQUENCE: 248

Asn Gln Ser Gly
1

<210> SEQ ID NO 249
<211> LENGTH: 8
<212> TYPE: PRT
<213> ORGANISM: H. sapiens

<400> SEQUENCE: 249

Ser Met Ile Phe Leu Gly Phe Arg
1               5

<210> SEQ ID NO 250
<211> LENGTH: 14
<212> TYPE: PRT
<213> ORGANISM: H. sapiens

<400> SEQUENCE: 250

Leu Glu Met Ile Cys Arg Arg Gln Phe Val Trp Asp Gln Thr
1               5                   10

<210> SEQ ID NO 251
<211> LENGTH: 9
<212> TYPE: PRT
<213> ORGANISM: H. sapiens

<400> SEQUENCE: 251

Lys His Lys Leu Ala Ala Ala Leu Glu
1               5

<210> SEQ ID NO 252
<211> LENGTH: 14
<212> TYPE: PRT
<213> ORGANISM: H. sapiens

<400> SEQUENCE: 252

Leu Val Asn Pro Leu Gly Pro Leu Asn Gly Lys Gly Val Asp
1               5                   10

<210> SEQ ID NO 253
<211> LENGTH: 24
<212> TYPE: PRT
<213> ORGANISM: H. sapiens

<400> SEQUENCE: 253

Leu Leu Glu Cys Gly Arg Lys Leu Met Leu Leu Cys Leu Ile Pro His
1               5                   10                  15

Lys Leu Pro Pro Thr Tyr His Phe
            20

<210> SEQ ID NO 254
<211> LENGTH: 28
<212> TYPE: PRT
<213> ORGANISM: H. sapiens

<400> SEQUENCE: 254

Ser Ser Lys Arg Lys Glu Asp His Gly Ser Thr Thr Leu Val Leu Gln
1               5                   10                  15

Val Arg Lys Leu Arg Arg Gly Phe Pro Leu Lys Leu
            20                  25

<210> SEQ ID NO 255
<211> LENGTH: 64
<212> TYPE: PRT
<213> ORGANISM: H. sapiens

<400> SEQUENCE: 255

Leu Thr Val Gln Gly Asp Leu Phe Cys Phe Lys Val Asp Leu Gln Pro
1               5                   10                  15

Leu Arg Phe Pro Phe Thr Ser Gly Phe Gly Asn Leu Ile Arg Asn Cys
            20                  25                  30

Pro Pro Pro Ala Gly Arg Lys Ile Pro Asn Arg Ser Gly Lys Leu
        35                  40                  45

Glu Phe Gly Ile Pro Ser Ile Thr Pro Asp Trp Asn Thr Thr Ser Phe
    50                  55                  60

<210> SEQ ID NO 256
<211> LENGTH: 17
<212> TYPE: PRT
<213> ORGANISM: H. sapiens

<400> SEQUENCE: 256

Lys Ile Ala Met Gln Cys Val Val Ala Glu Gln Arg Asn Asn Lys Val
1               5                   10                  15

Lys

<210> SEQ ID NO 257
<211> LENGTH: 22
<212> TYPE: PRT
<213> ORGANISM: H. sapiens

<400> SEQUENCE: 257

Gln Ile Thr Met Trp Arg Gly Asn Gln Phe Tyr Leu Met Arg Gly Glu
1               5                   10                  15

Arg Arg Arg Asp Thr Cys
            20

<210> SEQ ID NO 258
<211> LENGTH: 9
<212> TYPE: PRT
<213> ORGANISM: H. sapiens

<400> SEQUENCE: 258

Val Leu Asn Asn Leu Tyr Ile Gly Pro
1               5

<210> SEQ ID NO 259
<211> LENGTH: 15
<212> TYPE: PRT
<213> ORGANISM: H. sapiens

<400> SEQUENCE: 259

Lys Trp Lys Leu Ala Arg Gln Thr Gly Met His Met Lys Glu Ile
1               5                   10                  15

<210> SEQ ID NO 260
<211> LENGTH: 4
<212> TYPE: PRT
<213> ORGANISM: H. sapiens

<400> SEQUENCE: 260

Asn Asn Met Val
1

<210> SEQ ID NO 261
<211> LENGTH: 17
<212> TYPE: PRT
<213> ORGANISM: H. sapiens

<400> SEQUENCE: 261

Glu Leu His Ser Leu Glu Trp Leu Lys Tyr Lys Leu Ala Ala Ala Leu
1               5                   10                  15

Glu

<210> SEQ ID NO 262
<211> LENGTH: 11
<212> TYPE: PRT
<213> ORGANISM: H. sapiens

<400> SEQUENCE: 262

Leu Val Asn Pro Leu Gly Pro Leu Asn Leu Gly
1               5                   10

<210> SEQ ID NO 263
<211> LENGTH: 40
<212> TYPE: PRT
<213> ORGANISM: H. sapiens

<400> SEQUENCE: 263

Lys Gly Gly Gly Gly Pro Ile Ile Phe Leu Pro Phe Lys Asn Met
1               5                   10                  15

Trp Phe Lys Thr Leu Gly Leu Phe Phe Leu Phe Asn Gly Trp Ala Arg
            20                  25                  30

Gly Ala Phe Leu Ser Gly Lys Gly
        35                  40

<210> SEQ ID NO 264
<211> LENGTH: 15
<212> TYPE: PRT
<213> ORGANISM: H. sapiens

<400> SEQUENCE: 264

Lys Ile Lys Gly Ser Ser Phe Pro Pro Thr Pro Gly Arg Glu Phe
1               5                   10                  15

<210> SEQ ID NO 265
<211> LENGTH: 31
<212> TYPE: PRT
<213> ORGANISM: H. sapiens

<400> SEQUENCE: 265

Leu Glu Asn Leu Arg Gly Lys Thr Gly Ile Ile Leu Leu Arg Gly Asn
1               5                   10                  15

Leu Trp Gly Tyr Pro Gly Ser Gly Arg Val Gly Ser Lys Lys Pro
            20                  25                  30

<210> SEQ ID NO 266
<211> LENGTH: 7
<212> TYPE: PRT
<213> ORGANISM: H. sapiens

<400> SEQUENCE: 266

Gln Ser Arg Glu Ile Thr Lys
1               5

<210> SEQ ID NO 267
<211> LENGTH: 13
<212> TYPE: PRT
<213> ORGANISM: H. sapiens

<400> SEQUENCE: 267

Asn Asn Arg Ser Gln Cys Gly Glu Val Ile Ser Phe Thr
1               5                   10

<210> SEQ ID NO 268
<211> LENGTH: 11
<212> TYPE: PRT
<213> ORGANISM: H. sapiens

<400> SEQUENCE: 268

Gly Glu Lys Gly Gly Glu Thr His Val Glu Phe
1               5                   10

<210> SEQ ID NO 269
<211> LENGTH: 4
<212> TYPE: PRT
<213> ORGANISM: H. sapiens

<400> SEQUENCE: 269

Thr Ile Cys Ile
1

<210> SEQ ID NO 270
<211> LENGTH: 14
<212> TYPE: PRT
<213> ORGANISM: H. sapiens

<400> SEQUENCE: 270

Asp His Arg Asn Gly Ser Trp Pro Asp Arg Leu Ala Cys Ile
1               5                   10

<210> SEQ ID NO 271
<211> LENGTH: 13
<212> TYPE: PRT
<213> ORGANISM: H. sapiens

<400> SEQUENCE: 271

Lys Arg Tyr Glu Thr Thr Trp Phe Lys Asn Cys Ile Val
1               5                   10

<210> SEQ ID NO 272
<211> LENGTH: 10
<212> TYPE: PRT
<213> ORGANISM: H. sapiens

<400> SEQUENCE: 272

Asn Ile Ser Leu Arg Pro His Ser Ser Asn
1               5                   10

<210> SEQ ID NO 273
<211> LENGTH: 6
<212> TYPE: PRT
<213> ORGANISM: H. sapiens

<400> SEQUENCE: 273

Leu Thr Pro Trp Gly Leu
1               5

<210> SEQ ID NO 274
<211> LENGTH: 73

```
<212> TYPE: PRT
<213> ORGANISM: H. sapiens

<400> SEQUENCE: 274

Thr Trp Gly Lys Arg Gly Gly Gly Ala Arg Leu Tyr Phe Tyr Leu
1               5                   10                  15

Leu Lys Ile Cys Gly Leu Lys Pro Leu Gly Tyr Phe Phe Ser Thr
            20                  25                  30

Gly Gly Leu Gly Gly Pro Ser Tyr Gln Glu Lys Gly Lys Ser Arg
        35                  40                  45

Gly Pro Pro Phe Pro Pro Leu Gly Asn Phe Asn Trp Lys Ile
    50                  55                  60

Tyr Gly Gly Lys Arg Gly Leu Phe Tyr
65                  70

<210> SEQ ID NO 275
<211> LENGTH: 18
<212> TYPE: PRT
<213> ORGANISM: H. sapiens

<400> SEQUENCE: 275

Gly Glu Thr Ser Gly Gly Thr Gln Gly Arg Asp Gly Trp Asp Gln Lys
1               5                   10                  15

Asn Pro

<210> SEQ ID NO 276
<211> LENGTH: 11
<212> TYPE: PRT
<213> ORGANISM: H. sapiens

<400> SEQUENCE: 276

Gln Ser Lys Ile Thr Asp His Asn Val Glu Arg
1               5                   10

<210> SEQ ID NO 277
<211> LENGTH: 49
<212> TYPE: PRT
<213> ORGANISM: H. sapiens

<400> SEQUENCE: 277

Ser Val Leu Leu Asp Glu Gly Arg Lys Glu Arg His Met Leu Ser
1               5                   10                  15

Phe Lys Gln Ser Val Tyr Arg Thr Ile Glu Met Glu Ala Gly Gln Thr
            20                  25                  30

Asp Trp His Ala Tyr Glu Arg Asp Met Lys Gln His Gly Leu Arg Thr
        35                  40                  45

Ala

<210> SEQ ID NO 278
<211> LENGTH: 6
<212> TYPE: PRT
<213> ORGANISM: H. sapiens

<400> SEQUENCE: 278

Phe Arg Met Val Lys Ile
1               5

<210> SEQ ID NO 279
<211> LENGTH: 9
<212> TYPE: PRT
<213> ORGANISM: H. sapiens
```

```
<400> SEQUENCE: 279

Ala Cys Gly Arg Thr Arg Val Thr Ser
1               5

<210> SEQ ID NO 280
<211> LENGTH: 22
<212> TYPE: PRT
<213> ORGANISM: H. sapiens

<400> SEQUENCE: 280

Pro Leu Gly Ala Ser Lys Leu Gly Val Lys Gly Gly Gly Gly Pro
1               5                   10                  15

Asp Tyr Ile Phe Thr Phe
            20

<210> SEQ ID NO 281
<211> LENGTH: 4
<212> TYPE: PRT
<213> ORGANISM: H. sapiens

<400> SEQUENCE: 281

Lys Tyr Val Val
1

<210> SEQ ID NO 282
<211> LENGTH: 69
<212> TYPE: PRT
<213> ORGANISM: H. sapiens

<400> SEQUENCE: 282

Asn Pro Trp Val Ile Phe Ser Phe Gln Arg Val Gly Ser Gly Gly Leu
1               5                   10                  15

Leu Ile Arg Lys Arg Val Lys Asn Gln Gly Val Leu Leu Ser Pro His
                20                  25                  30

Pro Trp Glu Gly Ile Leu Ile Gly Lys Phe Thr Gly Glu Asn Gly Asp
            35                  40                  45

Tyr Phe Ile Lys Gly Lys Pro Leu Gly Val Pro Arg Val Gly Thr Gly
        50                  55                  60

Gly Ile Lys Lys Thr
65

<210> SEQ ID NO 283
<211> LENGTH: 14
<212> TYPE: PRT
<213> ORGANISM: H. sapiens

<400> SEQUENCE: 283

Pro Gln Glu Gln Ser Leu Lys Glu Thr Gly Leu Ser Gln Lys
1               5                   10

<210> SEQ ID NO 284
<211> LENGTH: 13
<212> TYPE: PRT
<213> ORGANISM: H. sapiens

<400> SEQUENCE: 284

Phe Cys Leu Gln Ala Cys Gly Arg Thr Arg Val Thr Ser
1               5                   10

<210> SEQ ID NO 285
<211> LENGTH: 33
```

```
<212> TYPE: PRT
<213> ORGANISM: H. sapiens

<400> SEQUENCE: 285

Pro Leu Gly Ala Ser Lys Arg Val Leu Arg Gly Ser Ser Tyr Ser Ser
1               5                   10                  15

Ala Ala Ala Ser Leu Gln Thr Glu Leu Phe Leu Ala Lys Ser Ser Phe
            20                  25                  30

Leu

<210> SEQ ID NO 286
<211> LENGTH: 10
<212> TYPE: PRT
<213> ORGANISM: H. sapiens

<400> SEQUENCE: 286

Ala Leu Phe Leu Trp Leu Leu Thr Ala
1               5                   10

<210> SEQ ID NO 287
<211> LENGTH: 4
<212> TYPE: PRT
<213> ORGANISM: H. sapiens

<400> SEQUENCE: 287

Glu Thr Val Trp
1

<210> SEQ ID NO 288
<211> LENGTH: 40
<212> TYPE: PRT
<213> ORGANISM: H. sapiens

<400> SEQUENCE: 288

Lys Cys Arg Lys Glu Phe Val Ser Pro Ser Ile Thr Pro Asp Trp Asn
1               5                   10                  15

Thr Thr Ala Pro Leu Leu Asn Leu Pro Thr Pro Asn Ile Ser Leu Phe
            20                  25                  30

Phe Phe Phe Phe Phe Leu His Thr
            35                  40

<210> SEQ ID NO 289
<211> LENGTH: 19
<212> TYPE: PRT
<213> ORGANISM: H. sapiens

<400> SEQUENCE: 289

Arg Lys Leu Asp Leu Ala Lys Asn Asn Ser Val Cys Lys Leu Ala Ala
1               5                   10                  15

Ala Leu Glu

<210> SEQ ID NO 290
<211> LENGTH: 11
<212> TYPE: PRT
<213> ORGANISM: H. sapiens

<400> SEQUENCE: 290

Leu Val Asn Pro Leu Gly Pro Leu Asn Gly Ser
1               5                   10

<210> SEQ ID NO 291
<211> LENGTH: 32
```

```
<212> TYPE: PRT
<213> ORGANISM: H. sapiens

<400> SEQUENCE: 291

Gly Val Leu Val Thr Arg Val Arg Pro Gln Ala Cys Arg Gln Asn Tyr
1               5                   10                  15

Phe Trp Leu Ser Pro Val Ser Phe Arg Leu Cys Ser Cys Gly Tyr Cys
                20                  25                  30

<210> SEQ ID NO 292
<211> LENGTH: 48
<212> TYPE: PRT
<213> ORGANISM: H. sapiens

<400> SEQUENCE: 292

Gln His Lys Lys Leu Ser Gly Glu Ser Ala Gly Lys Asn Ser Tyr Pro
1               5                   10                  15

Arg Ala Ser His Leu Thr Gly Ile Pro Gln Leu Leu Ser Leu Ile Cys
                20                  25                  30

Pro Pro Pro Ile Phe Pro Cys Phe Phe Phe Ser Ser Ile Leu
                35                  40                  45

<210> SEQ ID NO 293
<211> LENGTH: 15
<212> TYPE: PRT
<213> ORGANISM: H. sapiens

<400> SEQUENCE: 293

Pro Lys Ile Ile Leu Ser Ala Ser Leu Arg Pro His Ser Ser Asn
1               5                   10                  15

<210> SEQ ID NO 294
<211> LENGTH: 6
<212> TYPE: PRT
<213> ORGANISM: H. sapiens

<400> SEQUENCE: 294

Leu Thr Pro Trp Gly Leu
1               5

<210> SEQ ID NO 295
<211> LENGTH: 6
<212> TYPE: PRT
<213> ORGANISM: H. sapiens

<400> SEQUENCE: 295

Thr Gly Leu Glu Gly Phe
1               5

<210> SEQ ID NO 296
<211> LENGTH: 15
<212> TYPE: PRT
<213> ORGANISM: H. sapiens

<400> SEQUENCE: 296

Leu Leu Glu Cys Gly Arg Lys Leu Ala Asp Arg Ile Ile Phe Gly
1               5                   10                  15

<210> SEQ ID NO 297
<211> LENGTH: 34
<212> TYPE: PRT
<213> ORGANISM: H. sapiens

<400> SEQUENCE: 297
```

```
Val Gln Phe Pro Leu Gly Phe Pro Val Ala Ile Val Asp Ser Ile
1               5                   10                  15

Arg Asn Cys Leu Val Lys Val Gln Glu Arg Ile Arg Ile Pro Glu His
            20                  25                  30

His Thr
```

<210> SEQ ID NO 298
<211> LENGTH: 8
<212> TYPE: PRT
<213> ORGANISM: H. sapiens

<400> SEQUENCE: 298

```
Leu Glu Tyr His Ser Ser Ser Pro
1               5
```

<210> SEQ ID NO 299
<211> LENGTH: 17
<212> TYPE: PRT
<213> ORGANISM: H. sapiens

<400> SEQUENCE: 299

```
Ser Ala His Pro Gln Tyr Phe Pro Val Phe Phe Phe Leu Pro Pro
1               5                   10                  15

Tyr
```

<210> SEQ ID NO 300
<211> LENGTH: 12
<212> TYPE: PRT
<213> ORGANISM: H. sapiens

<400> SEQUENCE: 300

```
Leu Asp His Leu Tyr Gln Ile Leu Ile Ile Ser Ala
1               5                   10
```

<210> SEQ ID NO 301
<211> LENGTH: 5
<212> TYPE: PRT
<213> ORGANISM: H. sapiens

<400> SEQUENCE: 301

```
Leu Ile Asn Cys Asn
1               5
```

<210> SEQ ID NO 302
<211> LENGTH: 8
<212> TYPE: PRT
<213> ORGANISM: H. sapiens

<400> SEQUENCE: 302

```
Asn Ala Ala Ile Gln Ile Tyr Leu
1               5
```

<210> SEQ ID NO 303
<211> LENGTH: 4
<212> TYPE: PRT
<213> ORGANISM: H. sapiens

<400> SEQUENCE: 303

```
Thr Leu Lys Tyr
1
```

<210> SEQ ID NO 304

```
<211> LENGTH: 21
<212> TYPE: PRT
<213> ORGANISM: H. sapiens

<400> SEQUENCE: 304

Pro Arg Glu Leu Phe Ile Glu Glu Ser His Lys Ser Leu Ser Lys Phe
1               5                   10                  15

Ala Leu Leu Cys Arg
            20

<210> SEQ ID NO 305
<211> LENGTH: 17
<212> TYPE: PRT
<213> ORGANISM: H. sapiens

<400> SEQUENCE: 305

Ser Gly Asp Asn Tyr Leu Tyr Phe Arg Ser Leu Arg Pro His Ser Ser
1               5                   10                  15

Asn

<210> SEQ ID NO 306
<211> LENGTH: 6
<212> TYPE: PRT
<213> ORGANISM: H. sapiens

<400> SEQUENCE: 306

Leu Thr Pro Trp Gly Leu
1               5

<210> SEQ ID NO 307
<211> LENGTH: 17
<212> TYPE: PRT
<213> ORGANISM: H. sapiens

<400> SEQUENCE: 307

Thr His Gly Val Lys Val Leu Glu Ser Gly Arg Lys Val Leu Lys Tyr
1               5                   10                  15

Arg

<210> SEQ ID NO 308
<211> LENGTH: 21
<212> TYPE: PRT
<213> ORGANISM: H. sapiens

<400> SEQUENCE: 308

Leu Ser Thr Lys Tyr Ser Lys Leu Gly Ser Ala Leu Ile Lys Lys Ile
1               5                   10                  15

Leu Gly Glu Ile Phe
            20

<210> SEQ ID NO 309
<211> LENGTH: 10
<212> TYPE: PRT
<213> ORGANISM: H. sapiens

<400> SEQUENCE: 309

Gly Phe Lys Val Asn Trp Lys Trp Gly Phe
1               5                   10

<210> SEQ ID NO 310
<211> LENGTH: 5
<212> TYPE: PRT
<213> ORGANISM: H. sapiens
```

```
<400> SEQUENCE: 310

Thr Lys Phe Leu Ile
1               5

<210> SEQ ID NO 311
<211> LENGTH: 13
<212> TYPE: PRT
<213> ORGANISM: H. sapiens

<400> SEQUENCE: 311

Asn Ile Ser Lys Asp Lys Ser Tyr Lys Ala Asn Lys Tyr
1               5                   10

<210> SEQ ID NO 312
<211> LENGTH: 7
<212> TYPE: PRT
<213> ORGANISM: H. sapiens

<400> SEQUENCE: 312

Ile Gly Arg Gly Lys Thr His
1               5

<210> SEQ ID NO 313
<211> LENGTH: 18
<212> TYPE: PRT
<213> ORGANISM: H. sapiens

<400> SEQUENCE: 313

Thr Thr Tyr Thr Arg Phe Leu Ser Phe Leu Pro Glu Leu Phe Asp Phe
1               5                   10                  15

Ile Asp

<210> SEQ ID NO 314
<211> LENGTH: 17
<212> TYPE: PRT
<213> ORGANISM: H. sapiens

<400> SEQUENCE: 314

Ile Val Thr Lys Ser Phe Lys Met Pro Gln Phe Lys Phe Thr Phe Glu
1               5                   10                  15

His

<210> SEQ ID NO 315
<211> LENGTH: 8
<212> TYPE: PRT
<213> ORGANISM: H. sapiens

<400> SEQUENCE: 315

Asn Ile Asn Pro Glu Asn Tyr Leu
1               5

<210> SEQ ID NO 316
<211> LENGTH: 34
<212> TYPE: PRT
<213> ORGANISM: H. sapiens

<400> SEQUENCE: 316

Arg Arg Ala Thr Ser Arg Tyr Pro Ser Leu Leu Tyr Phe Val Asp Asn
1               5                   10                  15

Gln Gly Ile Ile Ile Tyr Ile Ser Glu Ala Cys Gly Arg Thr Arg Val
            20                  25                  30
```

Thr Ser

<210> SEQ ID NO 317
<211> LENGTH: 19
<212> TYPE: PRT
<213> ORGANISM: H. sapiens

<400> SEQUENCE: 317

Pro Leu Gly Ala Ser Lys Arg Met Gly Leu Arg Tyr Ser Arg Val Gly
1               5                   10                  15

Ala Arg Phe

<210> SEQ ID NO 318
<211> LENGTH: 19
<212> TYPE: PRT
<213> ORGANISM: H. sapiens

<400> SEQUENCE: 318

Asn Ile Asp Asn Tyr Pro Asp Tyr Gln Gln Ser Ile Ala Asn Leu Val
1               5                   10                  15

Ala Leu Leu

<210> SEQ ID NO 319
<211> LENGTH: 12
<212> TYPE: PRT
<213> ORGANISM: H. sapiens

<400> SEQUENCE: 319

Lys Lys Phe Leu Gly Lys Tyr Phe Lys Gly Ser Arg
1               5                   10

<210> SEQ ID NO 320
<211> LENGTH: 10
<212> TYPE: PRT
<213> ORGANISM: H. sapiens

<400> SEQUENCE: 320

Ile Gly Asn Gly Val Phe Lys Leu Asn Phe
1               5                   10

<210> SEQ ID NO 321
<211> LENGTH: 20
<212> TYPE: PRT
<213> ORGANISM: H. sapiens

<400> SEQUENCE: 321

Ala Lys Ile Asn Arg Ile Arg Leu Ile Asn Ile Asp Cys Lys Leu Gly
1               5                   10                  15

Gly Glu Lys His
            20

<210> SEQ ID NO 322
<211> LENGTH: 38
<212> TYPE: PRT
<213> ORGANISM: H. sapiens

<400> SEQUENCE: 322

Leu Arg Val Leu Lys Cys Arg Asn Ser Asn Leu Pro Leu Asn Ile Lys
1               5                   10                  15

Ile Leu Thr Gln Arg Ile Ile Tyr Arg Gly Glu Pro Gln Val Ala Ile
            20                  25                  30

Gln Val Cys Phe Thr Leu

<210> SEQ ID NO 323
<211> LENGTH: 4
<212> TYPE: PRT
<213> ORGANISM: H. sapiens

<400> SEQUENCE: 323

Ile Ile Arg Gly
1

<210> SEQ ID NO 324
<211> LENGTH: 12
<212> TYPE: PRT
<213> ORGANISM: H. sapiens

<400> SEQUENCE: 324

Leu Ser Ile Phe Gln Lys Leu Ala Ala Ala Leu Glu
1               5                   10

<210> SEQ ID NO 325
<211> LENGTH: 12
<212> TYPE: PRT
<213> ORGANISM: H. sapiens

<400> SEQUENCE: 325

Leu Val Asn Pro Leu Gly Pro Leu Asn Ala Trp Gly
1               5                   10

<210> SEQ ID NO 326
<211> LENGTH: 11
<212> TYPE: PRT
<213> ORGANISM: H. sapiens

<400> SEQUENCE: 326

Gly Thr Arg Glu Trp Ala Gln Gly Ser Glu Ile
1               5                   10

<210> SEQ ID NO 327
<211> LENGTH: 9
<212> TYPE: PRT
<213> ORGANISM: H. sapiens

<400> SEQUENCE: 327

Ile Ile Ile Leu Ile Ile Asn Lys Val
1               5

<210> SEQ ID NO 328
<211> LENGTH: 24
<212> TYPE: PRT
<213> ORGANISM: H. sapiens

<400> SEQUENCE: 328

Arg Ser Tyr Lys Lys Asn Ser Trp Gly Asn Ile Leu Arg Val Gln Gly
1               5                   10                  15

Lys Leu Glu Met Gly Phe Leu Asn
            20

<210> SEQ ID NO 329
<211> LENGTH: 9
<212> TYPE: PRT
<213> ORGANISM: H. sapiens

<400> SEQUENCE: 329

Ile Phe Asn Ile Lys His Lys Gln Arg
1               5

<210> SEQ ID NO 330
<211> LENGTH: 11
<212> TYPE: PRT
<213> ORGANISM: H. sapiens

<400> SEQUENCE: 330

Ile Leu Ile Val Asn Trp Glu Gly Lys Asn Thr
1               5                   10

<210> SEQ ID NO 331
<211> LENGTH: 62
<212> TYPE: PRT
<213> ORGANISM: H. sapiens

<400> SEQUENCE: 331

Met Gly Trp Gln Arg Asn Gly Arg Ser Arg Asp Ile Arg Thr Ala Cys
1               5                   10                  15

Phe Arg Val Cys Lys Gly Ser Glu Ala Ser Gln His Gln Thr Leu Cys
                20                  25                  30

Arg Pro Pro Ala Pro Ser Gly Ser Trp Gly Ser Gly His Gln Phe Lys
            35                  40                  45

Thr Val Gly Arg Val Thr Lys Lys Glu Ala Ser Arg Pro His
    50                  55                  60

<210> SEQ ID NO 332
<211> LENGTH: 124
<212> TYPE: PRT
<213> ORGANISM: H. sapiens

<400> SEQUENCE: 332

Val Thr Ile Asn Pro Leu Gly Pro Leu Asn Gly Leu Gly Gly Val Lys
1               5                   10                  15

Lys Ser Gly Gly Gly Ser Phe Phe Tyr Pro Pro Leu Arg Lys Lys
                20                  25                  30

Lys Asp Asp Pro Pro Ser Arg Glu Ala Asp Gly Gly Gly Ser
            35                  40                  45

Phe Phe Ala Pro Pro Lys Gly Pro Leu Arg Ser Val Tyr Ser Phe Cys
    50                  55                  60

Thr Ile Leu Cys Lys Asn Ser Pro Leu Met Pro Arg Glu Lys Gly Gly
65                  70                  75                  80

Asn Leu Lys Phe Phe Phe Leu Lys Lys Arg Val Phe Asn Phe Gly
                85                  90                  95

Lys Gly Phe Pro Lys Thr Glu Ser Phe Lys Gly Asn Gln Ile Gly Pro
            100                 105                 110

Asn Ser Pro Val Glu Lys Thr Ile Pro Arg Glu Asn
        115                 120

<210> SEQ ID NO 333
<211> LENGTH: 4
<212> TYPE: PRT
<213> ORGANISM: H. sapiens

<400> SEQUENCE: 333

Ile Lys Asn His
1

<210> SEQ ID NO 334

```
<211> LENGTH: 20
<212> TYPE: PRT
<213> ORGANISM: H. sapiens

<400> SEQUENCE: 334

Lys Gly Ala Met Ser Lys Ser Arg Glu Trp Val Gly Arg Glu Met Val
1               5                   10                  15

Glu Ala Glu Thr
            20

<210> SEQ ID NO 335
<211> LENGTH: 51
<212> TYPE: PRT
<213> ORGANISM: H. sapiens

<400> SEQUENCE: 335

Gly Gln Pro Ala Ser Glu Cys Ala Lys Glu Val Lys Pro Ala Ser Thr
1               5                   10                  15

Arg Pro Cys Ala Asp His Pro Pro Val Ala Ala Gly Gly Val Val
            20                  25                  30

Ile Ser Ser Arg Pro Trp Glu Gly Leu Gln Lys Lys Leu Arg Gly
        35                  40                  45

Arg Thr Glu
    50

<210> SEQ ID NO 336
<211> LENGTH: 7
<212> TYPE: PRT
<213> ORGANISM: H. sapiens

<400> SEQUENCE: 336

Leu Leu Thr Pro Trp Gly Leu
1               5

<210> SEQ ID NO 337
<211> LENGTH: 47
<212> TYPE: PRT
<213> ORGANISM: H. sapiens

<400> SEQUENCE: 337

Thr Val Trp Gly Gly Leu Lys Ser Arg Gly Gly Pro Phe Phe Thr
1               5                   10                  15

Pro Pro Pro Leu Gly Lys Lys Lys Met Thr Pro Leu Pro Gln Gly Arg
            20                  25                  30

Leu Met Val Val Val Leu Ser Leu His Leu Arg Arg Val Leu
        35                  40                  45

<210> SEQ ID NO 338
<211> LENGTH: 24
<212> TYPE: PRT
<213> ORGANISM: H. sapiens

<400> SEQUENCE: 338

Gly Arg Phe Thr Val Phe Ala Pro Phe Phe Val Lys Ile Pro Pro Leu
1               5                   10                  15

Cys Pro Gly Lys Lys Gly Glu Ile
            20

<210> SEQ ID NO 339
<211> LENGTH: 5
<212> TYPE: PRT
<213> ORGANISM: H. sapiens
```

```
<400> SEQUENCE: 339

Asn Ser Ser Phe Phe
1               5

<210> SEQ ID NO 340
<211> LENGTH: 41
<212> TYPE: PRT
<213> ORGANISM: H. sapiens

<400> SEQUENCE: 340

Lys Lys Gly Tyr Leu Ile Leu Glu Arg Val Ser Gln Lys Arg Arg Val
1               5                   10                  15

Leu Lys Val Ile Lys Ser Asp Pro Thr Pro Leu Trp Lys Lys Pro Ser
            20                  25                  30

Arg Gly Lys Thr Lys Leu Lys Thr Ile
        35                  40

<210> SEQ ID NO 341
<211> LENGTH: 29
<212> TYPE: PRT
<213> ORGANISM: H. sapiens

<400> SEQUENCE: 341

Arg Gly Gly Ser Leu Thr His Pro Pro Ala Trp Val Thr Glu Arg Gly
1               5                   10                  15

Arg Cys Leu Ser His Val Asn Gly Leu Ala Glu Lys Trp
            20                  25

<210> SEQ ID NO 342
<211> LENGTH: 15
<212> TYPE: PRT
<213> ORGANISM: H. sapiens

<400> SEQUENCE: 342

Lys Pro Arg His Lys Asp Ser Leu Leu Pro Ser Val Gln Arg Lys
1               5                   10                  15

<210> SEQ ID NO 343
<211> LENGTH: 42
<212> TYPE: PRT
<213> ORGANISM: H. sapiens

<400> SEQUENCE: 343

Ser Gln Pro Ala Pro Asp Leu Val Gln Thr Thr Arg Pro Gln Trp Gln
1               5                   10                  15

Leu Gly Glu Trp Ser Ser Val Gln Asp Arg Gly Lys Gly Tyr Lys Lys
            20                  25                  30

Arg Ser Phe Ala Ala Ala Leu Ser Asn Tyr
        35                  40

<210> SEQ ID NO 344
<211> LENGTH: 11
<212> TYPE: PRT
<213> ORGANISM: H. sapiens

<400> SEQUENCE: 344

Pro Leu Gly Ala Ser Lys Arg Phe Gly Gly Gly
1               5                   10

<210> SEQ ID NO 345
<211> LENGTH: 13
```

```
<212> TYPE: PRT
<213> ORGANISM: H. sapiens

<400> SEQUENCE: 345

Lys Val Gly Gly Gly Val Leu Phe Leu Pro Pro Pro
1               5                   10

<210> SEQ ID NO 346
<211> LENGTH: 4
<212> TYPE: PRT
<213> ORGANISM: H. sapiens

<400> SEQUENCE: 346

Glu Lys Lys Arg
1

<210> SEQ ID NO 347
<211> LENGTH: 7
<212> TYPE: PRT
<213> ORGANISM: H. sapiens

<400> SEQUENCE: 347

Pro Pro Ser Leu Lys Gly Gly
1               5

<210> SEQ ID NO 348
<211> LENGTH: 25
<212> TYPE: PRT
<213> ORGANISM: H. sapiens

<400> SEQUENCE: 348

Trp Trp Trp Trp Phe Phe Leu Cys Thr Ser Glu Gly Ser Phe Lys Val
1               5                   10                  15

Gly Leu Gln Phe Leu His His Ser Leu
            20                  25

<210> SEQ ID NO 349
<211> LENGTH: 24
<212> TYPE: PRT
<213> ORGANISM: H. sapiens

<400> SEQUENCE: 349

Lys Phe Pro Pro Tyr Ala Pro Gly Lys Arg Gly Lys Phe Lys Ile Leu
1               5                   10                  15

Leu Phe Phe Lys Lys Lys Gly Ile
            20

<210> SEQ ID NO 350
<211> LENGTH: 11
<212> TYPE: PRT
<213> ORGANISM: H. sapiens

<400> SEQUENCE: 350

Phe Trp Lys Gly Phe Pro Lys Asn Gly Glu Phe
1               5                   10

<210> SEQ ID NO 351
<211> LENGTH: 18
<212> TYPE: PRT
<213> ORGANISM: H. sapiens

<400> SEQUENCE: 351

Ser Asn Arg Thr Gln Leu Pro Cys Gly Lys Asn His Pro Ala Gly Lys
1               5                   10                  15
```

Leu Asn

<210> SEQ ID NO 352
<211> LENGTH: 7
<212> TYPE: PRT
<213> ORGANISM: H. sapiens

<400> SEQUENCE: 352

Ser Lys Lys Arg Gly Tyr Ser
1               5

<210> SEQ ID NO 353
<211> LENGTH: 11
<212> TYPE: PRT
<213> ORGANISM: H. sapiens

<400> SEQUENCE: 353

Arg Leu Ser Pro Pro Gly Ser Tyr Val Thr Pro
1               5                   10

<210> SEQ ID NO 354
<211> LENGTH: 4
<212> TYPE: PRT
<213> ORGANISM: H. sapiens

<400> SEQUENCE: 354

Phe Asn Ser Phe
1

<210> SEQ ID NO 355
<211> LENGTH: 57
<212> TYPE: PRT
<213> ORGANISM: H. sapiens

<400> SEQUENCE: 355

His Phe Pro His His Thr Phe Cys Ser Ser Lys Tyr Ile Pro Leu
1               5                   10                  15

Glu Lys Gln Met Cys Leu Leu Thr Thr His Asp Asn Leu Gly Asn Gly
                20                  25                  30

Cys Asn Cys Ser Cys Val Gly Leu Lys Lys Leu Lys Gln Asn Lys
            35                  40                  45

Thr Lys Lys Pro Gln Ala Asn Lys Ile
    50                  55

<210> SEQ ID NO 356
<211> LENGTH: 4
<212> TYPE: PRT
<213> ORGANISM: H. sapiens

<400> SEQUENCE: 356

Arg Pro Val Pro
1

<210> SEQ ID NO 357
<211> LENGTH: 17
<212> TYPE: PRT
<213> ORGANISM: H. sapiens

<400> SEQUENCE: 357

Gly Gln Met Ser Thr Lys Gly Leu Val Ser Pro Ser Lys Val Ser Gly
1               5                   10                  15

Val

```
<210> SEQ ID NO 358
<211> LENGTH: 9
<212> TYPE: PRT
<213> ORGANISM: H. sapiens

<400> SEQUENCE: 358

Arg Asp Leu Phe Ser Ile Phe Arg Pro
1               5

<210> SEQ ID NO 359
<211> LENGTH: 5
<212> TYPE: PRT
<213> ORGANISM: H. sapiens

<400> SEQUENCE: 359

Ala Ile Leu Phe Ala
1               5

<210> SEQ ID NO 360
<211> LENGTH: 9
<212> TYPE: PRT
<213> ORGANISM: H. sapiens

<400> SEQUENCE: 360

Ala Cys Gly Arg Thr Arg Val Thr Ser
1               5

<210> SEQ ID NO 361
<211> LENGTH: 12
<212> TYPE: PRT
<213> ORGANISM: H. sapiens

<400> SEQUENCE: 361

Pro Leu Gly Ala Ser Lys Arg Gly Gly Gly Val Ser
1               5                   10

<210> SEQ ID NO 362
<211> LENGTH: 55
<212> TYPE: PRT
<213> ORGANISM: H. sapiens

<400> SEQUENCE: 362

Ser Arg Gly Gly Gly Gly Ser Leu Arg Lys Thr Lys Ile Ala Asp Gly
1               5                   10                  15

Leu Lys Asn Gly Lys Tyr Pro Leu Ala Cys Leu Asn Trp Arg Thr Leu
            20                  25                  30

Thr Asn Thr Gly Pro Phe Gly Arg Val Phe Val Phe Leu Gly Gly Gly
        35                  40                  45

Val Phe Lys Phe Phe Phe Phe
    50                  55

<210> SEQ ID NO 363
<211> LENGTH: 17
<212> TYPE: PRT
<213> ORGANISM: H. sapiens

<400> SEQUENCE: 363

Pro Thr Leu Asn Pro Leu Gly Lys Lys Ile Val Phe Leu Arg Gly Gly
1               5                   10                  15

Phe
```

```
<210> SEQ ID NO 364
<211> LENGTH: 27
<212> TYPE: PRT
<213> ORGANISM: H. sapiens

<400> SEQUENCE: 364

Lys Lys Lys Met Gly Gly Lys Met Gly Lys Gly Ile Asn Pro Gly Gly
1               5                   10                  15

Glu Ser Arg Gly Lys Thr Lys Leu Lys Thr Ile
            20                  25

<210> SEQ ID NO 365
<211> LENGTH: 14
<212> TYPE: PRT
<213> ORGANISM: H. sapiens

<400> SEQUENCE: 365

Leu Pro Met Thr Ile Leu Glu Met Val Ala Thr Val His Val
1               5                   10

<210> SEQ ID NO 366
<211> LENGTH: 21
<212> TYPE: PRT
<213> ORGANISM: H. sapiens

<400> SEQUENCE: 366

Asn Lys Thr Lys Gln Lys Asn His Arg Gln Thr Lys Ser Arg Asp Leu
1               5                   10                  15

Cys His Lys Val Arg
            20

<210> SEQ ID NO 367
<211> LENGTH: 40
<212> TYPE: PRT
<213> ORGANISM: H. sapiens

<400> SEQUENCE: 367

Ala Arg Lys Gly Trp Leu Val His Pro Lys Ser Gln Gly Phe Arg Gln
1               5                   10                  15

Ala Arg Gly Ile Tyr Phe Pro Phe Leu Gly His Arg Gln Phe Cys Leu
            20                  25                  30

Leu Lys Leu Ala Ala Ala Leu Glu
        35                  40

<210> SEQ ID NO 368
<211> LENGTH: 13
<212> TYPE: PRT
<213> ORGANISM: H. sapiens

<400> SEQUENCE: 368

Leu Val Asn Pro Leu Gly Pro Leu Asn Gly Gly Gly Gly
1               5                   10

<210> SEQ ID NO 369
<211> LENGTH: 9
<212> TYPE: PRT
<213> ORGANISM: H. sapiens

<400> SEQUENCE: 369

Val Asn Arg Gly Gly Gly Gly Glu Ala
1               5

<210> SEQ ID NO 370
```

```
<211> LENGTH: 8
<212> TYPE: PRT
<213> ORGANISM: H. sapiens

<400> SEQUENCE: 370

Glu Lys Gln Lys Leu Pro Met Gly
1               5

<210> SEQ ID NO 371
<211> LENGTH: 6
<212> TYPE: PRT
<213> ORGANISM: H. sapiens

<400> SEQUENCE: 371

Lys Met Glu Asn Ile Pro
1               5

<210> SEQ ID NO 372
<211> LENGTH: 4
<212> TYPE: PRT
<213> ORGANISM: H. sapiens

<400> SEQUENCE: 372

Thr Gly Gly Leu
1

<210> SEQ ID NO 373
<211> LENGTH: 26
<212> TYPE: PRT
<213> ORGANISM: H. sapiens

<400> SEQUENCE: 373

Leu Thr Gln Ala Pro Leu Gly Gly Phe Leu Phe Phe Trp Gly Gly
1               5                   10                  15

Cys Leu Asn Phe Phe Phe Asn Pro Pro
            20                  25

<210> SEQ ID NO 374
<211> LENGTH: 9
<212> TYPE: PRT
<213> ORGANISM: H. sapiens

<400> SEQUENCE: 374

Thr His Trp Gly Lys Lys Leu Phe Phe
1               5

<210> SEQ ID NO 375
<211> LENGTH: 17
<212> TYPE: PRT
<213> ORGANISM: H. sapiens

<400> SEQUENCE: 375

Gly Glu Val Phe Asp Lys Lys Lys Trp Gly Glu Lys Trp Ala Lys
1               5                   10                  15

Glu

<210> SEQ ID NO 376
<211> LENGTH: 11
<212> TYPE: PRT
<213> ORGANISM: H. sapiens

<400> SEQUENCE: 376

Ile Arg Gly Gly Asn Pro Ala Gly Lys Leu Asn
1               5                   10
```

<210> SEQ ID NO 377
<211> LENGTH: 29
<212> TYPE: PRT
<213> ORGANISM: H. sapiens

<400> SEQUENCE: 377

Phe Leu Leu Thr Phe Ser Pro Ser Tyr Phe Leu Leu Phe Ile Lys Ile
1               5                   10                  15

His Pro Ser Arg Lys Thr Asn Val Leu Ile Asp Tyr Pro
            20                  25

<210> SEQ ID NO 378
<211> LENGTH: 45
<212> TYPE: PRT
<213> ORGANISM: H. sapiens

<400> SEQUENCE: 378

Gln Ser Trp Lys Trp Leu Gln Leu Phe Met Cys Arg Ile Lys Lys Lys
1               5                   10                  15

Ile Lys Thr Lys Gln Asn Lys Lys Thr Thr Gly Lys Gln Asn Leu Glu
            20                  25                  30

Thr Cys Ala Ile Arg Ser Asp Glu His Glu Arg Val Gly
        35                  40                  45

<210> SEQ ID NO 379
<211> LENGTH: 18
<212> TYPE: PRT
<213> ORGANISM: H. sapiens

<400> SEQUENCE: 379

Ser Ile Gln Ser Leu Arg Gly Leu Gly Lys Leu Glu Gly Phe Ile Phe
1               5                   10                  15

His Phe

<210> SEQ ID NO 380
<211> LENGTH: 16
<212> TYPE: PRT
<213> ORGANISM: H. sapiens

<400> SEQUENCE: 380

Ala Ile Gly Asn Phe Val Cys Leu Ser Leu Arg Pro His Ser Ser Asn
1               5                   10                  15

<210> SEQ ID NO 381
<211> LENGTH: 6
<212> TYPE: PRT
<213> ORGANISM: H. sapiens

<400> SEQUENCE: 381

Leu Thr Pro Trp Gly Leu
1               5

<210> SEQ ID NO 382
<211> LENGTH: 40
<212> TYPE: PRT
<213> ORGANISM: H. sapiens

<400> SEQUENCE: 382

Thr Gly Gly Gly Gly Lys Leu Ile Glu Gly Gly Gly Lys Leu Lys
1               5                   10                  15

Lys Asn Lys Asn Cys Arg Trp Ala Lys Lys Trp Lys Ile Ser Pro Ser

```
            20                  25                  30

Leu Pro Lys Leu Glu Asp Phe Asp
         35                  40

<210> SEQ ID NO 383
<211> LENGTH: 16
<212> TYPE: PRT
<213> ORGANISM: H. sapiens

<400> SEQUENCE: 383

His Arg Pro Leu Trp Glu Gly Phe Cys Phe Gly Gly Gly Gly Val
 1               5                  10                  15

<210> SEQ ID NO 384
<211> LENGTH: 46
<212> TYPE: PRT
<213> ORGANISM: H. sapiens

<400> SEQUENCE: 384

Ile Phe Phe Phe Leu Thr His Pro Glu Pro Ile Gly Glu Lys Asn Cys
 1               5                  10                  15

Phe Phe Glu Gly Arg Phe Leu Ile Lys Lys Lys Asn Gly Gly Lys Asn
             20                  25                  30

Gly Gln Arg Asn Lys Ser Gly Gly Gly Ile Pro Arg Glu Asn
         35                  40                  45

<210> SEQ ID NO 385
<211> LENGTH: 4
<212> TYPE: PRT
<213> ORGANISM: H. sapiens

<400> SEQUENCE: 385

Ile Lys Asn His
 1

<210> SEQ ID NO 386
<211> LENGTH: 30
<212> TYPE: PRT
<213> ORGANISM: H. sapiens

<400> SEQUENCE: 386

Gln Met Leu Leu Gln Asn His Val Val Ile Lys Ala Val Thr Leu Ile
 1               5                  10                  15

Lys Met Gly Phe Thr Arg Gly Phe Arg Tyr Asn Ser Cys Ser
             20                  25                  30

<210> SEQ ID NO 387
<211> LENGTH: 5
<212> TYPE: PRT
<213> ORGANISM: H. sapiens

<400> SEQUENCE: 387

Ile Ser Ile His Cys
 1               5

<210> SEQ ID NO 388
<211> LENGTH: 8
<212> TYPE: PRT
<213> ORGANISM: H. sapiens

<400> SEQUENCE: 388

Asn Lys Leu Ala Ala Ala Leu Glu
 1               5
```

```
<210> SEQ ID NO 389
<211> LENGTH: 14
<212> TYPE: PRT
<213> ORGANISM: H. sapiens

<400> SEQUENCE: 389

Leu Val Asn Pro Leu Gly Pro Leu Asn Gly Phe Lys Gly Tyr
1               5                   10

<210> SEQ ID NO 390
<211> LENGTH: 53
<212> TYPE: PRT
<213> ORGANISM: H. sapiens

<400> SEQUENCE: 390

Leu Leu Glu Cys Gly Arg Lys Leu Ile Leu Lys Asn Met Leu Thr Val
1               5                   10                  15

Asn Ser Ile Tyr Leu Glu Arg Cys Gly Glu Pro Leu Leu Lys Ala Phe
            20                  25                  30

Leu Ile Lys Asn Leu His Asn Asp Leu Ile Leu Gly Gln Pro Tyr Cys
        35                  40                  45

Gly Lys Asn Pro Pro
    50

<210> SEQ ID NO 391
<211> LENGTH: 34
<212> TYPE: PRT
<213> ORGANISM: H. sapiens

<400> SEQUENCE: 391

Arg Trp Ala Ser Gln Gly Val Ser Gly Thr Thr Ala Ala Val Lys Tyr
1               5                   10                  15

Leu Tyr Thr Val Asn Ile Phe Phe Lys Ile Ser Leu Arg Pro His Ser
            20                  25                  30

Ser Asn

<210> SEQ ID NO 392
<211> LENGTH: 6
<212> TYPE: PRT
<213> ORGANISM: H. sapiens

<400> SEQUENCE: 392

Leu Thr Pro Trp Gly Leu
1               5

<210> SEQ ID NO 393
<211> LENGTH: 16
<212> TYPE: PRT
<213> ORGANISM: H. sapiens

<400> SEQUENCE: 393

Thr Gly Leu Arg Gly Thr Ser Tyr Ser Ser Ala Ala Ala Ser Leu Phe
1               5                   10                  15

<210> SEQ ID NO 394
<211> LENGTH: 12
<212> TYPE: PRT
<213> ORGANISM: H. sapiens

<400> SEQUENCE: 394

Ile Val Phe Ile Trp Ser Ala Ala Gly Asn Pro Tyr
```

```
                        1               5                      10

<210> SEQ ID NO 395
<211> LENGTH: 6
<212> TYPE: PRT
<213> ORGANISM: H. sapiens

<400> SEQUENCE: 395

Arg Ile Cys Thr Met Ile
1               5

<210> SEQ ID NO 396
<211> LENGTH: 12
<212> TYPE: PRT
<213> ORGANISM: H. sapiens

<400> SEQUENCE: 396

Phe Leu Gly Asn His Ile Val Glu Lys Thr Pro Pro
1               5                   10

<210> SEQ ID NO 397
<211> LENGTH: 31
<212> TYPE: PRT
<213> ORGANISM: H. sapiens

<400> SEQUENCE: 397

Ser Ser Tyr Phe Asn Lys Asp Gly Leu His Lys Gly Phe Pro Val Gln
1               5                   10                  15

Gln Leu Gln Leu Asn Ile Tyr Thr Leu Leu Thr Tyr Phe Leu Lys
            20                  25                  30

<210> SEQ ID NO 398
<211> LENGTH: 20
<212> TYPE: PRT
<213> ORGANISM: H. sapiens

<400> SEQUENCE: 398

Gly Val Leu Val Thr Arg Val Arg Pro Gln Ala Tyr Phe Lys Lys Tyr
1               5                   10                  15

Val Asn Ser Glu
            20

<210> SEQ ID NO 399
<211> LENGTH: 21
<212> TYPE: PRT
<213> ORGANISM: H. sapiens

<400> SEQUENCE: 399

Tyr Leu Ser Gly Ala Leu Arg Gly Thr Leu Ile Lys Ser Phe Phe Asn
1               5                   10                  15

Lys Glu Phe Ala Gln
            20

<210> SEQ ID NO 400
<211> LENGTH: 14
<212> TYPE: PRT
<213> ORGANISM: H. sapiens

<400> SEQUENCE: 400

Ser Asp Ser Trp Ala Thr Ile Leu Trp Lys Lys Pro Pro Pro
1               5                   10

<210> SEQ ID NO 401
```

<211> LENGTH: 29
<212> TYPE: PRT
<213> ORGANISM: H. sapiens

<400> SEQUENCE: 401

```
Ser Gln Gly Ser Asn Tyr Ile Ser Ala Lys Thr Leu Leu Gly Leu Thr
1               5                   10                  15
Ser Ser Pro Arg Met Trp Thr Leu Val Arg Leu Pro Gly
            20                  25
```

<210> SEQ ID NO 402
<211> LENGTH: 4
<212> TYPE: PRT
<213> ORGANISM: H. sapiens

<400> SEQUENCE: 402

```
Glu Gly Val Ser
1
```

<210> SEQ ID NO 403
<211> LENGTH: 38
<212> TYPE: PRT
<213> ORGANISM: H. sapiens

<400> SEQUENCE: 403

```
Lys Leu Leu Phe Leu Cys Arg His Ser Met Cys Ser Leu Asp Ile Lys
1               5                   10                  15
Ala Asn Gly Leu Thr Asn Ser Phe Ser Leu Ser Lys Ile Glu Val Ser
            20                  25                  30
Trp Asn Tyr Leu Gly Pro
        35
```

<210> SEQ ID NO 404
<211> LENGTH: 4
<212> TYPE: PRT
<213> ORGANISM: H. sapiens

<400> SEQUENCE: 404

```
Gln Met Phe Leu
1
```

<210> SEQ ID NO 405
<211> LENGTH: 12
<212> TYPE: PRT
<213> ORGANISM: H. sapiens

<400> SEQUENCE: 405

```
Asn Lys Leu Arg Lys Leu Tyr Ile Phe Phe Phe Pro
1               5                   10
```

<210> SEQ ID NO 406
<211> LENGTH: 8
<212> TYPE: PRT
<213> ORGANISM: H. sapiens

<400> SEQUENCE: 406

```
Ser Leu Arg Pro His Ser Ser Asn
1               5
```

<210> SEQ ID NO 407
<211> LENGTH: 6
<212> TYPE: PRT
<213> ORGANISM: H. sapiens

<400> SEQUENCE: 407

Leu Thr Pro Trp Gly Leu
1               5

<210> SEQ ID NO 408
<211> LENGTH: 19
<212> TYPE: PRT
<213> ORGANISM: H. sapiens

<400> SEQUENCE: 408

Thr Val Arg Gly Gly Val Arg Gly Gly Gly Thr Asp Leu Arg
1               5                   10                  15

Arg Lys Ile

<210> SEQ ID NO 409
<211> LENGTH: 39
<212> TYPE: PRT
<213> ORGANISM: H. sapiens

<400> SEQUENCE: 409

Phe Arg Arg Val Val Ser Pro Lys Thr Ile Cys Gly Ala Arg Asn Phe
1               5                   10                  15

Gln Asn Leu Gly Arg Gly Gly Asn Pro Tyr Phe Tyr Leu Met Gly Gly
            20                  25                  30

Lys Lys Lys Phe Gln Asn Ser
        35

<210> SEQ ID NO 410
<211> LENGTH: 50
<212> TYPE: PRT
<213> ORGANISM: H. sapiens

<400> SEQUENCE: 410

Pro Gly Gly Gly Pro Asn Pro Phe Phe Gly Gly Gly Ala Thr Lys
1               5                   10                  15

Gly Phe Lys Lys Lys Lys Met Pro Gly Gly Phe Lys Lys Thr Phe Phe
            20                  25                  30

Phe Phe Cys Gly Lys Lys Arg Gly Glu Ile Phe Arg Gly Pro Pro Pro
        35                  40                  45

Pro Pro
    50

<210> SEQ ID NO 411
<211> LENGTH: 15
<212> TYPE: PRT
<213> ORGANISM: H. sapiens

<400> SEQUENCE: 411

Val Asp Cys Thr Asn Pro Ala Ala His Leu Cys His Ser Ser Lys
1               5                   10                  15

<210> SEQ ID NO 412
<211> LENGTH: 22
<212> TYPE: PRT
<213> ORGANISM: H. sapiens

<400> SEQUENCE: 412

Ala Thr Phe Thr Arg Val Phe Leu Asn Ser Pro Lys Asp Gln Ile Ile
1               5                   10                  15

Ser Leu Leu Lys His Cys
            20

<210> SEQ ID NO 413
<211> LENGTH: 32
<212> TYPE: PRT
<213> ORGANISM: H. sapiens

<400> SEQUENCE: 413

Leu Pro His Gln Glu Cys Gly Leu Trp Ser Asp Cys Gln Val Lys Arg
1               5                   10                  15

Ala Phe Leu Glu Asn Phe Cys Phe Phe Val Gly Thr Val Cys Ala His
            20                  25                  30

<210> SEQ ID NO 414
<211> LENGTH: 4
<212> TYPE: PRT
<213> ORGANISM: H. sapiens

<400> SEQUENCE: 414

Lys Leu Met Asp
1

<210> SEQ ID NO 415
<211> LENGTH: 8
<212> TYPE: PRT
<213> ORGANISM: H. sapiens

<400> SEQUENCE: 415

Leu Ile Pro Leu Ala Phe Pro Lys
1               5

<210> SEQ ID NO 416
<211> LENGTH: 6
<212> TYPE: PRT
<213> ORGANISM: H. sapiens

<400> SEQUENCE: 416

Arg Phe His Gly Thr Ile
1               5

<210> SEQ ID NO 417
<211> LENGTH: 31
<212> TYPE: PRT
<213> ORGANISM: H. sapiens

<400> SEQUENCE: 417

Ala His Asn Lys Cys Phe Cys Asp Glu Thr Asn Ser Gly Asn Cys Ile
1               5                   10                  15

Phe Ser Phe Ser Leu Lys Ala Cys Gly Arg Thr Arg Val Thr Ser
            20                  25                  30

<210> SEQ ID NO 418
<211> LENGTH: 7
<212> TYPE: PRT
<213> ORGANISM: H. sapiens

<400> SEQUENCE: 418

Pro Leu Gly Ala Ser Lys Arg
1               5

<210> SEQ ID NO 419
<211> LENGTH: 8
<212> TYPE: PRT
<213> ORGANISM: H. sapiens

```
<400> SEQUENCE: 419

Gly Gly Gly Gly Gly Ala Arg Ile
1               5

<210> SEQ ID NO 420
<211> LENGTH: 33
<212> TYPE: PRT
<213> ORGANISM: H. sapiens

<400> SEQUENCE: 420

Gly Gly Lys Tyr Ser Ser Gly Gly Leu Phe Pro Gln Lys Gln Phe Val
1               5                   10                  15

Gly Gln Glu Thr Ser Arg Thr Trp Gly Gly Gly Ile Leu Ile Phe
            20                  25                  30

Ile

<210> SEQ ID NO 421
<211> LENGTH: 61
<212> TYPE: PRT
<213> ORGANISM: H. sapiens

<400> SEQUENCE: 421

Trp Glu Gly Lys Lys Asn Ser Arg Thr Pro Asn Arg Gly Gly Asp Gln
1               5                   10                  15

Thr His Phe Leu Gly Gly Glu Gly Pro Gln Arg Val Leu Lys Lys Lys
            20                  25                  30

Lys Cys Arg Gly Ala Leu Lys Lys Leu Phe Phe Phe Val Gly Lys
        35                  40                  45

Lys Gly Gly Lys Phe Phe Gly Ala Pro Pro Pro Gln
    50                  55                  60

<210> SEQ ID NO 422
<211> LENGTH: 22
<212> TYPE: PRT
<213> ORGANISM: H. sapiens

<400> SEQUENCE: 422

Ile Ala Gln Ile Leu Gln Pro Ile Ser Ala Thr Ala Gln Ser Lys Gln
1               5                   10                  15

Leu Leu Leu Val Tyr Ser
            20

<210> SEQ ID NO 423
<211> LENGTH: 10
<212> TYPE: PRT
<213> ORGANISM: H. sapiens

<400> SEQUENCE: 423

Ile Val Pro Arg Ile Lys Leu Tyr Leu Cys
1               5                   10

<210> SEQ ID NO 424
<211> LENGTH: 31
<212> TYPE: PRT
<213> ORGANISM: H. sapiens

<400> SEQUENCE: 424

Asn Ile Val Arg Pro Asn Phe Leu Thr Lys Asn Val Asp Phe Gly Pro
1               5                   10                  15

Thr Ala Arg Leu Arg Gly Arg Phe Leu Lys Thr Phe Val Ser Leu
            20                  25                  30
```

```
<210> SEQ ID NO 425
<211> LENGTH: 10
<212> TYPE: PRT
<213> ORGANISM: H. sapiens

<400> SEQUENCE: 425

Ala Gln Tyr Val Leu Ile Arg Tyr Lys Ser
1               5                   10

<210> SEQ ID NO 426
<211> LENGTH: 40
<212> TYPE: PRT
<213> ORGANISM: H. sapiens

<400> SEQUENCE: 426

Pro Phe Gln Asn Arg Gly Phe Met Glu Leu Ser Arg Pro Ile Thr Asn
1               5                   10                  15

Val Ser Val Met Lys Gln Thr Gln Glu Thr Val Tyr Phe Leu Phe Pro
            20                  25                  30

Leu Lys Leu Ala Ala Ala Leu Glu
        35                  40

<210> SEQ ID NO 427
<211> LENGTH: 86
<212> TYPE: PRT
<213> ORGANISM: H. sapiens

<400> SEQUENCE: 427

Leu Val Asn Pro Leu Gly Pro Leu Asn Gly Glu Gly Gly Gly Lys Ala
1               5                   10                  15

Gly Gly Gly Gly His Gly Phe Lys Glu Glu Asn Ile Val Pro Glu Gly
            20                  25                  30

Cys Phe Pro Lys Asn Asn Leu Trp Gly Lys Lys Leu Pro Glu Pro Gly
        35                  40                  45

Glu Gly Gly Glu Ser Leu Phe Leu Ser Asn Gly Arg Glu Lys Lys Ile
    50                  55                  60

Pro Glu Leu Leu Thr Gly Gly Thr Lys Pro Ile Phe Trp Gly Gly
65                  70                  75                  80

Arg Gly His Lys Gly Phe
                85

<210> SEQ ID NO 428
<211> LENGTH: 8
<212> TYPE: PRT
<213> ORGANISM: H. sapiens

<400> SEQUENCE: 428

Lys Lys Lys Asn Ala Gly Gly Leu
1               5

<210> SEQ ID NO 429
<211> LENGTH: 23
<212> TYPE: PRT
<213> ORGANISM: H. sapiens

<400> SEQUENCE: 429
```

```
Lys Asn Phe Phe Phe Phe Leu Trp Glu Lys Lys Gly Gly Asn Phe Ser
1               5                   10                  15

Gly Pro Pro Pro Pro Pro Asn
            20
```